US012576000B2

(12) United States Patent
George et al.

(10) Patent No.: US 12,576,000 B2
(45) Date of Patent: Mar. 17, 2026

(54) SYSTEMS AND METHODS FOR TREATING NEUROLOGICAL DISORDERS

(71) Applicant: NOCIRA, LLC, Tempe, AZ (US)

(72) Inventors: David Mager George, Scottsdale, AZ (US); John Patrick Claude, Redwood City, CA (US); Kevin Willey, Fort Collins, CO (US)

(73) Assignee: NOCIRA, LLC, Tempe, AZ (US)

( * ) Notice: Subject to any disclaimer, the term of this patent is extended or adjusted under 35 U.S.C. 154(b) by 310 days.

(21) Appl. No.: 16/432,134

(22) Filed: Jun. 5, 2019

(65) Prior Publication Data

US 2020/0121544 A1      Apr. 23, 2020

Related U.S. Application Data

(63) Continuation of application No. PCT/US2017/064964, filed on Dec. 6, 2017.
(Continued)

(51) Int. Cl.
    *A61H 9/00*        (2006.01)
    *A61F 7/00*        (2006.01)
    (Continued)

(52) U.S. Cl.
    CPC ......... *A61H 9/0071* (2013.01); *A61F 7/0085* (2013.01); *A61H 21/00* (2013.01);
    (Continued)

(58) Field of Classification Search
    CPC ........ A61H 9/00; A61H 9/0081; A61H 9/005; A61H 9/0057; A61H 21/00; A61H 23/02;
    (Continued)

(56) References Cited

U.S. PATENT DOCUMENTS

| | | | |
|---|---|---|---|
| 787,443 A | 4/1905 | Godman et al. | |
| 841,146 A | 1/1907 | Hasbrouck | |

(Continued)

FOREIGN PATENT DOCUMENTS

| | | |
|---|---|---|
| AU | 2004/238090 | 11/2004 |
| CA | 1136751 | 11/1982 |

(Continued)

OTHER PUBLICATIONS

Akerman, et al. Pearls and pitfalls in experimental invivo models of migraine: Dural trigerninovascular nociception. Cephalagia, 2013, 33 (8), pp. 557-592.
(Continued)

*Primary Examiner* — Joseph D. Boecker
*Assistant Examiner* — Thomas W Greig
(74) *Attorney, Agent, or Firm* — Knobbe, Martens, Olson & Bear, LLP

(57)        ABSTRACT

Methods, systems, and apparatus, including computer programs encoded on computer storage media for treating medical conditions such as neurological disorders. A user device can be used to communicate with a user and can be used to control a treatment device. The treatment device can be an ear pressure treatment device. The system can execute treatment parameter profiles, and selection of the treatment parameter profiles can depend, at least in part, on feedback provided by the user, such as via the user device. One, two, or more nerves associated with target anatomical locations (e.g., one or both ears) can be stimulated. Some embodiments involve combination therapy including stimulating one or more nerves associated with at least one ear with a first stimulus modality, and a second stimulus modality that is the same as, or different from the first stimulus modality.

31 Claims, 67 Drawing Sheets

Related U.S. Application Data

(60) Provisional application No. 62/478,510, filed on Mar. 29, 2017, provisional application No. 62/452,864, filed on Jan. 31, 2017, provisional application No. 62/437,568, filed on Dec. 21, 2016, provisional application No. 62/430,423, filed on Dec. 6, 2016.

(51) Int. Cl.

| | |
|---|---|
| *A61H 21/00* | (2006.01) |
| *A61H 23/04* | (2006.01) |
| *A61N 1/20* | (2006.01) |
| *G16H 20/70* | (2018.01) |
| *H04R 1/10* | (2006.01) |

(52) U.S. Cl.
CPC .............. *A61H 23/04* (2013.01); *A61N 1/20* (2013.01); *G16H 20/70* (2018.01); *A61F 2007/0005* (2013.01); *A61F 2007/006* (2013.01); *A61H 2201/10* (2013.01); *A61H 2201/105* (2013.01); *A61H 2201/5012* (2013.01); *A61H 2201/5038* (2013.01); *A61H 2201/5046* (2013.01); *A61H 2201/5048* (2013.01); *A61H 2201/5071* (2013.01); *A61H 2201/5097* (2013.01); *A61H 2205/027* (2013.01); *A61H 2230/065* (2013.01); *H04R 1/1016* (2013.01)

(58) Field of Classification Search
CPC ...... A61H 23/04; A61H 9/0071; A61H 23/00; A61F 11/00; A61N 1/37247; G16H 50/50; G16H 40/63
See application file for complete search history.

(56) References Cited

U.S. PATENT DOCUMENTS

| | | | |
|---|---|---|---|
| 853,645 | A | 5/1907 | Meyer |
| 2,176,366 | A | 10/1939 | Smith |
| 2,437,490 | A | 3/1948 | Watson et al. |
| 2,570,675 | A | 10/1951 | Morris |
| 2,652,048 | A | 9/1953 | Joers |
| 3,757,769 | A | 9/1973 | Arguimbau et al. |
| 3,872,559 | A | 3/1975 | Leight |
| 4,002,161 | A | 1/1977 | Klar et al. |
| 4,133,984 | A | 1/1979 | Watson et al. |
| 4,160,449 | A | 7/1979 | Wade |
| 4,206,756 | A | 6/1980 | Grossan |
| 4,244,377 | A | 1/1981 | Grams |
| 4,289,143 | A | 9/1981 | Canavesio et al. |
| 4,325,386 | A | 4/1982 | Katz |
| 4,349,083 | A | 9/1982 | Bennett |
| 4,472,342 | A | 9/1984 | Carr |
| 4,552,137 | A | 11/1985 | Strauss |
| 4,594,058 | A | 6/1986 | Fischell |
| 4,632,104 | A | 12/1986 | Conrow |
| 4,667,676 | A | 5/1987 | Guinta |
| 4,688,582 | A | 8/1987 | Heller et al. |
| 4,754,748 | A | 7/1988 | Antowski |
| 4,757,807 | A | 7/1988 | Densert et al. |
| 4,775,370 | A | 10/1988 | Berry |
| 4,809,708 | A | 3/1989 | Geisler et al. |
| 4,896,380 | A | 1/1990 | Kamitani |
| 4,896,679 | A | 1/1990 | St. Pierre |
| 4,964,769 | A | 10/1990 | Hass |
| 4,984,579 | A | 1/1991 | Burgert et al. |
| 5,024,612 | A | 6/1991 | van den Honert et al. |
| 5,105,822 | A | 4/1992 | Stevens et al. |
| 5,131,411 | A | 7/1992 | Casali et al. |
| 5,228,431 | A | 7/1993 | Giarretto |
| 5,241,967 | A | 9/1993 | Yasushi et al. |
| 5,421,818 | A | 6/1995 | Arenberg |
| 5,431,636 | A | 7/1995 | Stangerup |
| 5,467,784 | A | 11/1995 | Mobley et al. |

| | | | |
|---|---|---|---|
| 5,476,446 | A | 12/1995 | Arenburg |
| 5,483,027 | A | 1/1996 | Krause |
| 5,483,975 | A | 1/1996 | Hirschebain |
| 5,488,961 | A | 2/1996 | Adams |
| 5,631,965 | A | 5/1997 | Chang et al. |
| 5,699,809 | A | 12/1997 | Combs et al. |
| 5,740,258 | A | 4/1998 | Goodwin-Johansson |
| 5,746,725 | A | 5/1998 | Shalon et al. |
| 5,755,234 | A | 5/1998 | Mobley et al. |
| 5,769,891 | A | 6/1998 | Clayton |
| 5,776,179 | A | 7/1998 | Ren et al. |
| 5,819,745 | A | 10/1998 | Mobley et al. |
| 5,865,183 | A | 2/1999 | Hirschebain |
| 5,868,682 | A | 2/1999 | Combe et al. |
| 5,944,711 | A | 8/1999 | Pender |
| 6,004,274 | A | 12/1999 | Nolan et al. |
| 6,016,499 | A | 1/2000 | Ferguson |
| 6,024,726 | A | 2/2000 | Hill |
| 6,129,174 | A | 10/2000 | Brown et al. |
| 6,139,507 | A | 10/2000 | Jeng |
| 6,159,171 | A | 12/2000 | Densert et al. |
| 6,186,959 | B1 | 2/2001 | Canfield et al. |
| 6,258,067 | B1 | 7/2001 | Hill |
| 6,296,652 | B1 | 10/2001 | Qingmin |
| 6,359,993 | B2 | 3/2002 | Birmhall |
| 6,430,443 | B1 | 8/2002 | Karell |
| 6,511,437 | B1 | 1/2003 | Nakamura et al. |
| 6,592,512 | B2 | 7/2003 | Stöckert et al. |
| 6,629,938 | B1 | 10/2003 | Engvall et al. |
| 6,725,568 | B2 | 4/2004 | Gronka |
| 6,748,275 | B2 | 6/2004 | Lattner et al. |
| 6,800,062 | B2 | 10/2004 | Epley |
| 6,820,717 | B2 | 11/2004 | Fleming et al. |
| 6,878,128 | B2 | 4/2005 | MacMahon et al. |
| 6,958,043 | B2 | 10/2005 | Hissong |
| 6,981,569 | B2 | 1/2006 | Stilp |
| 7,022,090 | B1 | 4/2006 | Engvall et al. |
| 7,162,039 | B1 | 1/2007 | Callahan |
| 7,179,238 | B2 | 2/2007 | Hissong |
| 7,189,252 | B2 | 3/2007 | Krueger |
| 7,268,466 | B2 | 9/2007 | Rasmussen |
| 7,352,871 | B1 | 4/2008 | Mozo |
| D570,457 | S | 6/2008 | Brown |
| 7,613,519 | B2 | 11/2009 | De Ridder |
| 7,766,858 | B2 | 8/2010 | Franz et al. |
| 7,779,844 | B2 | 8/2010 | Purcell et al. |
| 7,785,346 | B2 | 8/2010 | Blumberg |
| 7,797,042 | B2 | 9/2010 | Dietrich et al. |
| 7,833,282 | B2 | 11/2010 | Mandpe |
| 7,892,180 | B2 | 2/2011 | Epley |
| 7,959,597 | B2 | 6/2011 | Baker et al. |
| 7,988,657 | B2 | 8/2011 | Shapiro et al. |
| 8,020,563 | B2 | 9/2011 | Pfanstiehl |
| 8,047,207 | B2 | 11/2011 | Perez et al. |
| 8,052,693 | B2 | 11/2011 | Shahoian |
| 8,122,892 | B2 | 2/2012 | Johnson et al. |
| 8,142,373 | B1 | 3/2012 | Riles |
| 8,199,919 | B2 | 6/2012 | Goldstein et al. |
| 8,241,224 | B2 | 8/2012 | Keefe |
| 8,249,285 | B2 | 8/2012 | Killion et al. |
| 8,251,925 | B2 | 8/2012 | Keady et al. |
| 8,262,717 | B2 | 9/2012 | Rogers et al. |
| 8,267,983 | B2 | 9/2012 | Rogers et al. |
| 8,267,984 | B2 | 9/2012 | Rogers |
| 8,328,830 | B1 | 12/2012 | Pandit |
| 8,398,562 | B2 | 3/2013 | Keller |
| 8,414,521 | B2 | 4/2013 | Baker et al. |
| 8,442,632 | B2 | 5/2013 | Kullok et al. |
| 8,460,356 | B2 | 6/2013 | Rogers et al. |
| 8,506,469 | B2 | 8/2013 | Dietrich et al. |
| 8,515,552 | B2 | 8/2013 | Englehart |
| 8,550,206 | B2 | 10/2013 | Keady et al. |
| 8,568,348 | B2 | 10/2013 | Vlodaver |
| 8,603,152 | B2 | 12/2013 | Smith et al. |
| 8,625,833 | B1 | 1/2014 | Armwood |
| 8,666,502 | B2 | 3/2014 | Hartlep et al. |
| 8,688,239 | B2 | 4/2014 | Hartlep et al. |
| 8,696,724 | B2 | 4/2014 | Rogers |
| 8,858,430 | B2 | 10/2014 | Oyadiran et al. |

(56) References Cited

U.S. PATENT DOCUMENTS

| | | |
|---|---|---|
| 8,963,914 B2 | 2/2015 | Rawat et al. |
| 9,039,639 B2 | 5/2015 | George et al. |
| 9,168,171 B2 | 10/2015 | Rogers |
| 9,186,277 B2 | 11/2015 | George et al. |
| 9,283,111 B2 | 3/2016 | Rogers et al. |
| 9,526,653 B2 | 12/2016 | Rogers et al. |
| 9,532,900 B2 | 1/2017 | Smith et al. |
| 9,579,247 B2 | 2/2017 | Juto et al. |
| 9,655,772 B2 | 5/2017 | Smith et al. |
| 9,744,074 B2 | 8/2017 | Rogers |
| 9,849,026 B2 | 12/2017 | Rogers et al. |
| 10,076,464 B2 | 9/2018 | George et al. |
| 10,251,790 B2 | 4/2019 | George et al. |
| 10,271,992 B2 | 4/2019 | Hayahi et al. |
| 10,278,868 B2 | 5/2019 | George et al. |
| 10,319,475 B1 | 6/2019 | Croan et al. |
| 10,376,695 B2 | 8/2019 | Ericco et al. |
| 10,760,566 B2 | 9/2020 | George et al. |
| 10,772,766 B2 | 9/2020 | Sullivan |
| 11,065,444 B2 | 7/2021 | Ericco et al. |
| 11,090,194 B2 | 8/2021 | George et al. |
| 11,096,828 B2 | 8/2021 | George et al. |
| 11,246,793 B2 | 2/2022 | George et al. |
| 11,859,606 B2 | 1/2024 | George et al. |
| 12,016,816 B2 | 6/2024 | George et al. |
| 12,102,506 B2 | 10/2024 | Sullivan |
| 12,178,966 B2 | 12/2024 | George et al. |
| 2001/0025191 A1 | 9/2001 | Montgomery |
| 2002/0069883 A1 | 6/2002 | Hirchenbain |
| 2003/0105450 A1 | 6/2003 | Dimick |
| 2003/0195588 A1 | 10/2003 | Fischell et al. |
| 2003/0220536 A1 | 11/2003 | Hissong |
| 2003/0220585 A1 | 11/2003 | Hissong |
| 2004/0097839 A1 | 5/2004 | Epley |
| 2004/0163882 A1 | 8/2004 | Fleming et al. |
| 2004/0225178 A1 | 11/2004 | Kriewall |
| 2005/0065585 A1 | 3/2005 | Salas |
| 2005/0165460 A1 | 7/2005 | Erfan |
| 2005/0209516 A1 | 9/2005 | Fraden |
| 2005/0267388 A1 | 12/2005 | Hanna |
| 2006/0100681 A1 | 5/2006 | Salas Carpizo |
| 2006/0197412 A1 | 9/2006 | Rasmussen |
| 2006/0253087 A1 | 11/2006 | Vlodaver et al. |
| 2006/0272650 A1 | 12/2006 | Hoogenakker et al. |
| 2007/0040454 A1 | 2/2007 | Freudenberger et al. |
| 2007/0112279 A1 | 5/2007 | Iseberg et al. |
| 2007/0250119 A1 | 10/2007 | Tyler et al. |
| 2007/0299362 A1 | 12/2007 | Epley et al. |
| 2008/0011308 A1 | 1/2008 | Fleming |
| 2008/0154183 A1 | 6/2008 | Baker et al. |
| 2008/0168775 A1 | 7/2008 | Windheim et al. |
| 2008/0208100 A1 | 8/2008 | Wolff |
| 2008/0212787 A1 | 9/2008 | Goldstein et al. |
| 2008/0220092 A1 | 9/2008 | Dipierro |
| 2008/0240942 A1 | 10/2008 | Heinrich et al. |
| 2008/0249439 A1 | 10/2008 | Tracey et al. |
| 2008/0264464 A1 | 10/2008 | Lee et al. |
| 2009/0012420 A1 | 1/2009 | Keller |
| 2009/0082831 A1 | 3/2009 | Paul et al. |
| 2009/0173353 A1 | 7/2009 | Pursell et al. |
| 2009/0182399 A1 | 7/2009 | Sylvestre |
| 2009/0228103 A1 | 9/2009 | Clayton |
| 2009/0293886 A1 | 12/2009 | Dedrick et al. |
| 2010/0002897 A1 | 1/2010 | Keady |
| 2010/0030131 A1 | 2/2010 | Morris et al. |
| 2010/0071707 A1 | 3/2010 | Wohl |
| 2010/0071708 A1 | 3/2010 | Lenhardt |
| 2010/0113991 A1 | 5/2010 | Wu |
| 2010/0179490 A1 | 7/2010 | Connelly et al. |
| 2010/0198282 A1 | 8/2010 | Rogers |
| 2010/0211142 A1 | 8/2010 | Rogers |
| 2010/0322454 A1 | 12/2010 | Ambrose et al. |
| 2011/0079227 A1 | 4/2011 | Turcot et al. |
| 2011/0097141 A1 | 4/2011 | Browm |
| 2011/0098551 A1 | 4/2011 | Zhang |
| 2011/0130786 A1 | 6/2011 | Clayton et al. |
| 2011/0172739 A1 | 7/2011 | Mann et al. |
| 2011/0184341 A1 | 7/2011 | Baker et al. |
| 2011/0224493 A1 | 9/2011 | Oyadiran et al. |
| 2011/0245902 A1 | 10/2011 | Katz |
| 2011/0301572 A1 | 12/2011 | Vlodaver et al. |
| 2011/0313481 A1 | 12/2011 | De Vos |
| 2012/0046607 A1 | 2/2012 | Syk |
| 2012/0203309 A1 | 8/2012 | Englehart |
| 2012/0265093 A1 | 10/2012 | Allen et al. |
| 2012/0296268 A1 | 11/2012 | Vlodavaer et al. |
| 2012/0302859 A1 | 11/2012 | Keefe |
| 2012/0310077 A1 | 12/2012 | Rogers |
| 2012/0310313 A1 | 12/2012 | Rogers et al. |
| 2012/0318605 A1 | 12/2012 | Brown |
| 2013/0123889 A1 | 5/2013 | Katz et al. |
| 2013/0136285 A1 | 5/2013 | Naumann |
| 2013/0152949 A1 | 6/2013 | Simon |
| 2013/0177179 A1 | 7/2013 | Ambrose et al. |
| 2013/0183173 A1 | 7/2013 | Kohli et al. |
| 2013/0282070 A1 | 10/2013 | Cowan et al. |
| 2013/0303953 A1 | 11/2013 | Lattner |
| 2013/0304103 A1 | 11/2013 | Burres |
| 2013/0310907 A1 | 11/2013 | Rogers et al. |
| 2013/0324932 A1 | 12/2013 | Cogley |
| 2013/0331823 A1 | 12/2013 | Askem et al. |
| 2014/0069442 A1 | 3/2014 | Lewis et al. |
| 2014/0088671 A1 | 3/2014 | Rogers et al. |
| 2014/0243941 A1 | 8/2014 | Rogers et al. |
| 2014/0249608 A1 | 9/2014 | Rogers |
| 2014/0275827 A1* | 9/2014 | Gill ........................ G16H 40/67 607/18 |
| 2014/0309718 A1 | 10/2014 | Smith et al. |
| 2014/0334652 A1 | 11/2014 | Gebert |
| 2014/0344740 A1* | 11/2014 | Kaula ................. G06F 3/04842 715/771 |
| 2014/0365175 A1 | 12/2014 | Packer et al. |
| 2015/0000678 A1* | 1/2015 | Buckler ................... A61F 11/12 128/867 |
| 2015/0005661 A1 | 1/2015 | Trammell |
| 2015/0141879 A1* | 5/2015 | Harper ................... A61H 21/00 601/46 |
| 2015/0230989 A1* | 8/2015 | George ............... A61M 13/003 128/868 |
| 2015/0320591 A1 | 11/2015 | Smith et al. |
| 2015/0320592 A1 | 11/2015 | Black et al. |
| 2015/0324544 A1* | 11/2015 | Maslowski .......... A61B 5/0042 600/475 |
| 2015/0328413 A1 | 11/2015 | Cain |
| 2015/0335466 A1 | 11/2015 | Schöggler |
| 2015/0374538 A1 | 12/2015 | Rogers |
| 2016/0067099 A1* | 3/2016 | Hayashi ................. A61H 21/00 601/76 |
| 2016/0128897 A1 | 5/2016 | George et al. |
| 2016/0151206 A1 | 6/2016 | George et al. |
| 2016/0166203 A1 | 6/2016 | Goldstein |
| 2016/0279435 A1* | 9/2016 | Hyde ....................... A61N 7/00 |
| 2016/0346117 A1 | 12/2016 | Rogers et al. |
| 2016/0378945 A1 | 12/2016 | Mian et al. |
| 2017/0105876 A1 | 4/2017 | O'Connell, Sr. et al. |
| 2017/0109988 A1 | 4/2017 | O'Connell, Sr. et al. |
| 2017/0135854 A1 | 5/2017 | Rogers et al. |
| 2017/0235889 A1 | 8/2017 | Main et al. |
| 2018/0008457 A1 | 1/2018 | Smith et al. |
| 2018/0023558 A1 | 1/2018 | George et al. |
| 2018/0106244 A1 | 4/2018 | Wang et al. |
| 2018/0125748 A1 | 5/2018 | Goldenberg et al. |
| 2019/0231597 A1 | 8/2019 | Sullivan |
| 2020/0222272 A1 | 7/2020 | George et al. |
| 2021/0222684 A1 | 7/2021 | George et al. |
| 2021/0228414 A1 | 7/2021 | George et al. |
| 2021/0330928 A1 | 10/2021 | George et al. |
| 2022/0202617 A1 | 6/2022 | George et al. |
| 2022/0226158 A1 | 7/2022 | George et al. |
| 2022/0370286 A1 | 11/2022 | George et al. |

(56) References Cited

U.S. PATENT DOCUMENTS

| | | |
|---|---|---|
| 2024/0271609 A1 | 8/2024 | George |
| 2025/0120876 A1 | 4/2025 | George |

FOREIGN PATENT DOCUMENTS

| | | |
|---|---|---|
| CA | 1222464 | 6/1987 |
| CA | 1241152 | 8/1988 |
| CA | 2003452 | 6/1990 |
| CA | 2275057 | 10/1999 |
| CA | 2 337 076 | 1/2000 |
| CA | 2429560 | 1/2004 |
| CN | 2075517 U | 4/1991 |
| CN | 2418864 | 2/2001 |
| CN | 1308513 A | 8/2001 |
| CN | 2530645 | 1/2003 |
| CN | 2721057 Y | 8/2005 |
| CN | 1791370 A | 6/2006 |
| CN | 2912525 | 6/2007 |
| CN | 200945215 Y | 9/2007 |
| CN | 201143258 | 11/2008 |
| CN | 201164541 | 12/2008 |
| CN | 101668497 | 3/2010 |
| CN | 201505220 U | 6/2010 |
| CN | 201524178 | 7/2010 |
| CN | 201558360 | 8/2010 |
| CN | 201870809 | 6/2011 |
| CN | 202036187 | 11/2011 |
| CN | 202185057 | 4/2012 |
| CN | 102484761 | 5/2012 |
| CN | 102551957 | 7/2012 |
| CN | 202313927 | 7/2012 |
| CN | 102647966 | 8/2012 |
| CN | 202477966 | 10/2012 |
| CN | 202505833 | 10/2012 |
| CN | 102892392 A | 1/2013 |
| CN | 102986250 | 3/2013 |
| DE | 37 83 917 T2 | 8/1993 |
| DE | 102011008802 | 7/2012 |
| EP | 0 026 247 | 4/1981 |
| EP | 0 400 900 | 12/1990 |
| EP | 1 027 863 | 8/2000 |
| EP | 2 207 366 | 7/2010 |
| EP | 2 990 017 | 3/2016 |
| FR | 2 605 516 A1 | 4/1988 |
| FR | 2 779 944 | 12/1999 |
| GB | 1432572 | 4/1976 |
| GB | 1522031 | 8/1978 |
| GB | 2054387 | 2/1981 |
| GB | 2185688 | 7/1987 |
| GB | 2343263 | 5/2000 |
| GB | 2479891 | 11/2011 |
| IT | 1214840 | 1/1990 |
| JP | S 57-188245 | 11/1982 |
| JP | H 02-220650 | 9/1990 |
| JP | H 07-111987 | 5/1995 |
| JP | H 11-514898 | 12/1999 |
| JP | 2002-519150 | 7/2002 |
| JP | 2003-018359 | 1/2003 |
| JP | 2006-345903 | 12/2006 |
| JP | 2009-022699 | 2/2009 |
| JP | 2010-233643 | 10/2010 |
| JP | 2010-535542 | 11/2010 |
| JP | 2011-217986 | 11/2011 |
| JP | 2013-068448 | 4/2013 |
| JP | 2013-102784 | 5/2013 |
| JP | 2020-44371 | 3/2020 |
| KR | 10-1273296 | 6/2013 |
| MX | PA03005598 | 10/2004 |
| MX | 2010014470 | 2/2011 |
| MX | 2011006854 | 8/2011 |
| MX | 2012007726 | 8/2012 |
| RU | 90 333 U1 | 1/2010 |
| WO | WO 1986/01399 | 3/1986 |
| WO | WO 1994/22372 | 10/1994 |
| WO | WO 1996/23293 | 8/1996 |
| WO | WO 1997/23178 | 7/1997 |
| WO | WO 2000/001331 | 1/2000 |
| WO | WO 2000/001346 | 1/2000 |
| WO | WO 2000/010484 | 3/2000 |
| WO | WO 2000/010627 | 3/2000 |
| WO | WO 2000/010848 | 3/2000 |
| WO | WO 2001/19244 | 3/2001 |
| WO | WO 2003/075761 | 9/2003 |
| WO | WO 2004/064672 | 8/2004 |
| WO | WO 2004/100844 | 11/2004 |
| WO | WO 2006/003910 | 1/2006 |
| WO | WO 2006/009545 | 1/2006 |
| WO | WO 2007/084674 | 7/2007 |
| WO | WO 2007/118092 | 10/2007 |
| WO | WO 2007/145853 | 12/2007 |
| WO | WO 2008/036368 | 3/2008 |
| WO | WO 2008/064230 | 5/2008 |
| WO | WO 2008/086187 | 7/2008 |
| WO | WO 2008/128173 | 10/2008 |
| WO | WO 2008/153588 | 12/2008 |
| WO | WO 2009/020862 | 2/2009 |
| WO | WO 2009/050306 | 4/2009 |
| WO | WO 2009/077902 | 6/2009 |
| WO | WO 2010/005899 | 1/2010 |
| WO | WO 2010/016925 | 2/2010 |
| WO | WO 2010/085196 | 7/2010 |
| WO | WO 2011/075573 | 6/2011 |
| WO | WO 2011/075574 | 6/2011 |
| WO | WO 2012/007193 | 1/2012 |
| WO | WO 2012/083098 | 6/2012 |
| WO | WO 2012/083102 | 6/2012 |
| WO | WO 2012/083106 | 6/2012 |
| WO | WO 2012/083126 | 6/2012 |
| WO | WO 2012/083151 | 6/2012 |
| WO | WO 2013/075255 | 5/2013 |
| WO | WO 2014/120947 | 8/2014 |
| WO | WO 2014/175257 | 10/2014 |
| WO | WO 2014/210457 | 12/2014 |
| WO | WO 2015/009421 | 1/2015 |
| WO | WO 2015/074060 | 5/2015 |
| WO | WO 2016/022761 | 2/2016 |
| WO | WO 2017/040739 | 3/2017 |
| WO | WO 2017/040741 | 3/2017 |
| WO | WO 2017/040747 | 3/2017 |
| WO | WO 2017/079783 | 5/2017 |
| WO | WO 2017/197150 | 11/2017 |
| WO | WO 2018/106839 | 6/2018 |
| WO | WO 2018/157143 | 8/2018 |
| WO | WO 2019/246456 | 12/2019 |
| ZA | 200509787 | 1/2009 |

OTHER PUBLICATIONS

Baguley et al. Does caloric vestibular stimulation modulate tinnitus? Neuroscience Letters, Mar. 2011, 492(1), pp. 52-54.

Baier, et al.: "Vestibular-Evoked Myogenic Potentials In "Vestibular Migraine" and Meniere's Disease," Ann. N.Y. Acad. Sci., May 2009, 1164, pp. 324-327.

Becker: Weather and migraine: Can so many patients be wrong? Cephalalgia, Mar. 2011, 31(4), pp. 387-390.

Bolay et al.,: "Does Low Atmospheric Pressure Independently Trigger Migraine?" Headache, Oct. 2011, 51(9), pp. 1426-1430.

Breathometer. Breathometer—The World's First Smartphone Breathalyzer. Website, http://www.breathometer.co, originall downloaded Jun. 19, 2014, 8 total pages.

Cadwell. Sierra Wave. Website, http://www.cadwell.com, originally downloaded Feb. 27, 2014, 1 page.

Cranial Nerves—Wikipedia, https://en.wikipedia.org/aiki/Cranial_nerves, printed Aug. 16, 2019 in 12 pages.

DaSilva, et al.: "tdCS-Induced Analgesia and Electrical Fields in Pain-Related Neural Networks in Chronic Migraine," The Journal of Head and Face Pain, Sep. 2012, 52, pp. 1283-1295.

Dirckx et al. Human tympanic membrane deformation under static pressure. Hearing Research, Jan. 1991, 51(1), pp. 93-106.

Facebook. ð K: The first migraine and headache solution, Webpage, https://www.facebook.com, originally downloaded May 18, 2017, 10 pages total.

(56)　　　　　References Cited

OTHER PUBLICATIONS

Fasold et al. Human Vestibular Cortex as Identified with Caloric Stimulation in Functional Magnetic Resonance Imaging. Neuroimage, Nov. 2002, 17(3), pp. 1384-1393.

Ferrotec. Thermal Solutions. Website: http://thermal.ferrotec.com, originally downloaded Feb. 27, 2014, 1 page.

Ferrotec. Thermoelectric Technical Reference—Installation of Thermoelectric Modules. Website, http://thermal.ferrotec.com, originally downloaded May 21, 2014, 4 total pages.

Ferrotec. Thermoelectric Technical Reference—Introduction to Thermoelectric Cooling. Website, http://forrotec.com, originally downloaded Feb. 27, 2014, 2 total pages.

George et al. Safety and usability factors in development of a novel, automated treatment device for acute migraine. Biomedical sciences instrumentation. Biomedical sciences instrumentation, Jan. 2017, 53, pp. 398-403.

Hahn: "Let Me Blow in Your Ear, for Migraine Treatment, Of Course," Smile Columbia Dentistry, https://www.tmjtreatmentse.com, originally downloaded Apr. 25, 2016, 2 pages total.

Hu et al. Burden of migraine in the United States: disability and economic costs. Arch. Intern. Med., Apr. 1999, 159, pp. 813-818.

Janetta Neurovascular Compress in Cranial Nerve and Systemic Disease. Ann Surg, Oct. 1980, 192( 4), pp. 518-524.

Job et al. Cortical Representation of Tympanic Membrane Movements due to Pressure Variation: An ±MRI Study Human Brain Mapping, May 2011, 32(5), pp. 744-749.

Kickstarter. ŏ K: The first headache product that solves migraines and headaches. Website, https://www.funded.today, originally downloaded May 18, 2017, 3 pages total.

Klingner et al.: "Components of vestibular cortical function," Behavioral Brain Research, Jan. 2013, 236(1 ), pp. 194-199.

Kolev. How caloric vestibular irrigation influences migraine attacks. Cephalagia. Aug. 1990, vol. 10 issue 4, pp. 167-169 (abstract only).

Lifting the Burden. The Global Campaign Against Headache. Website, http://www.I-t-b.org, originally downloaded Feb. 27, 2014, 1 page.

Liszewski: Ear Pressure Equalizer. Website, http://www.ohgizmo.com, originally downloaded Dec. 18, 2013, 1 page.

Long Island News12.com. Long Island Naturally: Migraines. Website video, http://longisland.news12.com/multimedia/long-island-naturally-migraines-1.6501113, Nov. 26, 2013, 3 total pages.

Mayr: The Origins of Feedback Control. M.I.T. Press, 1970.

McGeoch et al. Vestibular stimulation can relieve central pain of spinal origin. Spinal Cord, Nov. 2008, 46(11), pp. 756-757.

Medscape. Peripheral Nerve Stimulator—Train of Four Monitoring. Website, http://emedicine.medscape.com, originally downloaded Feb. 27, 2014, 2 total pages.

Medtronic. Meniett Device for Meniere's Disease. Meniett Low-Pressure Pulse Generator device. Website, http://www.medtronic.com, originally downloaded Feb. 27, 2014, 2 total pages.

Medtronic. Restore Life's Balance with Meniett Therapy. The Meniett Device for Meniere's Disease. On-line article, http://www.medtronic.com, originally downloaded Mar. 13, 2015, 2 total pages.

Meng et al. Migraine Prevention with a Supraorbital Transcutaneous Stimulator: A Randomized Controlled Trial. Neurology, Sep. 2013, 81, pp. 1102-1103.

Minen. Tinnitus and Headache. American Migraine Foundation, website, downloaded Feb. 8, 2017, 3 pages total.

Mosqueria et al. Vagus Nerve Stimulation in Patients with Migraine. Rev Neurol, 2013, 57(2), English Abstract.

Nagai et al. Encapsulated nerve corpuscles in the human tympanic membrane. Archives of Otorhinolaryngology, 1989, 246(3), pp. 169-172.

New York Health Soultions. Migraine Headaches. Website, http://www.nyhealthsolutions.com, originally downloaded May 23, 2014, 2 pages.

Nihashi et al. Representation of the ear in human primary somatosensory cortex. Neuroimage, Feb. 2001, 13(2), pp. 295-304 (abstract only).

Olesen et al. Emerging Migraine treatments and drug targets. Trends in Pharmacological Sciences, 2011, 32( 6), pp. 352-359.

Pederson et al. Neurostimulation in cluster headache: A review of current progress. Cephalagia, 2013, 33(14 ), pp. 1179-1193.

Pietrobon, Migraine: new molecular mechanism. Neuroscientist. Aug. 2005, vol. 11, Issue 4, pp. 373-386 (abstract only).

Porta-Etessam et al. Neuro-otological symptoms in patients with migraine. Neurologia, Mar. 2011, 26(2), pp. 100-104.

Ramachandran et al. Rapid Relief of Thalamic Pain Syndrome Induced by Vestibular Caloric Stimulation. Neurocase, Jun. 2007, 13(3), pp. 185-188.

Sakata et al. Air pressure-sensing ability of the middle ear—Investigation of sensing regions and appropriate measurement conditions. Auris Nasus Larynx, Aug. 2009, 36(4), pp. 393-399.

Sameiro-Barbosa et al. Sensory Entrainment Mechanisms in Auditory Perception: Neural Synchronization Cortico-Striatal Activation. Frontiers in Neuroscience, Aug. 2016, vol. 10, Article 361, 8 pages.

Saunders, Tympanic membrane sensation. Brain. Jun. 1985, vol. 108, Issue 6,pp. 378-404 (abstract only) in 1 page.

Schoenen et al. Migraine prevention with a supraorbital transcutaneous stimulator. Neurology, 2013, 80(8), pp. 697-704.

Schulman. Breath-Holding, Head Pressure, and Hot Water: An Effective Treatment for Migraine Headache. Headache, Nov.-Dec. 2002, 42(10), pp. 1048-1050.

Scion Neurostim. Therapeutic Neuromodulation via Caloric Vestibular Stimulation. Thermoneuromodulation (TNM). Slides for presentation, dated Sep. 2015, 12 pages total.

Sheftell, F, Steiner, TJ, Thhomas, H. Harry Potter and the Curse of Headache. Headache: The Journal of Head and Face Pain. Jun. 2007, vol. 47, Issue 6, pp. 911-916 (abstract only) in 1 page.

Silberstein et al.: "Botulinum Toxin Type A as a Migraine Preventive Treatment," The Journal of Head and Face Pain, Jun. 2000, 40, pp. 445-450.

SmartProducts. Series 100—Cartridge Specialty Check Valves and Pressure Relief Valves. Online catalog, www.smartproducts,com, originally downloaded Mar. 28, 2014, 2 total.

Stender, Dr., "Easing Migraine Symptoms with a Simple Puff of Air into the Ear," Pasadena Pain Management, http://www.pasadenapainmanagement.com, downloaded Apr. 25, 2016, 5 pages total.

Stovnver, LJ, et al. The global burden of headache: a documentation of headache prevalence and disability worldwide. Cephalagia, 2007. vol. 27, pp. 193-210.

Sullivan: "Ear Insufflation As A Novel Therapy Which Produces Rapid Relief Of Migraine Headache—a Case Study," Funct Neurol Rehabil Egon 2013; vol. 3, Issue 1, pp. 93-107. Published on Jun. 7, 2013. Received on Jan. 2, 2013. Revised Jan. 28, 2013. Accepted Feb. 15, 2013.

Sullivan: "Ear Insufflation Produces Rapid and Significant Relief of Trigeminal Neuraliga," Funct Neurol Rehabil Egon 2013; vol. 3, Issue 4, pp. 1-6. Published on May 26, 2014. Received on Jun. 21, 2013. Revised Dec. 24, 2013. Accepted Jan. 12, 2014.

Transcript of News Story, Aug. 22, 2013, video available at: https://www.facebook.com/178787878873891/videos/10201196245541704/.

"New Migraine Therapy," Aug. 22, 2013, video available at https://www.facebook.com/178787878873891/videos/10201196245541704/.

Transcript of News Story, Nov. 13, 2013, video available at: https://www.facebook.com/178787878873891/videos/treatment-for-migraines-and-trigeminal-neuralgia/10201781732138503/.

"Revolutionary Pain Therapy," Nov. 13, 2013, video available at https://www.facebook.com/178787878873891/videos/treatment-for-migraines-and-trigeminal- neuralgia/10201781732138503/.

Transcript of News Story, Jul. 7, 2014, video available at: https://www.facebook.com/178787878873891/videos/681870651898942/.

"New Therapy for Migraines," Jul. 7, 2014, video available at https://www.facebook.com/178787878873891/videos/treatment-for-migraines-and-trigeminal- neuralgia/10201781732138503/.

Transcript of Webinar, Apr. 10, 2013, video available at: https://www.anymeeting.com/WebConference/RecordingDefault.aspx?c_psrid=ED57DC868548.

(56) References Cited

OTHER PUBLICATIONS

"A novel application to resolve migraine headaches—A Functional Neurology forum," Apr. 10, 2013, video available at: https://www.anymeeting.com/WebConference/RecordingDefault.aspx?c_psrid=ED57DC8685 48.

Ultimate Ears. Ultimate Ears Custom In-Ear Monitors. Website, http://pro.ultimatears.com, originally downloaded Feb. 27, 2014, 3 total pages.

Westone. Occupational Earpieces. Website, http://www.westone.com, originally downloaded Feb. 27, 2014, 2 total pages.

Wikipedia. Microcurrent electrical neuromuscular stimulator. Website, http://en.wikipedia.org, originally downloaded Feb. 27, 2014, 3 total pages.

Wikipedia. Somatosensory evoked potential. Website, http://en.wikipedia.org, originally downloaded Feb. 27, 2014, 5 pages total.

Wikipedia. Transcutaneous electrical nerve stimulation. Website, http://en.wikipedia.org, originally downloaded Feb. 27, 2014, 5 pages total.

World Health Organization. Headache disorders. Website, http://www.who.int, originally downloaded Feb. 27, 2014, 4 total pages.

International Preliminary Report on Patentability in Application No. PCT/US2017/064964, dated Jun. 11, 2019 in 19 pages.

Berthold Langguth, Verena Hund, Volker Busch, et al., "Tinnitus and Headache," BioMed ResearchInternational, vol. 2015, Article ID 797416, 7 pages, 2015. https://doi.org/10.115/2015/797416 (Year: 2015) in 7 pages.

Cathcart, et al., "Pain sensitivity mediates the relationship between stress and headache intensity in chronic tension-type headache", Nov. 2012 (Year: 2012) in 5 pages.

Croley, Christen, "Mechanicsburg doctor develops new migraine therapy," The Sentinel, Nov. 9, 2012.

Doherty, Colleen. "The Link Between Migraines and Tinnitus". Verywell Health, Nov. 23, 2019, https://www.verywellhealth.com/link-between-migraines-and-tinnitus-4077631#citation-10 (Year: 2019) in 4 pages.

Frangos E, Ellrich J, Komisaruk B. Non-invasive access to the vagus nerve central projections via electrical stimulation of the external ear: fMRI evidence in humans. Brain Stimul. Dec. 6, 2014. 8(3), 624-636 in 13 pages.

Kanzara T, Hall A, Virk J, Leung B, Singh A. Clinical anatomy of the tympanic nerve: A review. World J Otorhinolaryngol. Nov. 2014; 4(4), 17-22 in 8 pages.

Kiyokawa J., Yamaguchi K, Okada R, Maehara T, Akita K. Origin, course and distribution of the nerves to the posterosuperior wall of the external acoustic meatus. Anat Sci Int. Mar. 2014; 89(4), 238-245.

Saunders R, Tympanic membrane sensation. Brain. 1985, 108, 378-404 in 18 pages.

Shevel, "Headaches and tinnitus: correlation found", May 2008 (Year: 2006).

Tekdemir I, Aslan A, Elhan A., A clinico-anatomic study of the auricular branch of the vagus nerve and Arnold's ear-cough reflex. Surg Raiol Anat. 1998. 20(4), 253-257 in 5 pages.

Tekdemir I, Aslan A, Tuccar E, He C, Elhan A, Deda H. An anatomical study of the tympanic branch of the glossopharyngeal nerve (nerve of Jacobson). Ann Anat. Aug. 1998; 180(4): 349-52 in 4 pages.

Von Korff, et al., "Assessing headaches severity. New Directions", Jul. 1994 (Year: 1994).

Widemar L, Hellstrom S, Schultzberg M, Stenfors Le. Autonomic innervation of the tympanic membrane. An immunocytochemical and histofluorescence study. Acta Otolaryngol. Jul.-Aug. 1985;100(1-2):58:65 in 9 pages.

U.S. Appl. No. 61/841, 111, filed Jun. 28, 2013.

Teixido, Michael: "Migraine—More than a Headache," Dec. 15, 1999, ENT and Allergy of Delaware (Year: 1999).

U.S. Appl. No. 18/949,671, filed Nov. 15, 2024.

* cited by examiner

1100

2010

2000

2210

2112

2200

2112

2410

2400

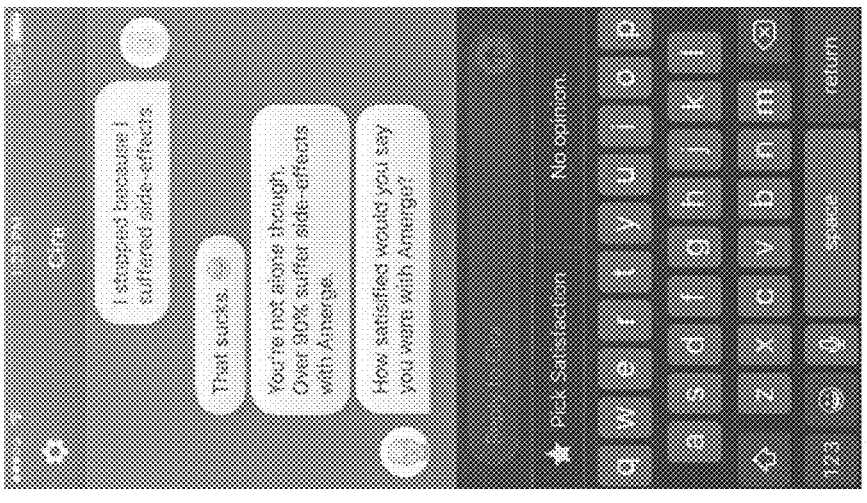
2510
2500
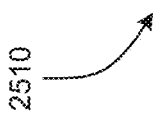
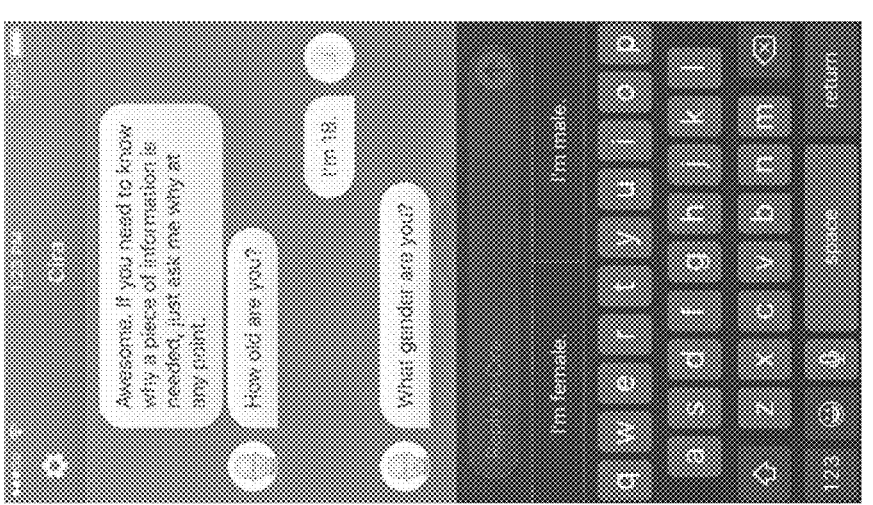
FIG. 35
FIG. 34

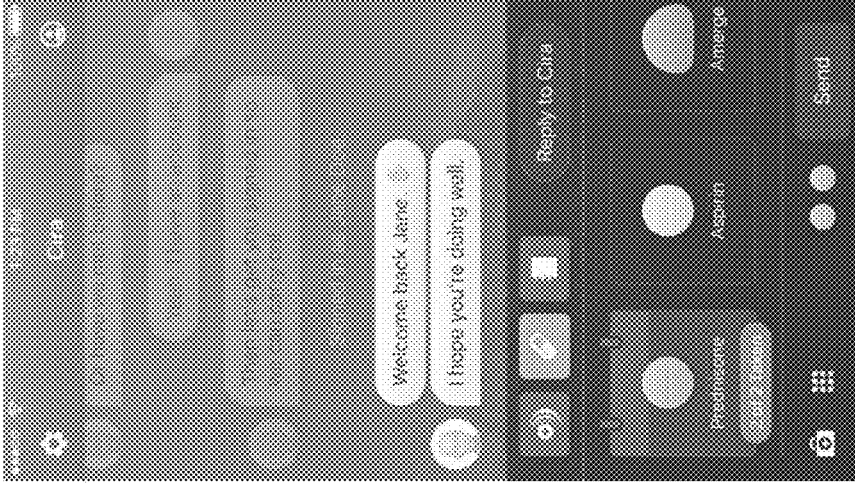
2600
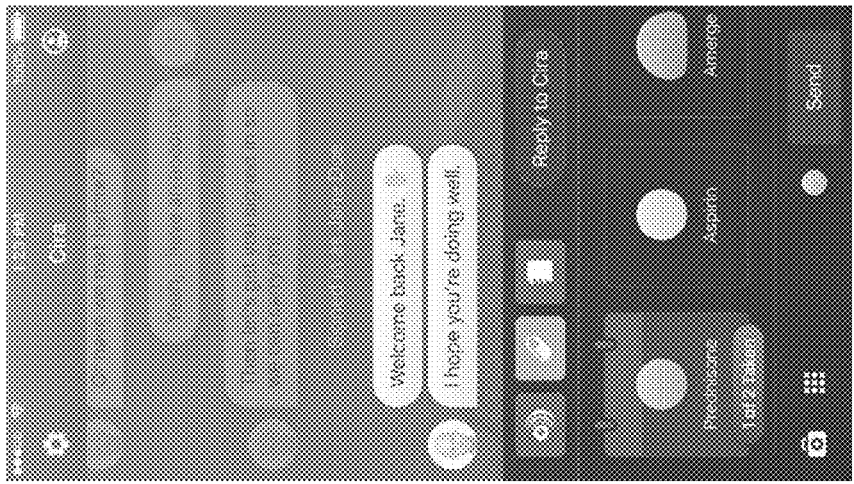
2610
FIG. 36
FIG. 37

2710

2700

2702

2800

2910

2900

2902

2904

2906

3000

3010

14.6 Sense of Equilibrium

Tonaudiogramm

SYSTEMS AND METHODS FOR TREATING NEUROLOGICAL DISORDERS

CROSS REFERENCE TO RELATED APPLICATIONS

The present application is a continuation of International Application No. PCT/US2017/064964 designating the United States, with an international filing date of Dec. 6, 2017, titled "SYSTEMS AND METHODS FOR TREATING NEUROLOGICAL DISORDERS," which claims priority to and the benefit of U.S. Provisional Patent App. No. 62/430,423, filed Dec. 6, 2016, titled "TREATMENT DEVICE CONTROL SYSTEM;" U.S. Provisional Patent App. No. 62/437,568, filed Dec. 21, 2016, titled "SYSTEMS AND METHODS FOR TREATING NEUROLOGICAL DISORDERS;" U.S. Provisional Patent App. No. 62/452,864, filed Jan. 31, 2017, titled "SYSTEMS AND METHODS FOR TREATING NEUROLOGICAL DISORDERS;" and U.S. Provisional Patent App. No. 62/478,510, filed Mar. 29, 2017, titled "SYSTEMS AND METHODS FOR TREATING NEUROLOGICAL DISORDERS," the entirety of each of which is incorporated by reference herein and should be considered a part of this specification.

INCORPORATION BY REFERENCE

The following references are incorporated by reference in their entirety and made a part of this specification for all that they disclose: U.S. Pat. No. 9,039,639 (the "'639 patent"), issued May 26, 2015, and titled EXTERNAL EAR CANAL PRESSURE REGULATION SYSTEM; United States Patent Application Publication No. 2015/0000678 (the "'678 Publication"), published Jan. 1, 2015, and titled METHOD FOR EXTERNAL EAR CANAL PRESSURE REGULATION TO ALLEVIATE DISORDER SYMPTOMS; United States Patent Application Publication No. 2016/0151206 (the "'206 Publication"), published Jun. 2, 2016, and titled EXTERNAL EAR CANAL PRESSURE REGULATION DEVICE; U.S. Pat. No. 7,797,042 (the "'042 patent"), issued Sep. 14, 2010, and titled DEVICE FOR APPLYING A TRANSCUTANEOUS STIMULUS OR FOR TRANSCUTANEOUS MEASURING OF A PARAMETER; U.S. Pat. No. 8,885,861 (the "'861 patent"), issued Nov. 11, 2014, and titled DEVICE FOR THE COMBINED APPLICATION OF A TRANSCUTANEOUS ELECTRICAL STIMULUS AND EMISSION OF AN ACOUSTIC SIGNAL; and United States Patent Application Publication No. 2014/0127666 (the "'666 Publication"), published May 8, 2014, and titled GALVANIC VESTIBULAR STIMULATION SYSTEM AND METHOD OF USE FOR SIMULATION, DIRECTIONAL CUEING, AND ALLEVIATING MOTION-RELATED SICKNESS.

BACKGROUND

This disclosure relates to systems and methods for treatment of medical conditions, including but not limited to systems and methods for treating neurological disorders. Neurological disorders can negatively affect quality of life, and indeed can be debilitating and cause numerous problems with relationships, employment, and so on. Some conditions, such as migraine headaches are sometimes treated with pharmaceuticals, which can have side effects. There remains a need for systems and methods for improving treatment of medical conditions.

SUMMARY

Particular embodiments of the subject matter described in this specification can be implemented so as to realize one or more of the following advantages. A treatment device is described that can treat neurological disorders, such as to safely eliminate, or reduce an intensity or frequency of, pain associated with headaches, which can include pain of the head or neck, and can optionally include pain not caused by underlying diseases or structural problems, such as primary headaches (e.g., migraines, cluster headaches, tension-type headaches, and so on). As will be described, the treatment device can manipulate pressure associated with one or more ears of a patient, such as manipulating pressure in an external ear canal of an ear (e.g., moving the tympanic membrane). The treatment device can utilize pressure profiles, for instance specific patterns of pressure applied to an ear (e.g., time series of pressure values), that are determined to reduce headache pain of individual users.

As will be described, the treatment device can receive information from a user device (e.g., a mobile device, such as a smart phone, a wearable device, a tablet, a laptop, a computer) being operated by a patient, with the information specifying treatment parameter profiles to utilize to reduce perceived pain by the patient. Through use of the user device, the patient can indicate pain he/she is experiencing (e.g., particular symptoms, particular locations such as areas of the head or neck being affected by one or more symptoms, intensity levels of the pain, and so on as will be described), and indicate whether applied treatment parameter profiles are effective. In monitoring information from the patient (e.g., patient specified or indicated information, or optionally physiological information from the patient, for instance a heart rate as determined by a device, such as a smartwatch or fitness tracker, worn by the patient), the user device can determine treatment parameter profiles that best reduce or alleviate pain symptoms. For example, the patient can specify particular symptoms the patient is experiencing, and the user device can determine a treatment parameter profile that best reduces the particular symptoms.

Some embodiments disclosed herein can relate to a computer implemented treatment device control system including a processor communicatively coupled to a memory element including a computer program having a condition symptoms assessment module executable to receive indications of condition symptoms. A treatment device control module can be executable to control a treatment device based on indications of condition symptoms. A symptom tracking module can receive indications of condition symptom relief or non-relief (e.g., based on prior control of the treatment device), which can be processed by the treatment control module to alter subsequent control of the treatment device to increase indications of condition symptom relief.

A broad object of the disclosure can be to provide a computer implemented treatment device control system including a processor communicatively coupled to a memory element containing a computer program including one or more of a condition symptoms assessment module executable to receive indications of condition symptoms, a treatment device control module executable to control a treatment device based on received indications of condition symptoms, and a condition symptom tracking module which receives indications of condition symptom relief or non-relief based on prior control of the treatment device which can be processed by the treatment control module in relation to indications of condition symptoms to alter subsequent control of the treatment device to increase indications of condition symptom relief.

Another broad object of the disclosure can be to provide a computer implemented treatment device control system including a processor communicatively coupled to a memory element containing a computer program including one or more of a condition symptoms assessment module executable to receive indications of condition symptoms including one or more of condition symptom intensity, condition symptom frequency, condition symptom duration, and condition symptom anatomical location, a treatment device control module executable to control a treatment device based on one or more of received indications of condition symptom intensity, frequency, or anatomical location, and a condition symptom tracking module which receives indications of condition symptom relief or non-relief based on prior control of the treatment device and the treatment device control module can process the indications of condition symptom relief or non-relief in relation to one or more of symptom intensity, frequency, duration or anatomical location to alter subsequent control of the treatment device toward increasing indications of symptom relief of the condition.

Another broad object of the disclosure can be to provide a computer implemented treatment device control system including a processor communicatively coupled to a memory element containing a computer program including one or more of a condition symptoms assessment module executable to receive a sensor signal which varies based on change in a sensed physiological parameter, a treatment device control module executable to control a treatment device in synchronization with the sensed physiological condition, and a condition symptom tracking module which receives indications of condition symptom relief or non-relief based on prior control of the treatment device which can be processed by the treatment device control module in relation to synchronization with the sensed physiological condition to alter subsequent control of the treatment device toward increasing indications of symptom relief of the condition.

Another broad object of the disclosure can be to provide a computer implemented treatment device control system including a processor communicatively coupled to a memory element containing a computer program which includes a graphical user interface module executable to depict a graphical user interface on the display surface of a computing device which includes a set up menu which includes one or more of: an anatomical representation of the body which by user interaction generates indications of condition symptom anatomical location, a symptom intensity rating scale which by user interaction generates indications of condition symptom intensity, a symptom frequency rating scale which by user interaction generates indications of condition symptom frequency, a condition symptom duration scale which by user interaction generates indications of condition symptom duration, and a physiological condition synchronization icon which by user interaction generates indications of treatment device control synchronization to a sensed physiological condition, each of the indications receivable by one or more of a condition symptoms assessment module, a treatment device control module, and condition symptom tracking module which subsequently function to variably control a treatment device based on one or more of the received indications of condition symptom intensity, frequency, anatomical location and treatment device control synchronization to a sensed physiological condition, and a condition symptom tracking module which receives indications of condition symptom relief or non-relief based on prior control of the treatment device which the treatment device control module can process in relation to one or more of symptom intensity, frequency, duration and anatomical location to alter subsequent control of the treatment device toward increasing indications of symptom relief of the condition.

Another broad object of the disclosure can be to provide a processor communicatively coupled to a memory element containing a computer program executable to implement one or more of: a condition symptoms assessment module, a treatment device control module, a condition symptom tracking module, and a graphical user interface module individually or in various combinations to control and variably adjust control of a treatment device to treat a condition or alleviate condition symptoms.

Naturally, further objects of the disclosure are disclosed throughout other areas of the specification, drawings, photographs, and claims.

The details of one or more embodiments of the subject matter of this specification are set forth in the accompanying drawings and the description below. Other features, aspects, and advantages of the subject matter will become apparent from the description, the drawings, and from the claims.

BRIEF DESCRIPTION OF THE DRAWINGS

FIGS. 32-35 illustrate example user interfaces in which chatting software interacts with a user of the user interfaces.

FIGS. 36-41 illustrate user interfaces for assisting a user to adhere to a medication regimen.

DETAILED DESCRIPTION

Figure 1:
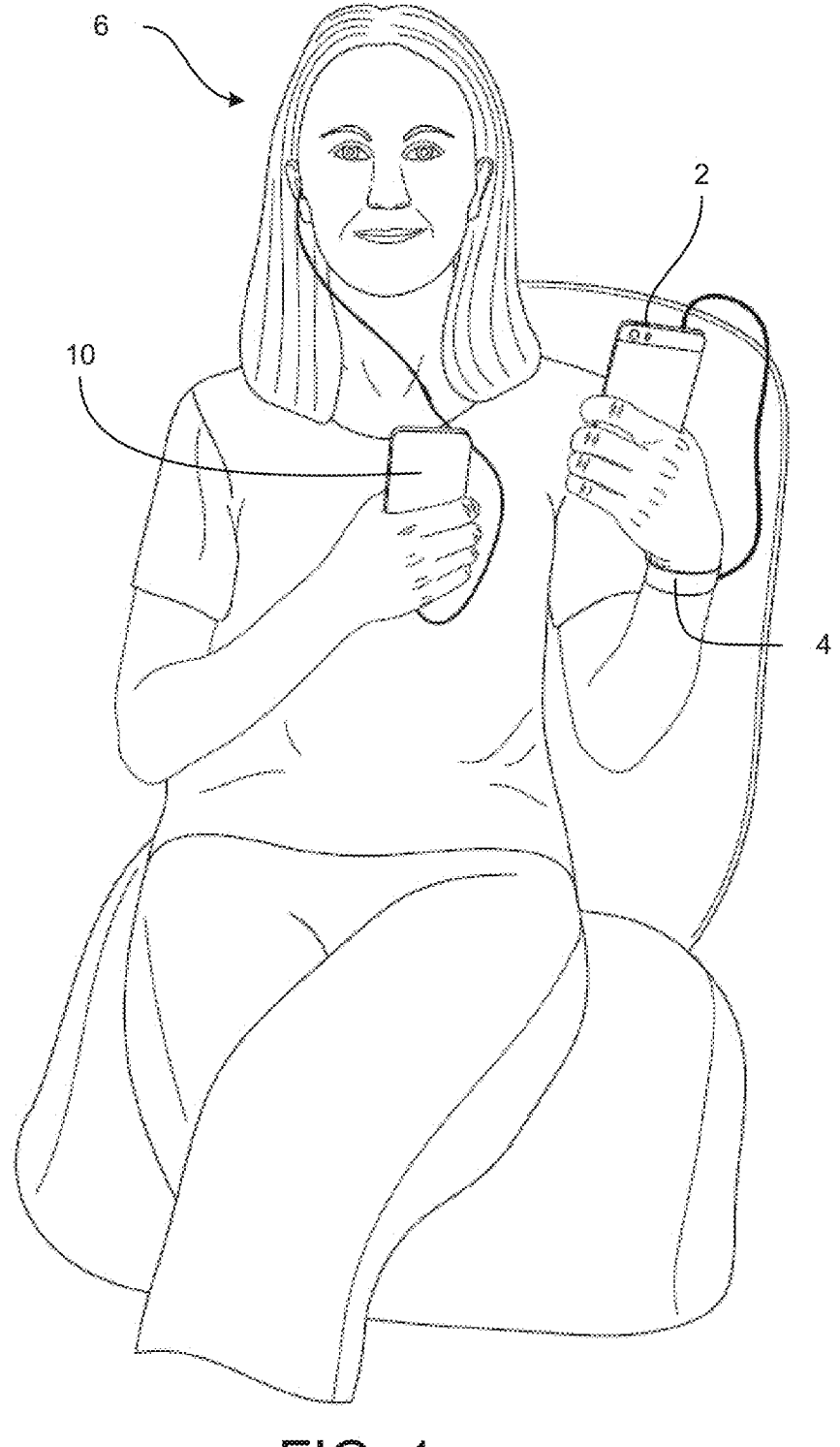
FIG. 1 illustrates a user utilizing a user device in combination with a treatment device to reduce or alleviate pain symptoms.

Some embodiments disclosed herein relate to systems and methods for treating medical conditions, such as neurological disorders and/or symptoms thereof (e.g., migraine headaches, other types of headaches, pain in other body portions, dizziness, nausea, etc.). In some implementations, the treatment system can include a user device, such as a smart phone, a wearable device, a tablet, a portable electronic device, a laptop, a computer, which, in combination with one or more treatment devices (e.g., the treatment device 10 described herein, such as with respect to FIG. 3), can reduce or alleviate symptoms of one or more conditions or symptoms experienced by a user (e.g., pain). For instance, an example treatment device can be configured to apply pressure to an ear canal of a patient. In some embodiments, a portion of the treatment device can be placed inside an ear cavity (e.g., the outer ear canal) of a user. The treatment device can maintain a seal with respect to the ear cavity (e.g., sealing against the walls of the external ear canal). The treatment device can produce and/or modify a pressure differential between the ear cavity (e.g., external ear canal) and an atmospheric pressure. As described herein, upon receiving information indicating a condition (e.g., a neurological disorder) and/or symptoms thereof being experienced by a user (e.g., a migraine, a cluster headache, motion sickness, etc.), a controller (e.g., on the user device or on the treatment device) can determine a treatment parameter profile to be implemented by the treatment device for treating the condition and/or the symptom(s) thereof. During treatment, the controller can change the treatment parameter profile in response to additional information regarding the condition and/or symptom(s) that is obtained from the user.

A treatment parameter profile can include information that is associated with various treatment parameters. For example, a treatment device that controls pressure in the external ear canal can be configured to execute one or more pressure treatment parameter profiles in order to provide treatment to a patient. By way of example, a pressure treatment parameter profile can include information indicative of one or more pressure values (e.g., a difference in pressure between an external ear cavity and an atmospheric pressure, or an absolute pressure) to be utilized over one or more times. The pressure treatment parameter profile can include time series information associated with pressure values (e.g., pattern information such as sinusoidal or sawtooth patterns, frequency information, amplitude information, and the like). A pressure treatment parameter profile can include pump settings (e.g., for one or more times) to achieve the desired pressure values for treatment. The treatment device can implement a treatment parameter profile to cause a pressure differential between, for example, the external ear canal and atmospheric pressure to be positive (e.g., pressure in the ear that is higher than ambient pressure), zero (e.g., pressure in the ear that is the same as ambient pressure), negative (e.g., pressure in the ear that is lower than ambient pressure), or combinations thereof. Optionally, the treatment parameter profile can be based on a baseline pressure (e.g., an average pressure), such that the treatment parameter profile can oscillate between applying pressure that is greater than, and/or less than, the baseline pressure. Similar treatment parameter profiles can have the same pressure oscillation frequency and/or amplitude but can be shifted upwards or downwards in pressure values. Increased pressure may be beneficial to some particular users, while decreased pressure may be beneficial to other particular users, with similar treatment parameter profiles being used that are centered around different baseline pressures. Some pressure treatment parameter profiles can apply a constant pressure for some or all of the length of the treatment parameter profile. Some pressure treatment parameter profiles can be regular (e.g., having relatively consistent pressure amplitudes and/or frequencies), while some pressure treatment parameter profiles can be relatively erratic (e.g., having irregular pressure amplitudes and/or frequencies). Various example pressure treatment parameter profiles are disclosed in the '639 patent (see FIGS. 37A to 39E), the '678 Publication (see FIGS. 4A to 6E), and the '206 Publication (see 14A to 15G).

Various other types of treatment parameter profiles can be used, such as for different types of treatment devices. By way of example, a treatment device that uses electrostimulation (e.g., to stimulate therapeutic neurological responses) can use electro stimulation treatment parameter profiles that include information indicative of parameters for the electro stimulation treatment. For example, an electro stimulation treatment parameter profile can indicate different amounts or types of electrical impulses to be applied at different times (e.g., having defined amplitudes and frequencies similar to the pressure treatment parameter profiles described herein). According to another example, a treatment device that uses sounds (e.g., to stimulate therapeutic neurological responses) can use audio treatment parameter profiles that include information indicative of parameters for the audio treatment (e.g., different tones, volumes, and durations, for sounds at different times). In some embodiments, a heat or cooling treatment can be applied (e.g., to the ear or to other portions of the body). In some embodiments, a vibration treatment can be applied. Various treatment types identified herein can be combined and can be used in conjunction with each other. For example, vibration treatment can be performed either separately or in conjunction with sound treatment and/or in conjunction with insufflation (e.g., of the ear canal to provide pressure treatment). In some embodiments, vibration can be delivered in the ear canal or via bone conduction delivered to the skull, such as at the temporal bone, including but not limited to the mastoid process. A treatment parameter profile might include sound, vibration, electrical stimulation, pressure waves, insufflations, or thermal stimulation (heat or cold), delivered independently or in conjunction with each other in any suitable combination. The aforementioned stimuli might be delivered into the ear canal or to the temporal bone, in some embodiments, or to any bone of the skull.

Although some embodiments discussed herein are described in the context of treating pain, such as caused by migraine headaches, the systems and methods disclosed herein can be used to treat and/or prevent various neurological disorders and other medical conditions, such as Meniere's disease, trigeminal neuralgia, morning sickness, nausea, dizziness, auditory and speech perception issues, disorders of equilibrium, oculomotor control problems (or vestibulo-oculo-motor disorders), disorders of cognition. Various systems and methods disclosed herein can be used for brain performance enhancement.

The user device can execute software or an application (e.g., an 'app' downloaded from an electronic application store) that can communicate (e.g., over a wireless or wired connection) with one or more treatment devices. The user device can receive input from the user and/or can output information or queries to the user. A controller (e.g., on the user device, on the treatment device, and/or on an intermediate device) can determine treatment parameter profiles that are to be used based on user indications of experienced condition symptoms. The controller can provide the determined treatment parameter profiles to the treatment device, which can execute treatment according to the determined treatment parameter profiles. A user can utilize one or more user interfaces presented on or via the user device, and through interactions with the user device, cause the treatment devices to apply treatment (e.g., pressure to the user's ear). In some embodiments, through this applied pressure a tympanic membrane of the ear can be precisely manipulated, and symptom(s) (e.g., pain) experienced by the user can be reduced or alleviated.

Figure 4:
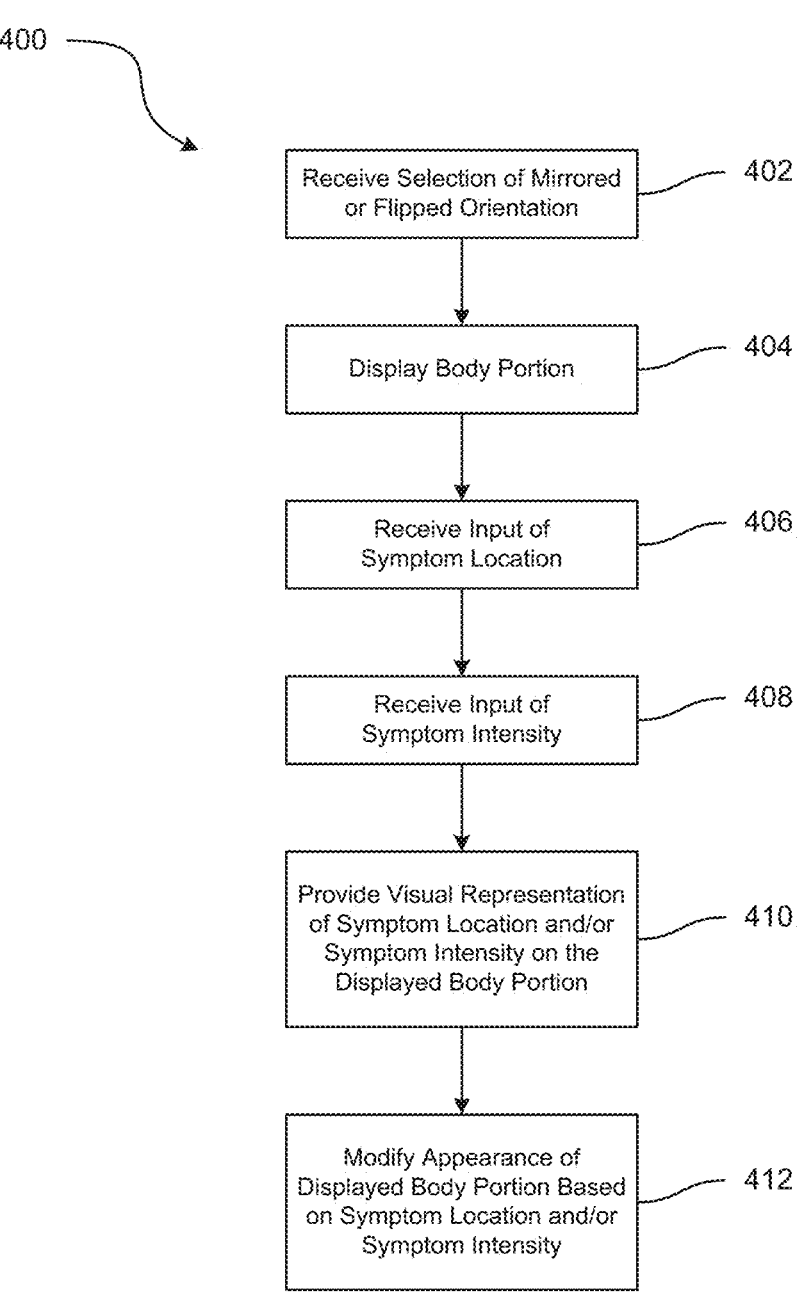
FIG. 4 illustrates an example process for describing pain information.
Figure 6:
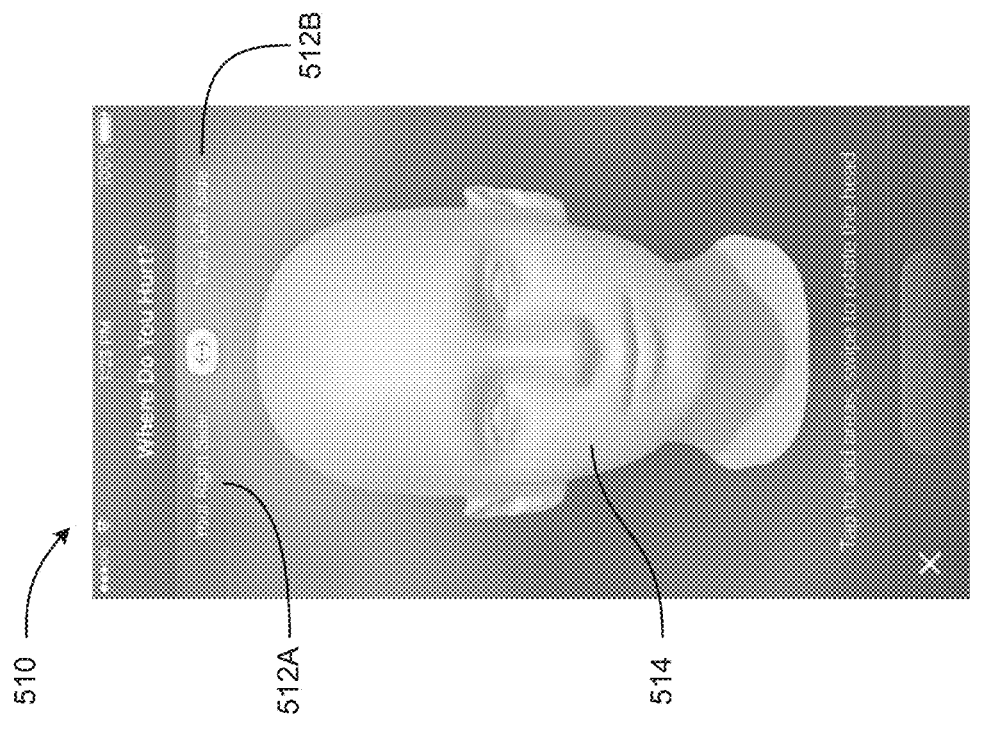
FIG. 6 illustrates and example user interface for identifying locations of pain symptoms on a graphical representation of a body portion.

As described herein, for instance with respect to FIG. 4, the user device can present one or more user interfaces for the user to describe symptom(s) (e.g., pain) being experienced. As illustrated in FIG. 6, the user device can present (e.g., display) an indicia or representation of a body portion (e.g., a head), and the user can specify locations for the symptom(s) (e.g., pain) on the body portion. The user interface can be configured to receive input of an indication of an intensity of the symptom(s) (e.g., pain). For instance, the user can select a particular location, such as a left eye, and indicate an intensity of pain he/she is experiencing at the left eye (e.g., pain that appears to be located at the left eye). Additionally, the user can specify or describe additional symptoms that may not be associated with a physical location, such as nausea, dizziness, vomiting, etc.

Upon receipt of the symptom information (e.g., pain information), the controller can determine a treatment parameter profile to attempt to reduce or alleviate the symptom(s) (e.g., pain) being experienced by the user. As described herein, the treatment system can maintain, or be able to access, historical information associated with the user, which can indicate treatment parameter profiles that have been determined to be effective for the particular user, and in some implementations effective with respect to the symptoms characteristics (e.g., pain location and/or intensity) set forth in the symptom information (e.g., pain information). The controller can select a previously utilized treatment parameter profile, or determine a new treatment parameter profile, based on the present described symptom (e.g., pain), and provide the treatment parameter profile for implementation by the at least one treatment device. The controller can try different treatment parameter profiles in connection with different symptoms to learn which treatment parameter profiles work particularly well for this particular user and/or for the particular symptom or type of symptom. Accordingly, the treatment system can get better at treating the particular patient as the treatment system learns the patient over time.

Furthermore, the controller (e.g., on the user device and/or the treatment device) can be in communication with an optimization system (e.g., the treatment parameter profile optimization system 100 described below) that monitors effectiveness of treatment parameter profiles with respect to described pain across a multitude of users, and that optimization system can, at least in part, determine or recommend a treatment parameter profile for implementation by the user's treatment device. The controller (e.g., on the user device and/or the treatment device) can send information to the optimization system about the effectiveness of the treatment parameter profiles on the particular user, and the optimization system can gather effectiveness data regarding treatment parameter profiles used on a multitude of users. The optimization can analyze the effectiveness data to identify generally effective treatment parameter profiles, and/or to correlate effectiveness links between particular treatment parameter profiles (or treatment parameter profile types) and various types of symptom data. For example, the optimization system can analyze the effectiveness of various profiles on a general population to determine that a certain treatment parameter profile is particularly effective in treating pain associated with the area at the right eye. Then the optimization system can distribute that correlation information to the treatment systems utilized by one or more users so that the controllers can use, or consider using, the certain treatment parameter profile when pain associated with the area at the right eye is identified by the pain information (e.g., input by a user).

In some embodiments, the controller can generate new treatment parameter profiles, such as be combining features of multiple effective treatment parameter profiles, to be used for treating the patient. Accordingly, the treatment system can develop unique treatment parameter profiles that are specifically tailored to the particular user. This can be an iterative process, where the treatment system can generate several generations of new treatment parameter profiles to optimize the treatment system for the user. The treatment system can use information received from the optimization system for generating new treatment parameter profiles. For example, the controller can generate an updated (e.g., combined) treatment parameter profile for implementation that incorporates aspects of one or more prior effective treatment parameter profiles for the user and one or more treatment parameter profiles effective across other users. In some embodiments, the optimization system can automatically generate new treatment parameter profiles based on multiple treatment parameter profiles (e.g., that were determined to be effective). Custom combinations of treatment parameter profile parameters can be generated for the individual user base on their own present and/or past response(s) to treatment, and/or by statistical probability of success based on overall distribution of multiple users (e.g., all users of the device being tracked or a pertinent category of users).

Figures 18, 19:
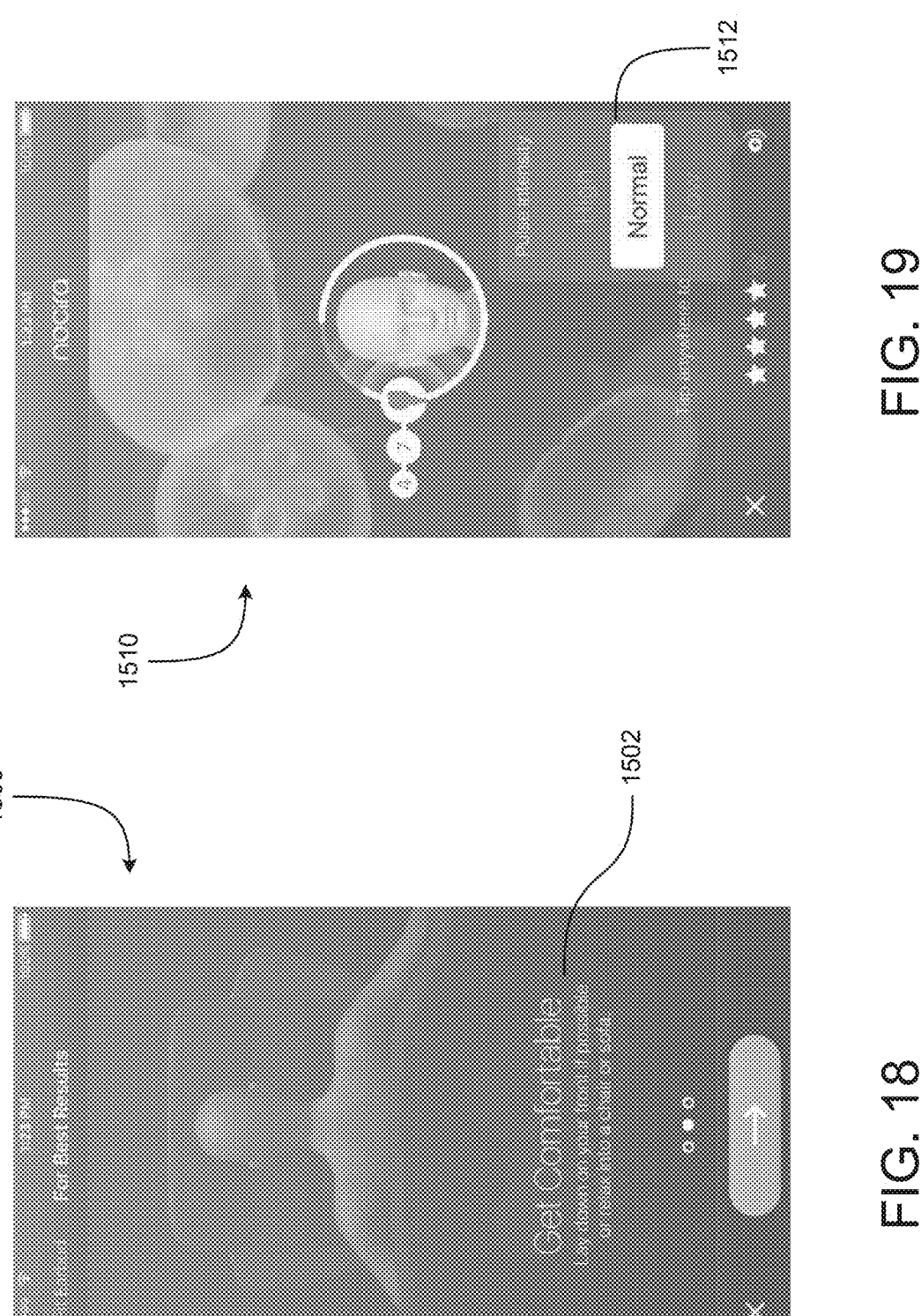
FIG. 18 illustrates an example user interface to prepare a user for treatment.
FIG. 19 illustrates an example user interface displayed on a user device while a treatment parameter profile is being implemented.

As will be described, effectiveness can be determined based on information received from the user, for instance as illustrated in FIG. 19 the user can indicate whether the experienced symptom (e.g., pain) is gone, reduced, the same, or has become worse. In some implementations, effectiveness scores can be maintained for the treatment parameter profiles. Multiple effectiveness scores can be used for multiple symptoms or symptom types. For example, a treatment parameter profile may have a low effectiveness score for right-side head pain but a high effectiveness score for left-side head pain. When a user provides feedback input, the treatment system can update the effectiveness score(s) based on that input. For example, if a user indicates that the pain has reduced, the effectiveness score of the preceding treatment parameter profile can be increased, and if the user indicates that the pain has become worse, the effectiveness score of the preceding treatment parameter profile can be decreased. In some embodiments, the score can be based on the degree of improvement or worsening of the symptom. For example, a treatment parameter profile may be determined to have some effectiveness even if the symptom worsens (e.g., if the rate of worsening decreases).

In some instances, after applying a treatment parameter profile, and upon the user indicating the treatment parameter profile was effective, the same treatment parameter profile can be continued. Once the user indicates the symptom has been resolved, the treatment can cease (e.g., and the treatment device can be removed). Alternatively, upon the user indicating that the treatment was ineffective (e.g., the pain or other symptom becomes worse, stays the same, improves the symptom by less than a threshold), a different treatment parameter profile can be determined and provided to the treatment device, or the same treatment parameter profile can be re-used by the treatment device (e.g., the treatment parameter profile may need to be applied again or for a longer period of time).

Figure 31:
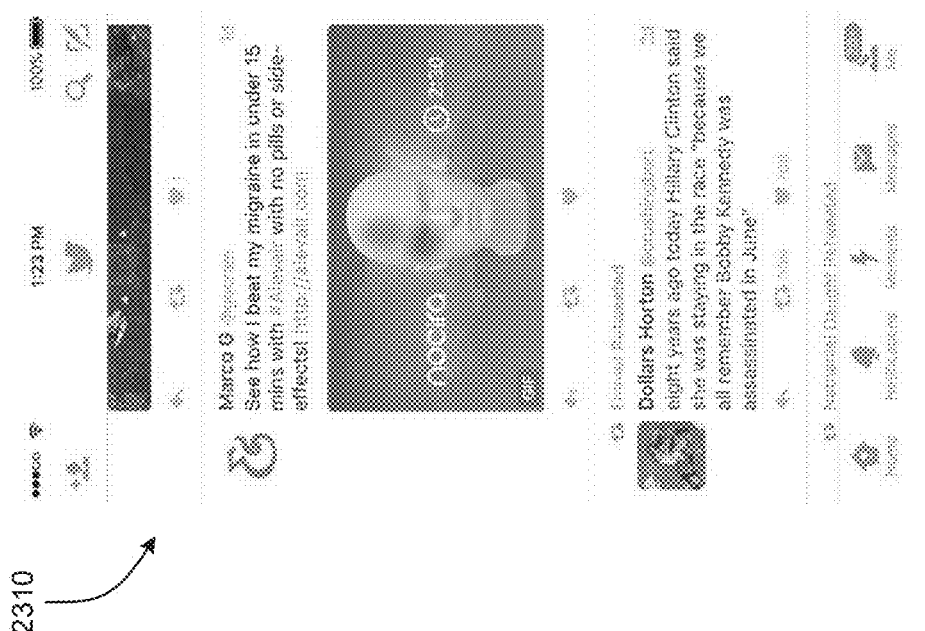
FIG. 31 illustrates an example of a shared relief replay.

In addition to reducing or alleviating symptom(s) (e.g., pain) being experienced, the treatment system can monitor medications or other therapies being taken/utilized by the user (e.g., the user can indicate times at which medications were taken and/or quantities of medication taken and/or types of medications taken), and provide incentives for the user to continue routinely taking any prescribed medication. For instance, the user can be associated with a user account, and the treatment system can assign one or more scores associated with the user's proper and routine adherence to a medication regimen. The treatment system can maintain a proactivity score for the user, and the proactivity score can be influenced by the medication information (e.g., score improves when the user properly uses medication and/or the score worsens when the user misses or misuses medication). The same proactivity score can be influenced by other factors, such as use of the treatment device, and activities that tend to improve the condition (e.g., adequate sleep, sufficient exercise, prudent eating, etc.). Additionally, the treatment system can monitor effectiveness of the treatment device, and provide indications (e.g., visual nudges) reminding the user of the effectiveness of the treatment, including any reduction in frequency and/or severity of condition symptoms (e.g., reduction in experienced migraines or other headaches, reduction in intensity of pain, etc.) (e.g., as illustrated in FIG. 31). In this way, the user can be reassured that his/her condition symptom(s) (e.g., pain) are being addressed, which can increase quality of life for the user based on knowing that the condition is, at least in part, under control—thus reducing worry associated with the conditions and providing a sense of calm that the treatment device is effective when required. This mental state of wellbeing can itself result in improvement of the neurological disorder, which can compound the benefit of the therapy.

As will be described, the user device can present a communications interface (e.g., FIG. 24, described herein), and software can include a chatbot feature executing on the user device or other component of the treatment system to communicate with the user to inquire about condition symptoms (e.g., pain parameters), medications being taken, effectiveness of the treatment device, the user's overall mental wellbeing, and so on. Additionally, the communications interface can prompt the user to take medications at particular times, and warn the user of possible medication misuse or neglect. Through analysis of user information, the communications interface can present incentives for the user to adhere to the medication regimen, including providing information about correlations showing reductions in frequency or intensity of symptom(s) (e.g., pain) while adhering to the regimen, etc.

FIG. 1 illustrates a user 6 (e.g., a patient) utilizing a user device 2 in combination with a treatment device 10 (e.g., to reduce or alleviate pain). As illustrated, the user is holding in one hand the user device 2, which in this example is a smart phone, while holding a body portion of the treatment device 10 in the other hand. The treatment device 10 can include an earpiece that is inserted into the user's ear canal. Tubing can connect the ear piece to a pressure generator (e.g., a pump in the body portion of the treatment device 10), which can apply pressure (e.g., through the tubing and earpiece) to the user's ear canal. A controller can be implemented on one or both of the user device 2 and the treatment device 10. In some embodiments, most of the controller functions (e.g., input and output of information via a user interface, treatment parameter profile selection, treatment parameter profile management, etc.) can be executed by the user device 2, and the treatment device 10 can be configured to execute treatment instructions received from the user device 2. In other embodiments, the user device 2 can primarily handle input and output of information (e.g., to and from the user and/or to and from an optimization system) and that information can be transmitted to the treatment device 10, which can handle the other controller functions (e.g., treatment parameter profile selection and management, etc.) In some embodiments, a separate inter- mediate controller device can be in communication with both the user device 2 and the treatment device 10, and the intermediate controller device can execute some of the controller functions discussed herein. Many other alterna- tives are possible. While FIG. 1 illustrates a single treatment device being used with the right ear of the user 6, it should be understood that the user 6 can utilize two treatment devices (e.g., a treatment device for each ear), or the single treatment device 10 can be configured to provide treatment to both ears. For example, the treatment device 10 can include two earpieces. In some embodiments, the treatment device 10 can include some or all of the features of the user device 2 (e.g., a user interface), and the user device 2 can be omitted. In some embodiments, the treatment device 10 can be a wearable unit that is configured to be worn by the user 6 (e.g., so that the user does not need to hold a portion of the treatment device 10 in a hand). The pressure generator (e.g., a pump) can be built into the ear piece, and the tubing can be omitted. Various details relating to the treatment device 10, as well as other features of the treatment system, are disclosed in the '639 patent, the '678 Publication, and the '206 Publication.

When the user 6 desires treatment for a condition and/or symptoms thereof, such as a migraine, nausea, motion sickness, etc., the user 6 can activate software, such as an application (e.g., an 'app' downloaded from an electronic application store), and describe the symptom(s) (e.g., pain) being experienced. As described herein, the user 6 can indicate a particular condition and/or the symptoms being experienced (e.g., sensitivity to light, locations and intensity of pain, etc.). As will be described below, with respect to FIGS. 8-10, the controller (e.g., on the user device 2) can determine a particular ear (e.g., the left or right ear) for treatment (e.g., the ear in which the user 6 is to insert the treatment device 10). For instance, if the user 6 is experi- encing pain largely or entirely on a particular side of his/her head or face, the user device 2 can prompt the user 6 to insert the treatment device 10 into the ear on that same particular side. Alternatively, if the pain is substantially symmetric (e.g., within a threshold intensity on each side) or located in the middle of the face or head, the user device 2 can prompt the user 6 to insert the treatment device 10 into a particular ear, such as for instance, the left ear.

Using the condition symptom information input by the user 6 (e.g., the described pain), the controller can determine a treatment parameter profile (e.g., select from among a multitude of stored treatment parameter profiles, or generate an updated or new treatment parameter profile), and provide (e.g., over Bluetooth or Wi-Fi or other wireless communi- cation protocol) the treatment parameter profile for imple- mentation by the treatment device 10. For instance, the treatment system (e.g., the user device 2) may store or be able to access an initial number of treatment parameter profiles (e.g., 10, 15, 30), and the controller (e.g., on the user device 2) can select a particular treatment parameter profile indicated as best matching the described pain (e.g., deter- mined to be effective for a multitude of users). As will be described, as the treatment system is utilized more by the user 6, the treatment system (e.g., the user device 2) can access historical information associated with the effective- ness of one or more treatment parameter profiles for the particular user 6, and can determine a treatment parameter profile that has been effective in the past (e.g., the user 6 had previously indicated that his/her pain was alleviated subse- quent to use of the treatment parameter profile). Addition- ally, the treatment system (e.g., the user device 2) can receive information from an optimization system (e.g., the treatment parameter profile optimization system 100 described herein) that monitors effectiveness of treatment parameter profiles across multitudes of users, and can utilize the information (e.g., a treatment parameter profile, features or aspects of treatment parameter profiles, such as an inten- sity, whether negative or positive pressure is utilized, fre- quency of a sinusoidal or saw tooth wave, etc.) to determine the treatment parameter profile for implementation by the treatment device 10. That is, the treatment system (e.g., via the user device 2) can receive updated or new treatment parameter profiles over time.

The treatment system (e.g., the treatment device 10) can perform an initial test (e.g., a leak test as will be described with respect to, at least, FIGS. 8 and 11), and upon satis- faction of the initial test, can create a pressure differential between an external cavity of the user 6 and an ambient or atmospheric pressure. As described herein, the pressure treatment parameter profile can indicate pressure values that are to be applied (e.g., pressure differentials), and can include a particular pattern (e.g., a sine wave pattern, a saw-tooth pattern, an arbitrary pattern) optionally at a par- ticular repeating frequency (e.g., the sine wave can be at a frequency, such that a range of pressure values are applied in each period associated with the frequency).

The pressure treatment parameter profile can oscillate between positive and negative pressure, and can repeat based on a frequency of the oscillation (e.g., a frequency of the sinusoidal wave). In other example pressure treatment parameter profiles, the pressure can be entirely negative or entirely positive, and can also be relatively static (e.g., below a threshold frequency). In some embodiments, treat- ment parameter profiles can be categorized into groups. For example, kinetic pressure treatment parameter profiles can be relatively dynamic (e.g., having a relatively high fre- quency of oscillation), whereas akinetic pressure treatment parameter profiles can be relatively static (e.g., having a relatively low frequency of oscillation or no oscillation such as a static pressured state that is held). In some embodi- ments, a kinetic pressure treatment parameter profile can have pressure that changes between increasing and decreas- ing pressure at a rate that is faster than 0.125 Hz, faster than 0.25 Hz, faster than 0.5 Hz, faster than 1 Hz, faster than 2 Hz, faster than 3 Hz, faster than 5 Hz, faster than 10 Hz, or more. Kinetic pressure treatment parameter profile can have pressure changes at rates up to 25 Hz, up to 50 Hz, up to 100 Hz, up to 200 Hz, and faster rates can be used in some implementations. An akinetic pressure treatment parameter profile can have pressure that changes between increasing and decreasing pressure at a rate that is slower than 10 Hz, slower than 5 Hz, slower than 3 Hz, slower than 2 Hz, slower than 1 Hz, slower than 0.5 Hz, slower than 0.25 Hz, slower than 0.125 Hz or less. Any of the above-identified values can be a threshold rate that separates the categories of kinetic and akinetic treatment parameter profiles.

In some instances, a pressure treatment parameter profile can be categorized as a kinetic or akinetic profile at least in part based on a sliding scale that considers both the ampli- tude and the frequency pressure changes during the profile. A profile that has a certain frequency may be considered a kinetic profile if its amplitude is higher than a threshold, whereas another profile with the same frequency may be considered an akinetic profile if its amplitude is lower than a threshold.

A treatment parameter profile can have a set amount of time. In some embodiments, each treatment parameter profile can have the same duration of time. A treatment session can be divided into treatment phases, where a treatment parameter profile can be applied during each treatment phase. In some embodiments, different treatment parameter profiles can have different times. In some embodiments, the same treatment parameter profile can be applied for various different durations of time (e.g., depending on other aspects of the treatment). For example, a treatment parameter profile could be used for a short time initially as a test of the profile, and the same treatment parameter profile could be executed for a longer time (e.g., without querying the user for feedback) once the treatment system has determined that the treatment parameter profile is producing beneficial effects. A treatment parameter profile can last for an amount of time set by the user. The user interface (e.g., on the user device 2) can be configured to receive input from the user, and in response the treatment system can set a treatment phase time for a treatment parameter profile, can extend or shorten a duration time for a treatment parameter profile, or can abort a treatment parameter profile. Treatment parameter profiles can generally have durations times between 10 seconds and 30 minutes in length, although other durations can be used, especially depending on the type of treatment associated with the treatment parameter profile. Treatment parameter profiles can have a duration time of at least 10 seconds, at least 30 seconds, at least 1 minute, at least 2 minutes, at least 3 minutes, at least 5 minutes, at least 10 minutes, at least 15 minutes, or at least 30 minutes, or at least 60 minutes, or at least 90 minutes, or more, and/or less than or equal to 120 minutes, less than or equal to 90 minutes, less than or equal to 60 minutes, less than or equal to 30 minutes, less than or equal to 15 minutes, less than or equal to 10 minutes, less than or equal to 5 minutes, less than or equal to 3 minutes, less than or equal to 2 minutes, less than or equal to 1 minute, less than or equal to 30 second, or less.

A treatment parameter profile may continue with the same pattern (e.g., amplitude and oscillation) for the entire length of the treatment parameter profile, or the treatment parameter profile may include multiple portions with different patterns. For example, a pressure treatment parameter profile can have a saw tooth pattern of a first amplitude and a first frequency centered on a first baseline pressure, followed by a sinusoidal wave pattern of a different frequency, a different amplitude, and/or centered around a different baseline pressure value, etc.). The treatment parameter profile may comprise one or more portions, may repeat regularly, irregularly, and may optionally be adaptable based on received user input. For instance, while the treatment device 10 is implementing a treatment parameter profile, the user 6 can utilize a user interface (e.g., on the user device 2) to indicate that the treatment parameter profile should be increased or decreased in intensity (e.g., an average pressure value can be shifted up or down, and/or the amplitude of the pattern can be increased or decreased). Also, in some implementations, the treatment system (e.g., the treatment device 10) can perform a pressure tolerance test (see FIG. 11, discussed herein) on the user 6 to determine a pressure tolerance level for the user. Although the treatment device 10 can be configured to produce pressures well below levels that would cause pain or serious discomfort under normal circumstances, some users may not be able unable to tolerate the full pressure produced by the treatment device 10 (e.g., due to ear infection, ear injury, unusual sensitivity to ear pressure, etc.) If a lower pressure tolerance level is determined, the treatment system can scale back the pressure amplitude for some or all of the pressure treatment parameter profiles delivered to the user 6, or the treatment system can select only pressure treatment parameter profiles that have peak pressures below the determined tolerance threshold. A new pressure tolerance test can be performed for each treatment session performed on the user 6.

The user 6 can specify updated condition symptom information (e.g., updated locations and/or intensity of pain). For example, the user 6 can indicate that pain on the forehead has moved to the left eye. The user can 6 can indicate additional symptoms (e.g., the user can indicate that a rapid onset of nausea is occurring), and can report changes in those additional symptoms as the treatment session progresses (e.g., between each treatment phase). The controller (e.g., on the user device 2) can then determine an updated treatment parameter profile and provide the updated treatment parameter profile (e.g., over a wireless connection) to the treatment device 10 for implementation.

Optionally, the user device 2 can be in communication with a sensor device 4, which can be a wearable device (e.g., over a wireless connection, for example a Bluetooth or Wi-Fi connection). The wearable device can be a smart watch, fitness tracker, and so on, and can receive physiological parameters of the user 6. As an example, the sensor device 4 can monitor a heart rate of the user 6. In some embodiments, the treatment can be synchronized with a physiological parameter (e.g., heart rate) measured by the sensor device 4, as discussed herein. The treatment system can cause modification to a treatment parameter profile being implemented by the treatment device 10, or cause replacement of the treatment parameter profile based on the physiological parameters measured by the sensor device 4. For instance, if the user's heart rate increases, the frequency of treatment (e.g., pressure pulses) can also increase (e.g., proportionally), and/or if the user's heart rate decreases, the frequency of treatment (e.g., pressure pulses) can also decrease (e.g., proportionally). Heart rate synchronization can be used in various manners. For example, pressure, vibration, electrical stimulation, sound waves, and/or other forms of treatment can be synchronized with specific phases of the cardiac cycle (e.g. systole). Heart rate can be analyzed to measure a patient's response to treatment. In some instances, an elevation in heart rate or determination of increased contractility can suggest an increase in sympathetic nervous system output, which may be interpreted as a negative response to treatment. In response, the treatment can be automatically altered (e.g., until a favorable physiologic response is noted). Heart rate variability (HRV) can be measure, and can be used as a measure of favorable/unfavorable physiologic response to treatment (e.g., any combination of inputs from a treatment device).

Other modifications can be made to the treatment parameter profile based on physiological information (e.g., measured by the sensor device 4). For example, if the user's heart rate increases (e.g., above a threshold or threshold rate of increase), an intensity of the treatment parameter profile may be changed (e.g., increase or decrease positive pressure, increase or decrease negative pressure, change the amplitude, change the frequency, and/or change the baseline pressure). As another example, a physiological parameter can indicate information associated with perspiration by the user 6 (e.g., the user 6 sweating may indicate an increase in stress), an increase or decrease in rapid movement by the user 6 (e.g., an increase in twitching or other movement of the arm or hand may indicate an increase in stress or pain), and so on. In this way, the user device 2 can receive empirically determined physiological characteristics of the user 6, instead of (or in addition to) descriptive information as inputted by the user 6.

The treatment device 10 can finish implementing the treatment parameter profile (e.g., after a period of time associated with the profile, after a user selectable amount of time, or after the user has requested the treatment end (e.g., via a user interface on the user device 2)). The user 6 can provide input, such as through interactions with the user device 2 (e.g., pressing a button, touching a virtual input element on a touchscreen, shaking the device, audibly telling the user device 2 to stop, removing the treatment device 10 from the ear, etc.). After (or during) the treatment parameter profile, a user interface (e.g., on the user device 2) can present one or more interfaces in which the user 6 can provide feedback information. The user can describe an effectiveness of the treatment parameter profile. The user can provide symptom information (e.g., pain information), which can be used to determine effectiveness of the treatment parameter profile (e.g., by comparison to prior symptom information from before the treatment parameter profile was performed). For instance, the user 6 can indicate that the symptom (e.g., pain) has been alleviated, reduced, stayed substantially constant, or is worse. Using the effectiveness information, the controller (e.g., on the user device 2) can determine a new, or updated, or different treatment parameter profile to use to try to reduce or alleviate the user's symptom(s) (e.g., pain). The effectiveness information associated with the treatment parameter profile can be used to inform a subsequent decision of whether to use the same treatment parameter profile for same, or similar, symptoms (e.g., pain). Optionally, one or more symptoms may be considered similar if they are associated with a same condition (e.g., all migraine pain may be treated as similar symptoms). Even if the specific symptoms may differ for different migraine attacks, these symptoms may still be considered similar since they are from a same root condition. Accordingly, a treatment parameter profile that is determined to be effective for treating a condition (e.g., migraines) can be used by the treatment system to treat later occurrences of the same condition (e.g., migraines) even if the specific symptoms of the later migraine are different (e.g., different pain location or intensity, or different secondary symptoms like nausea or sensitivity to light). In some embodiments, the effectiveness can be determined more granularly, such as based on more specific details regarding the symptoms. For example, a treatment parameter profile can be determined to be particularly effective for treating a user's migraines that cause pain on a left side of the head, or that are associated with a secondary symptom of intense nausea, etc. The treatment can continue during the period of time between treatment phases, such as while the user is providing feedback information to the system. Or the treatment can stop during the period of time between treatment phases.

The user 6 can provide updated symptom information (e.g., pain information). The user 6 can assign updated intensity values to the symptoms (e.g., pain), and/or the user 6 can indicate new pain locations, and/or the user 6 can indicate that pain has moved to a new location. The controller (e.g., on the user device 2) can determine a treatment parameter profile based on the updated symptom information, such as the updated pain intensity value(s). The user 6 can provide updated symptom information about secondary symptoms as well (e.g., a first symptom, such as nausea, might be reduced, while a second symptom, such as dizziness, might be increased or newly included). The controller (e.g., on the user device 2) can then select a treatment parameter profile and provide the treatment parameter profile for implementation by the treatment device 10, and subsequently the user 6 can again provide information relating to the effectiveness of the treatment parameter profile. The process can repeat until the condition or the symptoms thereof have been resolved.

The treatment system (e.g., the user device 2) can store information indicating effectiveness of treatment parameter profiles that have been implemented, and can utilize the effectiveness information when subsequently determining a treatment parameter profile. For example, the user device 2 can determine that a first treatment parameter profile was effective (e.g., based on information provided by the user, such being described by the user as alleviating pain associated with particular parameters), while a second treatment parameter profile was ineffective, and can thus select the first treatment parameter profile for later treatment (e.g., for treatment of pain having the same, or similar, pain parameters). Additionally, the treatment system (e.g., the user device 2) can provide the effectiveness information to the optimization system for storage and/or usage together with effectiveness information from other users to evaluate treatment parameter profiles and/or generate new treatment parameter profiles. In implementations in which user information is stored or utilized, including user profile information (e.g., user account information, personal information, as will be described), effectiveness information, pain information, and so on, the user information can be (1) encrypted, (2) anonymized, and/or (3) be 'opt-in'.

Figure 2:
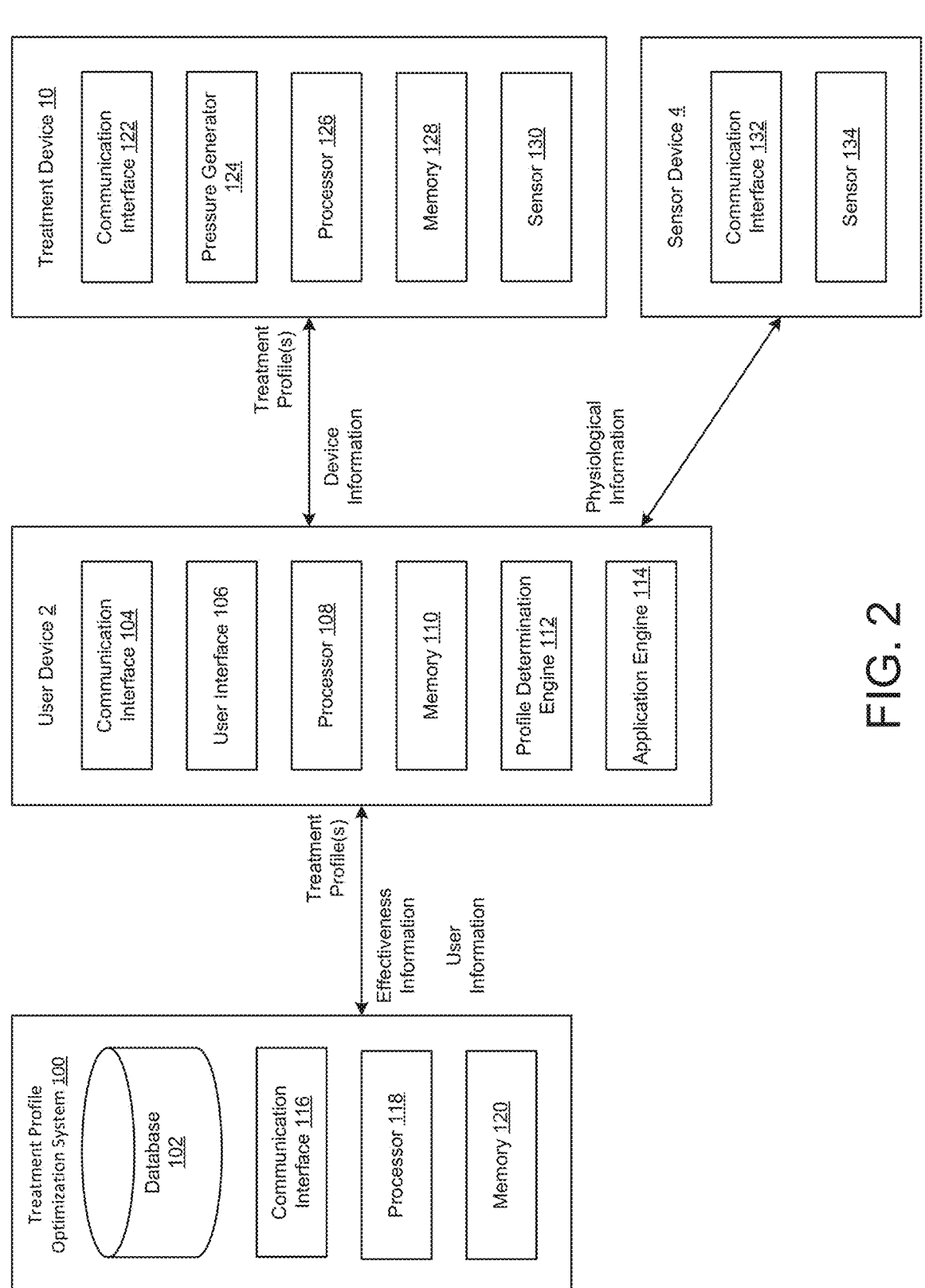
FIG. 2 illustrates a block diagram of a treatment system having a user device in communication with other systems and devices.

FIG. 2 illustrates a block diagram of a user device 2 in communication with other systems and devices. As illustrated, the user device 2 can include a communication interface 104, and can be in wired or wireless (e.g., Bluetooth, Wi-Fi) communications with a treatment device 10 (e.g., using a communication interface 122 on the treatment device 10). The communication interface 104 of the user device 2 can be in communication with a treatment parameter profile optimization system 100 over a network (e.g., the internet). The communication interface 104 can also be in wired or wireless communication with the sensor device 4.

The user device 2 can have one or more processors 108. The user device 2 can be a device such as a laptop, mobile device (e.g., smart phone), tablet, wearable device (e.g., smart watch), portable electronic device, etc. Optionally, the user device 2 can have one or more processors 108 (e.g., one or more field programmable gate arrays (FPGAs), specialized circuits, etc.) that are specific for executing at least some of the operations discussed herein, such as that are specific for use with the treatment device 10 (e.g., a specialized controller). In some embodiments, the at least one processor 108 can be configured to execute instructions (e.g., stored in memory 110) to perform at least some of the operations discussed herein as well. In some embodiments the at least one processor 108 can be a general purpose processor.

In some embodiments, the user device 2 can include a user interface 106, which can include a display or touchscreen display. The user interface 106 can be configured to receive input from a user. The user interface 106 can include one or more user input elements (e.g., such as buttons, switches, slides, knobs, etc.) for receiving input, such as from the user 6. The user input elements can be virtual user input elements, such as on a touchscreen display. The user interface 106 can include a microphone, or other input mechanisms. The user interface 106 can be configured to output information to a user. For example, the user interface 106 can include a display and/or speakers. Other output mechanism can be used, such as a vibrator, a printer, etc. In some implementations, the input and output elements can be incorporated together, such as in a touchscreen display.

The treatment parameter profile optimization system 100 can be a system of one or more computers, or a system of one or more virtual machines executing on a system of one or more computers. The optimization system 100 can be a remote system (e.g., a remote server system located far away from the user), which can be in communication with the user device 2 and/or the treatment device 10 over a network (e.g., the internet). The optimization system 100 can maintain or be in communication with at least one database 102 (e.g., one or more data storage systems) that can store user profile information of users and/or effectiveness information for treatment parameter profiles. The database 102 can include information (e.g., user profile information and/or treatment parameter profile effectiveness information) associated with multiple users of the treatment systems. The optimization system 100 can analyze aggregate data from a multitude of users and identify correlations, trends, patterns, etc. in the effectiveness data. The optimization system 100 can send new treatment parameter profiles to the user device 2 and/or to the treatment device 10, as discussed herein. The optimization system 100 can include at least one processor that is configured to execute computer-readable instructions stored in memory to execute the operations discussed herein. In some embodiments, the optimization system 100 can be omitted.

The user device 2 includes an application engine 114, which can be an application (e.g., 'app') downloaded from an electronic application store by a user of the user device 2, and can enable functionality described herein. Optionally, the user device 2 can include software installed, or otherwise being executed on, the user device 2, which can enable the functionality described herein. The software can be installed on memory 110 (which can be non-transitory computer readable memory). The software can run remotely (e.g., on the optimization system 100) and results, decisions, queries, etc. can be transmitted to the user device 2 and/or to the treatment device 10. The application engine 114 can operate the user interface 106 for presentation of information or queries to the user 6, and/or for receiving user interactions (e.g., user input) via the user interface 106. The user interactions can cause information to be provided to the treatment device 10, treatment parameter profile optimization system 100, etc. as discussed herein.

A user utilizing the application engine 114 can access information via the user interface 106 requesting user account information, and the application engine 114 can receive (via the user interface 106) a user name and password for authentication, or other identifying information (e.g., a thumbprint). Upon receipt, the application engine 114 can access stored information associated with the user account, or optionally can provide the user account information to the treatment parameter profile optimization system 100 for authentication. Upon authentication of the user account information, user profile information, such as treatment parameter profiles previously utilized by the user, symptom information (e.g., pain information) specified by the user, medications being taken by the user, personal information (e.g., name, address, and so on), can be accessed. Optionally, the user profile information can include one or more user scores associated with use of the treatment system (e.g., use of the application engine 114), such as one or more of a proactivity score (e.g., a score indicating (1) a degree to which the treatment device 10 is used (e.g., in response to pain or other symptoms experienced by the user, and/or preventative usage of the treatment device 10), (2) a proper adherence to a medication regimen, and/or (3) user actions that are preventative or therapeutic for the condition symptoms), a connectedness score (e.g., a score indicating a degree to which the user shares information with other users, such as through one or more social networks), and/or an understanding score (e.g., a score indicating a degree to which the user requests or views information, such as medical information, related to conditions the user is experiencing, such as migraines, headaches, nausea, motion sickness, and so on). User scores are described herein in more detail, with respect to, at least, FIGS. 21 and 31.

The application engine 114 can generate user interface outputs and update the user interface outputs upon interactions with the user. For instance an initial user interface output can present a representation of a body portion (e.g., a head), and the application engine 114 can receive information (e.g., via the user interface 106) describing pain being experienced by the user. Optionally, the application engine 114 can present interactive documents (e.g., web pages) received from the treatment parameter profile optimization system 100 to generate user interface outputs, or the application engine 114 can run as a native application (e.g., on the user device 2). As described herein, the symptom (e.g., pain) information can be indicative of a particular condition. In some embodiments, the condition (e.g., a neurological disorder) being treated can be specified (e.g., included in the symptom information), while in other embodiments, the symptom information can include information regarding one or more symptoms being experience without specifying an underlying condition. The symptom information can include symptoms parameters, which can be descriptive of the experienced symptom(s). For example, for the symptom of head pain, the pain parameters can include one or more locations of pain, one or more intensity values for the pain (e.g., corresponding to the identified pain location(s)), and/or one or more descriptions of type of pain, such as pounding, shooting, sharp, aching, burning, pressure, etc. (e.g., corresponding to the identified pain location(s)).

Upon receipt of symptom (e.g., pain) information, a treatment parameter profile determination engine 112 can determine a treatment parameter profile for implementation by the treatment device 10. The selected treatment parameter profile (e.g., a time series, such as discrete values according to a sample rate; one or more mathematical formulas that can generate the time series; an identifier of the treatment parameter profile, which the treatment device 10 can utilize to access stored treatment parameter profile information; etc.) can be provided to the treatment device 10. The treatment device 10, for instance, as further described with respect to FIG. 3, can then apply a range of positive and/or negative pressure values to an ear (e.g., via the external ear canal) of the user according to the treatment parameter profile (e.g., using a pressure generator 124). Furthermore, subsequent to implementation of the treatment parameter profile, the treatment parameter profile determination engine 112 can receive information (e.g., via the user interface 106) indicative of an effectiveness of the treatment parameter profile, and/or can determine an updated treatment parameter profile to be provided to the treatment device 10 for implementation. Determining an effectiveness of the treatment parameter profile is described in more detail herein, at least with respect to FIGS. 16-19. As discussed herein the treatment device can be configured to provide any combination of pressure therapy (e.g., insufflation), vibration therapy, sound therapy, thermal stimulus therapy (e.g., heating or cooling), electro-stimulation therapy, or any other type of therapy for stimulating therapeutic responses in the nervous system. By way of example, in many instances it can be useful to apply insufflation as a foundation therapy, and one or more additional therapies can be applied in addition to the foundation insufflation therapy (e.g., simultaneously or serially). Other therapies discussed herein can be used as a foundation therapy to which supplemental therapies can be added. In some embodiments, the supplemental therapies can improve or harmonize with the foundation therapy. A synergy can be produced in many instances where the combination of therapies can have therapeutic results that are superior to the sum of results of the individual therapies.

As will be described, to determine a treatment parameter profile based on received symptom (e.g., pain) information, the treatment parameter profile determination engine 112 can identify treatment parameter profiles that have been previously effective for the user (e.g., by access stored user profile information). In implementations in which the treatment parameter profile determination engine 112 can select a treatment parameter profile from a particular set of stored treatment parameter profiles, the engine 112 can select a treatment parameter profile that has been determined to have been previously effective at treating same, or similar, symptoms (e.g., pain) for the user (e.g., based on comparison of the current symptom information with the previously treated symptom information, or based on a categorization of symptom, which can be based on the provided symptom information). In some implementations the treatment parameter profile determination engine 112 can generate treatment parameter profiles, and the engine 112 can, for instance, combine treatment parameter profiles. In some instances, each treatment parameter profile being combined can be weighted according to (1) its effectiveness, (2) a similarity of symptom (e.g., pain) information for which the treatment parameter profile was effective to the user's current symptom information, etc.

Furthermore, the treatment parameter profile optimization system 100 can store or maintain information specifying the effectiveness of various treatment parameter profiles as indicated by a multitude of users. When determining a treatment parameter profile, the treatment parameter profile determination engine 112 can utilize the stored or maintained information (e.g., received from the treatment parameter profile optimization system 100, for instance in response to the user device 2 providing pain information to the optimization system 100) to select a treatment parameter profile, or to generate new or updated treatment parameter profiles. For example, if the user is experiencing a migraine that is associated with sensitivity to light, in which the pain is located largely on the left side of the body, the user device 2 can receive information from the optimization system 100 indicating treatment parameter profiles that have been effective for other users with the same, or similar, pain information. Optionally, the optimization system 100 can provide one or more new treatment parameter profiles to the user device 2 (e.g., along with information indicating the effectiveness of the one or more new treatment parameter profiles at alleviating or reducing symptoms having particular parameters or categorizations).

Additionally, the treatment parameter profile optimization system 100 can utilize demographic information of users when indicating one or more treatment parameter profiles that are effective for same, or similar, symptoms (e.g., pain) as the user. For instance, demographic information can include one or more of an age, gender, weight, height, race, location (e.g., people located in cities might be differently affected due to environmental stress), and so on. Optionally, when the treatment parameter profile determination engine 112 is determining a treatment parameter profile to utilize, the engine 112 can utilize the effectiveness information from multitudes of users that are associated with same or similar demographic information. In this way, the treatment parameter profile can be better tailored to the user. As an example, a very elderly person might have greater success with a first treatment parameter profile, while a younger person might have greater success with a second treatment parameter profile. For example, height and weight can be used in some cases to determine a probable volume of the ear canal to accordingly adjust output or modifiable configuration of the system (e.g., maximum pressure levels) to best suit the user.

Figure 22:
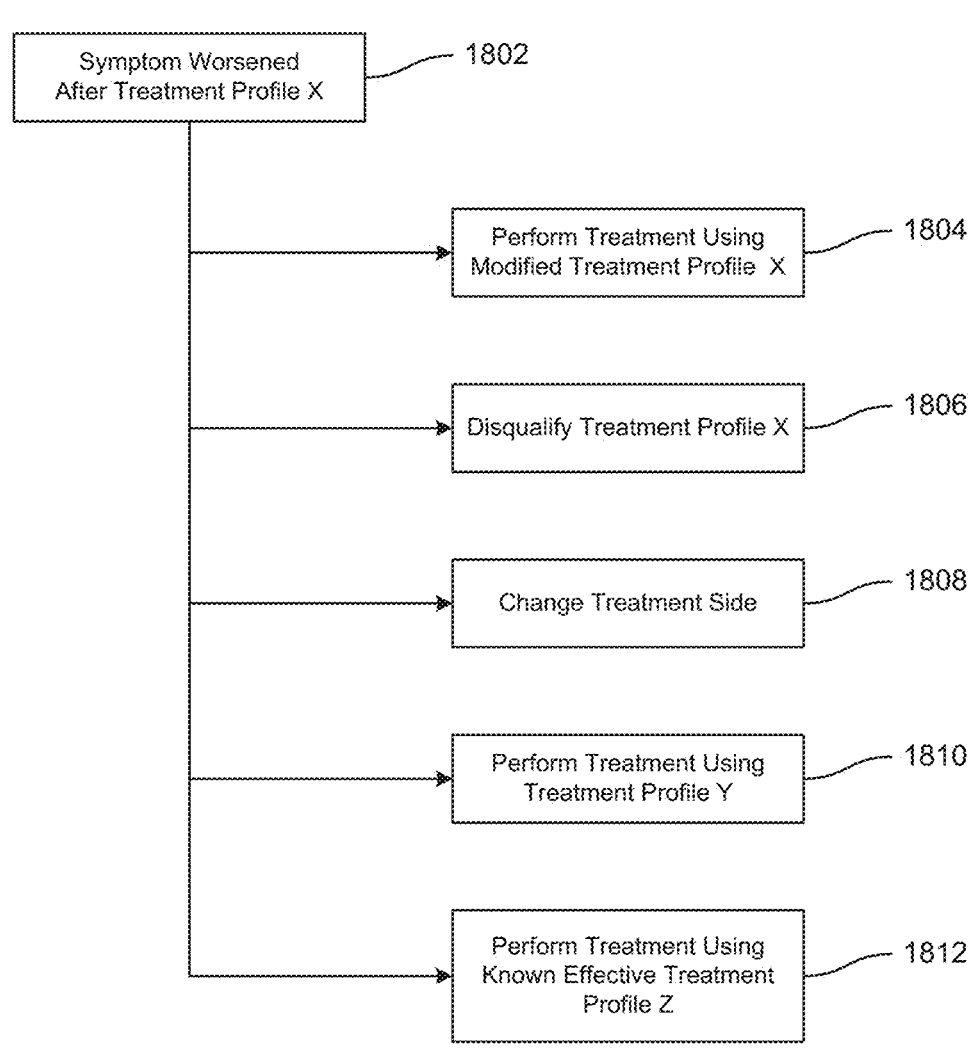
FIG. 22 is an example process for selecting a subsequent treatment parameter profile.

The application engine 114 can present summary information associated with a user undergoing treatment via the treatment device 10. For instance, while undergoing treatment the user can utilize the user device 2 to indicate that pain (or another symptom) increased or decreased at times during the treatment, optionally along with locations of the pain or other symptom (e.g., a pain in the left eye might decrease, while a pain in the neck might increase). At the end of the treatment, the application engine 114 can present a video clip of a graphical representation of the treatment, for instance a representation of a body portion (e.g., a head) and locations of pain (or other symptoms) on the head decreasing (for example) over time during the treatment (e.g., a relief replay video, as illustrated in FIG. 22). Optionally for the head described above, the expression on a face of the head can change to reflect the progress of the treatment (e.g., the expression be modified from an initial distressed state, such as a frowning face, to a content state, such as a happy face, as the pain, or other symptom, decreases during the treatment). In the case of non-cranial structures, the body posture/attitude may be altered to reflect a range of comfortable to stressed or painful states, potentially including "protective guarding" of the affected area.

This video clip can be uploaded to one or more social media accounts of the user, such that other users can congratulate the user on successfully treatment, and/or such that the user can inform others of the successfully treatment. Similarly, the application engine 114 can generate graphs or other representations of data that specify frequencies of the treatment device 10 being utilized, intensities of symptom(s) (e.g., pain) experienced during particular time periods (e.g., an average intensity of pain or other symptoms during each month, along with a frequency of occurrences of pain or other symptoms), and so on. In this way the user can quickly ascertain whether the occurrence of symptom(s) such as pain (e.g., occurrence of migraines) is being reduced. This summary information can further be shared with other users via one or more social media networks. Generating summary information is described in more detail herein, such as with respect to FIGS. 22-23, and 29-30.

The application engine 114 and/or the treatment parameter profile determination engine 112 can be implemented as computer-readable instructions (e.g., stored in memory 110) which can be executed by the at least one computer hardware processor 108 to perform the operations described. In some embodiments, the application engine 114 and/or the treatment parameter profile determination engine 112 can be implemented as application specific computer hardware (e.g., one or more field programmable gate arrays (FPGAs), specialized circuits, application specific integrated circuits, etc.) that are configured to perform the operations describe. Although the application engine 114 and/or the treatment parameter profile determination engine 112 are described as operating in connection with the user device 2, in some embodiments, one or both can operate on the treatment device 10 or on the treatment parameter profile optimization system 100.

The treatment parameter profile optimization system 100 can include a communication interface 116, which can communication with one or more treatment systems, which can be remotely located away from the treatment parameter profile optimization system 100, such as over a network (e.g., the internet). The treatment parameter profile optimization system 100 can include at least one processor 118 and computer-readable memory 120, which can have executable instructions that are executable by the at least one processor 118 to perform the functions of the treatment parameter profile optimization system 100 described herein. In some embodiments, the at least one processor 118 can be application specific computer hardware (e.g., one or more field programmable gate arrays (FPGAs), specialized circuits, application specific integrated circuits, etc.) that can be specially configured to perform the operations described herein. In some embodiments, the memory 120 can be omitted. The memory 120 and the database 102 can be stored together in common computer readable medium or separately.

The treatment device 10 can include at least one processor 126 and computer-readable memory 128, which can have executable instructions that are executable by the at least one processor 126 to perform the functions of the treatment device 10 described herein. In some embodiments, the at least one processor 126 can be application specific computer hardware (e.g., one or more field programmable gate arrays (FPGAs), specialized circuits, application specific integrated circuits, etc.) that can be specially configured to perform the operations described herein. In some embodiments, the memory 128 can be omitted. In some implementations, the treatment device 10 can have an earpiece and can be configured to provide pressure to an ear of the user 6 (e.g., using the pressure generator 124, which can be a pump). The treatment device 10 can receive a pressure treatment parameter profile or parameters for the treatment based on a pressure treatment parameter profile, and the at least one processor 126 can operate the pressure generator 124 to produce the pressure according to the pressure treatment parameter profile. In some embodiments, the treatment device 130 can include a sensor (e.g., a pressure sensor) that is configured to measure the pressure in the ear (e.g., in the external ear canal). The at least one processor 126 can monitor the pressure measured by the sensor 130 and can control the pressure generator 124 (e.g., pump) to achieve the pressures set by the pressure treatment parameter profile. The treatment device 10 can use the pressure sensor 130 to detect a leak, such as when the earpiece is not sealed properly in the user's ear. If the pressure measured by the sensor 130 does not increase or decrease as expected (e.g., within an acceptable threshold) when the pressure generator 124 (e.g., pump) attempts to change the pressure, or if the measured pressure is changing (e.g., outside of an acceptable threshold) when the pressure generator 124 (e.g., pump) is trying to hold the pressure steady, the treatment device 10 can determine that a leak is likely present.

In some embodiments, the treatment system can optionally include a sensor device 4. The sensor device 4 can be a wearable device. For example, in the embodiment of FIG. 1, the sensor device 4 can be a wrist strap. The sensor device 4 can be worn on the user's chest, head, arm, leg, finger, neck, ear lobe, etc. depending on the physiological parameter being tested. The sensor device 4 can include at least one sensor 134 that is configured to measure a physiological parameter, such as heart rate, respiratory rate, blood oxygenation level, temperature, and/or blood pressure, etc. A communication interface 132 on the sensor device 4 can communication physiological information (e.g., based on the sensor 134 measurement) to other components of the treatment system. In the embodiment illustrated in FIG. 1, the sensor device 4 can have a wired connection to the user device 2, although the communication can be wireless as well. In some embodiments, the sensor device 4 can communication the physiological information (e.g., hear rate) directly to the treatment device 10. In some embodiments the communication interface 132 can receive information as well. For example, the user device 2 and/or the treatment device 10 can send commands to the sensor device 4, such as regarding the sample rate for a sensor 134, an instruction to take a measurement, calibration instructions, etc. In some embodiments, the treatment system (e.g., the user device 2) can display the physiological information (e.g., heart rate), such as using the user interface 106.

In some embodiments, the treatment performed by the treatment device 10 can depend, at least in part, on the physiological information. The physiological information can be transmitted from the user device 2 to the treatment device 10, or directly from the sensor device 4 to the treatment device 10, or the user device 2 can send commands to control the treatment device 10 using the physiological information (e.g., among other things). In some embodiments, the treatment parameter profile can be synchronized with the physiological information. For example, the treatment can be synchronized with the user's heart rate. Since the human mind generally ignores or filters out the sensation created by a person's beating heart, synchronizing the treatment with the user's heart rate can cause the user's "mind" to ignore or filter out the sensations created by the treatment (e.g., the brain endogenous filtering systems, including but not limited to the basal ganglia, can be activated to actively inhibit "extraneous" information), which can make the treatment more comfortable for the user, and/or can help the mind ignore (e.g., brain inhibit) or filter out some or all of the symptom(s) (e.g., pain) experienced by the user. Without being limited by theory, it is believed that symptom relief due to synchronization of treatment with the user's heart rate can be linked to stimulation of the trigeminal system. By way of example, the treatment can stimulate the user's trigeminal nerve (e.g., by applying pressure to manipulate the tympanic membrane) in synchronization with the user's heart rate. This synchronization with the heart rate can cause the mind to ignore or brain filter out at least some neurological signals associated with the trigeminal nerve. The trigeminal nerve can also be associated with pain, or other symptoms, experienced by the user. By causing the mind to ignore or filter out at least some neurological signals associated with the trigeminal nerve (e.g., due to synchronization of the treatment with the heart rate) the pain, or other symptoms, can be alleviated.

In the example of a treatment device 10 that includes an external ear canal pressure regulation device, pressure wave frequency within the external ear canal can be correlated or matched to the sensed heart rate. However, this illustrative example, is not intended to preclude operation of the treatment device 10 synchronized with other sensed physiological parameters. Other types of treatment therapies can also be synchronized with the heart rate or other physiological parameters. For example, electro stimulation signals, sounds, or lights can be timed to synchronize with the physiological parameter (e.g., heart rate). At least one treatment parameter administered by a treatment device 10 can depend, at least in part, on a physiological parameter (e.g., heart rate), which can be sensed by the sensor device 4.

FIG. 2 shows an example implementation of a treatment system, and many alternatives are possible. For example, some or all features of the user device 2 can be incorporated into the treatment device 10. For example, the user can provide input and receive information directly to and from the treatment device 10 (e.g., via a user interface 106). In some embodiments, an intermediate control device (now shown) can be included (e.g., between the user device 2 and the treatment device 10). For example, the user device 2 can perform input and output functions to communicate with the user, the intermediate control device (not shown) can perform controller functions to implement at least some control features described herein, and the treatment device 10 can receive commands from the intermediate controller device (not shown) to implement the treatment. In some embodiments, the user device 2 can primarily operate to communicate with the user 6 (e.g., input and output via the user interface 106), and the at least some of the controller functions described in connection with the user device 2 can be performed by the treatment device 10. In some embodiments, at least some of the controller functions (e.g., described in connection with the user device 2, such as treatment parameter profile selection) can be performed by a remote system (e.g., the optimization system 100). Accordingly, the "controller" of the treatment system can be implemented as a combination of different components (e.g., the user device 2, the treatment device 10, and/or the optimization system 100), and the various control features described herein can be distributed between those different components in various manners. Although some embodiments are described as using pressure treatment, other types of treatment can be used, such as electro stimulation, audio sounds, lights, heating, cooling, vibration, etc. Accordingly, the treatment device 10 can include various treatment generator features in place of the pressure generator 124.

As described above, one or more user scores can be maintained for user accounts, and can be increased or decreased based on user actions. For instance, a proactivity score can be assigned to the user according to a frequency of use of the treatment device 10, an adherence to a medication regimen (e.g., the medication regimen can be used to proactively reduce occurrences of symptoms, such as migraine headache pain), and/or other user activities can be preventative or therapeutic (or causal or exacerbating) for the condition or symptoms. The user can be incentivized to increase his/her proactivity score, thus reducing a frequency and/or intensity of symptom(s) (e.g., pain) through gamification. The proactivity score can be a measure of the patient's efforts to manage their own condition. A connectedness score can be assigned to the user according to the user sharing information with others (e.g., other users of treatment devices). For instance, the connectedness score can be increased upon the user sharing a video clip of a treatment summary (e.g., as described herein), sharing the successful adherence to a medication regimen, and so on. An understanding score can be assigned to the user according to the user researching information associated with condition(s) and/or symptom(s) he/she is experiencing (e.g., migraines, cluster headaches, motion sickness), which can be accessed via the user device 2. Additionally, the understanding score can be increased upon the user viewing research information, and/or then accessing his/her summary information. For instance, the user might read that particular environmental triggers can be associated with migraines, and the user can view summary information and determine whether the environmental triggers could be a cause of the migraine pain. The understanding score can be an assessment of the patient's understanding of their condition. The system can make information (e.g., research, background information, or facts relating to a condition) available to the user, such as via the user device (e.g., via the application running on a smartphone). The system can track or store indications of what information the user has accessed, and the understanding score can be based at least in part on the information that the user has accessed.

Figure 3:
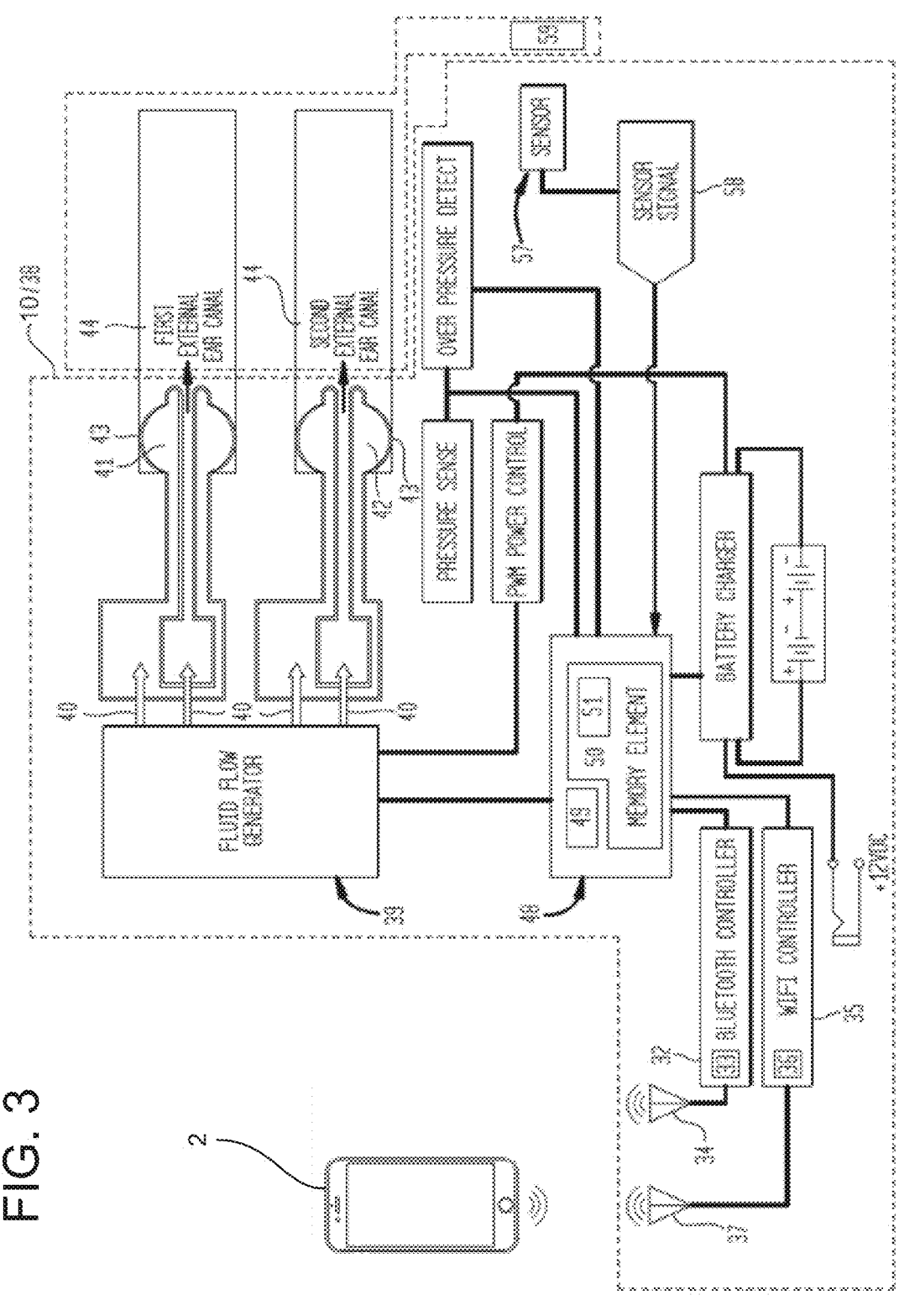
FIG. 3 illustrates a block diagram of an example treatment device.

FIG. 3 illustrates a block diagram of an example treatment device 10. The treatment device 10 can be an external ear canal pressure regulation device 38 including a fluid flow generator 39 (e.g., a pump), which can be configured to generating at least one fluid flow 40. The treatment device 10 can include one or more of a first earpiece 41 and a second earpiece 42, which can be jointly fluidicly coupled or discretely fluidicly coupled to the fluid flow generator 39. The earpiece 41 and/or 42 can have an earpiece external surface 43 configured to sealably engage an external ear canal 44 of an ear as a barrier between an external ear canal pressure and an ambient pressure. Although FIG. 3 shows two ear pieces 41 and 42 (e.g., to enable treatment to be applied to both ears), in some embodiments a single ear piece 41 can be used (e.g., for applying treatment to only one ear at a time). In some embodiments, the ear piece can seal outside the ear canal. For example, the ear piece can fit over the ear and seal against the side of the head that is next to the ear.

The external ear canal pressure regulation device 38 can further include a treatment device controller 48, which can include at least one treatment device processor 49 communicatively coupled with a treatment device memory element 50, which can contain treatment device computer code 51 executable by the processor 49 to control the fluid flow generator 39 to generate a pressure differential (e.g., positive or negative) between the external ear canal pressure and the ambient pressure which can be generated according to a received treatment parameter profile (e.g., from a wireless connection with a user device 2). For instance the treatment parameter profile can be a pre-selected static pressure differential, as pre-selected pressure waves having pre-selected amplitude or pre-selected frequency, or combination thereof (e.g., in which a pre-selected static pressure differential can be generated and superimposed by a pressure wave having a pre-selected frequency and pre-selected amplitude). The external ear canal pressure regulation device 38 can, but need not necessarily, further include a physiological parameter sensor 57, which can generate a sensor signal 58 which varies based on change in a sensed physiological parameter 59 receivable by the treatment device controller 48, which can further functions to synchronize operation of the fluid flow generator 39 (e.g., in regard to amplitude and frequency of the pressure differential generated in the external ear canal 44 with the sensed physiological parameter 59, as discussed herein.

The treatment device 10 can include a communication interface, which can communicate via a wired or wireless communication protocol. Wireless communication can use electromagnetic waves rather than some form of wire to carry a signal over all or a part of a communication path and can include, for example, BLUETOOTH® or Wi-Fi®, or combinations thereof, for the exchange of data over the communication path. As to particular embodiments, the treatment device 10 can, but need not necessarily, include a BLUETOOTH® controller 32 including the associated BLUETOOTH® transceiver 33 and BLUETOOTH® antenna 34. As to particular embodiments, the treatment device 10 can, but need not necessarily, include a Wi-Fi® controller 35 and the associated Wi-Fi® receiver 36 and Wi-Fi® antenna 37. As to other embodiments, the treatment device 10 can provide both a BLUETOOTH® controller 32 and a Wi-Fi® controller 35 including the associated transceivers 33, 36 and antennas 34, 37. The other devices described herein as having communication interfaces, can include similar features for communicating via one or more wireless communication protocols, and various other communication protocols can be used (e.g., short message service (SMS), 3G, 4G, cellular network, etc.)

The treatment device 10 can be placed in the active condition by a user such that the treatment device 10 seeks a connection with a computing device (e.g., a user device 2) containing or having access to a treatment program within the range of the transceiver 33, 36 (or vice versa). The software can cause pairing of the computing device (e.g., user device 2) with the treatment device 10.

Further details and examples of treatment devices are included in the '639 patent, the '678 Publication, and the '206 Publication.

FIG. 4 illustrates an example process 400 for describing symptom (e.g., pain) information (e.g., via a user device 2). For convenience, the process 400 will be described as being performed by a device having one or more processors (e.g., the user device 2), although it can be performed by a treatment device 10, or other device.

As described herein, the user device can execute software or an application (e.g., 'app') and provide interactive user interface outputs for presentation (e.g., display) to a user. The user can interact with the user interface via a touch screen display of the user device, or using a keyboard, mouse, his/her voice, and so on. The user can optionally provide user account information, which the user device or a system in communication with the user device (e.g., the treatment parameter profile optimization system 100) can authenticate. Upon authentication, the user's profile information can be accessed and utilized by the software or application, as will be described.

Figure 5:
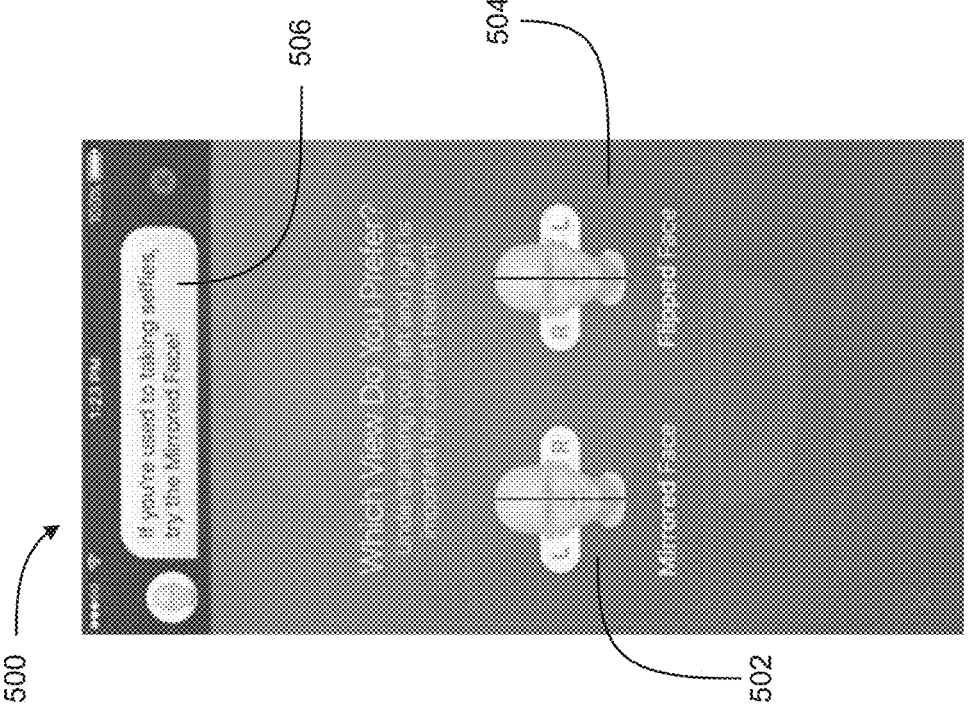
FIG. 5 illustrates an example user interface for selecting an orientation for a displayed body portion.

The user device can receive a selection of a mirrored or flipped orientation (e.g., via the user interface) (block 402). Upon the user interacting with the user device, the user device can initially present a representation or indicia of a body portion (e.g., a head) for the user to specify pain information on the body portion. Initially (e.g., a first time the user uses the treatment device and/or application on a user device, etc.), or each time the user uses the treatment device, or upon a command from the user, the user interface can enable the user to specifies a particular orientation associated with the body portion. For instance, as illustrated in FIG. 5, the body portion can be presented with an option to specify a mirrored orientation or a flipped orientation. In the mirrored orientation, a right side of the user's body portion is represented by the displayed right side of the body portion and the left side of the user's body portion is represented by the displayed left side of the body portion (e.g., like looking in a mirror). In the flipped orientation, a right side of the user's body portion is represented by the displayed left side of the body portion and the left side of the user's body portion is represented by the displayed right side of the body portion (e.g., as if the user were to turn around to assume the orientation of the displayed body portion (e.g., head)).

By way of example, FIG. 5 illustrates a user interface output to enable the user to indicate a preferred orientation of the body portion. User interface 500 provides two options, a first option being a mirrored face orientation 502, in which a left side of the graphical representation corresponds to a left side of the user (e.g., from his/her perspective), and a second being a flipped face orientation 504, in which a left side of the graphical representation corresponds to a right side of the user (e.g., from his/her perspective). The user interface 500 can present a textual description 506 describing the options, and/or providing a recommendation. For instance, the textual description 506 can include a reference to 'selfies' being oriented under the mirrored orientation. Many alternatives are possible. In some embodiments, the user device can request that the user hold the user device with a screen of the user device facing the user, and can request that the user touch a particular side of the body portion (e.g., touch a left side of the user's head or touch the right ear). The side that the user touches in response to the prompt can indicate whether the user intuitively prefers the mirrored or flipped orientation. The assignment of the mirrored face orientation 502 or the flipped face orientation 504 can update or be determined based on the indication of where the user touched in response to the prompt.

With reference again to FIG. 4, the user device can present (e.g., display) the body portion via the user interface (block 404). As illustrated in FIG. 6, the user device can display a representation of the body portion, which in this example is a head. In other examples the body portion can be an arm, a leg, torso, and so on. Optionally, the user device can access profile information associated with the user, and present an image of the user's head. For example, the user device can request one or images of the user, and the user can capture images (e.g., using a camera on the user device) of his/her head. As another example, the user device can request that a camera of the user device be rotated about the user's head, for instance starting at one side of the head, and being rotated about the head towards the other side. In this way the user device can store images of the head such that the user device can display a rotatable representation of the user's head.

The example user interface output 510 of FIG. 6 depicts a representation 514 of the body portion (e.g., head), and includes a designation of a right side 512A and left side 512B of the representation 514, which can be based on the selection of the mirrored or flipped orientation. The user interface 510 can receive user interactions to change the portions of the body portion that are visible on the representation 514, such as through user interactions with a touch screen (or other user input element) presenting the user interface 510. The representation 514 can be rotated around to show the front, side, back, top, etc. of the body portion (e.g., head).

Figure 7:
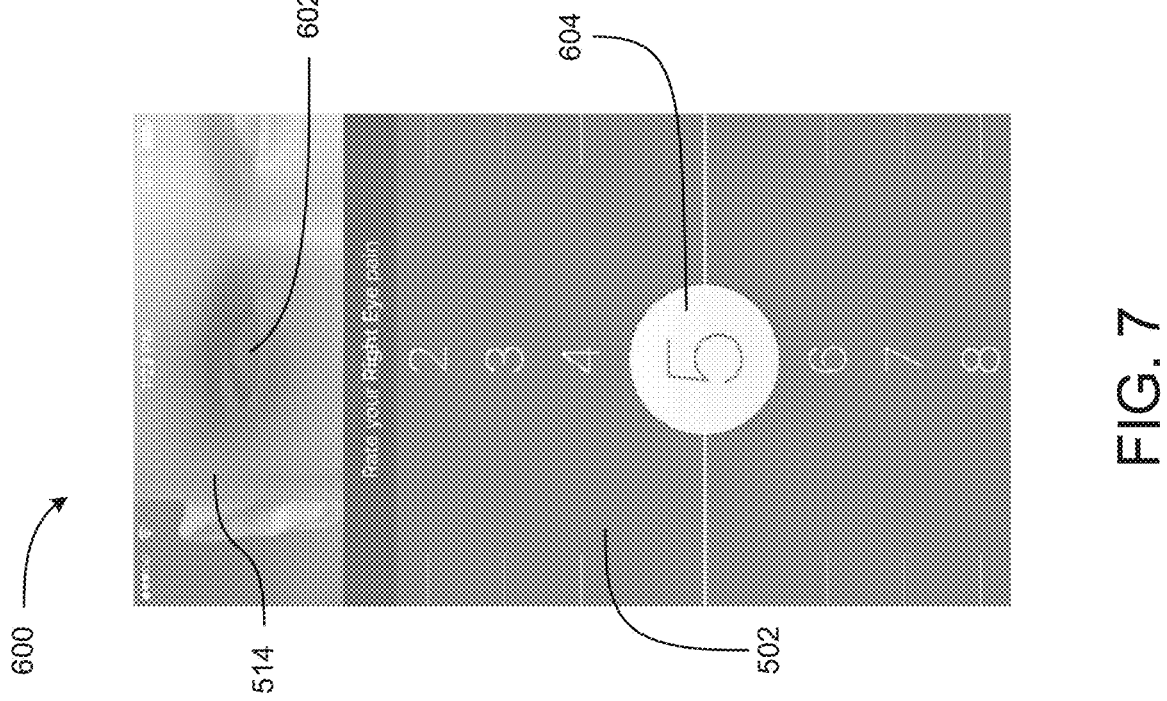
FIG. 7 illustrates an example user interface for describing intensity values of pain symptoms on a graphical representation of a body portion.

With reference again to FIG. 4, the user device can receive input indicating locations of symptom(s) (e.g., pain) (block 406). As illustrated in FIGS. 7-8, the user can select locations on the body portion that are associated with pain or other symptom(s) being experienced by the user. For instance, as illustrated in FIG. 7 the user has selected a right eye indicating that pain is located at the right eye of the user. Optionally the user interface can enable the user to specify a size of the location affected by the symptom (e.g., pain). For example, the user can initially select a location by pressing on a touch screen display presenting the user interface, and then dragging a circle or ellipse into existence using one or more fingers, with the circle or elapse representing roughly a size of the location of the pain. The representation or indicia of the body portion can be divided into predefined selectable areas. In some embodiments, the representation or indicia of the body portion can have between 5 and 50 selectable areas, between 10 and 30 selectable areas, between 15 and 25 selectable areas, although other values can be used. Although many examples herein are discussed in the context of headache pain, the principles disclosed can be applied to other body portions and other pain areas, such as back pain, for example. In some cases lower back pain can be associated with anxiety or numbness.

Optionally, the user device can receive input indicating that the user device is to activate a camera of the user device facing the user (e.g., a front camera on a mobile device). The user device can then monitor a location of the user's finger as seen via images (e.g., live video) captured by the camera facing the user, and select locations of pain symptoms based on one or more positions of the user's finger. As an example, the user device can utilize computer vision techniques, such as feature matching, blob detection, and so on, to identify the finger (e.g., identify a rough shape of the finger). Upon the finger resting at a particular portion of the user's head for greater than a threshold period of time, the user device can record the location as associated with the symptom (e.g., pain). The determined location can be displayed on the representation of the body portion and the user interface can request that the user confirm the location is accurate. For instance, the user device can determine a shape of the user's head, and determine a location on the representation that corresponds to the location at which the user pointed. The user can confirm via an additional user input, or optionally provide a verbal confirmation (e.g., the user can say "yes," and the user device can process the received audio to determine that a yes was said). Additionally the user can modify a location on the representation, such as by selecting the location on the representation and moving (e.g., dragging) the location to a different location on the representation. In this way, if the user is particularly sensitive to light he/she can choose not to stare at a bright display (e.g., selecting locations via the display), and instead can turn the user device towards his/her head and point to affected portions.

The user device can receive input specifying an intensity associated with a pain symptom (block 408 of FIG. 4). As described above, the user can indicate a location at which he/she is experiencing symptom(s) (e.g., pain), such as a location on his/her head or neck. The user can additionally specify an intensity value, which for instance, can be a value within a particular range (e.g., 1 to 10, 1 to 20, and so on).

FIG. 7 illustrates a user interface output for enabling a user to describe pain symptoms (e.g., on a graphical representation of a head). Upon selection of a location on the graphical representation of the body portion (e.g., a selection on the large representation 514 described above), the user interface output 600 of FIG. 7 can be presented. The user interface 600 can include a close-up view of a specified location 602 on the body portion indicated as being associated with a pain symptom (e.g., the right eye). The user can select an intensity value from amongst a range of intensity values using the user interface. For instance, the user has selected an intensity value of '5' 604 from the range '1-10' through manipulations of a scroll wheel. While a scroll wheel is illustrated, other user input elements to select the intensity value can be utilized, such as elements for entering the value, manipulating a pointer located in a circle with values spaced around the circumference of the circle, and so on.

Optionally, as described herein, the user device can be turned towards the user (e.g., a screen of a smart phone facing the user, or a back of the smart phone facing the user), such that the user device can obtain images of the user. The user can then point to a particular portion of his/her body portion (e.g., head or neck), and can verbally speak an intensity value (e.g., the user device can optionally verbally describe the particular range, such as "Please identify an intensity value between 1 and 10," and the user can say a number included in the particular range while pointing to an affected portion).

Optionally, for a user device that can detect a pressure or force being applied to a touch screen display of the user device, the user can first (1) select a location on the representation corresponding to an experienced pain while applying a pressure or force to the touch screen, and (2) upon applying a greater pressure or force to the touch screen, the user device can present user selectable options to indicate an intensity value. In this way, the user device can reduce a number of user required for the user to specify a location and intensity of each pain symptom. In some embodiments, the user can select the location for the symptom (e.g., pain) by the location that the user touches, and/or the user can specify the intensity of the symptom (e.g., pain) by the amount of pressure applied when touching that location. For example, a pain value of '2' can be specified by applying light pressure, whereas a pain value of '8' can be specified by applying more pressure. The pain value specified by the pressure can be displayed. The user can modify the pressure to adjust the intensity value until a desired value is reached. The user can stop the touch to select the intensity value. In some implementations, the user can swipe in a first direction (e.g., up) to increase the intensity value, and can swipe in a second direction (e.g., downward) to decrease the intensity value.

The user device can present a visual representation of the one or more locations and/or associated intensity values of the symptom (e.g., pain) (block 410 of FIG. 4). The user device can present a graphical representation of the location and intensity on the representation of the body portion (e.g., head). For instance, the graphical representation can include an identification of the location, such as highlighting the location, outlining the location, modifying a color of the location of the representation of the body portion, etc. Additionally, the graphical representation can be modified according to an intensity value (e.g., a color assigned to the location can depend on an intensity value, such as red being associated with a higher intensity and a different color, such as green, being associated with a lower intensity value). In some embodiments, different shades of the same color can be used. For example, a light reddish coloring for a location can indicate light or moderate symptom(s) (e.g., see the pain value of 4 in FIG. 8), whereas a dark and/or solid red color for a location can indicate more severe symptom(s) (e.g., see the pain value of 7 in FIG. 8).

Figure 8:
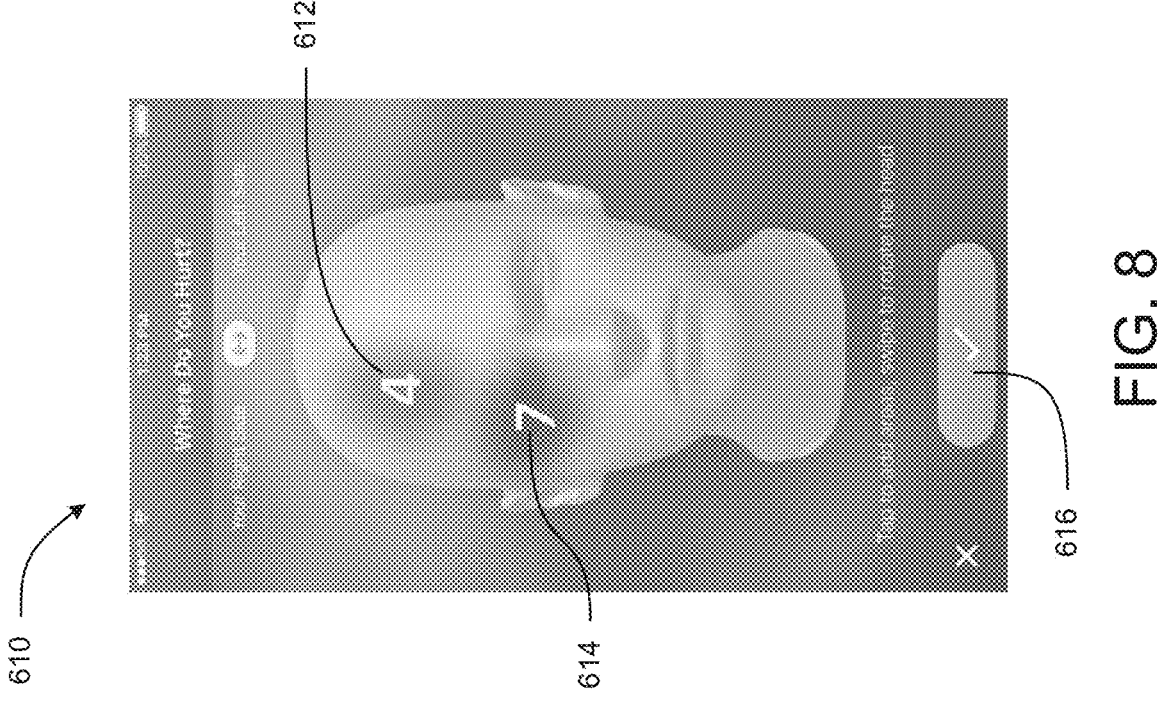
FIG. 8 illustrates an example user interface for displaying pain symptoms being experienced by a user.

User interface 610 of FIG. 8 illustrates a summary of the described physical pain information, including locations of each pain symptom and an associated intensity value. For instance, the graphical representation of the body portion includes a first location 612 of a pain symptom, along with an indicated intensity value (e.g., '4'), and a second location 614 of a pain symptom, along with an indicated intensity value (e.g., '7'). The user can continue adding additional pain symptoms through selections with other locations on the graphical representation of the body portion. Alternatively, the user can select an option 616 to complete the described physical pain information.

The user device can modify an appearance of the body portion based on the pain symptom intensity (block 412). For an example body portion of a head, the head can display a face having an expression based on the intensity values of pain symptoms. For instance, the head can display a face based on one or more face pain scales, indicating a level of pain and severity being experienced by the user. In the example of FIG. 8, the face has an expression that reflects the pain illustrated (e.g., having a frown and a knit brow). The background can also depend on the symptom(s) identified. For example, more severe symptom(s) can result in a darker background. The appearance of the body portion (e.g., the expression of the face) can reinforce to the user that the pain indicated on the user interface corresponds to the actual pain that the user is feeling.

Figure 9:
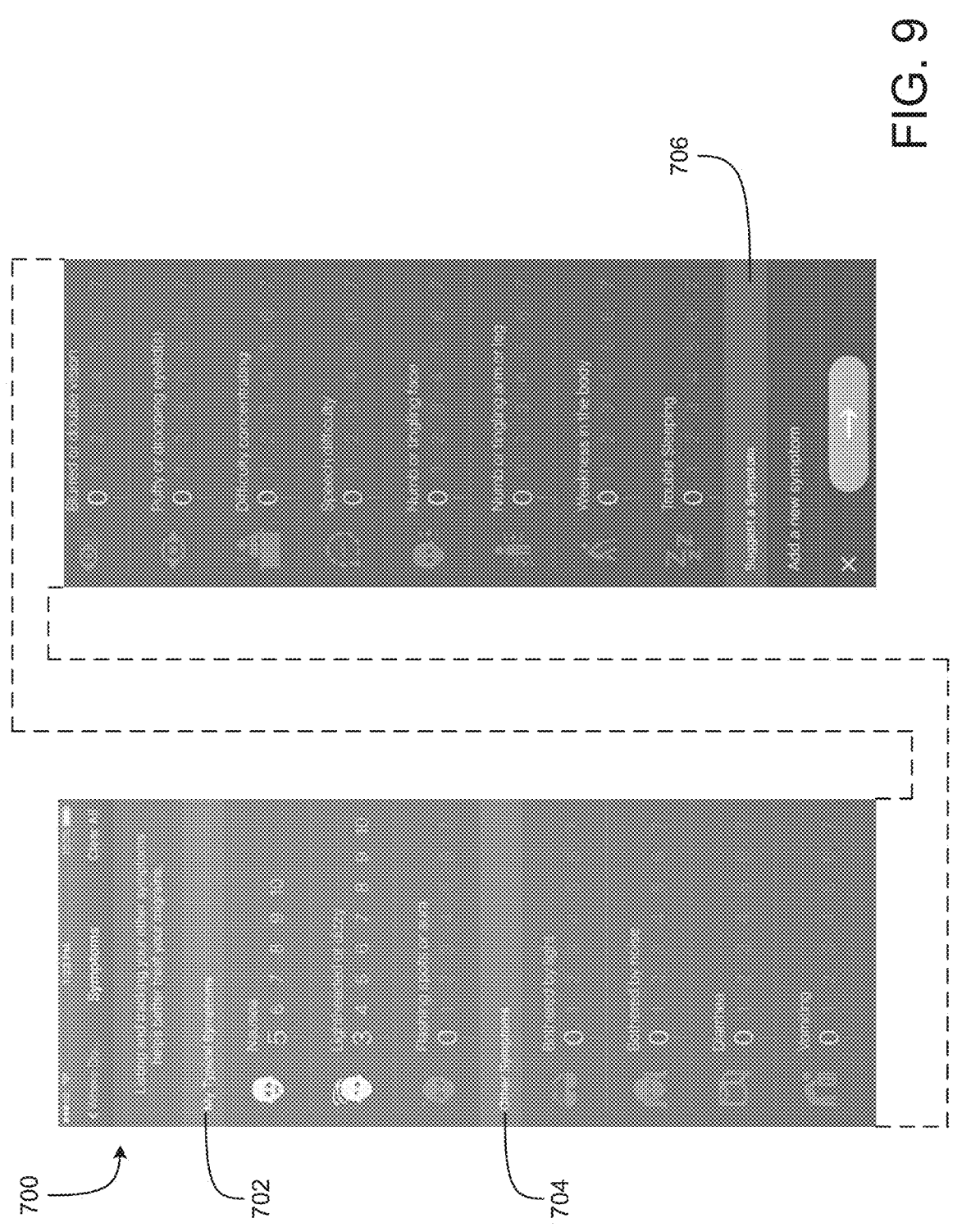
FIG. 9 illustrates an example user interface selecting associated symptoms.

FIG. 9 illustrates an example user interface 700 for describing symptom(s) (e.g., secondary symptoms or symptoms associated with a primary symptom, such as pain) being experienced by a user. As described herein, a user can specify locations of the user's body that are associated with symptoms(s) (e.g., pain) and an intensity of the symptom(s) (e.g., pain) at each specified location. For other symptoms, the symptom may not be associated with an identifiable location. Utilizing user interface 700 the user can indicate descriptions of symptoms he/she is experiencing, along with an intensity value associated with the symptom(s). For instance, symptoms can include nausea, dizziness, flashing spots or aura, being bothered by light or noise or touch, diarrhea, vomiting, blurred or double vision, puffy or drooping eyelid(s), difficulty concentrating, speech difficulty, numb or tingling face or arm or leg or other body portion, weakness in the body, trouble sleeping, and so on. As described herein, these descriptive symptoms can be utilized by the user device when determining a treatment parameter profile to alleviate or reduce symptom(s) being experienced by the user.

The user interface 700 can present typical symptoms 702 associated with the user, such as symptoms the user has previously experienced, or experiences at greater than a threshold occurrence with respect to other symptoms (e.g., a top 5 symptoms), and/or experienced more recently than other symptoms. These typical symptoms 702 can be associated with a selection of a particular condition (e.g., top symptoms associated with a migraine may be different than top symptoms associated with motion sickness). In the example of FIG. 9, the user's typical symptoms 702 include nausea, dizziness, and flashing spots. In this way, the user can easily access common symptoms without searching through a larger list. Remaining symptoms 704 are similarly included in the user interface 700 (e.g., listed below the typical symptoms). In some embodiments, the user can search for additional symptoms 706 not included in the user interface 700 (e.g., enter one or more words describing a symptom, and the user device presenting the user interface 700 can search for a corresponding symptom, such as by searching an outside search system), or the user can specify his/her own additional symptom 706. In some embodiments, the suggested symptom(s) specified by a plurality of users can be reviewed (e.g., using an optimization system 100) to determine whether additional symptoms should be added to the listing.

Various components and operations discussed in connection with FIG. 4 are optional and can be omitted or modified. For example, for some body portions the selection of a mirrored or flipped orientation can be omitted. In some embodiments, the user can specify a body portion from multiple selectable body portions (e.g., the user can select between the right arm, left arm, right leg, and left leg). In some embodiments, the symptom might not be associated with a location, or a symptom may be either present or absent (as opposed to having a variable intensity value). In some embodiments, the system can omit displaying visual representations of the inputted symptom(s) (e.g., pain) to the user and/or can omit the modification of the appearance of the body portion.

FIG. 8 illustrates an example process 800 for selecting and causing performance of a treatment parameter profile. For convenience, the process 800 will be described as being performed by a user device having one or more processors (e.g., the user device 2) in combination with a treatment device (e.g., the treatment device 10), although various alternatives are possible, as discussed herein.

The user device can query the user regarding symptom(s) being experienced (block 802). As described herein, the user device can present user interfaces, and the user can select or describe a particular condition and/or symptom(s), such as a migraine, headache pain, specific pain parameters, nausea, etc. The user device can receive symptom (e.g., pain) information (block 804). As described herein, for instance with respect to FIGS. 4-9, the user device can receive descriptions of symptom(s) (e.g., pain) being experienced, such as locations of the pain and associated intensity values, and descriptions of other symptoms such as sensitivity to light.

The user device can determine an ear in which to insert the treatment device (block 806). As described herein (e.g., at least with respect to FIGS. 11-12, the user device can determine whether a left ear or a right ear of the user is to be utilized. For instance, the user device can determine that all, or a threshold percentage of, the locations of pain are on a particular side, and can select the ear located on that particular side for treatment. The user device can prompt the user to apply the treatment device (e.g., insert the eyepiece) to the left ear (block 807) or the right ear (block 809) based on the determination. In some embodiments, treatment may be applied to both ears.

The treatment device can perform a treatment threshold test (block 808). For example, prior to initiation of a treatment parameter profile (e.g., described below with respect to block 814), the treatment device can perform an initial treatment threshold test to determine whether the user can likely sustain a planned pressure differential between an external ear cavity and atmospheric pressure. For instance, the user device can determine a maximum pressure that is to be applied (e.g., a maximum positive pressure, or a lowest negative pressure), and the treatment device can ramp up an applied pressure over a threshold amount of time until reaching the maximum pressure. During the ramping up process, the user can utilize the user device to indicate discomfort, and upon any such indication, the user device can provide information to the treatment device to stop the ramping process or to restore the external ear cavity pressure to atmospheric pressure. An example of a threshold test is provide at least at FIGS. 13 and 15, and determining the initial maximum pressure is described herein with respect to FIG. 14.

The treatment device can perform a leak test to determine whether the treatment device is properly applied (e.g., inserted into the user's ear) (block 810). While ramping up an applied pressure, the treatment device can determine whether a seal between the treatment device and the user's ear is maintaining the pressure differential. For instance, the treatment device can include a sensor to measure a value of an applied pressure, and can determine whether the value is ramping up according to the ramp up process, or whether it detects sudden or periodic drops in pressure. If the treatment device detects that the treatment device is leaking, the treatment device can provide information to the user device, and the user device can present information describing the incorrect insertion. Optionally, the user device can present an animation or video illustrating a proper technique of insertion.

The user device can select a treatment parameter profile for implementation by the treatment device (block 812). As described herein, the user device can select a treatment parameter profile based on the provided symptom (e.g., pain) information. That is, the user device can select from amongst multiple pre-defined treatment parameter profiles. In some implementations, the treatment parameter profiles can be associated with indications (e.g., stored in memory on the user device or optimization system) of symptoms they are likely to be effective to reduce or alleviate. In some implementations, the treatment parameter profile can be selected in part based on historical information associated with the user (e.g., treatment parameter profiles that were indicated as being (or otherwise determined to be) effective by the user. For instance a treatment parameter profile can be indicated as reducing pain being experienced greater than a threshold. Treatment parameter profiles that were indicated as being effective for same, or similar, symptom (e.g., pain) information from other users utilizing a treatment device can be used to select a treatment parameter profile for the current user. For instance, a system in communication with the user device can be queried, or the user device can maintain effectiveness information received from the system, and the user device can select a treatment parameter profile based in part on the effectiveness information (e.g., from the user and/or from other users). Selecting a treatment parameter profile is described below in more detail, with respect to FIG. 17.

Figure 10:
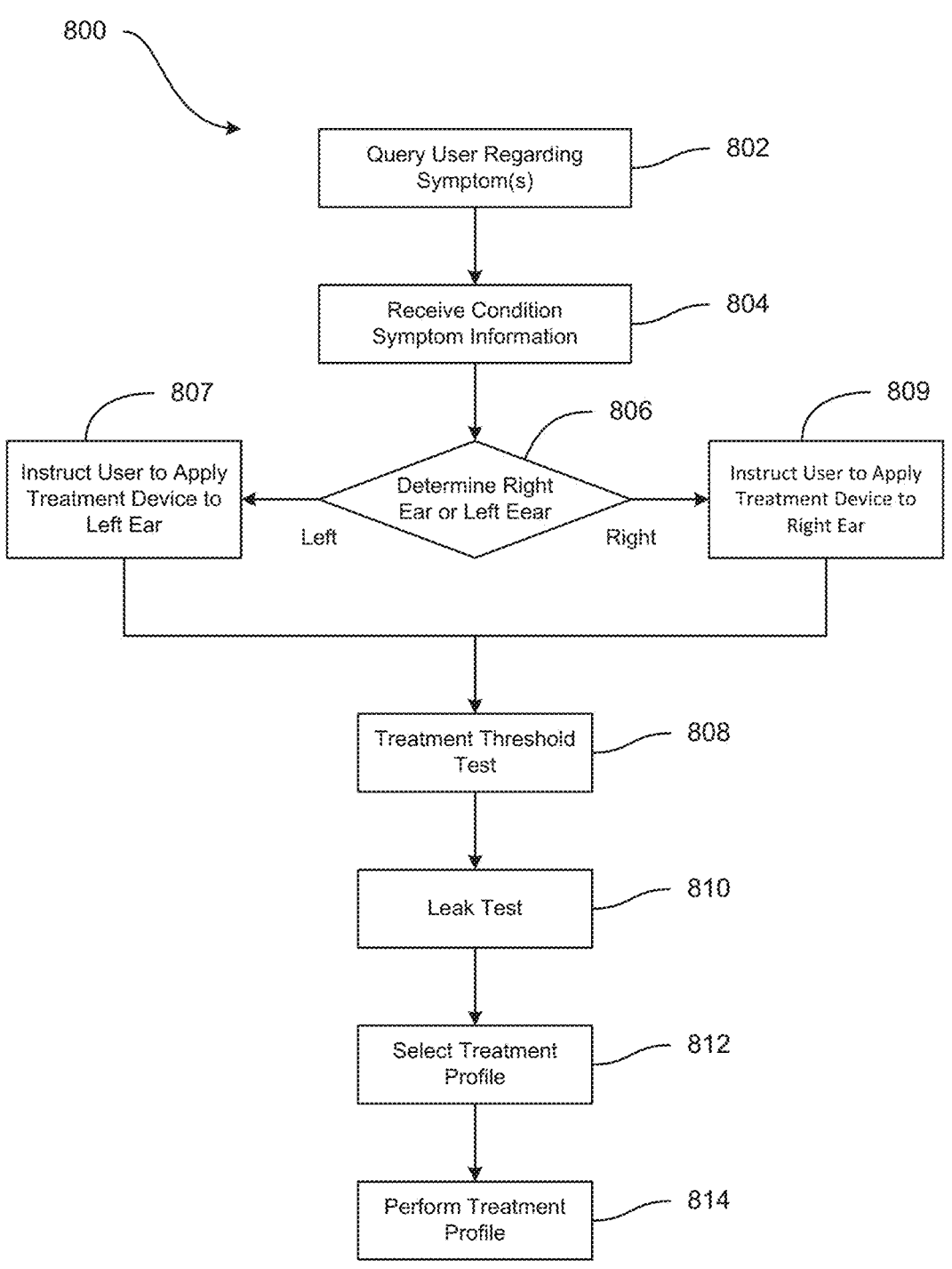
FIG. 10 illustrates an example process for selecting and performing a treatment parameter profile.

The treatment device can implement the selected treatment parameter profile (block 814). The user device 2 can provide information to the treatment device 10 associated with the selected treatment parameter profile, such that the treatment device 10 can implement the treatment parameter profile. In some embodiments, the user device 2 can send the treatment parameter profile to the treatment device 10, which can interpret and implement the treatment parameter profile. Many variations are possible. For example, the user device 2 and treatment device can be incorporated into a single device. Various components and operations discussed in connection with FIG. 10 are optional and can be omitted or modified. For example, some treatments don't apply pressure to the ear.

Figure 11:
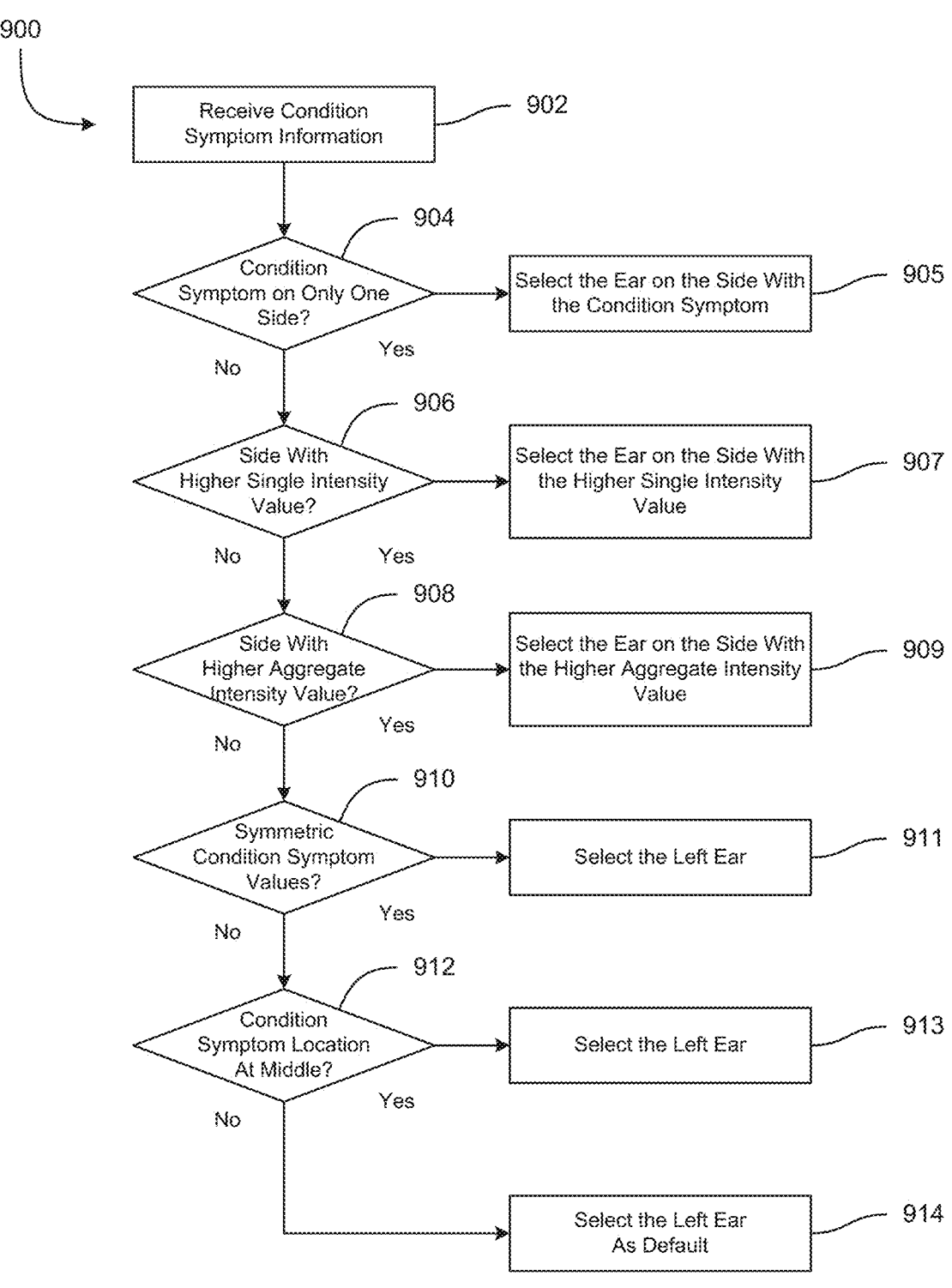
FIG. 11 illustrates an example process for selecting an ear in which a user is to apply a treatment device.

FIG. 11 illustrates an example process 900 for selecting an ear to which a user is to apply a treatment device (e.g., by inserting an earpiece into the external ear canal). For convenience, the process 900 will be described as being performed by a user device having one or more processors (e.g., the user device 2). The user device can receive symptom (e.g., pain) information (block 902). As described herein, the user device can receive symptom (e.g., pain information) from the user. For example, the pain information can specify locations of pain being experienced by the user along with associated intensity values.

The user device can determine whether the symptom (e.g., pain) information is associated with only one side of the user (e.g., one side of the user's head and/or neck) (block

904), and upon a positive determination selects that side for the user to insert the treatment device (block 905). For example, if the identified pain is all located on the right side of the user's head, the system can instruct the user to use the treatment device 10 with the right ear. In some embodiments, symptoms that are located in the center can be disregarded for this determination. For example, if the identified pain is located on the right side, and some on the center of the head, the process 900 can still proceed to block 905 to instruct the user to use the treatment device with the right ear.

The user device can determine a side associated with a highest intensity value for the symptom (e.g., pain) (block 906), and the user device can select that side with the highest intensity value as the side for treatment (block 907). For example, the user can input pain information for locations on the right side having intensity values of 3, 4, and 5, and for locations on the left side having intensity values of 5 and 7, the user device can instruct the user to use the treatment device with the left side.

The user device can determine a side associated with a highest aggregate intensity value (e.g., a sum associated with the intensity values per side) (block 908), and can select the determined side with the highest aggregate value as the side for treatment (block 909). The user device can determined, for example, a weighted sum of intensity values based on side, with the weights being associated with particular locations. For instance, the user device can weight an intensity value associated with eye pain higher than an intensity value associated with cheek pain. Similarly, the user device can weight intensity values higher based on a distance associated locations are from a middle of the user. For instance, the user device can weight an intensity value higher if it is located near the ear of the user when compared to an intensity value located near the nose of the user.

The user device can select the left ear for treatment (blocks 911 and 913) if the symptom(s) (e.g., pain) are symmetric about the user (e.g., the body portion) (block 910), or the pain symptoms are located in the middle of the user (e.g., the body portion), such as within a threshold distance from the middle, a threshold number or percentage of the intensity values are within the threshold distance of the middle, or a threshold percentage of the aggregate intensity values are from within the threshold distance of the middle (block 912). The user device can select the left ear by default (block 914). If the selection of the user is ambiguous, or insufficient information is provided, the user device can select the left ear for treatment as the default selection. Many variations are possible. The order of the determinations in FIG. 11 can be rearranged, and some can be omitted or modified.

Figure 12:
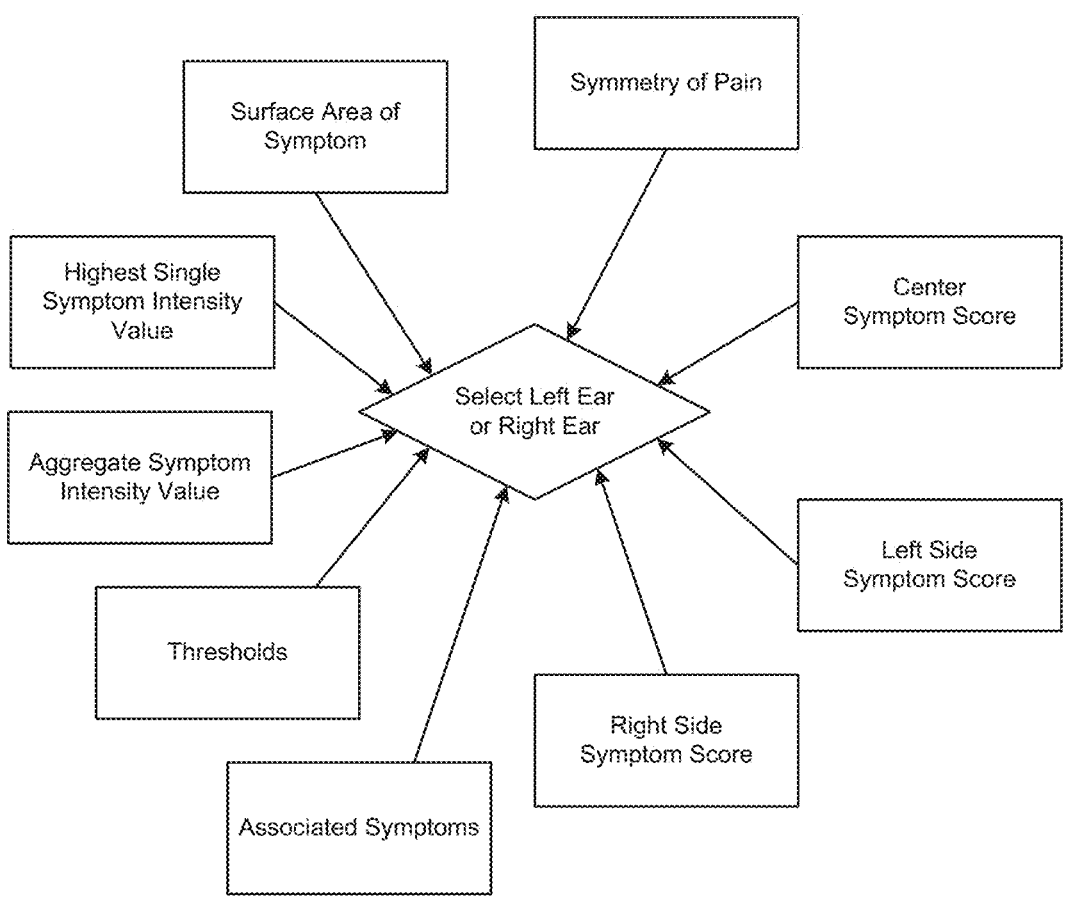
FIG. 12 illustrates factors used in selecting an ear in which a user is to apply the treatment device.

FIG. 12 illustrates another example of selecting an ear to which a user is to apply the treatment (e.g., by insert the earpiece of the treatment device into the ear canal so that pressure can be applied). The illustration of FIG. 12 includes identifications of factors that can be utilized (e.g., by the user device) in determining an ear for treatment. In some embodiments, the factors can be provided to one or more machine learning algorithms (e.g., implemented on the optimization system 100) trained on, for example, effectiveness of treatment parameter profiles being implemented by treatment devices across multitudes of users, or the user. For instance, users can describe effectiveness of a same treatment parameter profile when implemented by a treatment device in each of the users' ears. The user device can then utilize the identified factors to determine an ear that is determined to be the most effective based on the described symptom (e.g., pain) information.

For example, a right side symptom score, left symptom side score, and/or center symptom score, can be determined based on the symptom information. The scores can be determined, for example, based on one or more of the following: an aggregate intensity value, locations of the symptoms, number of symptom locations, duration of the symptoms, etc. In some implementations, the right-side, left-side, and center symptom scores can be pain scores. In some cases, if the left-side symptom score or the center symptom score is highest, the left ear can be selected for treatment, whereas if the right-side symptom score is highest the right ear can be selected for treatment. Additionally, locations of highest symptom intensity values, an indication of a symmetry associated with the pain information (e.g., a measure associated with how different the pain information is for each side), surface area of the symptom, aggregate symptom intensity value, and so on, can be used as factors in selecting the ear for treatment. The factors can then be utilized by the user device to determine a side expected to be more effective based on the symptom (e.g., pain) information, including descriptions of symptoms that are not associated with a side (e.g., sensitivity to light, and so on as illustrated in FIG. 9). In some embodiments, thresholds can be applied when comparing the right and left sides. For example, if a left side has pain values of 2, 4, 6, and 7 whereas the right side has pain values of 2, 4, 6, and 8 that can be within a threshold such that the pain is considered symmetrical, resulting in treatment of the left ear, even though the right side has one pain value that is higher.

Subsequent to a treatment device being utilized, the user device can receive effectiveness information and determine whether a proper side of the user was selected. For instance, the user device can request that the user try the same treatment parameter profile on the other side (e.g., if treatment is not sufficiently effective on the first-selected side), and update the machine learning algorithms based on received effectiveness information for the other side.

Figure 13:
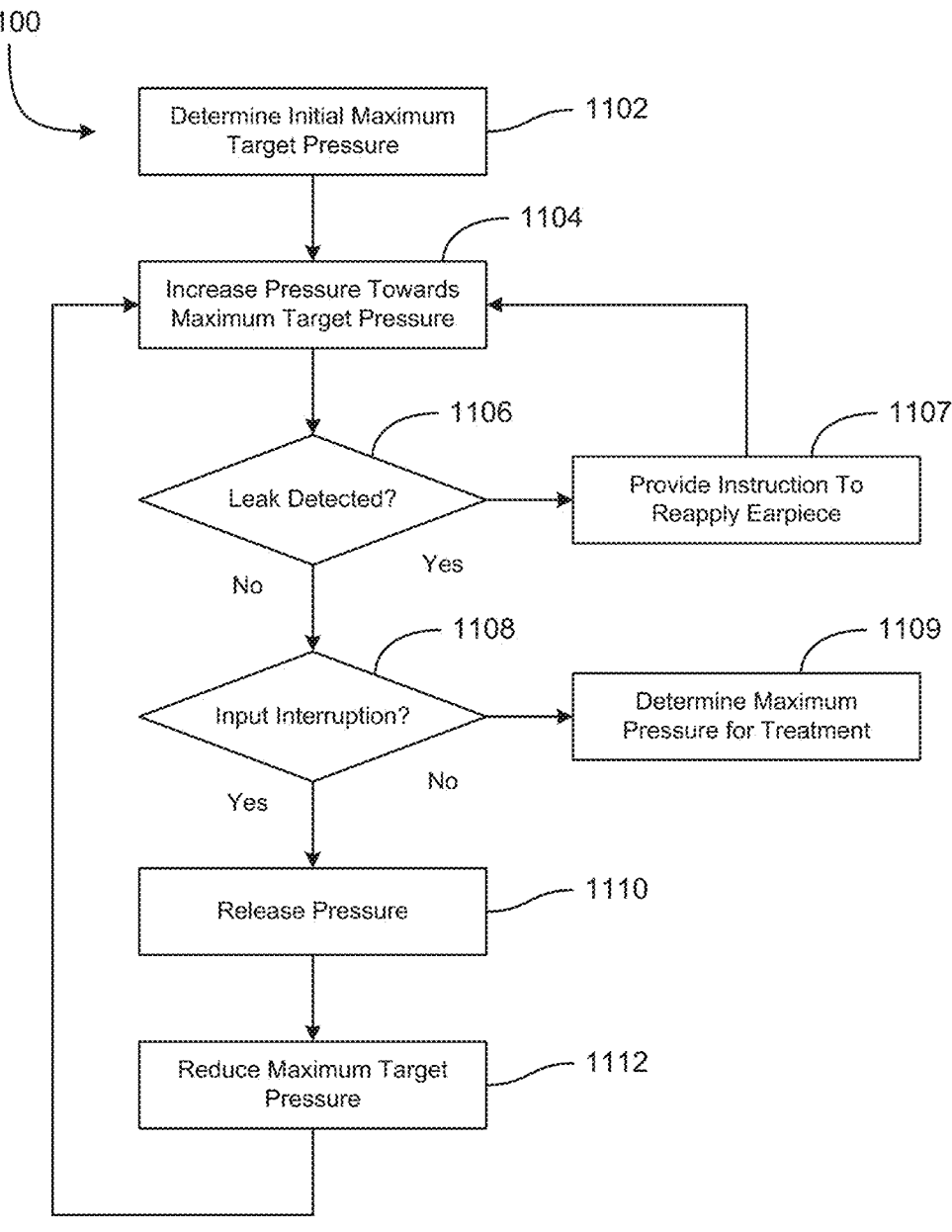
FIG. 13 illustrates an example process of an initial preparation or calibration of a treatment device.

FIG. 13 illustrates an example process 1100 of an initial preparation or calibration of a treatment device. For convenience, the process 100 will be described as being performed by a user device having one or more processors (e.g., the user device 2) in combination with a treatment device (e.g., the treatment device 10), although many variations are possible, as discussed herein.

The user device can determine an initial maximum target pressure (block 1102). As described herein, the user device determines a maximum target pressure, which can be a maximum target positive pressure that is to be utilized during treatment, and/or a minimum negative target pressure that is to be utilized. In some cases, the maximum target pressure indicates a maximum absolute value of a pressure differential that would be applied to the user. As disclosed, at least with respect to FIG. 14, the user device can determine the initial maximum target pressure based on one or more factors, such as an age of the user, a gender of the user, an ethnicity of the user, a height of the user, a weight of the user, a body mass index of the user, etc. For example, a woman that is 80 years old and weighs 110 pounds can receive a lower initial maximum starting pressure than a man that is 35 years old and is 6'4" and 225 pounds. In some embodiments, the system can have a set or a default initial maximum starting pressure that is applied regardless of the user's demographic information.

The initial maximum target pressure can indicate a pressure that is determined to be (1) likely effective for the user (e.g., the user device can monitor, or receive from a system, effectiveness information, and can determine a maximum target pressure that is determined to be likely effective) and (2) likely comfortable for the user (e.g., the pressure is determined to be at a value capable of being tolerated by the user, according to the factors). In some instances, a user might not tolerate the pressure that was determined to be likely comfortable (e.g., due to ear infection, injury of the ear, etc.).

The treatment device can increase pressure towards the initial maximum target pressure (block 1104). The treatment device can receive (e.g., over a wireless connection, such as Bluetooth or Wi-Fi) information identifying the initial maximum target pressure (such as from the user device). The treatment device can increase a positive or negative pressure towards the initial maximum target pressure. For instance, the treatment device can ramp up the pressure differential over a particular amount of time, which can depend on the maximum target pressure. In this way, the user is given time to stop the treatment device from modifying the pressure (e.g., in the event of discomfort or ear pain). In some implementations, the treatment device can increase the pressure by a step values, and pause upon reaching the step value, only continuing to the next pressure step value after receiving confirmation from the user to proceed (e.g., the user device can prompt the user to confirm that the treatment device can continue) or after an amount of time passed without input from the user. In some embodiments, the treatment device can first apply one of the maximum target positive pressure and the maximum target negative pressure, and then apply the other of the maximum negative pressure and the maximum positive pressure. For example, a user might be able to tolerate more positive pressure than negative pressure (and vice versa).

The treatment device can determine whether a leak is detected (block 1106), and if so the user device prompts the user to re-insert the treatment device (block 1107). As described herein, the treatment device (or the user device, based on information received from the treatment device) can determine that a leak is present due to a loss of pressure. Upon a positive determination of a leak, the treatment device can provide information to the user device confirming the leak, and the user device can prompt the user to reapply (e.g., re-insert) the treatment device. Optionally, the user device can present an animation or video clip explaining proper insertion.

If the treatment device reaches the maximum target pressure(s) without interruption, the process can proceed to block 1109 and determine a maximum pressure for treatment. If no interruption was made, the initial maximum target pressure(s) can be used as the actual maximum pressure(s) at block 1109.

Figures 15, 16:
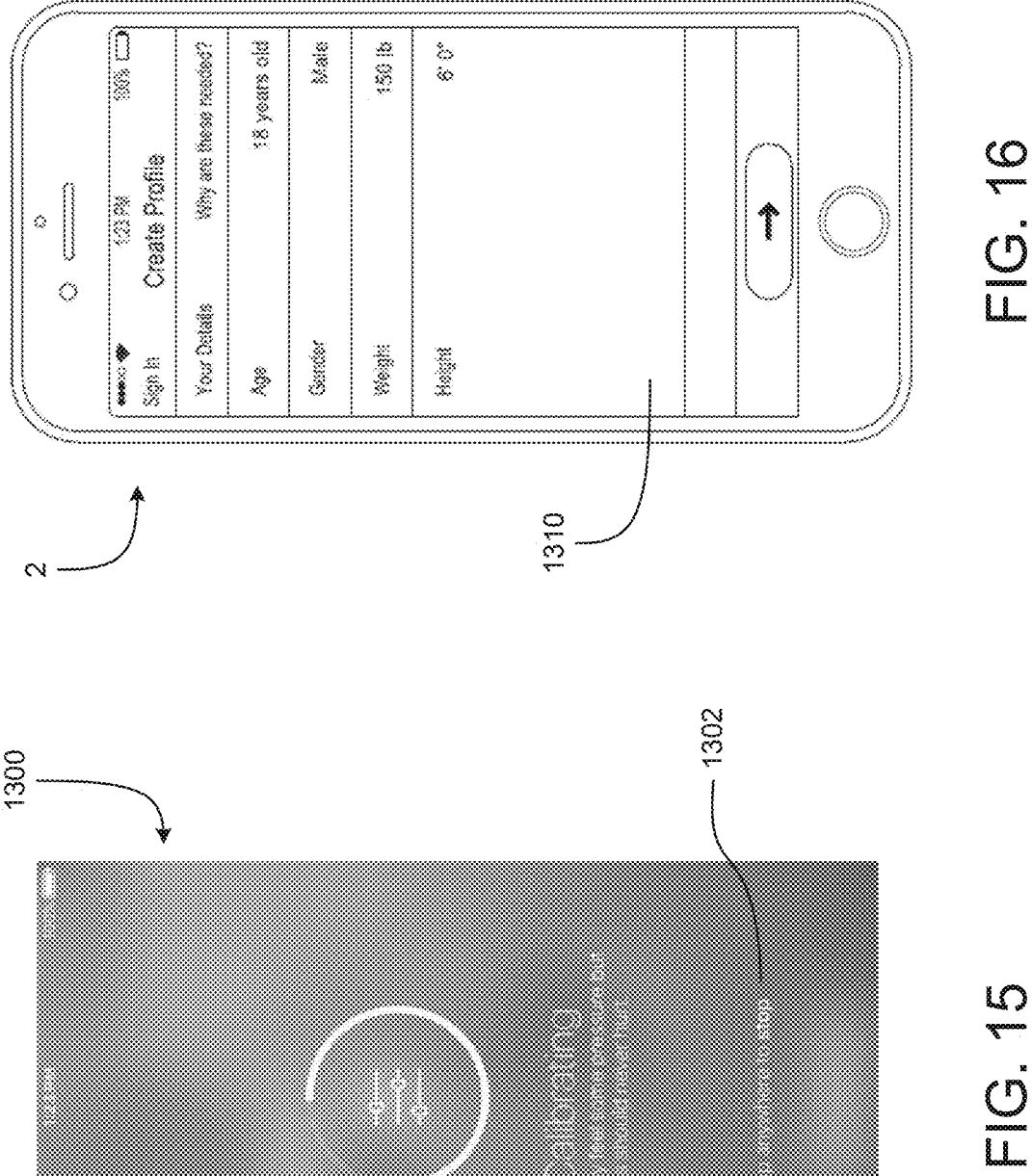
FIG. 15 illustrates an example user interface that can be presented while the treatment device ramps up pressure for a pressure tolerance test.
FIG. 16 illustrates an example user interface for inputting user demographic information.

The system can be configured to interrupt the increase in pressure (e.g., negative or positive pressure) upon an interruption triggered by the user (e.g., via input delivered to a user device) (block 1108). The system can decreases or release the pressure (block 1110) in response to the interruption input received from the user. As illustrated in FIG. 15, the user can select an option on the user interface of the user device to stop the increase in pressure. Upon the triggering of the interruption (e.g., selecting the option, verbally indicating the increase is to stop, etc.), the user device can provide information to the treatment device to stop the increase in pressure. The treatment device can then reduce the pressure, and the user device, or optionally treatment device, can store information indicating a pressure at which the user triggered the interruption.

The user device can reduce the maximum target pressure based on the user interruption (block 1112). As described above, the user device, or optionally treatment device, can store information identifying the pressure at which the user triggered the interruption. The user device can reduce the maximum target pressure to a pressure at or below the identified pressure where interrupted. In some embodiments, the identified pressure where the user interrupted the process can be used as the new maximum target pressure. In other embodiments, the new maximum target pressure can be set at some level below the interrupted pressure level (e.g., a value between 20% and 1% below, between 15% and 5% below, between about 12% and 8% below, although other values can be used). The system can update user profile information to indicate the reduced maximum target pressure.

Additionally, since the maximum target pressure may depend on pain information being experienced by the user, the user device can store the reduced maximum target pressure as being associated with the pain information. For instance, while the user is experiencing pain at greater than an average intensity, or within a threshold distance of an ear in which the treatment device is inserted, a reduced maximum target pressure can be utilized, while generally the user may able to tolerate a higher maximum target pressure (or vice-versa).

The process 1100 can proceed from block 1112 back to block 1104 where the system can retry the pressure tolerance test but at the new, lower maximum target pressure(s) (e.g., positive and/or negative pressures). If the new maximum target pressure(s) is/are reached without interruption input, then the new lower maximum target pressure can be used for the maximum pressure value during treatment (block 1109). If the user again provides an interruption input, the process can again proceed through blocks 1110 and 1112 to further reduce the maximum target pressure. In some cases, the process can repeat until a tolerable pressure is reached. In some embodiments, after a number of attempts or at a threshold low pressure level, the system can cancel the treatment session.

In some embodiments, the system can perform an initial leak test before initiating the pressure therapy (e.g., using a pressure profile that is specific to detecting leaks). In some embodiments, the system can perform ongoing leak tests (e.g., during pressure treatment). For example, as the pressure treatment device applies pressure to the ear, the system can monitor the pressure (e.g., using a pressure sensor) and can check for leaks (e.g., periodically or continuously). The system can have an ongoing function that measures for optimal ear plug placement, such as by continuously checking for leaks during operation.

The system can have two leak state categories. A detected gross leak can be a leak that is so robust that it prevents sufficient generation of pressure or delivery of pressure waves to sufficiently deflect or oscillate the structures of the external ear (e.g., including the tympanic membrane) and/or the middle (e.g., including the ossicles of the middle ear) and/or the inner ear. If a gross leak is detected, the system can advise the user to replace the ear plug and/or correct the leak. The treatment device in the meanwhile can go into a "holding pattern" wherein it can still be therapeutic if applied to the ear (e.g., so as not to delay therapy). A partial leak can be determined when the treatment device identifies a slight leak (e.g., a leak that is not sufficient so as to render the treatment ineffective, but that does make the treatment less than optimal). For example, the treatment device may be able to apply pressure up to the maximum pressure level even with a partial leak, but it may be inefficient in doing so. In the case of a partial leak, the user can be prompted by the system with a "soft warning" to replace or reposition the ear plug without interrupting treatment.

Figure 14:
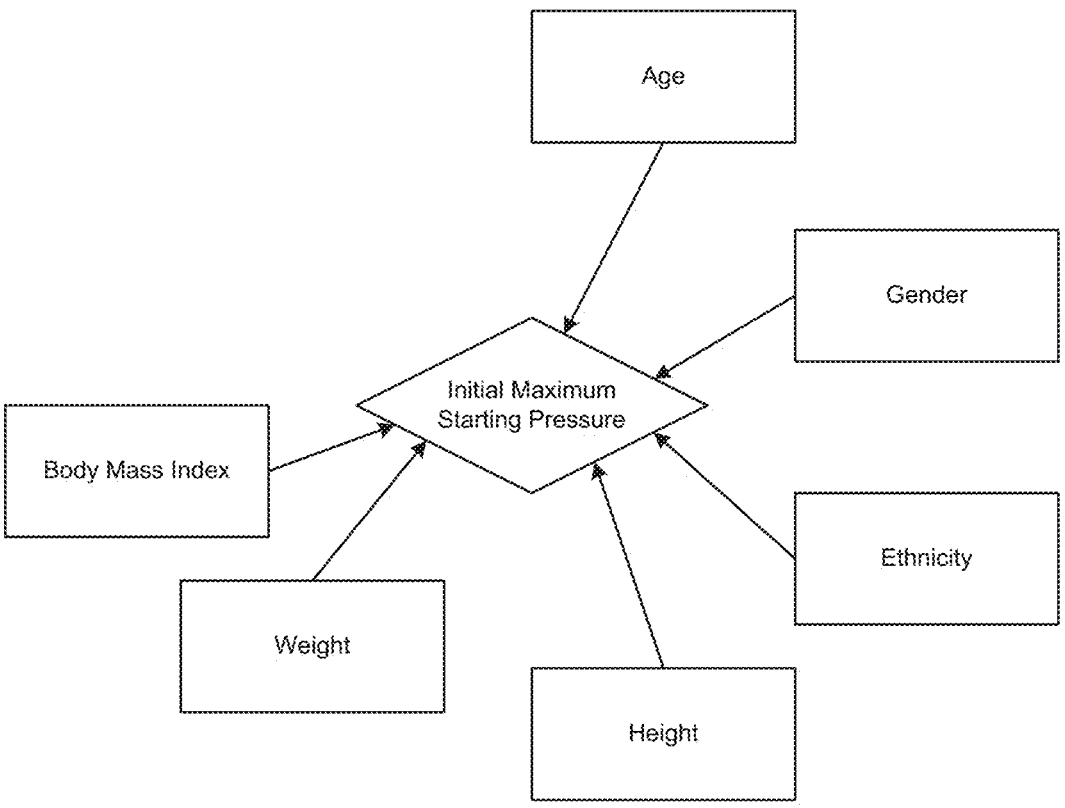
FIG. 14 illustrates an example of determining an initial maximum starting pressure for a user.

FIG. 14 illustrates an example of determining an initial maximum starting pressure for a user. As described herein, the user device can determine the initial maximum starting pressure utilizing factors associated with the user (e.g., demographic information about the user), including body mass index, weight, height, ethnicity, gender, age, and so on.

A system (e.g., the treatment parameter profile optimization system 100) that monitors use of treatment devices, including effectiveness of implemented treatment parameter profiles, and maximum starting pressures utilized during the treatment parameter profiles, can utilize the above-described factors across multitudes of users to determine an estimate of an initial maximum starting pressure for the user. As an example, the system can generate one or more machine learning algorithms, such as a k-means clustering algorithm, that can determine an estimated initial maximum starting pressure using the various factors. In this way, the factors associated with the user can be utilized by the machine learning algorithm (e.g., k-means clustering), such that other users' experiences with the treatment devices (e.g., effectiveness information, whether the users indicated the maximum target pressure had to be reduced, and so on) can be grouped together and used to inform an initial maximum target pressure of the user. Optionally, the symptom (e.g., pain) information can be taken into account. For instance as described above, depending on the intensity and/or location of pain or other symptoms, users may be more or less able to comfortably deal with pressure.

As described herein, the treatment system may be configured to collect various patient information. The collected patient information may comprise at least one of patient biographical information (e.g., height, weight, gender, age, race and/or ethnicity, etc.), treatment device use information (e.g., treatment duration, applied treatment parameter profiles, etc.), supplemental medication usage information (e.g., medication dosage, medication usage frequency, etc.), patient migraine information (e.g., timing of migraine, severity of migraines, pain location, secondary symptoms, migraine triggering events, etc.), patient geographic location information (e.g., atmospheric temperature, barometric pressure, humidity, light exposure, etc.), other contextual information from use of the user mobile device (e.g., amount of mobile device usage, contact information, communication information, etc.), user activity and/or exercise information (e.g., information acquired from mobile device applications, biometric information acquired from wearable devices, etc.), and any other information discussed herein. In some cases information can be obtained from an outside source. For example a user device can supply the location where a migraine event happened, such as using the GPS features of the user device (e.g., smartphone). Using that location data, the weather, temperature, barometric pressure, air quality, and other parameters can be looked up, such as using a weather database.

In some embodiments, the treatment system may incorporate one or more machine learning algorithms and/or predictive analytics to analyze the various patient information. The treatment system may be configured to incorporate the algorithms and/or analytics to develop predictive information as to whether and/or when a patient may experience a migraine (e.g., in the future). The system may identify similarities and correlations between various collected patient information to determine significant migraine triggering events. The treatment system, in some instances, may alert a user that a migraine may occur as a result of the user being exposed to one or more migraine triggering events. A user may be prompted to utilize the treatment device before the onset of a migraine and/or a headache phase of a migraine. Early use of the treatment device before the onset of a migraine headache may provide a user with the opportunity to pretreat a migraine and avoid a resultant headache.

In some instances, the patient information can be sent to a remote optimization system (e.g., a server), which can receive patient information from a multitude of users. The patent information, along with information from others, can be analyzed by the optimization system to identify patterns, trends, migraine triggering events, etc. In some instances, the optimization system can send a notification to the treatment system of a predicted migraine event. The optimization system can send parameters to the treatment system for predicting future migraine events, such as information about migraine triggering events. The treatment system (e.g., the user device) can monitor patient activities, time, locations, weather parameters, etc. and identify migraine triggering events, and it can issue a notification to the user.

FIG. 15 illustrates an example user interface output presented while the treatment device ramps up pressure (e.g., for pressure tolerance testing). The user interface 1300 can be presented subsequent to the treatment device receiving an indication of (or determining) an initial maximum starting pressure. The user can interact with user input element 1302 to interrupt the increase in pressure (e.g., as described herein, at least with respect to FIG. 13).

FIG. 16 illustrates an example user device 2 (e.g., a smart phone) having a user interface 1310 that can be utilized for the user to specify one or more of the factors described in FIG. 14, for instance the user can specify his/her age, gender, weight, and height. As described above, these factors can be used to inform a determination of an initial maximum starting pressure.

Figure 17:
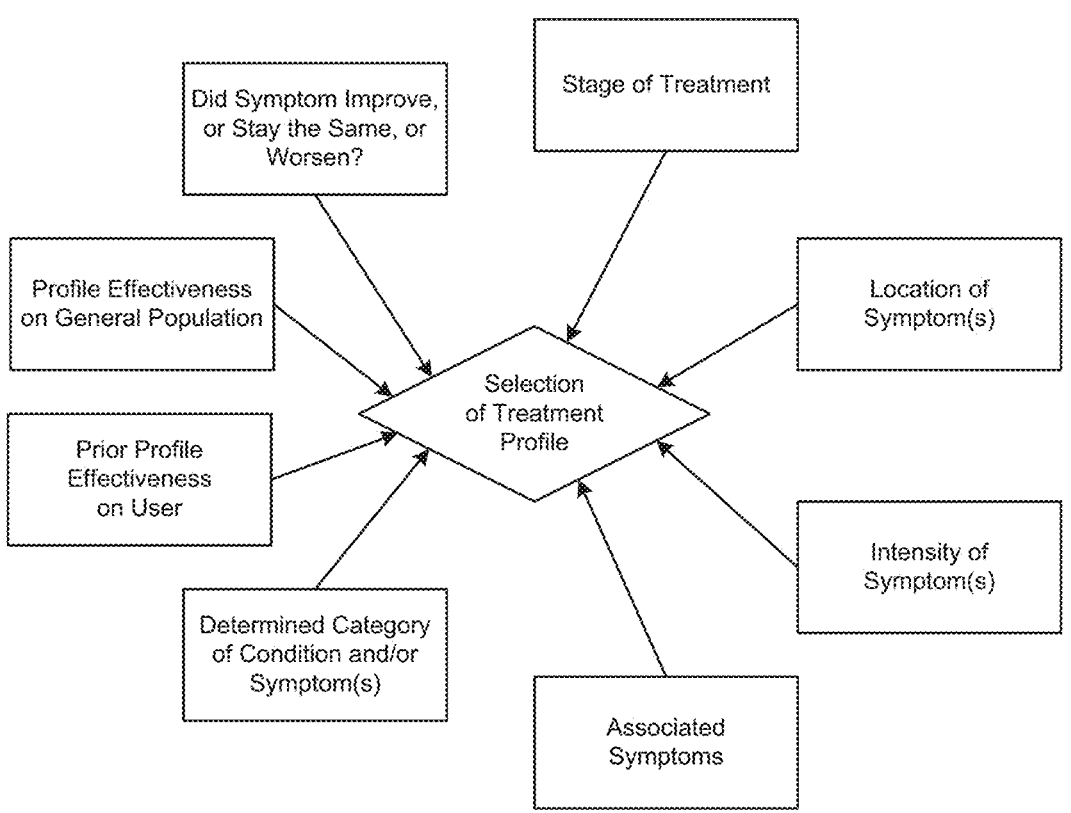
FIG. 17 illustrates example factors utilized in selecting, or determining, a treatment parameter profile to alleviate or reduce pain being experienced by a user.

FIG. 17 illustrates example factors utilized in selecting, or determining, a treatment parameter profile (e.g., to attempt to alleviate or reduce pain or other symptoms being experienced by a user). As described herein, at least with respect to FIG. 10, a user device can select a treatment parameter profile that is determined to be likely to reduce or alleviate pain or other symptom(s) being experienced by the user. The treatment parameter profile can be selected based on various factors, including a location and/or intensity of the symptom(s), secondary or associated symptoms (e.g., not associated with locations) such as sensitivity to light, effectiveness information of prior treatment parameter profiles on the user (e.g., when treating same, or similar, symptom(s) of the user), treatment parameter profiles effectiveness with respect to multitudes of users (e.g., when treating same, or similar, symptoms), and/or the stage of the treatment session. For example, if a treatment parameter profile is not effective after one usage (e.g., one treatment phase), the treatment parameter profile can be tried again. However, if the treatment has proceeded to a stage where the same treatment parameter profile has been ineffective multiple times (e.g., some preset number of attempts), then a different profile can be selected. Selection of a treatment parameter profile can base based at least in part on whether pain symptoms worsened, improved, or stayed the same, with respect to a prior application of a treatment parameter profile. The above-described factors can be analyzed (e.g., using a machine learning algorithm, such as an algorithm trained on effectiveness information) and used to inform selection of a particular treatment parameter profile to be utilized in attempting to alleviating the user's symptom(s) (e.g., pain).

As described herein, optionally the user device or system can generate a new or updated treatment parameter profile based on effectiveness information associated with the user or from multitudes of users. For instance, a new treatment parameter profile can include pieces, or snippets, of other treatment parameter profiles, including a first treatment parameter profile being used for a threshold amount of time, followed by one or more other treatment parameter profiles being used.

Additionally, the treatment parameter profile can be based on the maximum starting pressure, as described above, and/or on an average pressure to be used. That is, the treatment parameter profile can define a particular time series of pressure differentials to apply, and the maximum starting pressure and/or average pressure can move the time series upwards or down in applied pressure.

FIG. 18 illustrates an example user interface output (e.g., displayed on a user device 2), which can be presented to a user while a treatment parameter profile is being implemented or in preparation for the treatment parameter profile. The user interface 1500 includes descriptive information 1502 for the user, including text indicating that the user should lay down and/or relax in some manner, turn off the lights, close eyes, etc. Optionally, the user interface 1500 can specify that a dark atmosphere is conducive to the treatment parameter profile being effective.

FIG. 19 illustrates an example user interface 1510, which can be displayed on the user device while the selected treatment parameter profile is being applied. The user interface 1510 can include an animation of the body portion (e.g., the head) being affected by the treatment that is based on the treatment parameter profile. The user interface 1510 can include an option 1512 to modify an intensity associated with the treatment parameter profile. The intensity can modify, for example, a maximum pressure, an average pressure being applied, and so on. That is, if the user finds the treatment parameter profile to be uncomfortable or not profound enough, he/she can interact with the option 1512 to reduce or increase the intensity. In some embodiments, later treatment phases can go back to using the intensity from before the user made the modification using the user input element 1512. In some embodiments, later treatment phases can use the new, modified intensity. Adjusting the intensity can modify the amplitude of pressure oscillations produced by the treatment device.

In some embodiments, the user interface can display a visual indicator that is associated with the active treatment parameter profile. For example, an image or a video can be displayed on the user interface (e.g., as a shorthand reference for the user to recognize and/or reference the treatment parameter profile). In the embodiment illustrated in FIG. 19, a video of jelly fish swimming can play while the treatment parameter profile is implemented. Other visual depictions can be used, such as a running stream, waves rolling on a beach, a lava lamp, etc. The visual shorthand can facilitate communication between users regarding the treatment parameter profiles. For example, one user can inform other user(s) that the "jelly fish" treatment parameter profile was particularly useful. It can be easier for a common user to identify the treatment parameter profile based on the shorthand representation, as opposed to the parameters of the treatment parameter profile (e.g., pressure amplitude and frequency).

Figure 20:
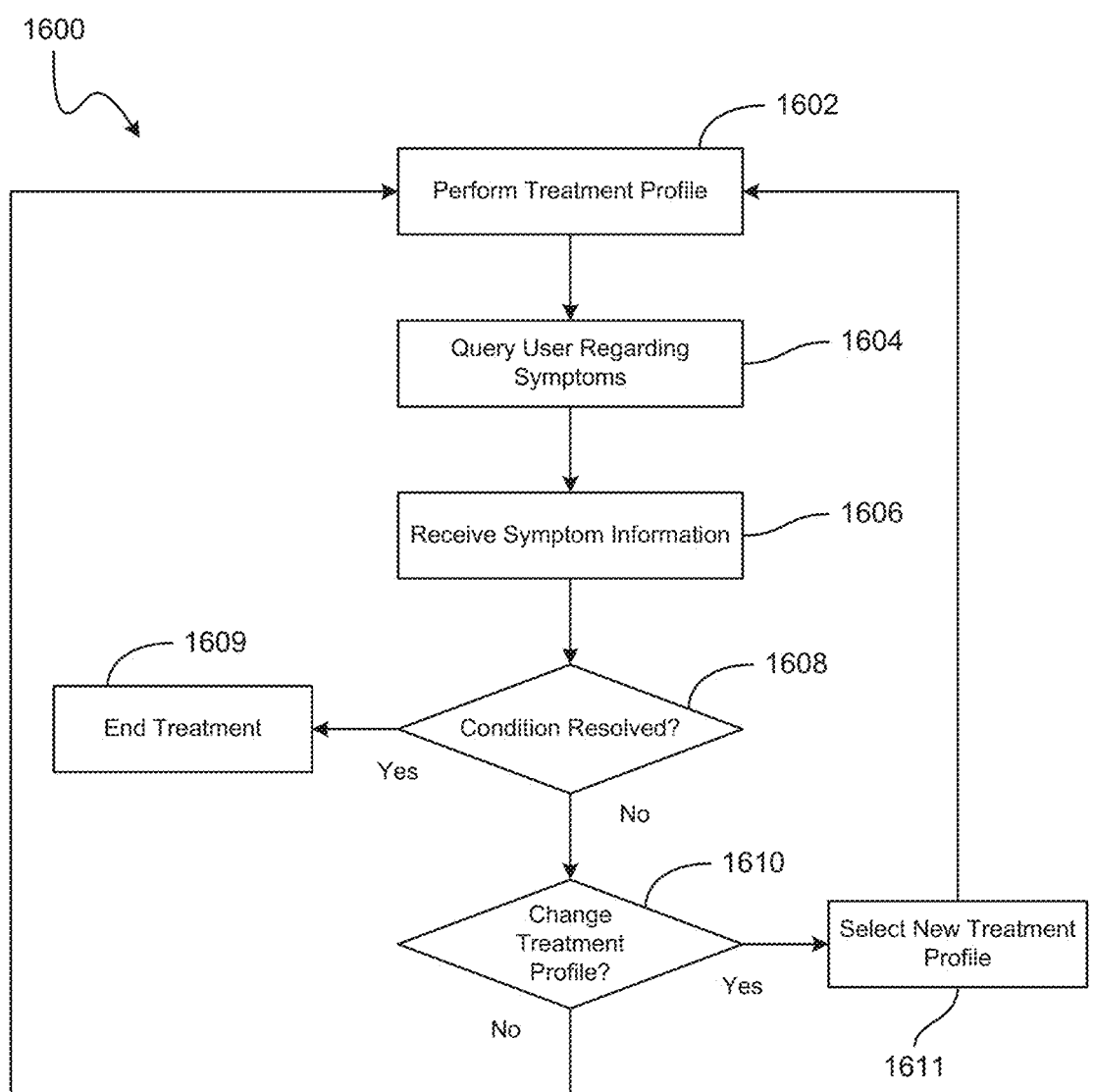
FIG. 20 illustrates an example process for selecting a new treatment parameter profile.

FIG. 20 illustrates an example process 1600 for performing a treatment session. The process can include selecting a treatment parameter profile based on effectiveness information received from a user. For convenience, the process 1600 will be described as being performed by a user device having one or more processors (e.g., the user device 2) in communication with a treatment device 10. The treatment device can implement a treatment parameter profile (block 1602). As described herein, the treatment device can receive a treatment parameter profile or operating parameters based on the treatment parameter profile, and the treatment device can be configured to implement treatment based on the treatment parameter profile.

Figures 23, 24:
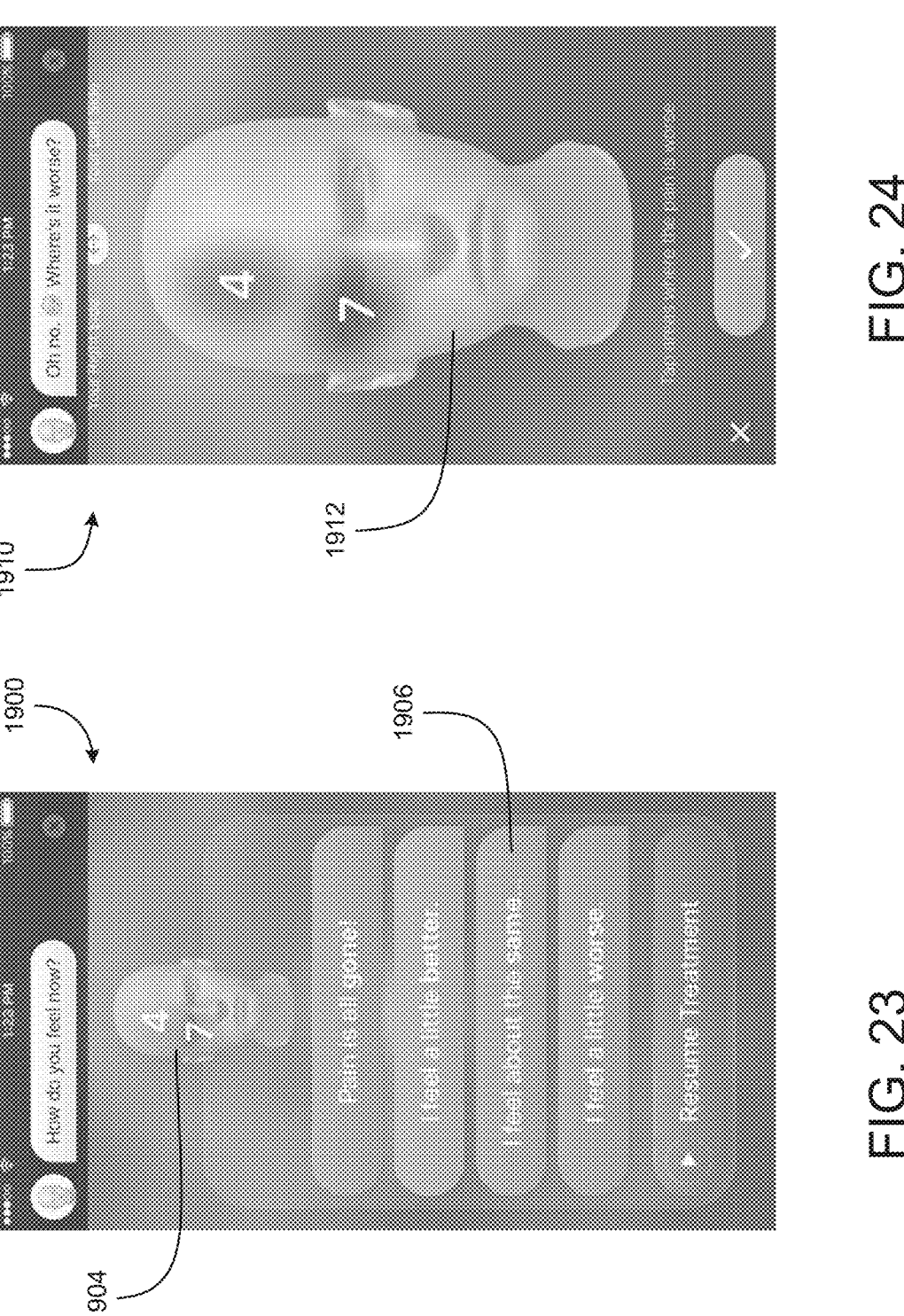
FIGS. 23-26 illustrates an example user interface for the user to indicate updated symptom information.

Subsequently, the user device can query the user regarding symptom (e.g., pain) information (block 1604). At block 1606, symptom information can be received (e.g., from the user via a user interface on the user device). For example, after the treatment parameter profile is implemented, the user can indicate whether the described symptom (e.g., pain) has been reduced or alleviated. For instance, FIG. 23 illustrates an example user interface that enable the user to specify whether the treatment parameter profile was effective, or whether pain locations are now worse or substantially the same.

Upon an indication by the user that the user's experienced pain has been resolved (e.g., alleviated to the satisfaction of the user) (block 1608), the treatment can be ended (block 1609). Alternatively, if symptom(s) (e.g., pain) remain unresolved (e.g., the same pain, or different pain), the user device can determine whether to change the treatment parameter profile (block 1610). In some instances, the process can determine to continue using the same treatment parameter profile, and the process can proceed to block 1602 where the process 1600 can repeat. In some instances, the process select a new treatment parameter profile (block 1611) and can proceed to bock 1602 to repeat the process 1600 only using a different treatment parameter profile. As be described herein, such as at least with respect to FIG. 21, the user device can determine whether the same treatment parameter profile is to be utilized again (e.g., in a same or different ear), or whether a new treatment parameter profile is to be selected.

Figure 21:
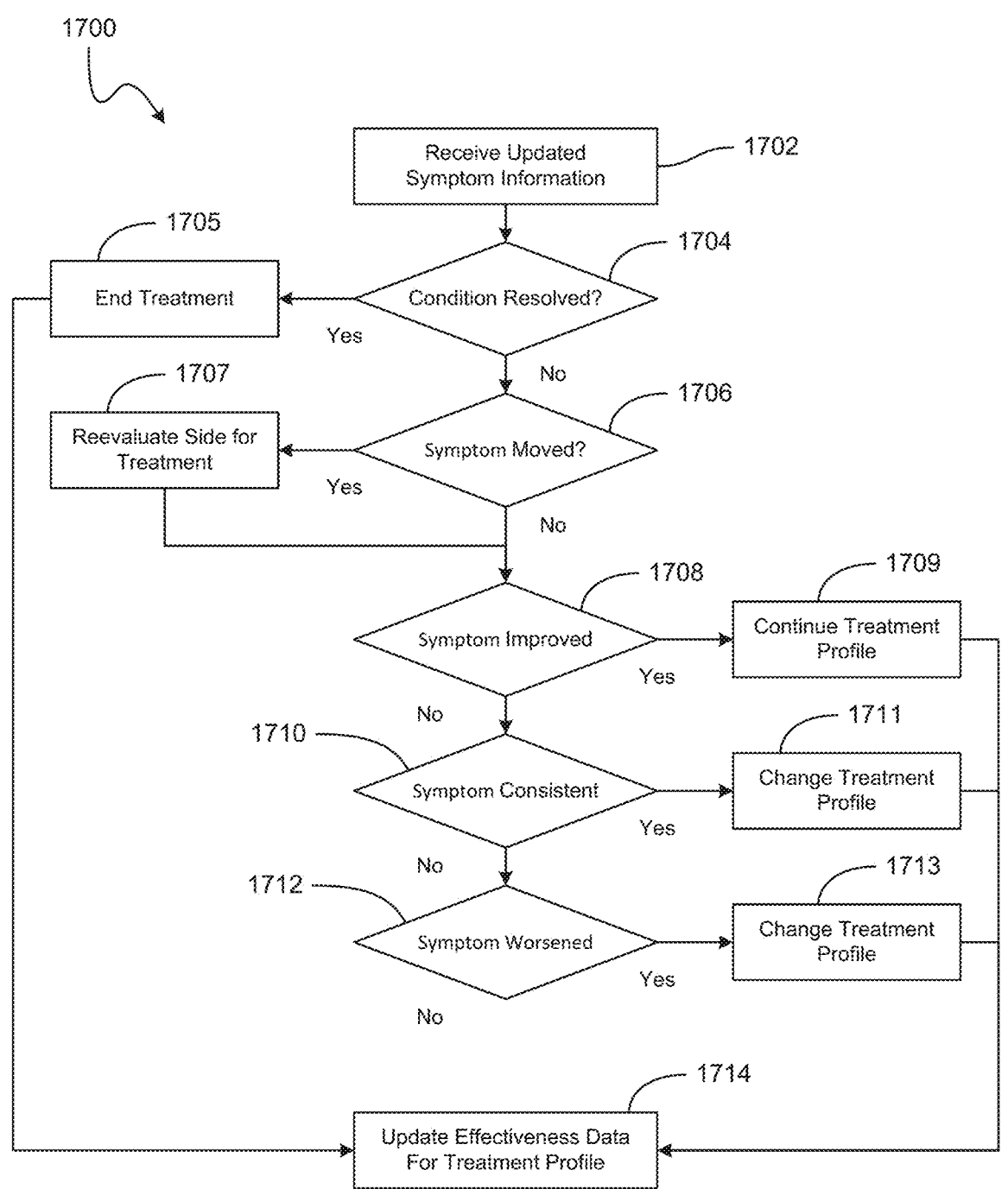
FIG. 21 illustrates an example process for executing treatment.

FIG. 21 illustrates an example process for determining whether to implement a subsequent treatment parameter profile. For convenience, the process 1700 will be described as being performed by a user device of one or more processors (e.g., the user device 2), although various alternatives are possible.

The user device can receive updated symptom (e.g., pain) information (block 1702). As described herein, the user can indicate whether his/her pain has been reduced, whether locations of pain have moved, whether the intensities have increased or decreased, and so on. If the user indicates that the pain or other symptom(s) have been reduced or alleviated to the user's satisfaction (block 1704), the treatment can be ended (block 1704). Alternatively, if the user indicates that the symptom(s) is not resolved the treatment can continue. At block 1706, if a symptom (e.g., pain) has moved locations or changed in intensity, the user device can determine whether the treatment device is to remain in a same ear, or be moved to a different ear. The determination can be made similar to the determination described in connection with FIGS. 10-12.

If the user indicates that the pain symptoms have improved (block 1708) (e.g., improved greater than a threshold), such as an aggregate or average intensity value has been reduced (e.g., by a threshold percentage or amount), then the same treatment parameter profile can be re-applied (block 1709). If the pain symptoms are consistent with the initially described pain information (block 1710), or worse (block 1712) than the previously described pain information, then the treatment parameter profile can be changed, as described at least with respect to FIG. 22.

The user device can update effectiveness information associated with the treatment parameter profile that was previously performed (block 1714). The user device can update effectiveness information for that treatment parameter profile with respect to the described symptom information (e.g., pain information). For instance, if the treatment parameter profile reduced or alleviated the symptom(s), the user device can store information indicating that the treatment parameter profile was effective. Optionally, the effectiveness information can be provided to a system (e.g., the treatment parameter profile optimization system 100) for storage and use when selecting treatment parameter profiles (e.g., the effectiveness information can be anonymized and used to inform the effectiveness of the treatment parameter profile with respect to same, or similar, pain symptoms).

FIG. 22 is an example process 1800 for selecting a subsequent treatment parameter profile in the event that the symptom(s) worsen. For convenience, the process 1800 will be described as being performed by a user device of one or more processors (e.g., the user device 2), although many alternatives are possible. The user device can receive information indicating that the symptom(s) have worsened, or optionally not been reduced by a threshold (block 1802). As described herein, the user can specify updated symptom (e.g., pain) information. In some embodiments, the user device can determine to update the previously applied treatment parameter profile, and provides the updated treatment parameter profile for implementation by the treatment device (block 1804). The user device can update the treatment parameter profile by, for example, increasing an average pressure or a maximum pressure (e.g., a negative and/or positive pressure). For instance, the user device can determine that the pain information was indicated as being reduced, and that if the treatment parameter profile was made more pronounced then the pain information would be alleviated. In another instance, the user device can determine that a longer application of the treatment parameter profile is needed, and so can determine that the same, or updated, treatment parameter profile is to be implemented again.

Alternatively, the user device can determine to disqualify the previously applied treatment parameter profile (block 1806). The user device can determine that none of the pain symptoms were sufficiently reduced, and can remove the treatment parameter profile so that it is not utilized during later treatment for the user. Additionally, the user device can update the optimization system 100, such that for other users that have same, or similar, symptom information, the treatment parameter profile that was disqualified will be less recommended (e.g., the overall effectiveness information can be reduced). Since the user may be an outlier, the treatment parameter profile might not be disqualified for other users, but will be indicated as being questionable, which can inform the aggregate experience of users with the treatment parameter profile. In some embodiments, a treatment parameter profile can be used multiple times without sufficient positive effect before the treatment parameter profile is disqualified. The user device can have a set of available treatment parameter profiles, and the user device can replace a disqualified treatment parameter profile with a new treatment parameter profile (e.g., obtained from the optimization system 100).

The user device can determine to select a different treatment parameter profile, or a treatment parameter profile that is known to be effective with at least one or more of the pain symptoms (blocks 1808 and 1810). The user device can select an entirely different treatment parameter profile (e.g., as described herein), such as a new treatment parameter profile that the user has not experienced, or the user device can select a treatment parameter profile that is known to reduce at least one or more of the symptoms experienced by the user (e.g., during prior treatment). Optionally, the user device can combine multiple treatment parameter profiles based on the pain symptoms (e.g., generate an updated time series through a weighted sum of treatment parameter profiles based on a number of pain symptoms they are known to treat, or based on an intensity of the pain symptoms being experienced by the user).

In some embodiments, the user device can instruct the user to change the treatment side (e.g., from the left ear to the right ear, or vice versa). For example, if multiple different treatment parameter profiles are not effective, the treatment can be changed to the other side. In some cases, the treatment on the new side can be a treatment parameter profile that was known to be effective (e.g., combining blocks 1808 and 1812). Many other variations and combinations are possible.

FIG. 23 illustrates an example user interface for the user to indicate updated pain information. User interface 1900 includes a representation 1904 of the previously described pain information, such as on the body portion (e.g., a head). Selectable options 1906 to describe the effectiveness of the applied treatment parameter profile can be included. The user can specify whether the treatment parameter profile resolved the pain, reduced the pain, had little effect on the pain, or made the pain worse.

Optionally, and as described herein, the user interface 1900 can be presented to the user while a treatment parameter profile is being applied. The user can therefore indicate a live update regarding the effectiveness of the treatment parameter profile, and if the treatment parameter profile is indicated as making the pain worse, the treatment parameter profile can be immediately stopped and a new treatment parameter profile can be selected. Optionally, if the treatment parameter profile is increasing the pain, but the treatment parameter profile has been implemented for less than a threshold amount of time (e.g., 30 seconds, 45 seconds), the user device can either (1) cause the stopping of the treatment parameter profile and recommend that the treatment parameter profile resume since it may not have had enough time to be effective, or (2) recommend that the treatment parameter profile resume and include an option to stop the treatment parameter profile. In some implementations, the user interface 1900 can be presented after the treatment parameter profile has ended. In some embodiments, the user interface 190 can be presented after the treatment parameter profile has run for a preset time, and the treatment parameter profile can continue while the user interacts with the user interface 1900.

With reference to FIG. 24, user interface 1910 can include the graphical representation 1912 of the body portion, and the user can indicate updated pain information on the graphical representation (e.g., as described above, with respect to FIGS. 7 and 8). The user device can then update effectiveness information for the previously applied treatment parameter profile, to indicate one or more of, the ineffectiveness of the treatment parameter profile, the ineffectiveness of the treatment parameter profile with respect to particular pain symptoms (e.g., the effectiveness information can indicate that for pain symptom locations that were made worse, the treatment parameter profile is particularly ineffective).

Figure 26:
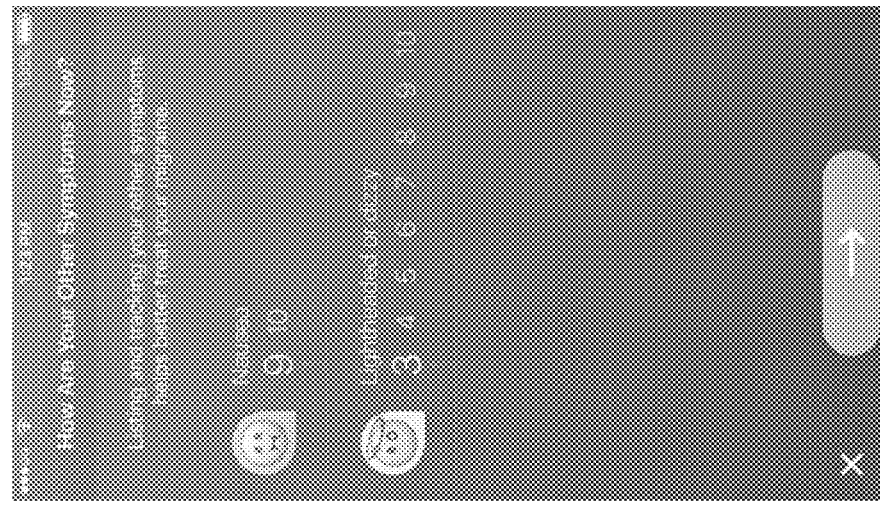
Figure 25:
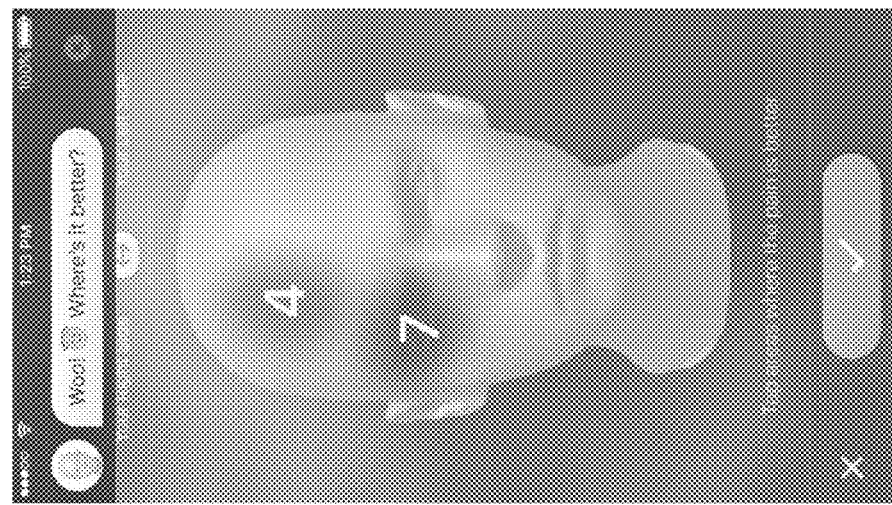

FIG. 25 illustrates an example user interface for describing effectiveness information of a treatment parameter profile. User interface 2000 enables the user to specify previously indicated locations of pain that are now better. The user can update an intensity value associated with one or more locations to indicate a reduction in pain. With reference to FIG. 26, user interface 2010 can enable the user to update previously described symptoms that are not associated with locations, such as updating an intensity value associated with "nausea," or dizziness. In this way, the effectiveness information can be updated in accordance with the empirically determined reduction in symptom(s) of the user.

Figure 27:
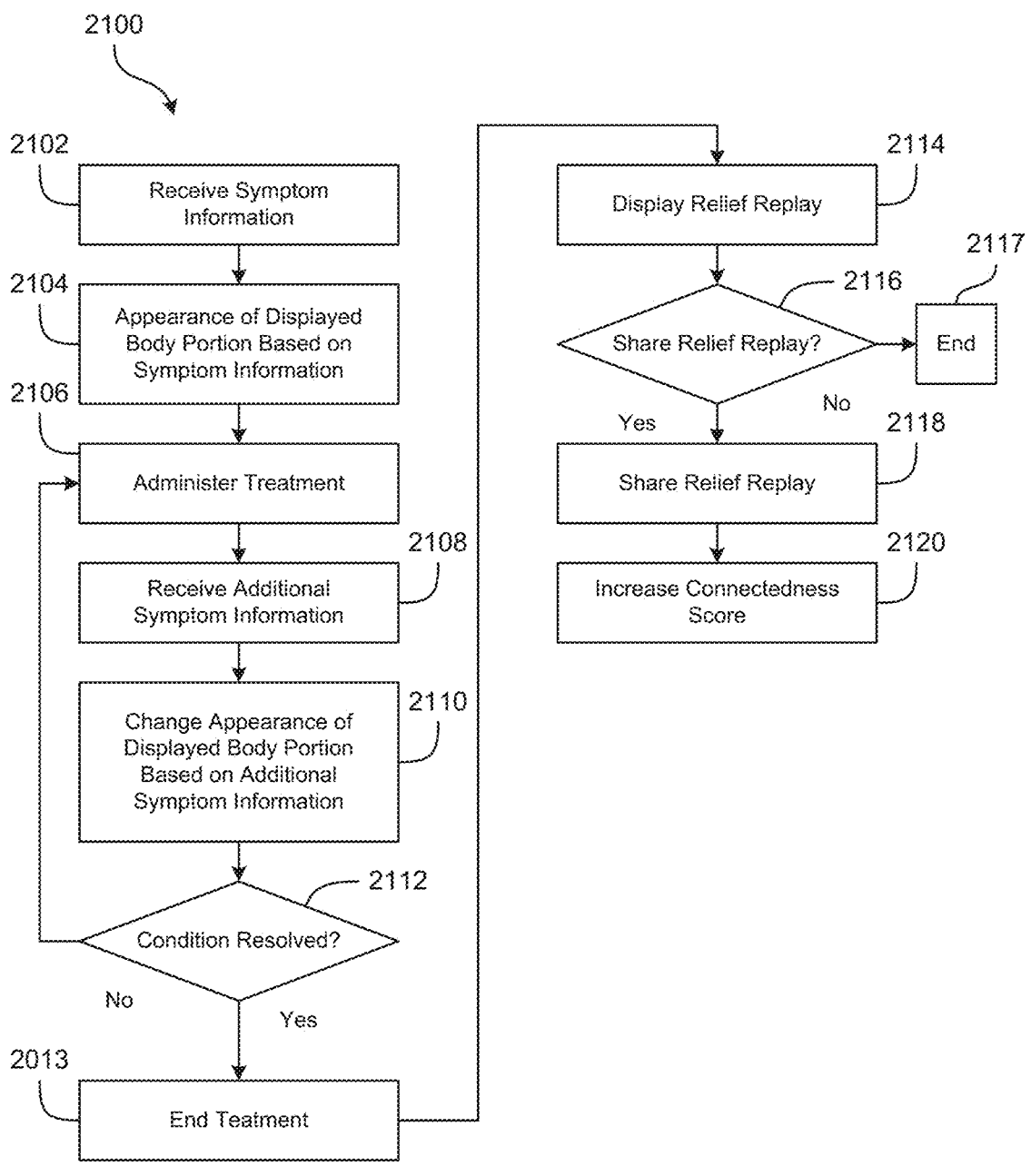
FIG. 27 illustrates an example process for generating and sharing a relief replay.

FIG. 27 illustrates an example process 2100 for generating and sharing a relief replay. For convenience, the process 2100 will be described as being performed by a user device of one or more processors (e.g., the user device 2), although many alternatives are possible. The user device can receive symptom (e.g., pain) information (block 2102), and can present a graphical representation of the symptom information on a body portion (block 2104). The user device can select a treatment parameter profile and a treatment device can implement the treatment parameter profile (block 2106). The user can specify additional symptom information, which can be indicative of the effectiveness of the treatment parameter profile (block 2108). The user device can store the real-time effectiveness information that can be determined based on the additional symptom information of block 2108. The user device can update the graphical representation according to the updated symptom information (block 2110). For instance, a facial expression on the graphical representation can be made more content as symptom(s) (e.g., pain) reduces and/or the visual representations of the symptoms (e.g., displayed pain location shading and intensity values) can change as the symptom(s) change. The treatment system can perform multiple treatment phases. Once the symptom(s) are resolved (block 2112), the treatment session can end (block 2013).

The user device can generate a relief replay, which can be displayed to the user (e.g., via the user interface on the user device) (block 2114). The user device can generate a graphical representation based on the effectiveness information as specified by the user during the treatment parameter profile being implemented. For instance, the relief replay can be a shortened version of the graphical representation presented to the user, showing in a reduced amount of time (e.g., 15 seconds, 30 seconds) where the user started (e.g., high pain—see FIG. 28), and where the user ended (e.g., pain resolved—see FIG. 29). Optionally, the graphical representation can be based on physiological information received from the user. For instance, a sensor (e.g., wearable) device can monitor a heart rate, perspiration, shaking, and so on, of the user, and can update the graphical representation as these physiological values become more in line with a user not being in pain.

The user device can receive information regarding whether to share the generated relief replay (e.g., to one or more social networks, and/or one or more other users via a notification (e.g., text message, MMS message, and so on)) (block 2116). If the relief replay is not shared, the process can end at block 2117. If the user shares the generated relief replay (block 2118), the user device can increase a connectedness score assigned to the user, as described herein (block 2120). As described herein, sharing the relief replay (e.g., via social media or otherwise) can result in others being incentivized to use the treatment device, or be given hope that a effective treatment is possible through watching the relief replay. Connecting with and helping others people that suffer from the same condition and/or symptoms can help the user's state of mind, which can further benefit the treatment.

Figure 29:
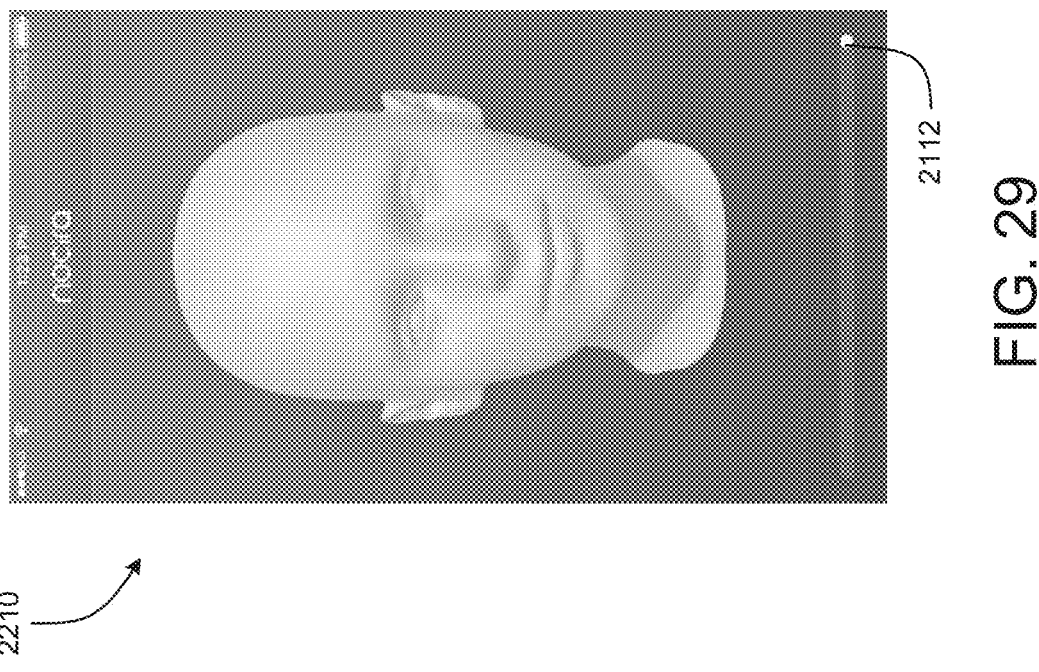
FIGS. 28-29 illustrates example images from a generated relief replay.
Figure 28:
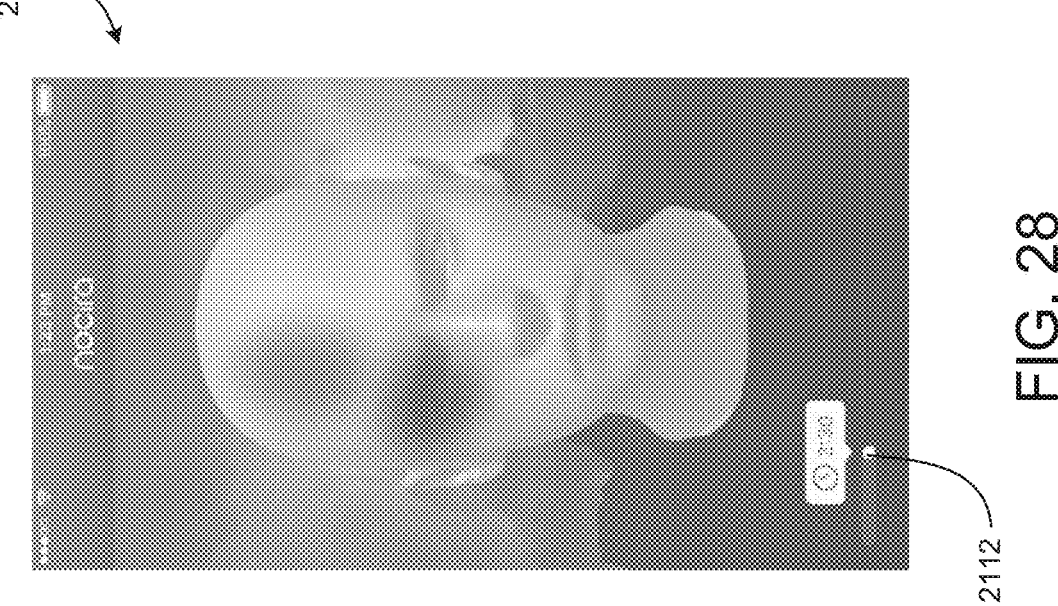

FIGS. 28 and 29 illustrate examples images from a generated relief replay. The relief replay can be a video that provides an accelerated summary of the treatment session that was performed for the user. For example, the video can last 2 minutes, while summarizing a treatment session that lasted 20 minutes. The relief reply can have a duration that is 1% to 50%, or 5% to 35%, or 10% to 20% the length of the treatment session, although other values can be used. FIG. 28 illustrates an image from a generated relief replay taken relatively early in the treatment (e.g., at 2:30). The image 2200 includes a graphical representation of a body portion along with indications of locations of pain that correspond to the pain information from the associated time of the treatment (e.g., at 2:30). As the relief replay proceeds in time, the graphical representation is updated (e.g., as described above) based on the symptom information that was provide during the treatment. The image 2210 of FIG. 29 illustrates the graphical representation at the end of the video of the relief replay, which corresponds to the end of the treatment session when the symptom(s) have been resolved. Thus, the facial expression shown in the graphical representation is content at the end, indicating that the treatment parameter profile was effective. By way of example, between the images of FIGS. 28 and 29, the video relief replay can show the two pain areas gradually lighten in color as the facial expression transmissions from the upset expression of FIG. 28 to the content expression of FIG. 29, and the time indicator 2202 progresses at an accelerated rate (as compared to the real time treatment session that is being summarized).

Figure 30:
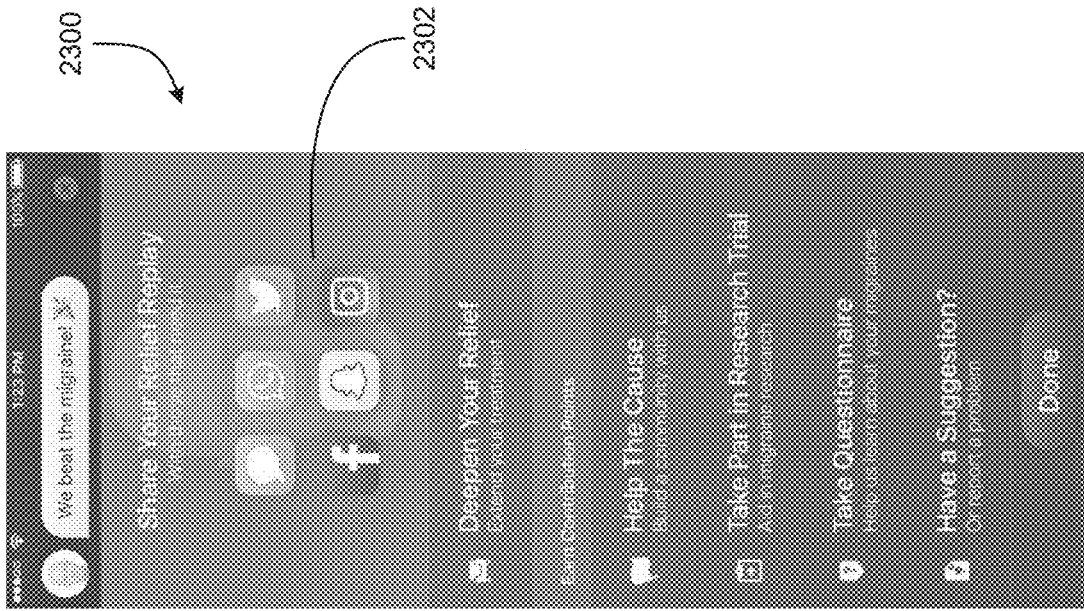
FIG. 30 illustrates an example user interface for sharing a generated relief replay.
Figure 33:
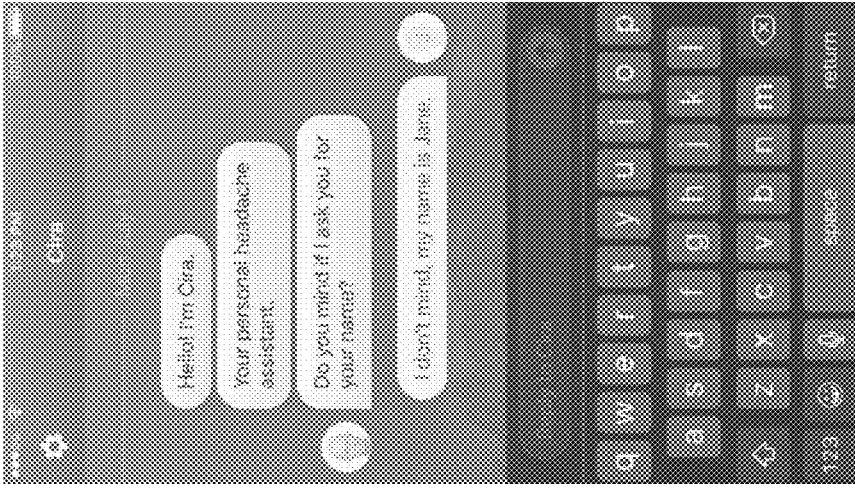
Figure 32:
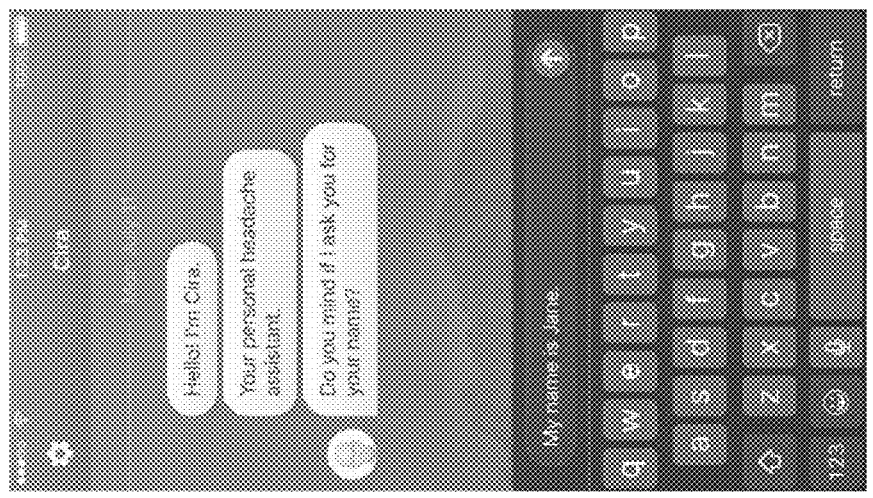

FIG. 30 illustrates an example user interface implementation for sharing a generated relief replay. As described herein, the generated relief replay can be shared to one or more social network sites. For instance, the user interface 2300 includes available social network site links 2302, and the user can specify one or more social networks with which he/she has an account, and the relief replay video can be shared via the user's profile with the one or more social networks. User interface 2310 illustrates an example social network site with a relief replay video shared to it.

As described above, automated chatting software, such as a chatbot, can execute on the user device, or the user device can be in communication with a system that receives text entered by a user and determines updated responses to provide the user, and the chatting software can provide useful information to the user. For instance, the chatbot can act as an easy gateway into setting up a user profile, inquiring about effectiveness of medications or treatment parameter profiles and so on. Additionally, the chatbot can assist the user to stick a regimen of medications and/or determine whether contraindications may exist between medications the user is taking, or is about to take.

FIGS. 32-35 illustrate example user interface outputs in which chatting software, such as a chatbot, interacts with a user of the user interfaces. User interface 2400 includes a chat between the user and a chatbot (e.g., 'Cira'). As illustrated, the chatbot is asking for the user's name, and upon receipt of the name the chatbot can generate a user profile for the user. In this way, users that are less familiar with operation of user devices can have an easy way into the application executing on the user device through a series of questions being posted to the user. User interface 2410 illustrates the user having a name, 'Jane'. Optionally, the user may merely type in the word 'Jane,' and the chatbot can create a sentence that includes the entered word. For instance, the chatting software can parse the entered text for a name, and generate a sentence, 'I don't mind, my name is Jane,' that includes the entered name.

Similarly, user interface 2500 illustrates the chatbot requesting an age of the user and a gender. This information can be utilized, for instance, when determining an initial maximum starting pressure as described above. The system can present a texting interface for the user to response to queries. In some situations, the general texting keyboard interface can be replaced with or supplemented with additional, context-specific user input elements. For example, in FIG. 34, the user input elements for "I'm female" and "I'm male" can be presented in addition, or instead of, the normal texting keyboard.

User interface 2510 illustrates the chatbot requesting information regarding a particular pharmaceutical, and then upon the user indicating that the pharmaceutical was stopped due to side-effects, the chatbot states the commonality of side effects being evident during use. In this way the user can be made to feel like the user's problems are not uniquely associated with the user, and are indeed a commonly experienced thing.

FIGS. 36-41 illustrate user interface outputs for assisting a user to adhere to a medication regimen. User interface 2600 can illustrate the user specifying that the user took 1 pill a particular medication. For example, the user can touch the icon associated with the medication to indicate that one pill was taken. The system can have the user's prescription information stored in memory. The system can indicate whether the user should take additional pills to satisfy the prescription. For example, in FIG. 36, the user interface states "1 of 2 taken," and a progress bar is shown partially completed. When the user indicates medication was taken, the medication taken can be logged (e.g., by the user account). In FIG. 37, the user interface 2610 displays "2 of 2" taken for the medication, and the progress bar is shown completed.

Figure 38:
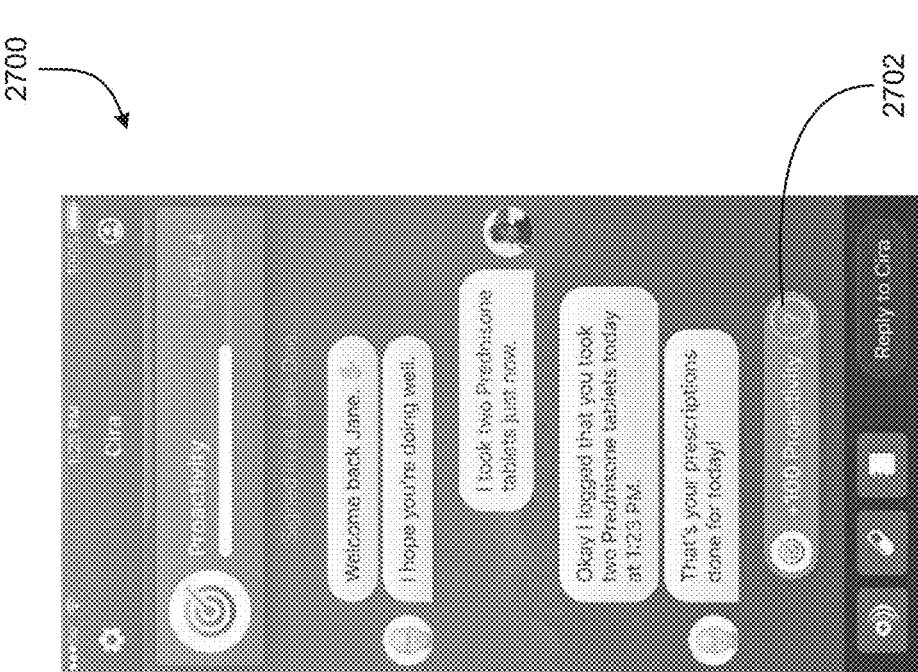
Figure 41:
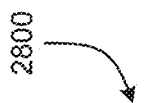
Figure 41:
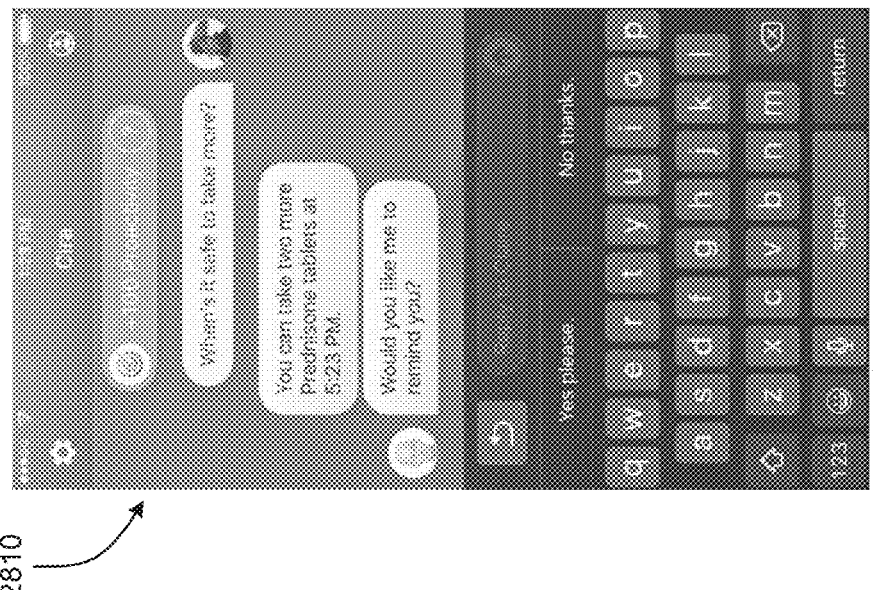

With reference to FIG. 38, the system can generate a "text message" from the user to the system indicating the medications that were taken. The message can be generated based on the user merely pressing the icon(s) relating to the medication(s) taken, and the system can generate text message that relays that information via the text or chat interface. This is another example of the message from the user in the text or chat interface was not typed out by the user, but rather was generated by the system based on simpler inputs from the user.

Figure 39:
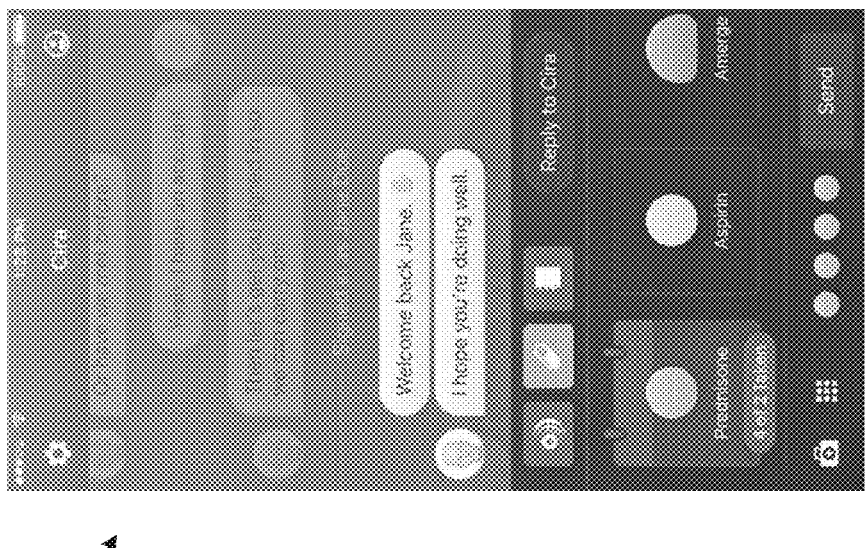

In FIG. 38, a proactivity score can be associated with the taking of medication, and upon the user indicating that the medication was taken properly, the user's proactivity score can be increased (e.g., the score was increased by 100 in FIG. 38 at 2702). In contrast to the user specifying the name of the medication, user interface 2700 includes a graphical representation of the user's medications, which the user can select. The user can initially specify the medications, for example the user can capture an image of a prescription using a camera of the user device, and so on. In this way the user can easily select a medication, and specify an amount the user has consumed. FIG. 39 shows "4 out of 2 taken" for the medication, which can be an indication that the user is overusing the medication. A warning indicator can be provided (e.g., displayed), such as the progress bar turning red.

In some cases the proactivity score can be reduced when the medication is taken improperly.

Figure 40:
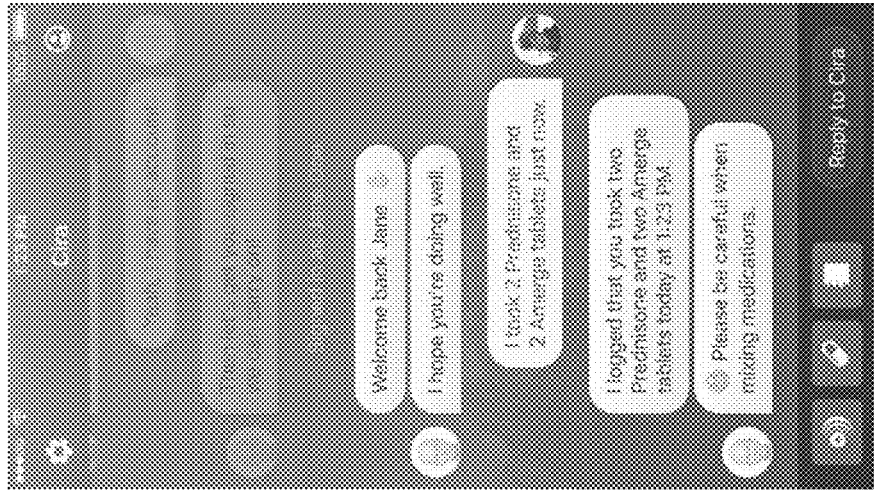

With reference to FIG. 40, user interface 2800 includes a recommendation (e.g., a warning) regarding mixing of two different medications. The chatbot can access medical databases and contraindication information, and determine whether mixing medications are considered to be safe. Additionally, the chatbot can respond to questions, as in user interface 2810 of FIG. 41, in which the user requests when it is safe to consume additional medication (e.g., the chatbot can access or search for information specifying a safe time delta). Furthermore, the user interface 2810 can be used to set reminders for the user to consume medication, and optionally the user interface 2810 can be used to begin or initiate a use of the treatment device (e.g., treatment device 10) in response to medication not being available to take again.

Figure 43:
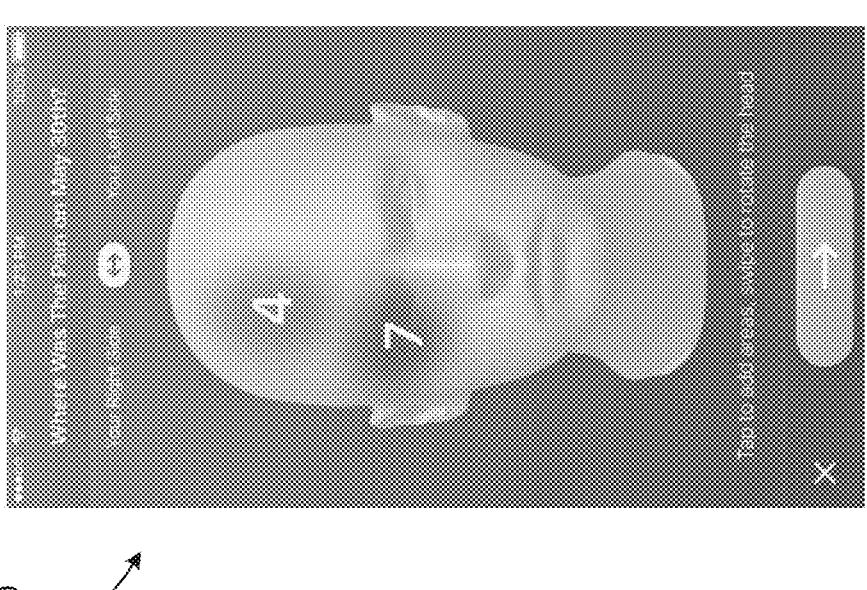
FIGS. 43 and 44 illustrates example user interfaces for entering information to the logging feature.
Figure 42:
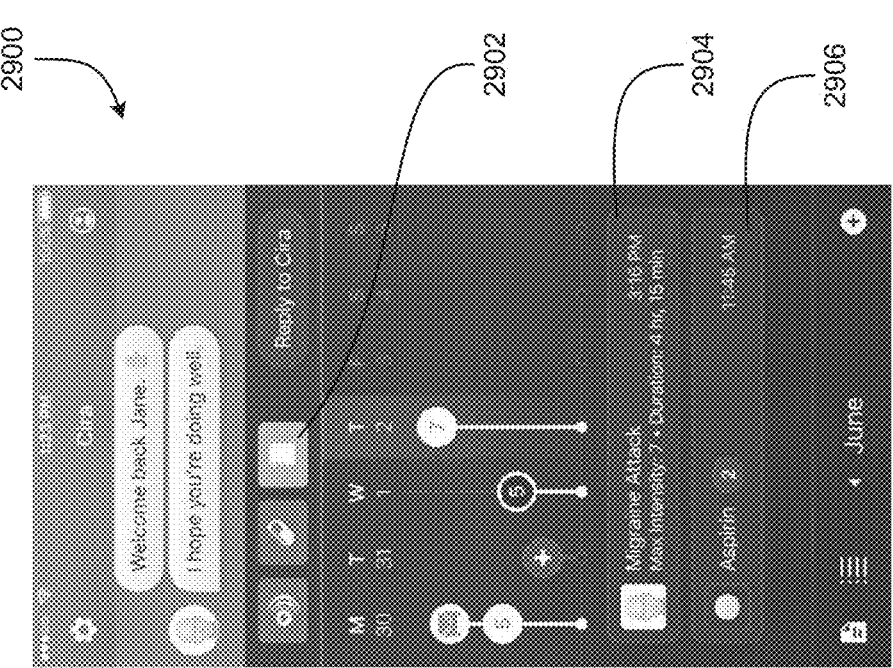
FIG. 42 illustrates an example user interface that presents logged information.
Figure 44:
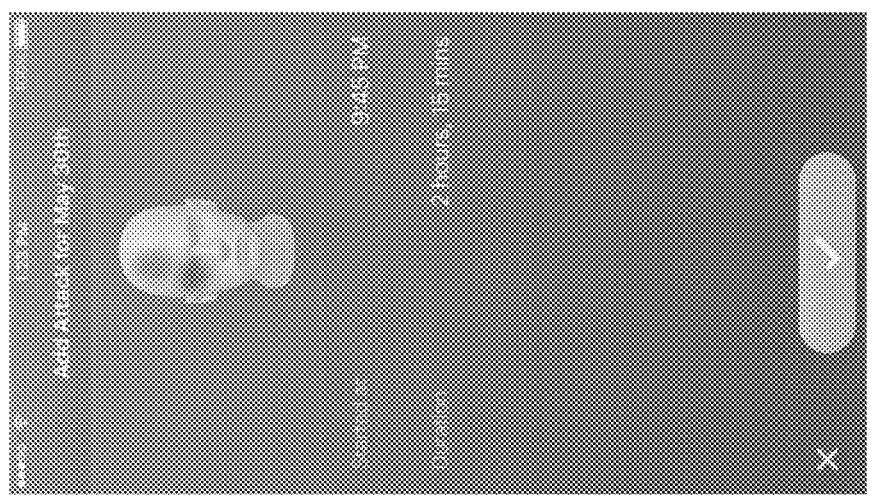

FIG. 42 illustrates an example user interface output 2900 that presents logged information. The user interface 2900 illustrates that the user has selected a particular selectable option 2902 associated with viewing logged information. Upon selection of the option 2902, symptom (e.g., pain) information can be presented, including a highest pain intensity value for each occurrence of the condition or symptom (e.g., each migraine event) and descriptive information (e.g., indicating a condition, which in this example is a 'migraine' 2904). For instance, the user interface 2900 indicates that for a particular date, the highest pain intensity value was a '7' 2904. The user interface 2900 further includes information identifying medications taken, which in the example of FIG. 42 includes an 'aspirin' 2906. The user can retroactively input condition or symptom information into the log. FIGS. 43-44 shows an example user interface for enabling the user to enter pain information for a migraine that occurred in the past. The user can indicate locations and intensity values for the pain via interface 2910, similar to the other discussion herein. FIG. 44 shows a summary display 3000 of the inputted information regarding the past migraine event.

Figure 45:
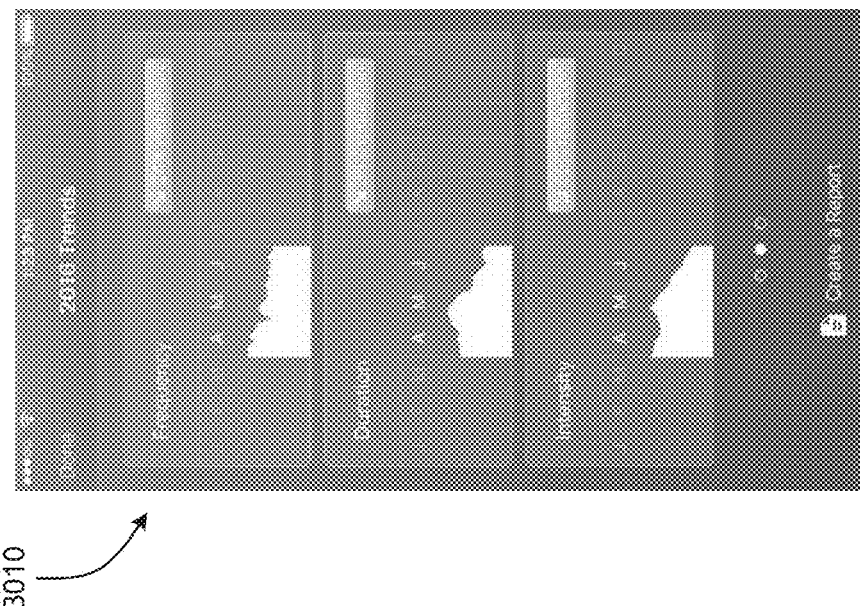
FIG. 45 illustrates an example user interface that includes summary information showing trends over time.
Figure 45:
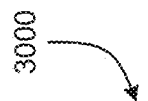

FIG. 45 illustrates an example user interface 3010 presenting summary information of the user's use of the treatment device, or of pain being experienced in general. For instance, the user interface 3010 includes summary information for a user selectable time period (e.g., the year 2016), and includes charts describing frequency, duration, and intensity, of experienced pain. Additionally, the summary information includes any reductions (e.g., a '24% reduction') or optionally increases associated with the summary information.

Figure 46:
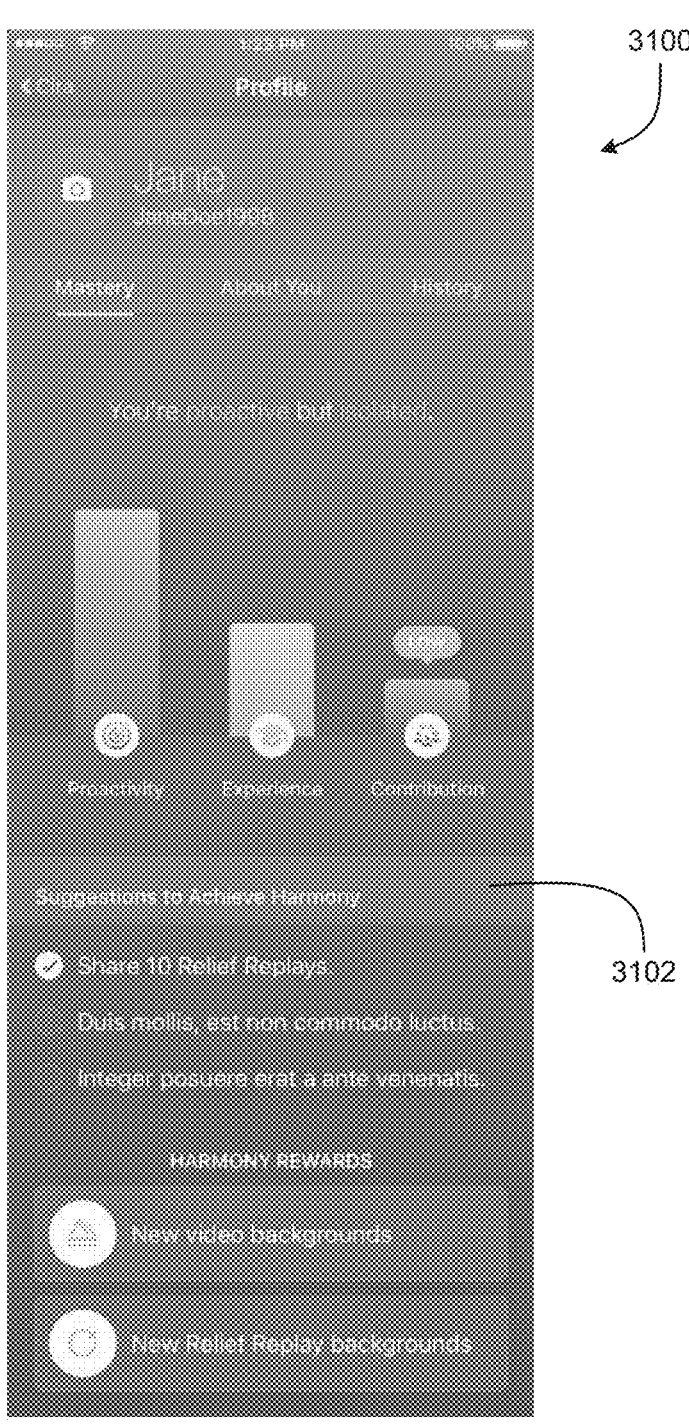
FIG. 46 illustrates an example user interface that includes score information assigned to the user.

FIG. 46 illustrates an example user interface 3100 that includes score information assigned to the user. As described above, the user device can monitor and assign scores to the user, including a proactivity score, a connectedness score, and an understanding score. The user interface 3100 presents the scores as, for instance, a bar chart, and can include recommendation's 3102 to increase the respective scores. Optionally, the user interface 3100 can include scores associated with friends of the user, and the users can compete to obtain higher scores.

Figure 47:
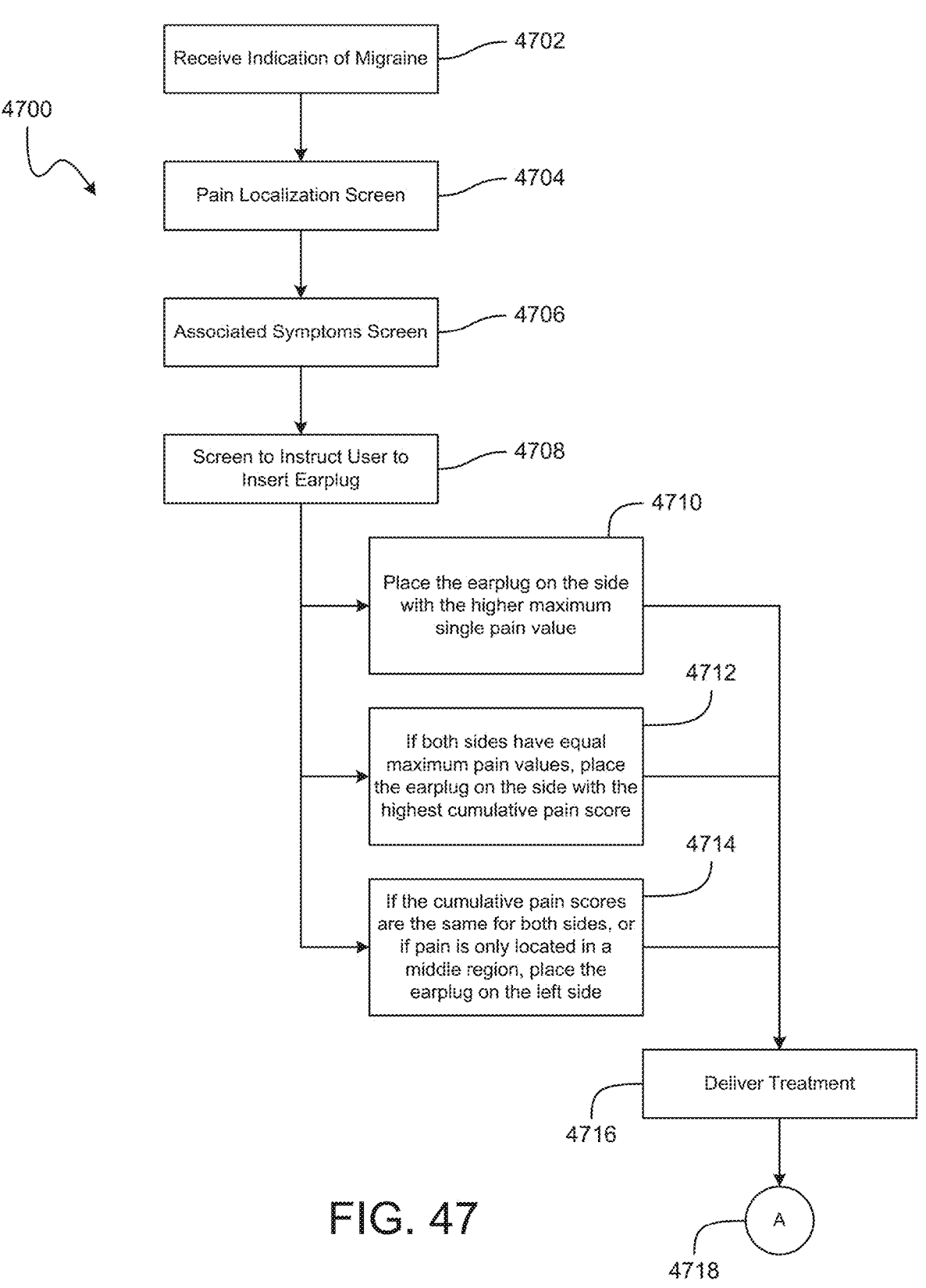
FIGS. 47 and 48 show a flowchart of a process for an example embodiment of a treatment session.
Figure 48:
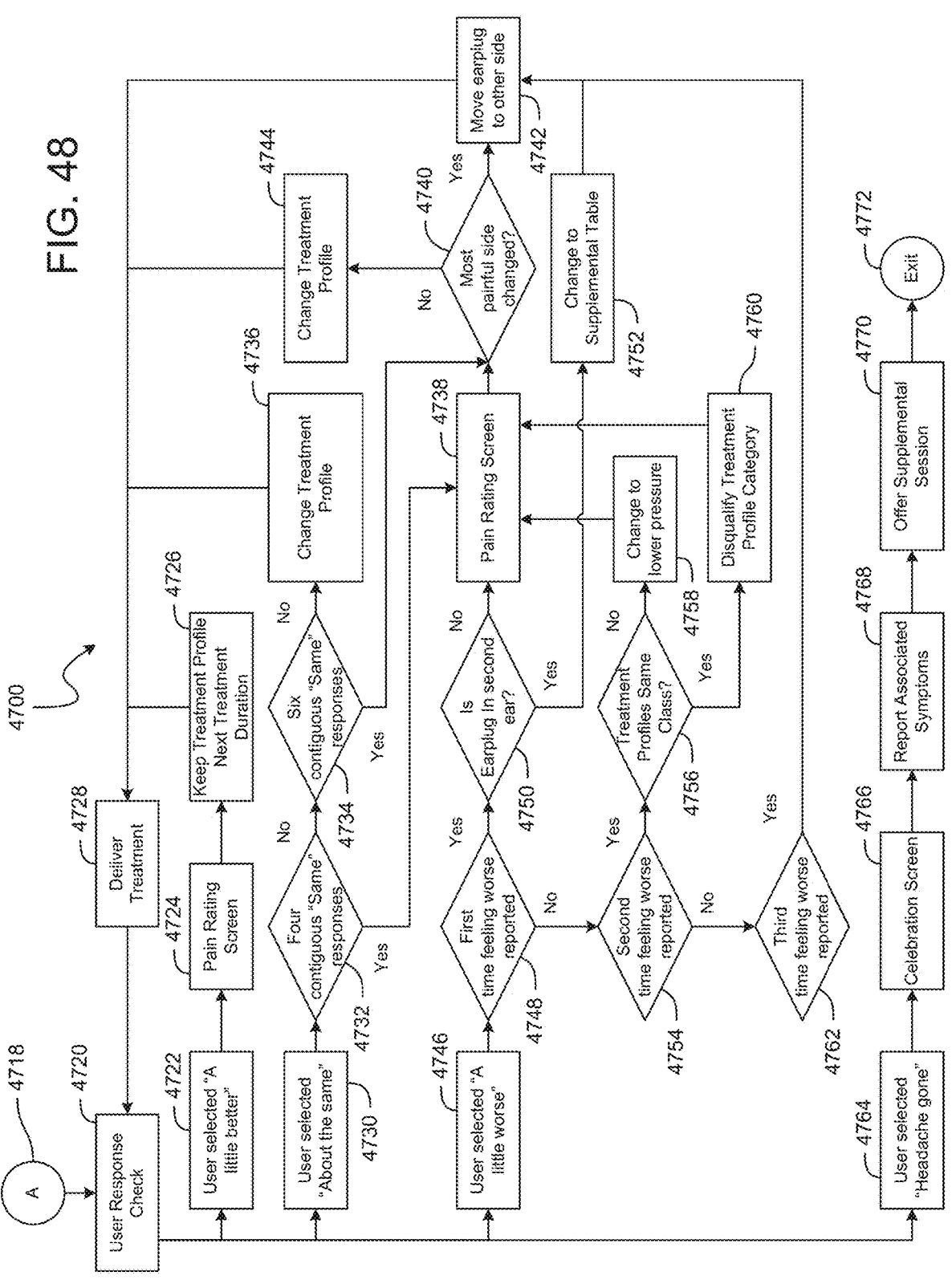
Figure 49:
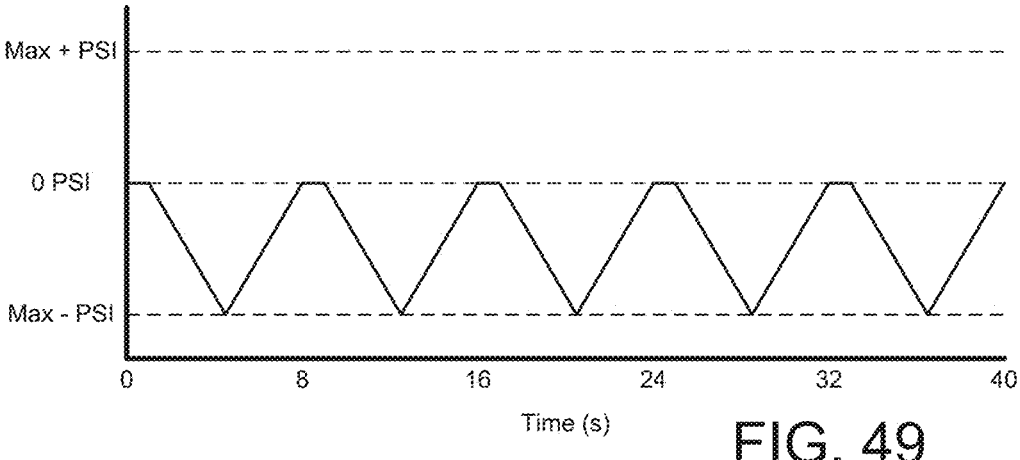
FIGS. 49 to 61 show example embodiments of pressure treatment parameter profiles.

FIGS. 47 and 48 are flow charts that illustrate an example embodiment of a process 4700 of a treatment session. FIGS. 47 and 48 are discussed in detail, and it should be understood that many variations to the treatment session process 4700 are possible. Although the discussion of FIGS. 47 and 48 relate to treatment of migraine headaches using pressure applied to an ear, other treatment types can be used and the treatment(s) can be used to treat other conditions, as disclosed herein. The treatment session process embodiments discussed herein can be performed using the various treatment systems discussed herein. At block 4702, an indication of a migraine can be received. By way of example, a user can use a smartphone to run an app that is associated with the treatment system, and the user can provide user input (e.g., via the app) to indicate that the user is experiencing a migraine. The treatment session can be initiated in other suitable manners.

At block 4704, the user interface can present a pain localization screen to the user. The user can provide input to identify one or more locations for the pain. The user can also provide one or more intensity values for the pain. In some embodiments, the user can identify categorizations for the pain (e.g., dull pain, sharp pain, deep pain, pressure, etc.). FIGS. 6-8 show examples of pain localization screens. At block 4706, the user interface can present an associated symptoms screen to the user. FIG. 9 is an example of an associated symptoms screen. The user can identify and/or quantify one or more associated symptoms that are being experienced by the user with the migraine.

At block 4708, the user interface can instruct the user to insert the earplug into one of the user's ears. Although various embodiments are described in connection with an ear plug that seals inside the user's ear, in some implementations an earpiece can seal outside the ear (e.g., similar to a headphone unit). The system can determine which ear should receive the earplug. In a first case, at block 4710, if one side of the user's head has a higher maximum single pain value than the other side of the head, the side with the higher maximum single pain value can be determined to be the most painful side and can receive the ear plug. For example, if a left side had pain values of 2, 4, and 5 while the right side had pain values of 1 and 6, the system could instruct the user to put the earplug into the right ear. In a second case, at block 4712, if both sides have equal maximum single pain values, then side with the higher cumulative pain score can be determined to be the most painful side and can receive the ear plug. For example, if the left side had pain values of 3, 4, and 6 while the right side had pain values of 5 and 6, the system could instruct the user to put the earplug into the left ear. In a third case, at block 4714, if the maximum single pain value and the cumulative pain scores are the same for both sides, or if the pain locations are only in the middle region, the system can instruct the user to place the earplug in the left ear. The left side can be the most painful side by default. For example, if the left side had pain values of 1, 4, and 6, and the right side had pain values of 5 and 6, and the middle region(s) (e.g., crown of the head) have a pain value of 3, the system can default to the instruction to the user to put the earplug in the left ear.

Many variations are possible. For example, in some cases the number of pain areas can affect the determination of which ear will receive treatment. For example, if the left side had pain values of 5 and 6 while the right side had pain values of 1, 4, and 6, the maximum single pain values and the cumulative pain scores would be equal. The system could instruct the user to apply the earplug to the right ear, instead of the default left ear, because the right side has 3 pain areas as compared to the 2 pain areas of the left side. Although FIGS. 47 and 48 are described for a system having one ear plug, in some embodiments the treatment system can include two ear plugs, and the system can instruct the user to apply a right ear plug to the right ear and a left ear plug to the left ear. The system could selectively apply treatment to the right ear only, to the left ear only, or to both ears, at different times during the treatment session (as discussed herein) without the user needing to reposition the ear plug.

At block 4716, the system can deliver the first phase of the treatment session. A first treatment parameter profile can be used for the first treatment phase. The system can select the first treatment parameter profile based on the pain information, based on effectiveness information from one or more prior treatment sessions performed on the individual patient, based on effectiveness on other users (e.g., a general population or population category that includes the individual patient). In some embodiments, the system can have a default first treatment parameter profile.

The first treatment phase can last for a predetermined amount of time. In some embodiments, the system can use different amounts of time for different treatment phases during the treatment session. A pattern or algorithm can be used to determine the lengths of time for the various treatment phases performed. In some cases, a treatment duration pyramid can be used. The time durations of the treatment phases can increase until a treatment phase having a maximum time duration is performed, and then the time durations of the treatment phases can decrease until a treatment phase having minimum time duration is performed. The time durations of the treatment phases can then start increasing again. By way of example, a first treatment phase can last for 120 seconds, a second treatment phase can last for 150 seconds, a third treatment phase can last for 180 seconds, a fourth treatment phase can last for 150 seconds, and a fifth treatment phase can last for 120 seconds. The pyramid pattern can be repeated until the treatment session is completed. Other time duration patterns can be used. For example, the time durations can alternate between a shorter time duration and a longer time duration. The time durations can decrease to a minimum time and then increase to a maximum time (e.g., a time duration valley). The time durations for the treatment phases can be randomized (e.g., randomly selected time duration values between a minimum time and a maximum time).

Block 4718 links FIG. 47 and FIG. 48. After the treatment phase (e.g., after the treatment duration time has been completed), the process can proceed to block 4720 to perform a user response check. In some embodiments, the treatment (e.g., pressure treatment, etc.) can continue during the user response check. In some embodiments, the treatment can be continuous. For example, the system can change from a first treatment parameter profile to a second treatment parameter profile seamlessly, without a pause or time gap in the treatment. The user interface can display a user response check screen (see, FIG. 23, for example), and the user can provide information regarding the pain. In some embodiments, the user interface can enable the user to select between an indication that the pain is a little better, an indication that the pain is about the same, an indication that the pain is a little worse, and an indication that the pain is gone. Many variations are possible.

If the user selects that the pain is a little better (block 4722), the process can proceed to block 4724 and a pain rating screen can be presented via the user interface. The user can provide input regarding how the pain has changed. For example, the user can edit (e.g., increase or decrease) previously reported pain values. The user can indicate that pain has moved to a different location. The user can indicate that one pain location has resolved. The user can indicate new pain locations. In some cases, the option can be provided for the user to indicate that there was no change in the pain levels. For example, in some cases a patient can feel that the pain has improved slightly but not enough to change the pain values.

At block 4726, the system can keep the same treatment parameter profile. The time duration for the next treatment phase can be determined, and can be different than the time duration of the previous treatment phase. The system can use the treatment duration pyramid and can advance to the next time value in the pyramid. Other techniques can be used to determine the time duration for the next treatment phase, as disclosed herein. The method can advance to block 4728, and the treatment can be delivered for the next treatment phase. The user interface can display a treatment in progress screen (e.g., FIG. 19), such as until the time duration for that treatment phase ends. In some embodiments, the same treatment parameter profile can be used so long as the user reports that the pain is getting better. In some implementations, the system can change to a different profile even when the user indicates that the pain is getting better, such as if the rate of improvement is below a threshold, or to test exposure to other profiles to assess their effectiveness, or to vary the treatment in order to avoid reduced effectiveness of the profile by the user getting accustomed to the profile after repeated use, etc.

If the user indicates that the pain is about the same, at block 4730, the system can take different actions depending on how many times the user had indicated that the pain has stayed the same. By way of example, at block 4732, if the user indicates that the pain has stayed the same for four contiguous responses, the process can proceed to block 4738. At block 3734, if the user indicates that the pain has stayed the same for six contiguous responses, the process can proceed to block 4740. Otherwise (e.g., for at least the first three contiguous responses that the pain has stayed the same), the process can proceed to block 4736, and the treatment parameter profile can be changed. The treatment parameter profile can change to the next profile on a list (e.g., stored locally on the treatment system or stored remotely on a server). In some embodiments, the available profiles can be categorized. For example, as discussed herein, a treatment parameter profile can be categorized as kinetic or akinetic. At block 4736, the system can select a profile from a different category than the profile that was used previously. For example, if a kinetic profile was used and the user indicated that the pain stayed about the same, the system can select the next profile from the akinetic category for the next treatment phase. In some cases, a profile or category of profiles can be disqualified, as discussed herein, and the system can select a profile that is not disqualified or in a disqualified category. For example, the system can select a next profile from the same category if another category of profiles has been disqualified. The process can proceed to block 4728 to perform the deliver treatment for the next treatment phase.

At block 4732, if the user indicates that the pain has stayed the same for four contiguous responses, the process can proceed to block 4738, and a pain rating screen can be presented via the user interface, similar to block 4724. The user can input updated pain information or indicate no change. The process can proceed to block 4740 where the system can reevaluate which ear will receive treatment. The system can determine the most painful side according to updated pain information. For example, the system can make a determination similar to the discussion in connection blocks 4708 to 4714 of FIG. 47. If the determination is that the ear receiving treatment should change (e.g., the most painful side of the head has changed based on the updated pain information), the process can proceed to block 4742. The user interface can instruct the user to move the earpiece to the other ear. In embodiments, where the system has two ear pieces, the treatment can change from one ear to the other without the user taking action. The process can proceed to block 4728 and treatment can be delivered to the other ear. In some cases, the same treatment parameter profile that was previously used can be applied to the other ear, or the treatment parameter profile can be changed (e.g., similar to the discussion of block 4736). If block 4740 determines that the ear for treatment will not change, the process can proceed to block 4744, and the treatment parameter profile can be changed, and might be selected from a different category of profiles (e.g., similar to the discussion of block 4736). The process can then proceed to block 4728. At block 3734, if the user indicates that the pain has stayed the same for six contiguous responses, the process can proceed to block 4740 (e.g., bypassing block 4738). Many variations are possible.

If the user indicates that the pain has become worse, at block 4746, the system can take different actions depending on how many times the user had indicated that the pain has become worse. For the first time the user indicates that the pain has become worse (block 4748), the process can proceed to block 4750. If the earplug is in the first ear (e.g., the process has not moved the earplug at block 4742), the process can move to block 4738, which is discussed herein. If the earplug is in the second ear (e.g., the earplug was previously moved at block 4742), the process can move to block 4752, and the system can select a treatment parameter profile from a supplemental table. The supplemental table can include one or more supplemental treatment parameter profiles in addition to the treatment parameter profiles that are part of the one or more categories discussed herein (e.g., the kinetic profile category and the akinetic profile category). The one or more profiles of the supplemental table or group can be used when changing the treatment from one ear to the other and/or changing the profile category (e.g., kinetic to akinetic or vice versa) has not worked and the pain has become worse. The one or more supplemental profiles can be "last resort" treatment parameter profiles in some instances. The process can then proceed to blocks 4742 and 4728 to change back to the first ear and apply the treatment based on the treatment parameter profile from the supplemental table.

For the second time the user indicates that the pain has become worse (block 4754), the process can proceed to block 4756. If the two treatment parameter profiles that resulted in an indication that the pain has become worse are both from the same category (e.g., both kinetic or both akinetic), the profile category can be disqualified at block 4760. At block 4760, the system can change to a different category of treatment parameter profiles. The system can select the next profile from the other category of profiles. In some embodiments, the system can also reduce the pressure to be applied during the next treatment phase (e.g., similar to block 4758). For example, a profile can have a low pressure version, which can have the same frequency and shape, except that the amplitudes of the applied pressures can be lower. The process can proceed to block 4738 and on, as discussed herein.

If the two treatment parameter profiles that resulted in an indication that the pain has become worse are not from the same category of profiles, the process can move to block 4758 and the pressure for one or more of the later treatment phases can be reduced. For example, a profile can have a low pressure version, which can have the same frequency and shape, except that the amplitudes of the applied pressures can be lower. In some embodiments, all subsequent treatment phases can use the reduced pressure level (e.g., until the pressure level is later changed). The process can proceed to block 4738 and on, as discussed herein.

For the third time the user indicates that the pain has become worse (block 4762), the process can proceed to block 4742 and the treatment can be moved from one ear to the other ear. The process can proceed to block 4728 and deliver treatment to the other ear. Accordingly, in some instances treatment can be applied to the ear on the opposite side of the determinations of 4710, 4712, and 4714 and the like. In some embodiments, the same treatment profile that was used for the previous treatment phase can be used on the other ear. This can help the system determine whether changes in the treatment effectiveness are due to the change from one ear to the other or due to a change of the treatment profile. In some embodiments, the treatment profile can be changed when the treatment is moved from one ear to the other. For example, in some implementations, the system can utilize a treatment profile that has previously been determined to be effective for the particular patient when the treatment is moved to the other ear.

In some embodiments, if the user indicates that the pain has become worse a certain number of times (e.g., a fourth time) (not shown in FIG. 48), the treatment can be suspended for that session. In some embodiments, the progression from blocks 4748 to 4754 to 4762 can occur for consecutive indications that the pain has become worse. The process can treat and indication that the pain has become worse as the first indication (at block 4748), even if there were one or more previous indications that the pain had become worse, if there were one or more intermediate indications that the pain had not become worse. For example, a user can indicate that the pain becomes worse two consecutive times (e.g., at blocks 4748 and 4754), and the user can then indicate that the pain has gotten a little better (e.g., at block 4722), and then if the user indicates that the pain has gotten worse again the process can move to block 4748 and treat that as a first indication that the pain has become worse. In some embodiments, the process can progress from block 4748 to block 4754 to block 4762 even if there were intermediate indications that the pain had become better or stayed the same. For example, a user can indicate that the pain becomes worse two consecutive times (e.g., at blocks 4748 and 4754), and the user can then indicate that the pain has gotten a little better (e.g., at block 4722), and then if the user indicates that the pain has gotten worse again the process can move to block 4762 and treat the indication as a third indication that the pain has become worse.

If the user indicates that the pain is gone, at block 4764, the user interface can present a celebration screen at block 4766. At block 4768, updated information can be received regarding the associated symptoms. The user can input information about the associated symptoms, similar to the discussion of block 4706. In some embodiments, at least one additional treatment phase can be performed after the user indicates that the pain is gone. The additional treatment phase can be for relaxation and/or can decrease the likelihood that the migraine headache will return. The at least one additional treatment phase can be optional, in some implementations. For example, at block 4770 the system can offer the supplemental session to the user. The user can accept the supplemental session offer and the supplemental treatment phase can be performed. The supplemental treatment phase can use relatively gentle treatment profiles, and can be designed to help the patient relax (e.g., after pain relief has been achieved). For example, a supplemental treatment phase can use the profiles of FIGS. 49-53 and the like, while not using the profiles of 54-57 and the like. In some embodiments, for the supplemental session, the system can provide treatment phases based on one or more treatment profiles, which can be changed randomly (e.g., in duration and/or in profile selection from the appropriate set of profiles). The supplemental treatment phase can be delivered over a prolonged period of time, such as in the range from 5 minutes to 2 hours or 10 minutes to 1 hour, for example. The supplemental treatment phase can last until the user provide input to terminate the session. The supplemental treatment phase can deliver the one or more treatment profiles without interruption (e.g., without input or feedback from the user) during the supplemental session. The user can reject the supplemental session offer and the supplemental treatment phase can be omitted. The process can end at block 4772. The supplemental session (e.g., relaxation session) can run without requesting feedback from the user. It can change treatment profiles at random, in some cases. The relaxation session or supplemental session can prevent habituation or tolerance build up to the treatment or to particular treatment profiles.

FIGS. 49 to 58 include example embodiments of pressure treatment parameter profiles. In the treatment parameter profile of FIG. 49, no pressure is applied for a time (e.g., about 1 second), then increasing negative pressure can be applied (e.g., for about 3.5 seconds) until a predetermined negative pressure (e.g., the maximum negative pressure) is reached, then the negative pressure can be released (e.g., for about 3.5 seconds) until the 0 PSI state is reached. This cycle can repeat for the duration of the treatment phase. The pattern can have a cyclical rate of 0.125 Hz. Other values and many other variations are possible.

Figure 50:
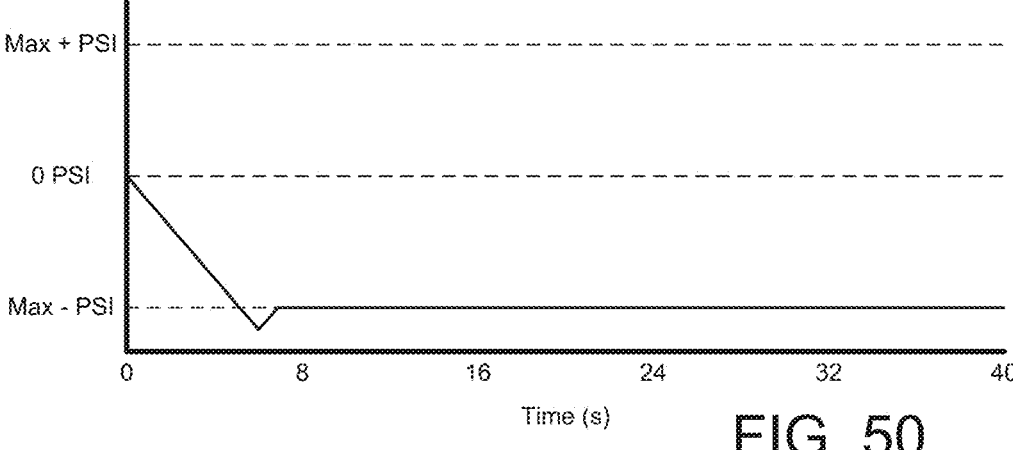

In the treatment parameter profile of FIG. 50, increasing negative pressure can be applied until a predetermined negative pressure (e.g., the maximum negative pressure) is reached after a first time (e.g., after about 6 seconds). The system can maintain the predetermined negative pressure (e.g., the maximum negative pressure) for the duration of the treatment phase. In some embodiments, the pressure can exceed the predetermined pressure (e.g., the maximum pressure value) for a brief time, such as for 0.25 to 5 seconds, or 1 to 3 seconds, or for about 2 seconds, for example. For example, in the treatment profile of FIG. 50, more negative pressure than the maximum negative pressure value can be applied for 2 seconds (from the 5-second to the 7-second times). This can help the ear plug seat correctly with the ear. Alternatively, the treatment parameter profile may not provide a more negative pressure than the maximum negative pressure value. In such an embodiments, the treatment system may apply a negative pressure until the predetermined negative pressure value is reached. For each of the pressure treatment profiles that have a portion that passes outside the Max positive or Max negative pressure (e.g., see FIGS. 50, 51, 54-57) the portion that passes outside the Max pressure values can be omitted, such as so that the plots would stay within the bounds set by the Max pressure values.

The treatment system may utilize the treatment parameter profile of FIG. 50, in some instances, to determine whether the ear plug is sealed correctly within the ear or whether the ear plug is unseated or leaking. For example, the treatment system may apply a predetermined pressure and utilize a pressure sensor (as described herein) to determine if and/or how the applied pressure is changing over time. In some embodiments, if the pressure does not change as expected when activating a pressure generator, then the treatment system may determine that the ear plug is not correctly seated and/or that a leak condition is occurring. Alternatively, if the treatment system determines that the pressure does change as expected and/or maintains an expected pressure value for a set threshold of time, the treatment system may determine that the ear plug is correctly seated and/or that a leak has not occurred. The treatment system, in some embodiments, may proceed to a subsequent treatment parameter profile once the system determines that the ear plug is correctly seated and/or that a leak is not occurring. The pressure treatment profile of 49 can be used for seating the earpiece and/or testing for leaks. The negative pressure (e.g., FIGS. 49, 50, and 51) can help pull the earplug into the ear canal.

At an initiation of treatment, the treatment system, in some embodiments, may utilize the treatment parameter profile of FIG. 50 to facilitate proper seating and/or sealing of the ear plug against a user's ear canal. For example, the treatment system may instruct a user to insert the ear plug and then perform one or more negative pressure "pulls." The treatment system, as discussed herein, may determine whether the ear plug is properly seated and/or if a leak condition is occurring. In some instances when the treatment system determines that there is a leak or other problem, the treatment system may apply the treatment parameter profile of FIG. 49, FIG. 50, or similar to attempt to establish a proper seal between the ear plug and the ear canal. If a seal can be reestablished, the system can return to the treatment profile that was being used when the leak was detected.

Various other treatment profiles (e.g., FIGS. 51 and 54-57) can include similar brief over-pressure portions that can help seat the ear plug. In some instances, the pressure applied during the over-pressure portions can be within a safe pressure limit. Some embodiments can enable the user to specify maximum pressure values, or the system can perform pressure tolerance tests to determine maximum pressures values for a user, as discussed herein. In some implementations, the over-pressure events can briefly exceed the specified or determined maximum pressure values (e.g., a maximum negative pressure value). In some implementations, the over-pressure events do not exceed the maximum pressure values (e.g., a maximum negative pressure value). For example, in FIG. 50, the dwell period shown from the 7-second time to the 40-second time can use a pressure that is slightly reduced from the maximum negative pressure value, and the over-pressure event from the 5-second time to the 7-second time can be within the maximum negative pressure value.

Figure 51:
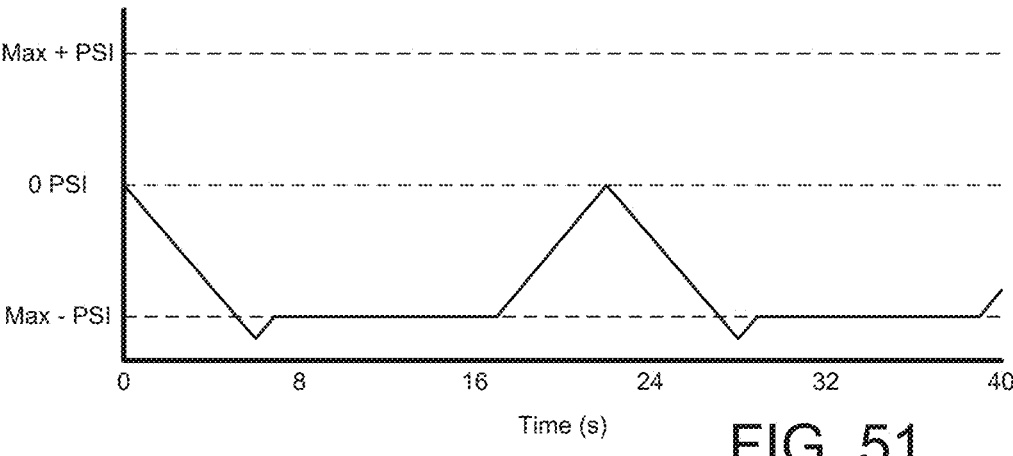

In the treatment parameter profile of FIG. 51, increasing negative pressure can be applied until a predetermined negative pressure (e.g., the maximum negative pressure) is reached after a first time (e.g., after about 6 seconds). The predetermined negative pressure (e.g., the maximum negative pressure) can be held substantially constant for a second amount of time (e.g., about 10 seconds). Then the negative pressure can be released during a third time (e.g., about 5 seconds). This pattern can repeat for the duration of the treatment phase.

In some embodiments, the treatment parameter profiles of FIGS. 49 to 53 can be categorized as akinetic profiles, and the treatment parameter profiles of FIGS. 54 to 57 can be categorized as kinetic profiles. In some embodiments, the treatment parameter profiles of FIG. 52 and/or 53 can be sufficiently dynamic to be categorized as kinetic profiles. The treatment parameter profiles of FIGS. 58 and 59 can be categorized as supplemental profiles (e.g., as discussed above in connection with the supplemental profiles of FIG. 48).

Figures 52, 53:
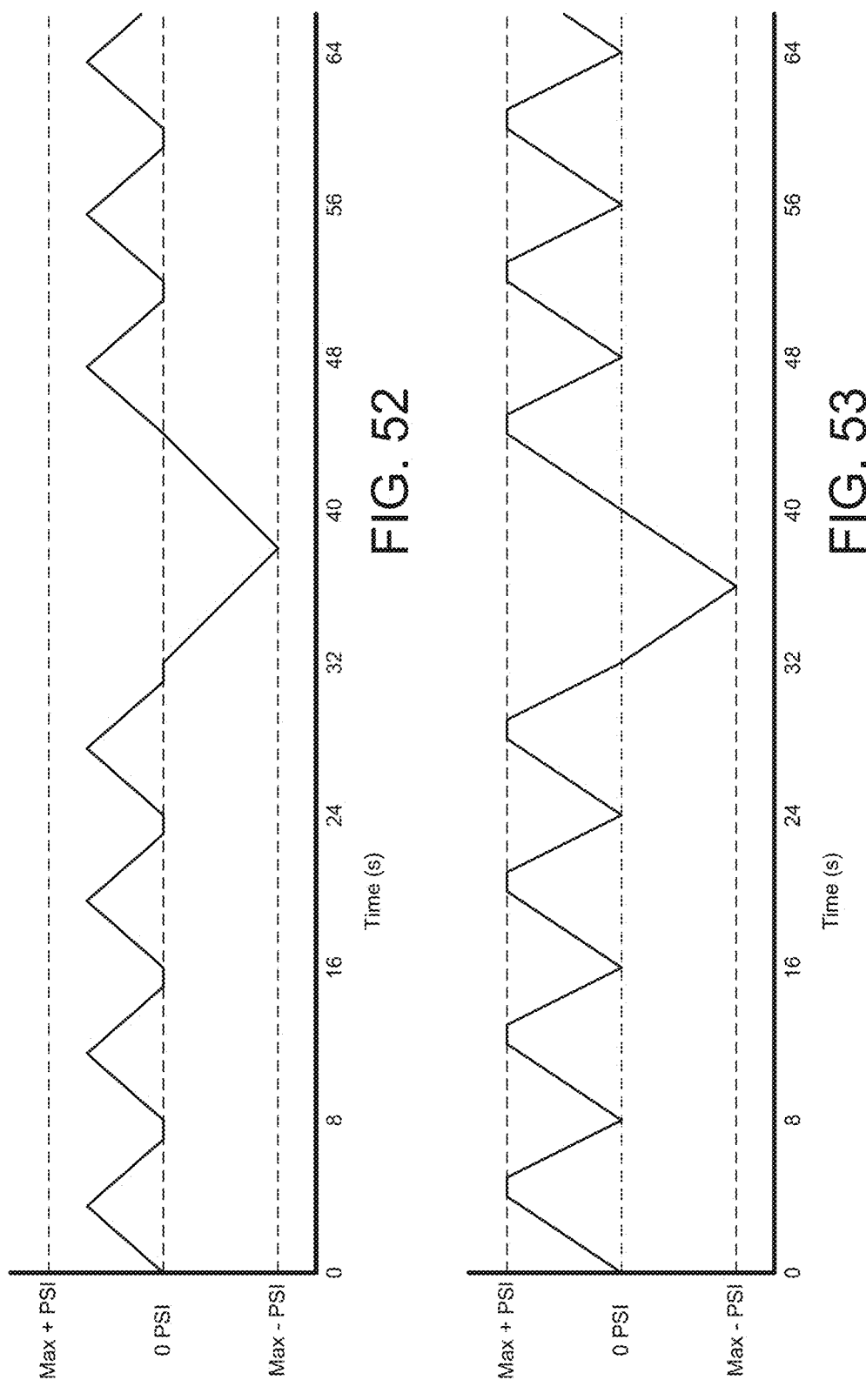

In the treatment parameter profile of FIG. 52, increasing positive pressure can be applied (e.g., for about 3.5 seconds) until a predetermined positive pressure is reached. The predetermined positive pressure can be some percentage (e.g., 66%) over the maximum positive pressure, although the maximum positive pressure can be used in some cases. Then the positive pressure can be released (e.g., for about 3.5 seconds) until the 0 PSI state is reached. A no pressure state can be held for a time (e.g., about 1 second). This pattern can be repeated for a number of times (e.g., 4 times). Then an increasing negative pressure can be applied for a time (e.g., about 6 seconds) until a predetermined negative pressure (e.g., the maximum negative pressure) is reached. Then the negative pressure can be released over a time (e.g., about 6 seconds). Then the overall pattern can repeat, and this pattern can be repeated for the duration of the treatment phase.

The treatment parameter profile of FIG. 53 can be similar to the profile of FIG. 52 in some regards. The positive pressure peaks can reach the maximum positive pressure value. The dwell times at the no pressure state can be omitted. In some embodiments, the profile can include a dwell at the peak of the positive pressure events. In some embodiments, the dwells at the positive pressure peaks can be omitted. By way of example, in FIG. 53, increasing positive pressure can be applied (e.g., for about 4 seconds) until a predetermined positive pressure is reached (e.g., the maximum positive pressure). The positive pressure can be held for a time (e.g., about 1 second). Then the positive pressure can be released (e.g., for about 3 seconds) until the 0 PSI state is reached. This pattern can be repeated for a number of positive pressure events (e.g., 4 times). Then an increasing negative pressure can be applied for a time (e.g., about 4 seconds) until a predetermined negative pressure (e.g., the maximum negative pressure) is reached. Then the negative pressure can be released over a time (e.g., about 4 seconds). Then the overall pattern can repeat, and this pattern can be repeated for the duration of the treatment phase. Many other alternatives are possible.

Figures 54, 55:
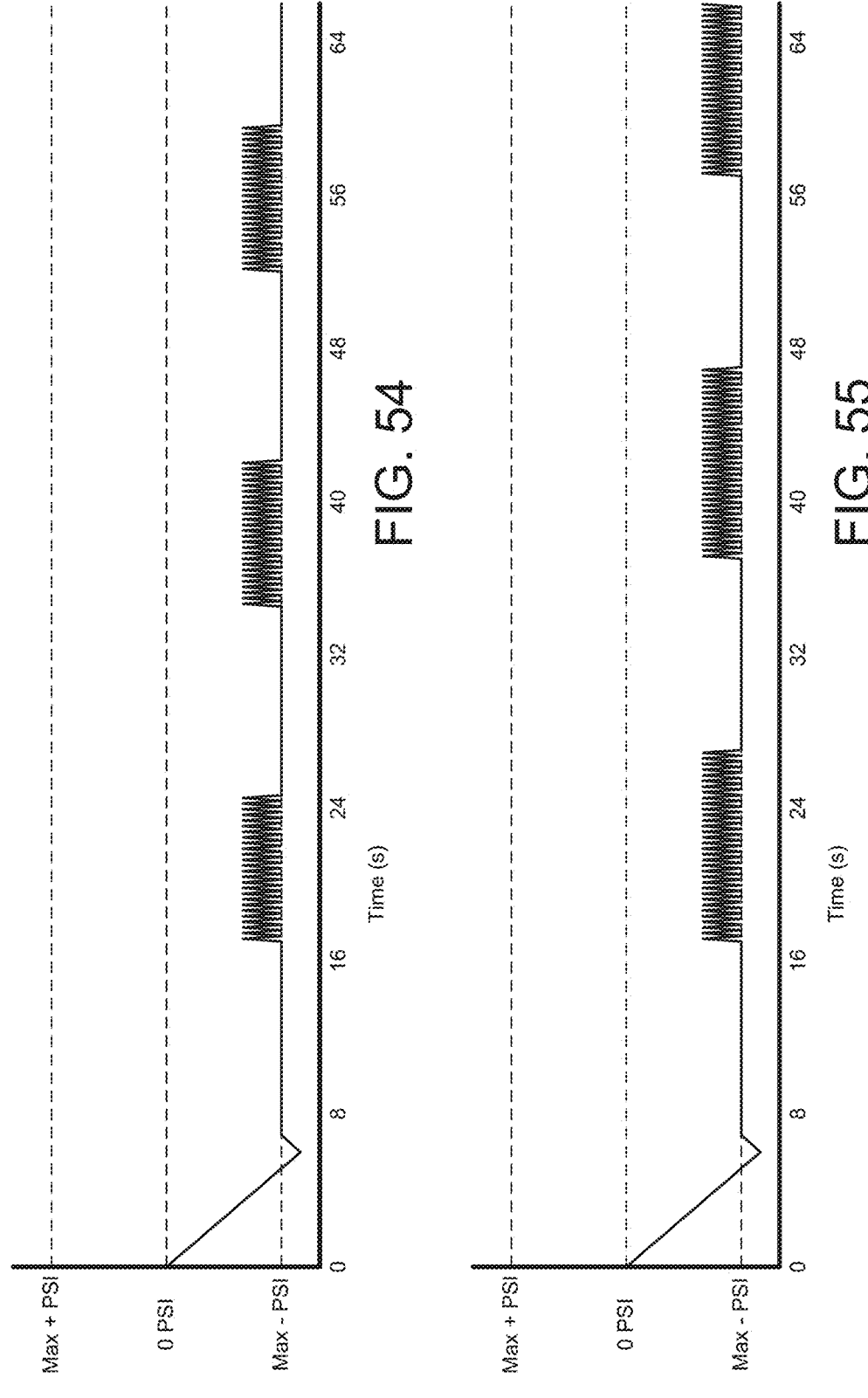

In the treatment parameter profile of FIG. 54, increasing negative pressure can be applied until a predetermined negative pressure (e.g., the maximum negative pressure) is reached after a first time (e.g., after about 6 seconds). The predetermined negative pressure (e.g., the maximum negative pressure) can be held substantially constant for a second amount of time (e.g., about 10 seconds). Then the pressure can oscillate rapidly between the higher and lower negative pressures (e.g., between the maximum negative pressure and a lower negative pressure) for a third amount of time (e.g., about 7.5 seconds). While the incorporation of rapid oscillation within a treatment parameter profile is disclosed in the context of the treatment parameter profile of FIG. 54, it will be understood by one of skill in the art that the treatment system may incorporate rapid oscillations within any variation of treatment parameter profiles disclosed herein. The treatment system can be configured to apply a treatment parameter profile incorporating rapid oscillations about any set base line, such as a set point of a positive pressure value relative to atmosphere, a negative pressure value relative to atmosphere, and/or a pressure value equal to atmosphere. For example, the treatment system may provide a treatment parameter profile that generates a rapid oscillation about 0 PSI, such as 30 mPSI to 40 mPSI. In some embodiments, the rapid oscillations may have a frequency of 100 Hz-200 Hz.

The oscillations can have a frequency between 0.5 Hz and 10 Hz, between 1 Hz and 6 Hz, between about 2 Hz and 4 Hz, although other frequencies can be used. In some embodiments, the oscillation frequency can be at least 1 Hz, at least 5 Hz, at least 10 Hz, at least 25 Hz, at least 50 Hz, at least 100 Hz, at least 150 Hz, at least 200 Hz, or more depending on the capabilities of the treatment device. The oscillation frequency can be up to 10 Hz, up to 25 Hz, up to 50 Hz, up to 100 Hz, up to 150 Hz, up to 200 Hz, up to 250 Hz, up to 300 Hz, or more, again depending on the capabilities of the treatment device.

In some instances, the use of rapid oscillations within a treatment parameter profile may be used as a treatment for various disorders. For example, it has been found that rapid oscillations at certain frequencies can be used to treat and/or prevent various neurological disorder and other medical conditions, such as traumatic brain injury, movement disorders (e.g., Parkinsons and dystonia), balance disorders, conscientiousness and sleep disorders, pain syndromes, epilepsy, and other central nervous disorders.

With reference again to FIG. 54, after the occurrence of a rapid oscillation, the predetermined negative pressure (e.g., the maximum negative pressure) can be held substantially constant for the second amount of time (e.g., about 10 seconds), followed by the rapid oscillations for the third amount of time. The pattern of constant negative pressure and rapid oscillations in negative pressure can repeat for the duration of the treatment parameter profile. The treatment parameter profile of FIG. 55 can be similar to the profile of FIG. 54, but the rapid oscillations can last for a longer time (e.g., about 10 seconds). The constant negative pressure time and the rapid oscillation time can be the same such that the pattern alternates between equal times of rapid oscillations and the constant negative pressure for at least a portion of the treatment phase. Many other alternatives are possible.

Figures 56, 57:
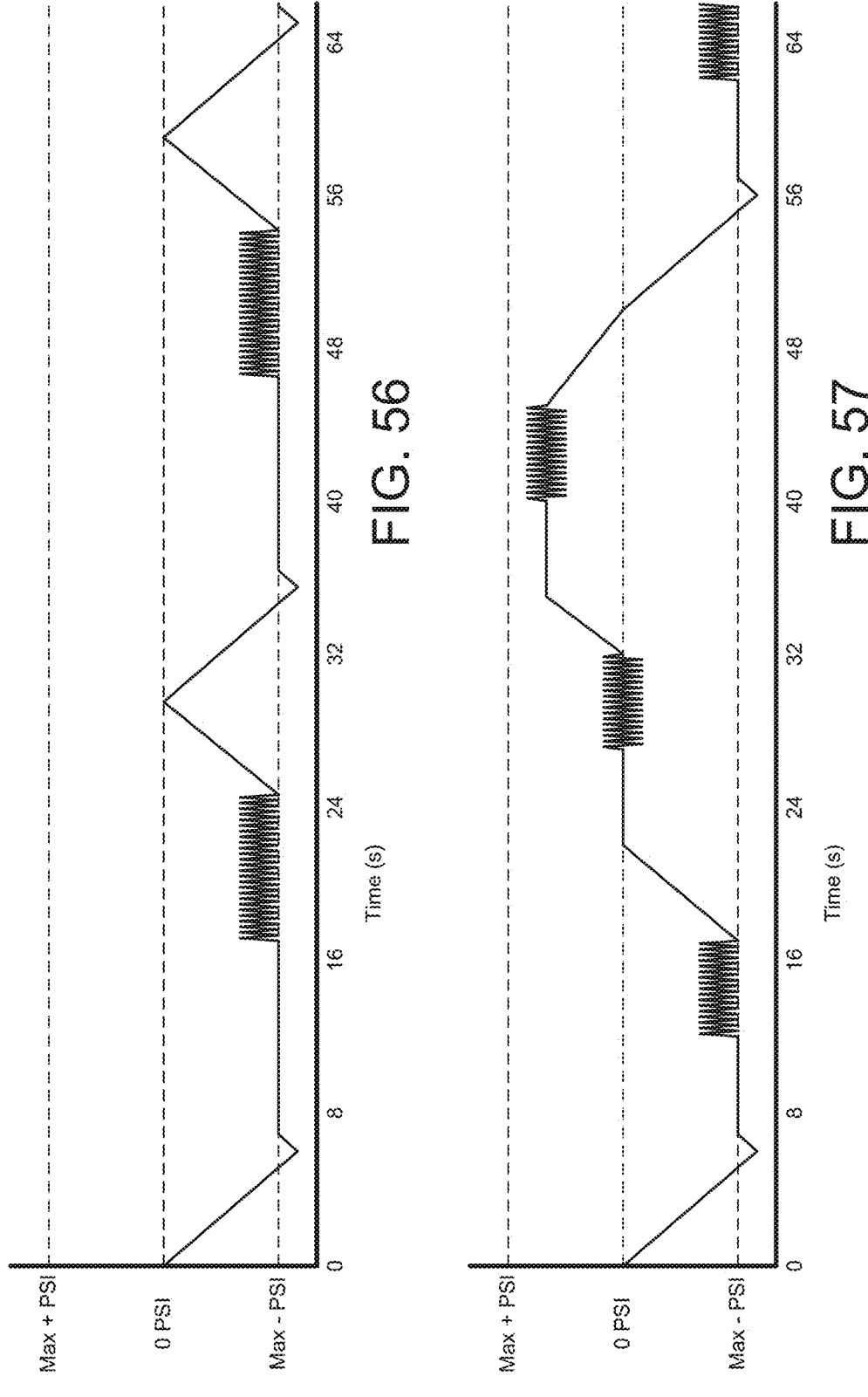

In the treatment parameter profile of FIG. 56, increasing negative pressure can be applied until a predetermined negative pressure (e.g., the maximum negative pressure) is reached after a first time (e.g., after about 6 seconds). The predetermined negative pressure (e.g., the maximum negative pressure) can be held substantially constant for a second time (e.g., about 10 seconds). Then the pressure can oscillate rapidly between the higher and lower negative pressures (e.g., between the maximum negative pressure and a lower negative pressure) for a time (e.g., about 7.5 seconds). The rapid oscillations can have a frequency between 0.5 Hz and 10 Hz, between 1 Hz and 6 Hz, between about 2 Hz and 4 Hz, although other frequencies can be used. In some embodiments, the oscillation frequency can be at least 1 Hz, at least 5 Hz, at least 10 Hz, at least 25 Hz, at least 50 Hz, at least 100 Hz, at least 150 Hz, at least 200 Hz, or more depending on the capabilities of the treatment device. The oscillation frequency can be up to 10 Hz, up to 25 Hz, up to 50 Hz, up to 100 Hz, up to 150 Hz, up to 200 Hz, or more, again depending on the capabilities of the treatment device. Then the negative pressure can release over a time (e.g., about 5 seconds). The pattern can repeat for the duration of the treatment parameter profile.

In the treatment parameter profile of FIG. 57, increasing negative pressure can be applied until a predetermined negative pressure (e.g., the maximum negative pressure) is reached after a first time (e.g., after about 4 seconds). The predetermined negative pressure (e.g., the maximum negative pressure) can be held substantially constant for a second amount of time (e.g., about 5 seconds). Then the pressure can oscillate rapidly between the higher and lower negative pressures (e.g., between the maximum negative pressure and a lower negative pressure) for a third amount of time (e.g., about 5 seconds). The rapid oscillations can have a frequency between 0.5 Hz and 10 Hz, between 1 Hz and 6 Hz, between about 2 Hz and 4 Hz, although other frequencies can be used. In some embodiments, the oscillation frequency can be at least 1 Hz, at least 5 Hz, at least 10 Hz, at least 25 Hz, at least 50 Hz, at least 100 Hz, at least 150 Hz, at least 200 Hz, or more depending on the capabilities of the treatment device. The oscillation frequency can be up to 10 Hz, up to 25 Hz, up to 50 Hz, up to 100 Hz, up to 150 Hz, up to 200 Hz, or more, again depending on the capabilities of the treatment device. Then the negative pressure can release over time (e.g., about 5 seconds) until a non-pressurized state is reached. The non-pressurized (e.g., same pressure as ambient pressure) state can be maintained for a time (e.g., about 5 seconds). Then the pressure can oscillate rapidly between a mild positive pressure and a mild negative pressure (e.g., centered on 0 PSI) for a time (e.g., about 5 seconds). Then increasing positive pressure can be applied over time (e.g., about 3 seconds) until a predetermined positive pressure is reached. The predetermined positive pressure can be a predetermined percentage of the maximum positive pressure, or it can be a set value (e.g., 0.2 PSI). The pressure can be held at the predetermined positive pressure for a time (e.g., about 5 seconds), and the pressure can then oscillate rapidly between higher and lower positive pressures (e.g., centered on the predetermined positive pressure) for a time (e.g., about 5 seconds). The positive pressure can then release over a time (e.g., about 5 seconds). This pattern can be repeated for the duration of the treatment phase.

Figure 58:
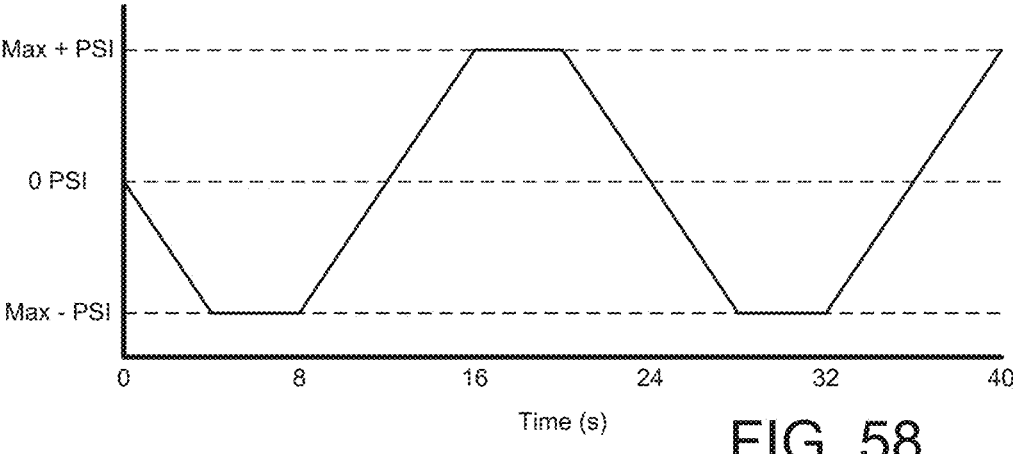

In the treatment parameter profile of FIG. 58, increasing negative pressure can be applied until a predetermined negative pressure (e.g., the maximum negative pressure) is reached after a time (e.g., after about 4 seconds). The predetermined negative pressure (e.g., the maximum negative pressure) can be held substantially constant for a second amount of time (e.g., about 4 seconds). Then the negative pressure can release over time (e.g., about 4 seconds) until a non-pressurized state is reached. Increasing positive pressure can be applied until a predetermined positive pressure (e.g., the maximum positive pressure) is reached after a time (e.g., after about 4 seconds). The predetermined positive pressure (e.g., the maximum positive pressure) can be held substantially constant for a second amount of time (e.g., about 4 seconds). Then the positive pressure can release over time (e.g., about 4 seconds) until a non-pressurized state is reached. This pattern can be repeated for the duration of the treatment phase.

Figure 59:
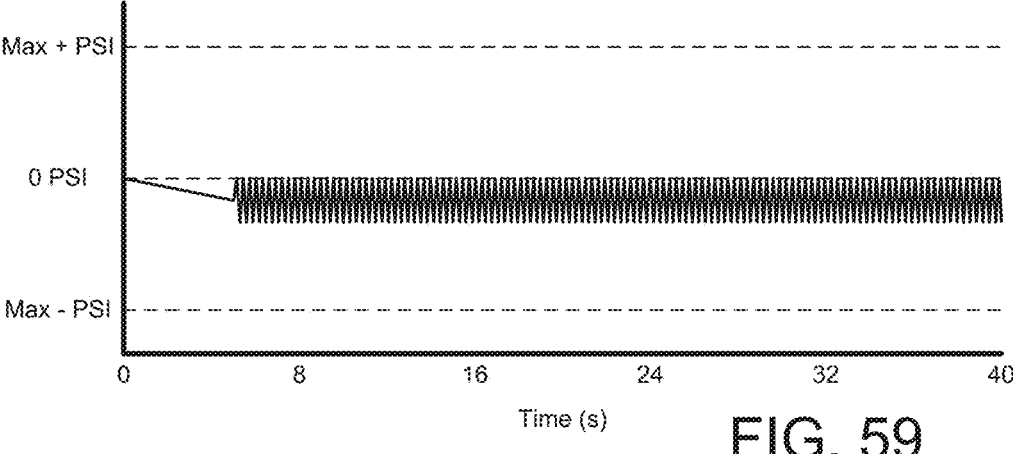

The treatment parameter profile of FIG. 59 can include low amplitude rapid oscillations of pressure. The oscillations of pressure can be centered around a mild negative pressure base line (e.g., less than 50%, less than 30%, less than 20%, less than 10%, or less than 5% of the maximum negative pressure). In some embodiments, the pressure oscillations can be centered on the non-pressurized state or on a mild positive pressure (e.g., less than 50%, less than 30%, less than 20%, less than 10%, or less than 5% of the maximum positive pressure). The pressure can oscillate between the non-pressurized state and a mild negative pressure (e.g., less than 50%, less than 30%, less than 20%, less than 10%, or less than 5% of the maximum negative pressure), such as the example depiction of FIG. 58. Many variations are possible. The pressure can oscillate between a mild negative pressure and a milder negative pressure, between a mild negative pressure and a mild positive pressure, between a non-pressurized state and a mild positive pressure, or between a mild positive pressure and a milder positive pressure. The rapid oscillations can have a frequency between 0.5 Hz and 10 Hz, between 1 Hz and 6 Hz, between about 2 Hz and 4 Hz, although other frequencies can be used. In some embodiments, the oscillation frequency can be at least 1 Hz, at least 5 Hz, at least 10 Hz, at least 25 Hz, at least 50 Hz, at least 100 Hz, at least 150 Hz, at least 200 Hz, or more depending on the capabilities of the treatment device. The oscillation frequency can be up to 10 Hz, up to 25 Hz, up to 50 Hz, up to 100 Hz, up to 150 Hz, up to 200 Hz, or more, again depending on the capabilities of the treatment device. In some embodiments, the profile can start with the pressure changing to the baseline pressure during a time (e.g., about 5 seconds in FIG. 58). The rapid oscillations can repeat during the duration of the treatment phase.

Figure 60:
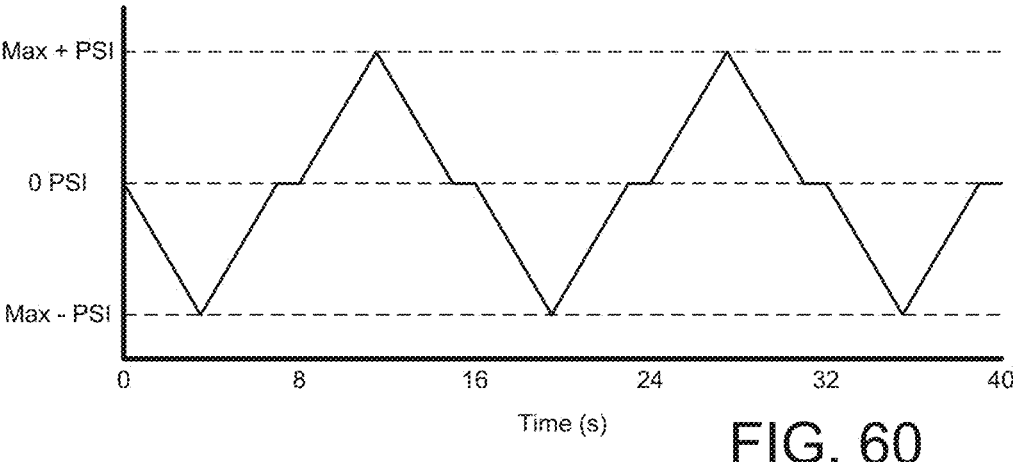

In the treatment parameter profile of FIG. 60, increasing negative pressure can be applied (e.g., for about 3.5 seconds) until a predetermined negative pressure (e.g., the maximum negative pressure) is reached, then the negative pressure can be released (e.g., for about 3.5 seconds) until the 0 PSI state is reached. A non-pressurized state can be held for a time (e.g., about 1 second). Maintaining the non-pressure state between pressure changes may advantageously provide a controlled transition through atmospheric pressure to facilitate a smooth transition and prevent placing excessive strain on one or more components of the treatment system. Then increasing positive pressure can be applied until a predetermined positive pressure (e.g., the maximum positive pressure) is reached after a time (e.g., after about 3.5 seconds). The positive pressure can then be released over a time (e.g., about 3.5 seconds) until the non-pressurized state is reached. The non-pressurized state can be maintained for a time (e.g., about 1 second). This pattern can be repeated for the duration of the treatment phase.

The treatment parameter profile of FIG. 60, in some instances, may be altered to maintain the maximum negative pressure, maximum positive pressure, and/or the non-pressurized state for a longer period of time. In some embodiments, the time to reach the maximum negative pressure and/or maximum positive pressure may be decreased. This would result is a steeper slope than the treatment parameter profile illustrated in FIG. 60. In some embodiments, the treatment parameter profile of FIG. 60 may be altered to only apply negative pressure or positive pressure.

In some embodiments, the pattern of the profile of FIG. 60 can be used for leak detection. Other pressure patterns can be used for leak detection, such as other patterns that extend to the maximum positive pressure and the maximum negative pressure (e.g., FIG. 58). The leak test profile (e.g., FIG. 60) can be executed in connection with FIGS. 10 and 13, discussed herein. In some embodiments, the system can distinguish between a gross leak and a less severe, fine leak (sometimes referred to as a slow leak). For example, if the system is not able to reach a threshold pressure during the leak test (e.g., FIG. 60) or during a treatment phase applying any treatment parameter profile, such as the maximum positive or negative pressure or a predetermined value (e.g., 0.15 PSI) the system can determine that a gross leak is present. If a gross leak is detected during a treatment phase, the system can stop the treatment profile and automatically initiate the leak detection profile (e.g., FIG. 60), in order to assess the leak. If the pressure drops by a threshold amount (e.g., 0.01 PSI or more) during a dwell time (e.g., about 5 seconds), then the system can determine that a slow leak is present. The detection of a slow leak and be based on the slope or rate of decline in the pressure. For example, a pressure loss of more than a threshold value (e.g., 0.002 PSI per second) can be identified by the system as a fine leak (e.g., so long as the system is able to maintain enough pressure to avoid identification of a gross leak). The threshold value for the fine leak can be any value between 0.0001 PSI per second to 0.1 PSI per second, or between 0.001 PSI per second to 0.01 PSI per second, although values outside these ranges can be used in some instances. When a fine leak is detected, the system can continue with the treatment phase, without changing the treatment parameter profile. In many instances, the treatment device can compensate sufficiently for a minor leak, such that the treatment can continue without interruption. In some cases, the system can prompt the user to reseat the earpiece after the treatment phase has completed in response to a detection of a fine leak. In some embodiments, the leak detection pattern can include a pressurized dwell stage, such that the leak detection profile can test for a fine leak.

Different users can have ear canals that are different shapes and sizes. Also, in some instances, a user may position an earpiece in a suboptimal position. These factors can result in leaks. In some embodiments, the system can depend on a closed-loop between the pressure generator and the ear canal, such that a significant leak could degrade or compromise treatment. It can be desirable to limit interruptions in the treatment (e.g., to present a continuous user experience, and/or to avoid interruptions that could affect therapeutic affects). Accordingly, there can be tension between prompting the user to reposition the ear piece in order to reduce or eliminate leaks and tolerating a leak in order to avoid interruption of the treatment. The system can include two categories of leaks: slow leaks and fast or gross leaks. The system can accommodate for slow leaks by detecting the leak and adjusting the pressure generator to compensate for the slow leak (e.g., thereby maintaining a consistent pressure in the ear canal, despite the slow leak). When the system is not able to compensate for the leak, the system can determine the leak to be a fast or gross leak (e.g., a gross leak flag can be raised in the system), and the user can be prompted to correct the seal of the ear piece. Accordingly, if the system is able to compensate for a leak, the system does not need to interrupt the treatment, which can result in a smoother user experience.

A slow leak can be detected during a dedicated leak detection test, or during delivery of treatment based on a pressure treatment parameter profile. For example, a pressure treatment parameter profile can call for a sustained or constant pressure segment (e.g., FIG. 51 from about 7 seconds to about 17 seconds), and the device pressure control loop can attempt to maintain the target pressure (e.g., based on pressures measured by a pressure sensor such as sensor 130). In the event of a slow leak, the system can increase the output of the pressure generator 124 to compensate for the slow leak. One or more parameters (e.g., such as pulse-width modulation) of a motor of the pressure generator can be adjusted (e.g., by changing the frequency, amplitude, and/or widths of pulses) in order to increase the pressure output by the pressure generator. The pressure generator can include a diaphragm or other movable element, and a motor can position the diaphragm or other movable element at different positions to achieve different pressures. In the event of a slow leak, the diaphragm or other movable element may need to be actuated further in order to obtain a target pressure. In some embodiments, the pressure generator can become maxed out, where it is unable to increase the pressure output any further to compensate for a slow leak. For example, a diaphragm or other movable element of the pressure generator can be pegged at its highest pressure state. When the pressure generator becomes maxed out, or when the pressure output exceeds a threshold value, the system can stop the treatment and release pressure down to a non-pressurized state (ambient pressure). Then the system can then restart treatment (e.g., restart the same treatment parameter profile that was being executed, or resume the same treatment parameter profile at the position where the treatment was aborted). For a slow leak, the system may then be able to complete the treatment parameter profile after restarting.

By way of example, treatment may start with the pressure generator using about 60% of its pressure-generating capacity (e.g., the diaphragm or other movable element actuated to 60% of its range) in order to obtain the maximum pressures called for by the treatment profiles. Due to a slow leak, the pressure generator gradually needs to use more of its capacity in order to obtain the maximum pressures, and the 60% value increases to 70%, then 80%, then 90%. The system may operate during this time without interrupting treatment and without prompting the user to reposition the ear piece. Eventually, the pressure generator cannot obtain the target pressure even at 100% of its capacity (e.g., with the diaphragm or other movable element is actuated to the end of its range). The system may have been able to perform a part of a treatment profile, or a full treatment profile, or multiple treatment profiles before the system is no longer able to compensate for the slow leak. In this example, the system was able to operate for about 5 minutes and perform two full treatment profiles while the required pressure generator capacity ramped up from 60%, and the treatment was stopped during the third treatment profile. The system can then performed a controlled release of the pressure to ramp down to a non-pressurized state (e.g., where the ear pressure is the same as ambient pressure). The system can reset the pressure generator to the non-pressurized state (e.g., by moving the diaphragm or other movable element to a non-pressurized position). In some embodiments, the pressure generator can include a vent to ambient pressure than can be opened to enable the diaphragm or other movable element to move to the non-pressurized position without changing the pressure in the ear canal. When the pressure generator has been reset at ambient pressure, the treatment can be restarted. In this example, the third pressure treatment parameter profile can be restarted or it can be resumed at the position where treatment was stopped. The system may then be able to operate for another 5 minutes, for example, and complete more treatment profiles before the pressure generator needs to be reset again.

In some embodiments, the system can reset the pressure generator to the ambient pressure position when the treatment parameter profile calls for ambient pressure (e.g., a non-pressurized state). For example, in the treatment profile of FIG. 49, the system can use ambient pressure from about 8 seconds to about 9 seconds. When the treatment calls for a non-pressurized state (e.g., ambient pressure), the diaphragm or other movable element of the pressure generator can be moved to its non-pressurized position. In some embodiments, a vent can be opened when the pressure generator is reset (e.g., so that ear canal pressure can remain at ambient pressure when the diaphragm or other movable element moves to the non-pressurized position). Then the vent can be closed when the pressure generator applies pressure. The example profile of FIG. 49 has multiple short dwells at ambient pressure. The system could reset the pressure generator to ambient pressure at each opportunity, or it could reset the pressure generator to ambient pressure when it is compensating for a slow leak beyond a threshold amount of its capacity (e.g., when the diaphragm or other movable element is positioned at more than 80%, for example, of its range in order to obtain the maximum target pressures). In some profiles, the pressure crosses ambient pressure to reaches ambient pressure only momentarily. For example, in the example profile of FIG. 51, the pressure reaches ambient pressure only momentarily at about 22 seconds. In some embodiments, the system can cause the treatment profile to pause at ambient pressure and to reset the pressure generator to ambient pressure (e.g., when the pressure generator is beyond a threshold amount of its capacity). For example, if the system determines that the pressure generator should be reset to ambient, the example profile of FIG. 51 could be modified to have a brief delay or dwell at 0 PSI (ambient pressure) (e.g., from about 22 seconds to about 23 seconds) and the treatment profile can then resume.

For example, a diaphragm or other movable element can be movable between a −100% position (to produce a maximum negative pressure) and 100% position (to produce a maximum positive pressure), with a 0% position corresponding to the non-pressurized position. If the pressure generator where to compensate for a slow leak while maintaining a negative pressure (e.g., at about seconds 7 to 17 in FIG. 51), then the position of the diaphragm or other movable element could be offset in the negative direction (e.g., at the −20% position) when producing ambient pressure (e.g., at about 22 seconds in FIG. 51). They system could reset the diaphragm or other movable element to the 0% position at ambient pressure. As mentioned above, the system can open a vent when the diaphragm or other movable element is reset to the 0% position (the non-pressurized position). The profile can pause at ambient pressure while the pressure generator is reset to the non-pressurized state. In some embodiments, the system can reset the pressure generator at ambient pressure only when the diaphragm or movable element is offset by a threshold value when at ambient pressure. The threshold value can be plus or minus 10%, plus or minus 20%, plus or minus 30%, plus or minus 40%, plus or minus 50%, or any values therebetween, or any ranges bounded by any combination of these values, although values outside these ranges can be used in some instances.

In some embodiments, the system can set a slow leak flag when the treatment is stopped. The slow leak flag can be cleared when the treatment device reaches a target pressure. A temporary slow leak, such as a leak caused by the patient temporarily laying in a particular position, could cause only a single slow leak flag, for example. A constant slow leak could result in periodic slow leak flags, where the system interrupts treatment to reset the pressure generator (e.g., each time the pressure generator gets maxed out). A more severe slow leak would cause the slow leak flags to occur more frequently, at shorter intervals. In some embodiments, the system can prompt the user to take action if the frequency of interruptions (e.g., slow leak flags) is above a threshold. For example, the system can prompt the user to reposition the earpiece if the system has interrupted treatment due to a slow leak more than once per treatment profile, more than once per half-a-minute, more than once per minute, more than once per 2 minutes, more than once per 3 minutes, more than once per 4 minutes, more than once per 5 minutes, more than once per 7 minutes, more than once per 10 minutes, or any values therebetween, or any ranges bounded by any of these values, although values outside these ranges could also be used.

In some embodiments, slow leaks can be detected during sustained or constant pressure segments. In some embodiments slow leaks could be detected during changes in pressure, such as if the pressure generator needs to increase its capacity (e.g., increase the rate of moving the diaphragm or other movable element) in order to achieve the desired rate of pressure change.

Gross leaks can be detected when pressure (either negative pressure or positive pressure) is being increased, such as during a dedicated leak detection test or during a ramp section of a pressure treatment parameter profile. If the treatment device cannot reach a threshold pressure, the system can detect a gross leak. The system can release the pressure until a zero pressure state is reached (e.g., ambient pressure). The system can prompt the user to reposition the ear piece. In some embodiments, the system can be configured to receive input from the user as a confirmation that the user has repositioned the earpiece. The system can resume in response to the user input. In some embodiments, the system can provide a time for the user to reposition the earpiece, and the system can resume after that time has expired. In some embodiments, the system can retry the treatment after the non-pressurized state has been reached, without prompting the user for action. The system can prompt the user if the system failed a second time to reach the threshold pressure. The system can set a gross leak flag when a gross leak is detected. And the system can clear the gross leak flag when a threshold or target pressure is reached (e.g., after the user has repositioned the earpiece).

In some embodiments, the system can detect a gross leak when the system is not able to reach a pressure value with a certain amount of effort by the pressure generator. For example, if the system can achieve the minimum threshold pressure, but by actuating a diaphragm or other movable element of the pressure generator beyond a threshold amount, the system can detect a gross leak. In some embodiments, the system can have threshold pressure and pulse width modulation values for detecting a gross leak. In some embodiments a gross leak can be detected during a period where constant pressure is desired (e.g., a dwell portion of a treatment profile). For example, if the pressure drops suddenly or severely, the system can detect a gross leak.

Many alternatives to the treatment parameter profiles described herein are possible. In some embodiments, the treatment profiles discussed herein can be inverted, such that negative pressures are used in place of positive pressure and such that positive pressures are used in place of negative pressures. The over-pressure events (see FIGS. 50-51 and 54-57) can be omitted. The amplitudes of applied pressure can be increased or reduced. Although the charts shown in FIGS. 49-60 show maximum positive pressure and maximum negative pressure values of equal scale, in some instances the treatment device can have different pressure values for the maximum negative pressure and the maximum positive pressure. For example, the maximum negative pressure value can be 0.5 PSI of pressure while the maximum positive pressure can be 0.2 PSI of pressure. The treatment device can be configured to apply positive or negative pressures up to 0.1 PSI, up to 0.2 PSI, up to 0.5 PSI, up to 0.75 PSI, up to 1.0 PSI, up to 1.5 PSI, up to 2.0 PSI, or more.

Figure 61:
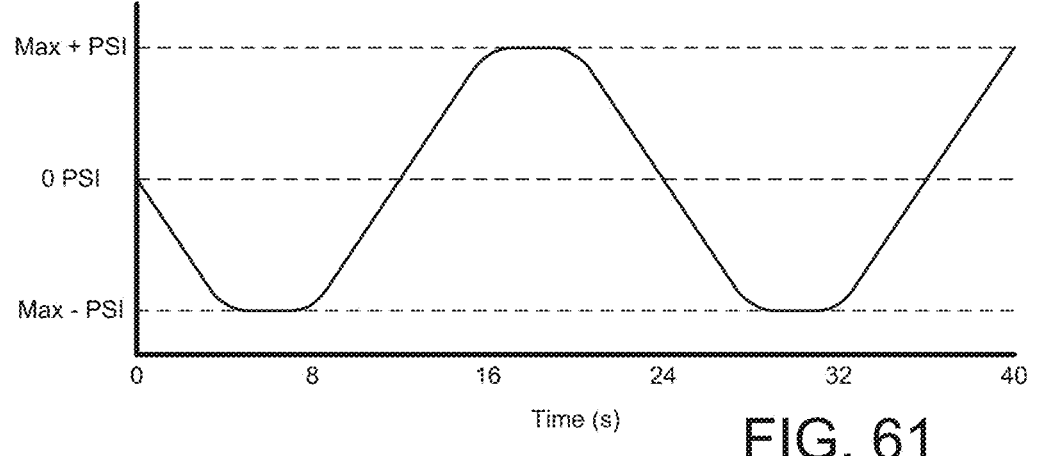

In some embodiments, the pressure changes applied by the treatment device can be softened as compared to the profiles shown in FIGS. 49-60. For example, FIG. 61 shows an example plot of pressure produced by a pressure treatment parameter profile similar to that of FIG. 58, where the transitions between increasing pressure, stable pressure, and decreasing pressure are smoother than shown in FIG. 60. The smoother transitions in pressure changes can be more comfortable to the patient's ear. In some instances, abrupt changes in pressure can be perceived by the user as sounds, which can be distracting to the patient and can interfere with the treatment in some cases. The smoother transitions in pressure changes can reduce this effect and can result in improved treatment. In some embodiments, the electronics of the treatment device can be configured to have a slew rate of around 0.1 V per microsecond, 0.125 V per microsecond, 0.2 V per microsecond, 0.25 V per microsecond, 0.5 V per microsecond, 0.75 V per microsecond, 1.0 V per microsecond, or any values therebetween, or any ranges bounded by the listed values, in order to smooth changes in voltage applied to a motor of the pressure generator in order to soften the pressure changes. In some embodiments, slew rate values outside of these ranges can also be used. Softened waveforms can be used for some or all of the pressure changes in a pressure treatment parameter profile, such as one or more of a baseline to positive pressure cycle, a baseline to negative pressure cycle, a positive pressure to negative pressure (e.g., through a baseline pressure) transition, or a negative pressure to positive pressure (e.g., through a baseline pressure) transition. The pressure generation system can include a motor and is able to generate negative and positive pressures in the ear canal and generate vibration or oscillation patterns about a neutral pressure (relative to atmosphere) state, a positive pressure (e.g., pressurized) state, and/or a negative pressure (e.g., depressurized) state in the ear canal.

In some embodiments, the treatment system can be configured to be used by a patient without direct supervision by a medical professional. The system can include safety feature to avoid over-pressure events that could damage the patient's ear or cause discomfort. The system can have a maximum pressure threshold for positive and/or negative pressure, which can be 1.5 PSI, 1.2 PSI, 1.0 PSI, 0.8 PSI, 0.6 PSI, 0.5 PSI, 0.4 PSI, 0.25 PSI, 0.1 PSI, or any values therebetween, or any ranges bounded by any combination of these values, although values outside these ranges can be used in some instances. The maximum pressure threshold can be at a level the does not cause discomfort in most patients. However, a patient may have an ear injury or may be especially sensitive to ear pressure. The system can enable the user to provide input to change the maximum pressure level. For example, as shown, for example, in connection with FIG. 19, the user can select a high, normal, or low setting, which can correspond to high, normal, and low maximum pressure threshold values. The system can enable the user to adjust the maximum pressure while continuing treatment.

A pressure sensor (e.g., pressure sensor 130) can monitor the pressure applied to the ear. The system can have an over pressure detector. If the measured pressure is above the maximum pressure value (e.g., in either the positive or negative pressure direction), the system can release pressure (e.g., by opening a vent) to reduce the pressure to a level that does not exceed the maximum pressure value. In some embodiments, the treatment system can continue treatment if an overpressure event occurs and is resolved. In some embodiments, the system can interrupt treatment if an over-pressure event occurs, such as to instruct the user to evaluate the ear piece placement.

The maximum pressure threshold value can be higher than a maximum intended operating pressure. For example, in some embodiments, the treatment system can be configured to produce a maximum pressure of plus or minus 0.6 PSI during treatment. The system can have a higher maximum pressure threshold value of plus or minus 0.8 PSI, where the system will take action outside the normal treatment when the pressure exceeds the maximum pressure threshold value. In this example, if the pressure exceeds 0.6 PSI by a small amount, but does not exceed 0.8 PSI, the treatment can continue. They system can adjust the pressure by adjusting the pump or other pressure generator in order to reduce the pressure to the desired value. If the pressure exceeds the 0.8 PRI threshold, the system can open a vent to release the pressure, can cut power to or otherwise stop the pump or other pressure generator, can stop the treatment cycle, and/or can provide a message to the patient to evaluate the ear piece placement.

The treatment device can be configured to deliver only low amounts of noise to the patient's ear. The pump or pressure generator can be located on a treatment device 10 that is not positioned adjacent to the ear (e.g., a hand-held unit). The treatment device 10 can be connected to the earpiece by tubing, which can transmit pressure (e.g., via air) to the ear. Some sound (e.g., from the pump or other pressure generator) can be transmitted to the ear (e.g., via the tubing). The movement of air in the ear can also be perceived by the user as sound, in some instances. The treatment device can be configured to deliver less than 50 dB, less than 30 dB, less than 20 dB, less than 15 dB, less than 10 dB of sound to the patient's ear, or any values therebetween or any ranges bounded by any combination of these values, although values outside these ranged could be used in some implementations.

Figure 61A:
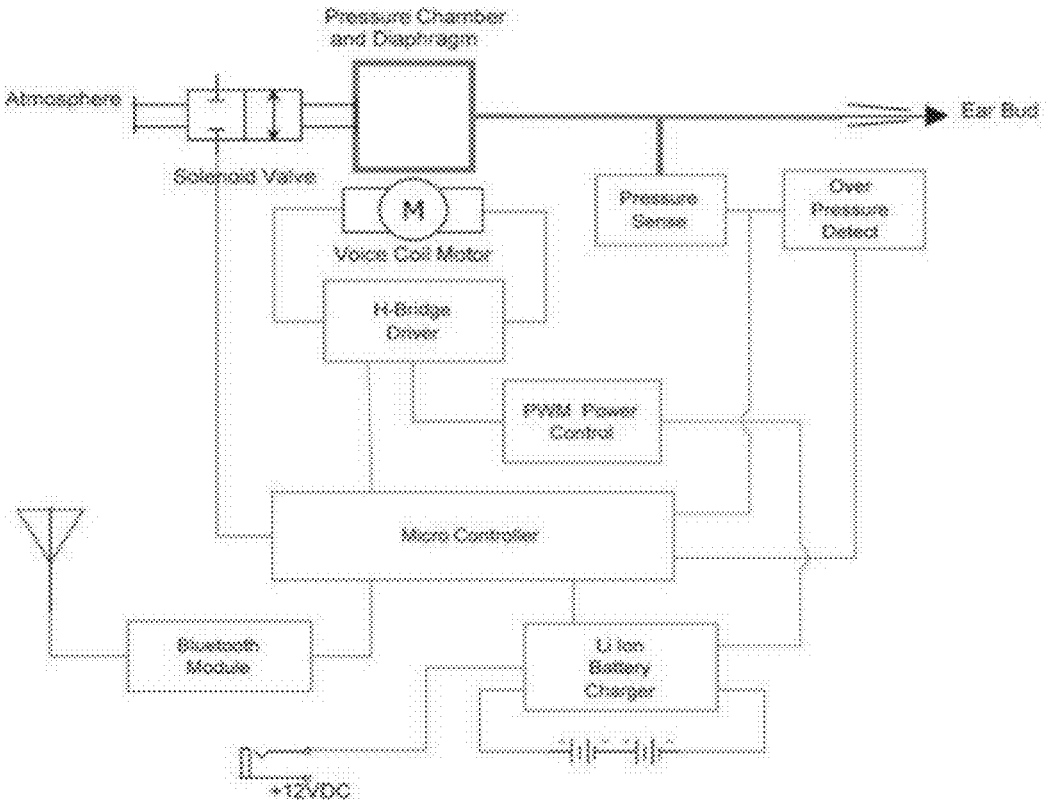
FIG. 61A is a schematic drawing shows an example embodiment of a treatment device.

The pressure generator can have a motor that is configured to produce low amounts of noise (e.g., low amounts of electromechanical noise). With reference to FIG. 61A, the motor can be a voice coil motor, although various other types of motors can be used. In some embodiments, the system can use an H-bridge to control the direction of the motor (e.g., one direction to increase pressure and another direction to decrease pressure). The H-bridge can have four switches. With a first pair of switches on and a second pair of switches off, the H-bridge can drive the motor in a first direction (e.g., to increase pressure). With the second pair of switches on and the first pair of switches off, the H-bridge can drive the motor in a second direction (e.g., to decrease pressure). The H-bridge can use electromechanical switches in some embodiments. The H-bridge can use solid state switches in some embodiments. The motor can use solid state switches to reduce the amount of noise produced. The power delivered to the motor can be controlled by a pulse width mode buck circuit or a constant current source (e.g., a constant current sink). In some embodiments, a solid state H-bridge and a constant current sink can be used to make a system the produced low amounts of noise. The system can have a solenoid valve, or other type of valve, which can be used to vent the system to atmosphere, such as to release pressure in the system.

Without being limited by theory, the ear pressure therapy therapeutic mechanism of action is thought to result from the stimulation of sensory receptors, primarily at the tympanic membrane but also in the ear canal, middle and inner ear. The tympanic membrane and external ear canal have overlapping sensory innervation by cranial nerves V, VII, IX and X, whereas the middle ear is supplied by cranial nerves V and IX, and the vestibulocochlear nerve (cranial nerve VIII) contains afferent fibers from the sensory organs of inner ear. With respect to vestibulocochlear contributions, since both vestibular (saccule) and auditory (cochlea) transducers are situated in the close proximity of stapes, the movement of stapes can stimulate the cochlea as well as the vestibule (saccule). The therapeutic, antinociceptive effects may be mediated via the following potential pathways: auriculotemporal nerve afferent modulation of sensory traffic within the trigeminal nucleus caudalis (TNC) and other sites including the sensory thalamus and cortex; vestibulocochlear nerve to vestibular nucleus to thalamus to parieto-insular vestibular cortex; vagus nerve afferent modulation of sensory traffic within the TNC, rostral sensory modulatory centers, and autonomic centers including the nucleus tractus solitarius.

Disclosed herein are systems and methods of stimulating one, two, or more nerves associated with target anatomical locations. The target anatomical locations could be in some cases one or both ears. In some embodiments, one, two, or more nerves associated with at least one ear are stimulated via at least a first stimulus modality. Some embodiments involve combination therapy including stimulating one or more nerves associated with at least one ear with a first stimulus modality, and a second stimulus modality that is the same as, or different from the first stimulus modality. The nerves stimulated by the first stimulus modality can be the same as, or different than the nerves stimulated by the second stimulus modality. In some cases, combination therapies such as those disclosed herein can create unexpectedly synergistic therapeutic effects in treating or preventing a variety of medical conditions. The stimulus modalities can include, for example, one, two, or more of ear canal pressure regulation stimuli, galvanic stimuli, acoustic (air and/or bone conduction) stimuli, and cold or warm caloric stimuli.

In certain embodiments, disclosed is a method for treating a patient, by administering a combination of regulating ear canal pressure (and in some cases delivering vibration and/or oscillation) in addition to one, two, or more other non-ear canal pressure regulation modalities to a target region of a patient for a synergistic therapeutic effect. In some embodiments, either the ear canal pressure regulation therapy, the other non-ear canal pressure regulation therapy, or both therapies may provide a therapeutic effect when administered separately, but have an enhanced therapeutic effect when administered in a combination therapeutic regimen. For example, in one embodiment where the ear canal pressure regulation therapy has a first therapeutic effect and the non-ear canal pressure regulation therapy has a second therapeutic effect, the combination therapeutic effect has a third therapeutic effect that is greater than the sum of the first and second therapeutic effects. In some embodiments, one or more non-ear canal pressure regulation modalities can be used alone, or independently of the ear canal pressure regulation modality.

In some embodiments, a first stimulation modality can stimulate a nerve associated with the ear, and a second stimulation modality different from the first stimulation modality can stimulate a nerve associated with the ear, which can synergistically effect somatotopic remapping. The therapy can be concurrent, overlapping, or one prior to or after the other therapy. In some embodiments, a first stimulation modality can stimulate a nerve associated with the ear, and a second stimulation modality can stimulate sensory nerves over a different non-ear region of the body experiencing pain, in order to effect somatotopic remapping. The different region of the body can be cutaneous, or visceral organs in some embodiments.

One, two, or more of the stimulus modalities can be synchronized to the cardiac cycle to, for example, increase patient comfort and tolerance of the stimulation. In some embodiments, the stimulus modalities can be synchronized with, and utilize heart rate variability as a closed-loop feedback parameter for adjusting the stimulus based upon heart rate variability measured parameters. The stimulus modalities can be randomized or pseudorandomized, such as via a randomization generator. A variety of otologic, vestibular, neurologic, and other medical and psychiatric conditions can be treated or prevented by systems and methods as disclosed herein, including but not limited to hearing loss, tonic tensor tympani syndrome, acute or chronic pain, trigeminal neuralgia, vertigo, otitis media, and others.

Figure 62:
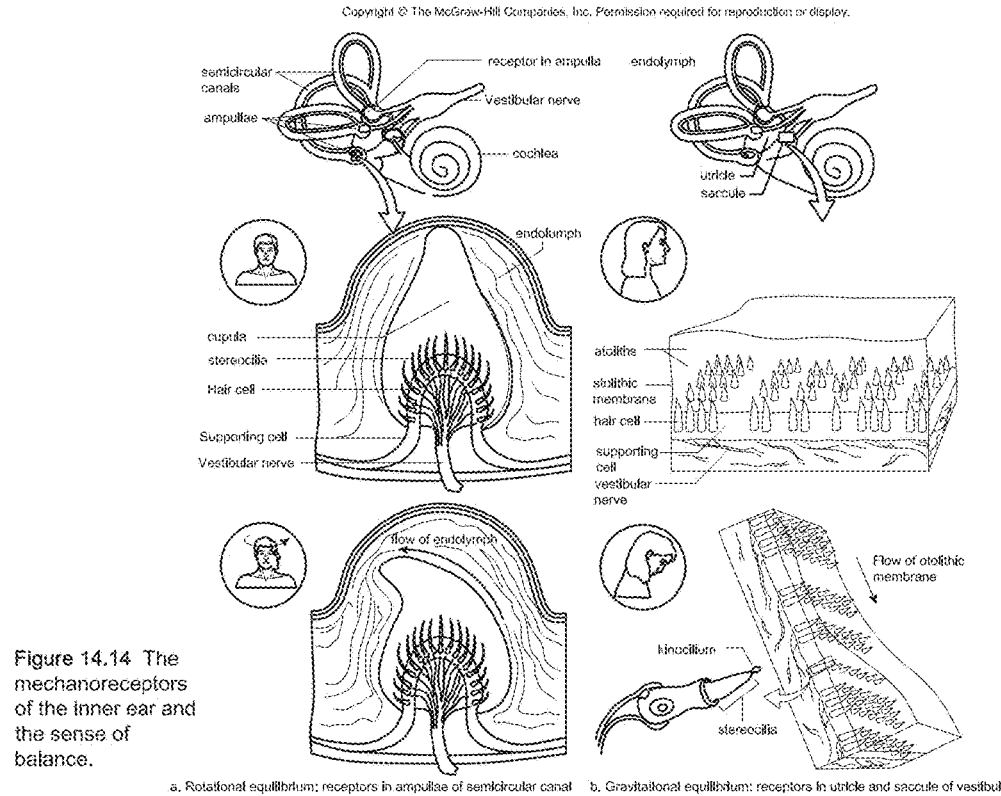
FIGS. 62-62A illustrates the anatomy of selected anatomical structures associated with bone conduction and air conduction.

FIG. 62 is a schematic illustration describing the role of the otolithic organs in controlling position of the eyes and activation of postural stabilizing muscles in response to head tilt; transducing linear acceleration into neural signals in the brain (allowing brain to sense linear acceleration). A shift of position of the otolithic membrane can deflect the stereocilia to or away from the kinocilium, resulting in stimulation or inhibition. Receptors in the ampullae of the semicircular canal can be associated with rotational equilibrium, while receptors in the utricle and saccule of the vestibule can be associated with gravitational equilibrium. Not to be limited by theory, vestibular receptors can be activated by stimulation modalities including sound and vibration, which can both cause fluid pressure waves in the inner ear and that it is these pressure waves which can displace the hair bundles on vestibular receptor hair cells and result in activation of type I receptor hair cells and phase locking of the action potentials in the irregular vestibular afferents, which synapse on type I receptors. In addition to activating cochlear receptors, air conducted sound (ACS) and bone conducted vibration (BCV) activate vestibular otolithic receptors. ACS can activate both saccular and utricular afferents, just as BCV activates both saccular and utricular afferents. Galvanic stimulation by surface electrodes on the mastoids can activate afferents from some or all vestibular sense organs. As one example, low-intensity 500 Hz bone-conducted vibration (BCV) or 500 Hz air-conducted sound (ACS) activate a high proportion of otolith irregular neurons from the utricular and saccular maculae. Saccular neurons have a strong projection to neck muscles and a weak projection to the oculomotor system. Utricular afferents have a strong projection to eye muscles.

Ear Pressure Regulation Stimulation Modalities

U.S. Pat. No. 9,039,639 to George et al., which is hereby incorporated by reference in its entirety and considered part of the specification, discloses in some embodiments of stimulus modalities that can involve external ear canal pressure regulation devices. These devices can include fluid flow generators and an earpiece fluidly coupled to the fluid flow generator. The earpiece can include a compliant earpiece external surface configured to sealably engage an external ear canal as a barrier between an external ear canal pressure and an ambient pressure, and can be used on one or both ears depending on the desired clinical result.

Not to be limited by theory, fluid pressure differentials generated by the fluid flow generators can be capable of moving a tympanic membrane, which lies across the first external ear canal to separate the first external ear canal from a middle ear, effective to alleviate one or more disorder symptoms or treat one or more disorders. The tympanic membrane includes three layers, including an intermediate layer (lamina propria) which is disposed between an external epidermal layer and an internal mucosal layer. The intermediate layer includes modified mechanoreceptive vaterpacinian corpuscles ("mechanoreceptors"), which can be sensitive to deformation or stretch of the tympanic membrane. As such, these mechanoreceptors can function as baroreceptors and transmit afferent signals to the central nervous system associated with inward ("toward the middle ear") or outward ("away from the middle ear") movement of the tympanic membrane. The mechanoreceptors can transmit the afferent signals to the auriculotemporal nerve via A-β pseudounipolar fibers, which subsequently merges with the mandibular nerve. The mandibular nerve converges with the maxillary nerve and the ophthalmic nerve to form the trigeminal ganglion, where the cell bodies of the primary afferent pressure-conveying fibers reside. The afferent fibers are conveyed through the sensory root of the trigeminal nerve to the ventrolateral aspect of the midbelly of the pons. In this way, the trigeminal nerve can transmit sensory signals including nociceptive signals ("pain signals") from the cranium and face to the central nervous system. The afferent fibers then enter the brainstem and synapse on various parts of the trigeminal nuclear system, including the deep lamina of the Trigeminal Nucleus Caudalis, where the afferent fibers can induce GABAergic interneurons to hyperpolarize nociceptive fibers and interneurons in the superficial laminae to block nociceptive transmission.

The pressure differentials between the corresponding first or second external ear canal pressures and the ambient pressure generated by the fluid flow generators can induce an anti-nociceptive barrage of mechanoreceptor-derived neural impulses such that the various related nuclei of the brainstem pain matrix can become attenuated and resume normal, steady-state activity. Also, parasympathetically-induced intracranial vasodilation can cease, restoring resting vascular flow and tone within the cranial vasculature, a portion of which can be associated with the trigeminal nerve and trigeminal nerve fibers as part of the trigeminal system. In addition to modulating vascular dynamics, biochemical alterations can be induced, such as a down-regulation of inflammatory cytokines or other pain-promoting compounds within or around the cranial vascular beds, whereby the vascular normalization can lead to further quiescence of trigeminal nociceptive afferentation which can culminate in the alleviation of one or more disorder symptoms or treatment of one or more disorders. Such systems and methods can also deliver varying frequency patterns, including oscillation/vibration of air and surrounding tissues of the ear, including the ear canal and the tympanic membrane.

Acoustic Stimulation Modalities

The hearing system can be differentiated into two components: conductive and sensorineural. Some anatomical structures relevant to the conductive hearing system including the ear canal, the tympanic membrane, and the ossicles of the middle ear (e.g., the stapes, the malleus, and the incus).

Figure 62A:
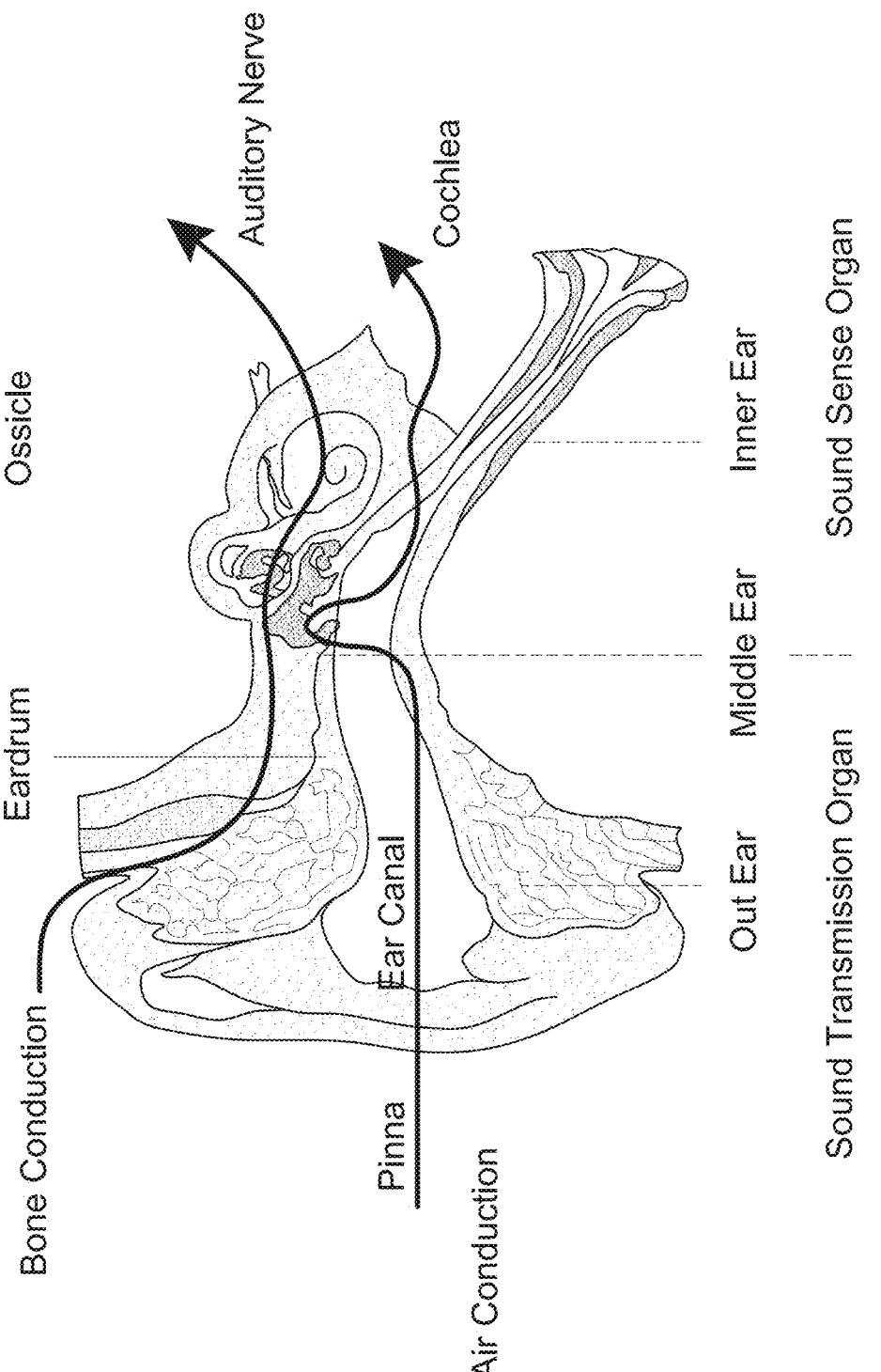

The anatomy of selected anatomical structures associated with bone conduction and air conduction are illustrated in FIG. 62A. Not to be limited by theory, by using bone conduction, systems and methods as disclosed herein can bypass the tympanic membrane sending audio signal to the cochlea through temporal bone. This can advantageously allow for manipulation of the tympanic membrane (e.g., through insufflation) without affecting the transmission of tones and intended sounds, which might otherwise be altered when the tympanic membrane is oscillated, arrested or stimulated by combination therapy with pressure regulation, causing pressure changes in the ear canal.

Acoustic stimulation modalities can involve tone generation via air and/or bone conduction, either as a stand-alone therapy or combination therapy with one or more other modalities as described herein. Tones can be introduced to the patient at set frequencies, rates, and other parameters while the user engages in any form of exercise or therapy. In some embodiments, acoustic stimulation can include rhythmic tones and/or variable pitch, and lead to improvements in variety of brain functions.

In some embodiments, a method for acoustic stimulation involves delivering a force such as a mechanical force to the ear canal, which can mobilize or manipulate the elements of the conductive aspect of the hearing system. The force could include, for example, one, two, or more of stretching, oscillating, warming, cooling, vibrating, and/or deforming one or both ears via an external source, including the auricle, ear canal, tympanic membrane, and/or the ossicles. Prior to, during, and/or subsequent to the delivering of the mechanical force, a selected frequency or range of frequencies of pressure waves can be delivered to the auditory system. Pressure waves can be delivered to the auditory canal, but can also be delivered to the bones of the skull (including but not limited to the temporal bone, for example at the mastoid—as one might associate with bone conduction auditory ear phones). A variety of systems can be utilized to provide acoustic stimulation therapy, including but not limited to bone conduction headphones from, e.g., Aftershokz (Syracuse, NY); or dual mode bone and air conduction headphones from Hanics (Incheon, South Korea). In some embodiments, an acoustic stimulation system includes a speaker and/or audio output. In some embodiments, a system can include a headphone that is operatively coupled to an ear pressure regulation device for multi-modality therapy. In some embodiments, pressure, vibratory, and/or sound waves can be within the range of human hearing (in which case they are referred to as "tones") but these may be, in some cases, above or below the normal human hearing range. Tones can be presented, for example, within the audible hearing range of between about 20 Hz to about 20,000 Hz, such as between about 100 Hz and about 8,000 Hz, or between about 200 Hz to about 1,500 Hz (e.g., continuous pure tones). In some embodiments, the tones can be presented in a range of between about 1 Hz and about 5,000 Hz, such as about 10 Hz, 50 Hz, 100 Hz, 200 Hz, 300 Hz, 400 Hz, 500 Hz, 600 Hz, 700 Hz, 800 Hz, 900 Hz, 1,000 Hz, 1,100 Hz, 1,200 Hz, 1,300 Hz, 1,400 Hz, 1,500 Hz, 2,000 Hz, or ranges incorporating any of the aforementioned values. In some embodiments, a system includes delivery of tones using a plurality of stimulation modalities (e.g., proximate the ear) that can be in phase or out of phase with respect to each other. For example, a first stimulation modality could deliver sound, while a second stimulation modality could deliver vibration (e.g., both in-phase generating a 500 Hz tone, or out of phase with a first stimulation modality generating a 500 Hz tone and a second stimulation modality generating a 1,000 Hz tone). In some embodiments, a pressure-based ear stimulation modality (alone or coupled with sounds and/or air or bone conduction vibration) could cycle at a selected frequency, such as about 10 Hz to facilitate transitional brain states. In some embodiments, a pressure-based/insufflation ear stimulation modality could be coupled with, for example, a vibratory and/or sound delivery modality, and generate a burst of mechanical/pneumatic oscillation at the alternative or same frequencies as the sound or vibratory component.

In some embodiments, one, two, or more stimulation modalities can be used at set frequencies (e.g., a pressure-based ear stimulation modality alone (with sustained single pulses or bursts of pressure pattern pulses in a negative or positive pressure state), or together with sound and/or vibration for example) to create a robust stimulus to stimulate the central nervous system via sensory entrainment.

Figure 62B:
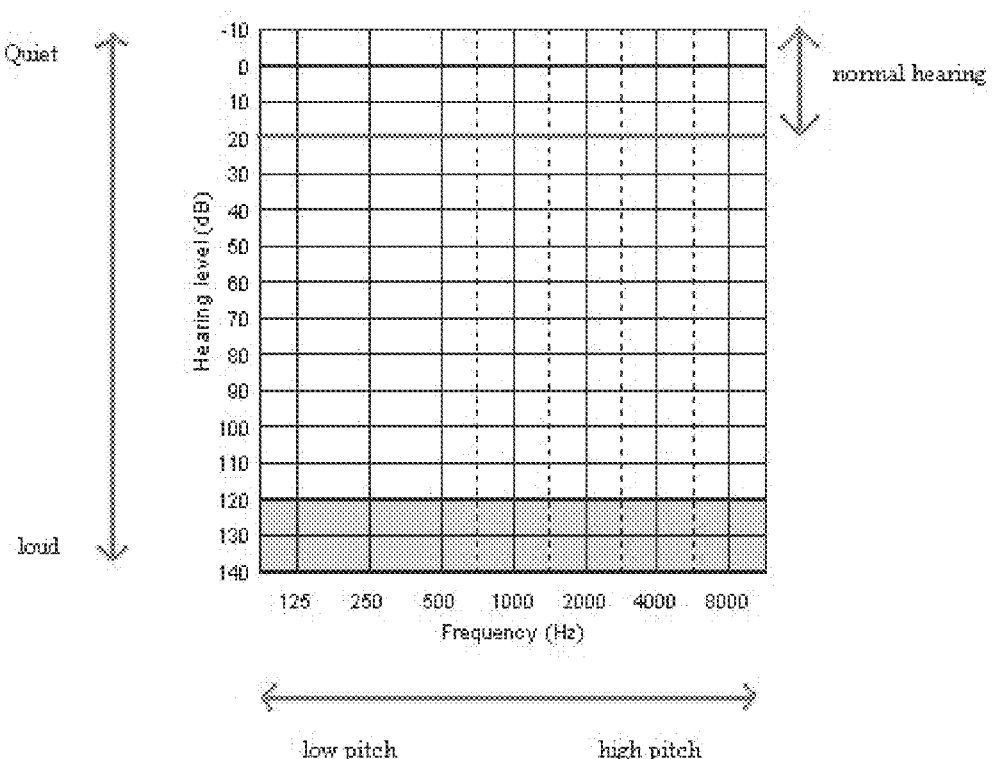
FIG. 62B schematically illustrates a table illustrating non-limiting ranges and values for tone intensity (dB) and frequency (Hz), and illustrating the "normal hearing" range.
Figure 62C:
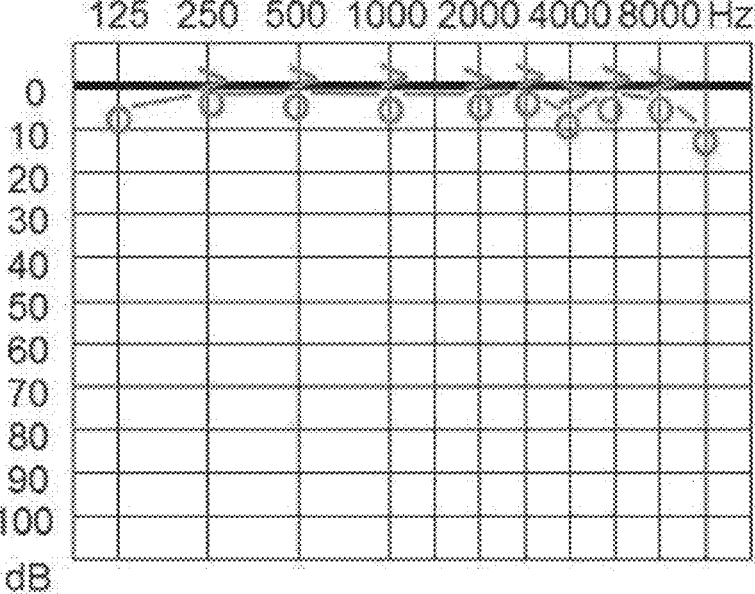
FIG. 62C schematically illustrates an example of a tonaudiogram test, illustrating non-limiting ranges and values for tone intensity (dB) and frequency (Hz), and a range of pitch for tones delivered.

FIG. 62B schematically illustrates a table illustrating non-limiting ranges and values for tone intensity (dB) and frequency (Hz), and illustrating the "normal hearing" range. FIG. 62C schematically illustrates an example of a tonaudiogram test, illustrating non-limiting ranges and values for tone intensity (dB) and frequency (Hz), and a range of pitch for tones delivered.

In some embodiments, the intensity (loudness) of the tones could be, for example, between about 5 dB and about 20 dB, such as between about −10 dB and 15 dB at the hearing level (HL). The intensity could be constant, or variable in some embodiments. Tones can be delivered for any duration depending on the desired clinical result. In some embodiments, tones can be delivered from time periods ranging from a fraction of a second (e.g., about or at least about 5 ms, 10 ms, 50 ms, 100 ms, 250 ms, or 500 ms) to 1 s, 5 s, 10 s, 15 s, 30 s, 60 s, 2 mins, 3 mins, 4 mins, 5 mins, or more as a continuous tone. In some embodiments, tones can be presented as a single burst tone, or a series (train) of tones of a certain duration separated by set or variable pauses of no sound (e.g., a 1,000 Hz tone for a 3 second burst, separated by 2 second pauses). In some embodiments, a tone can be delivered for between about 5 seconds to about 20 seconds, separated by a pause of between about 5 seconds to about 20 seconds, and/or cycled at a desired frequency (e.g., about 10 Hz to facilitate transitional brain states). In some embodiments, the frequencies of stimulus could be matched, or asynchronous.

In some embodiments, acoustic stimulation therapy can be synchronized with electrical activity of the heart as described further below. For example, acoustic stimulation can be configured to fire in sync with a selected phase of the cardiac cycle, and/or adjust filing rate based on feedback information relating to the heart rate or other parameters.

In some embodiments, acoustic stimulation can be used, for example, as hearing restoration therapy; as treatment for hyperacusis (sound sensitivity); as treatment for tonic tensor tympani syndrome; and/or as an adjunct to pain therapy (including but not limited to for headache).

Not to be limited by theory, certain sub-populations with hearing loss suffer from impaired tympanic membrane mobility, leading to reduced potential range of hearing acuity, a portion of the hearing range lost, and deafferentation (and consequence hypofunction) of associated areas of the brain (including the tonotopic map in temporal lobe), causing one or more of peripheral and centrally-mediated components of hearing loss. Insufflation (mechanical mobilization of tympanic membrane through sustained positions, e.g., stretching of the tympanic membrane, and/or vigorous oscillation (of the tympanic membrane and ossicular chain) can allow the tympanic membrane to freely move. The CNS/brain may still remain hypofunctional after movement of the tympanic membrane is restored. As such, providing acoustic stimulation tones to stimulate those areas of the brain through driving plasticity by repetitive tones of various durations can be advantageous. Tones can be configured, for example, to stimulate the neural elements of the auditory system, including the tonotopic map of the temporal lobe and brainstem.

Caloric Stimulation Modalities

In some embodiments, systems and methods can be configured for caloric vestibular stimulation, either above or below body temperature. As disclosed in, for example, U.S. Pat. No. 9,039,639 incorporated by reference in its entirety, e.g., FIGS. 8, 9B, 28, 29A, 40, and the accompanying description, caloric vestibular stimulation systems can include and/or be combined with an external ear canal pressure regulation device including a fluid flow temperature regulator fluidicly coupled between the fluid flow generator and the axial earpiece conduit. The fluid flow temperature regulator can be operable, for example, to regulate a fluid flow temperature of the fluid flow.

In some embodiments, one, two or more fluid flow temperature regulators can be fluidicly coupled to one or more fluid flow generators. The fluid flow temperature regulator can be operated to generate a fluid flow temperature greater or less than a body temperature. In some embodiments, a fluid flow temperature can be selected from one or more of the group including or consisting of: between about 10 degrees Celsius to about 20 degrees Celsius, between about 15 degrees Celsius to about 25 degrees Celsius, between about 20 degrees Celsius to about 30 degrees Celsius, between about 25 degrees Celsius to about 35 degrees Celsius, between about 30 degrees Celsius to about 40 degrees Celsius, between about 35 degrees Celsius to about 45 degrees Celsius, and between about 40 degrees Celsius to about 50 degrees Celsius.

One or a plurality of fluid flow temperatures can be generated with the external ear canal pressure regulation device depending upon the method of use, which can be further influenced by factors such as user anatomy, physiology, or biochemistry of the auditory meatus; disorder symptom targeted for alleviation; disorder targeted for treatment; observable effect(s) of using one or a plurality of fluid flow temperatures (or pre-selected fluid flow temperatures) in a particular method of using the external ear canal pressure regulation device; or the like; or combinations thereof; whereby the one or the plurality of fluid flow temperatures (or third pre-selected fluid flow temperatures) can be effective to alleviate one or more disorder symptoms or treat one or more disorders, but not so much as to cause discomfort to the user or injury to the auditory meatus or the tympanic membrane. In some embodiments, TIAs, strokes, balance disorders, pain, or other disorders or symptoms can be treated using caloric stimulation therapy.

Galvanic Stimulation Modalities

Figure 63:
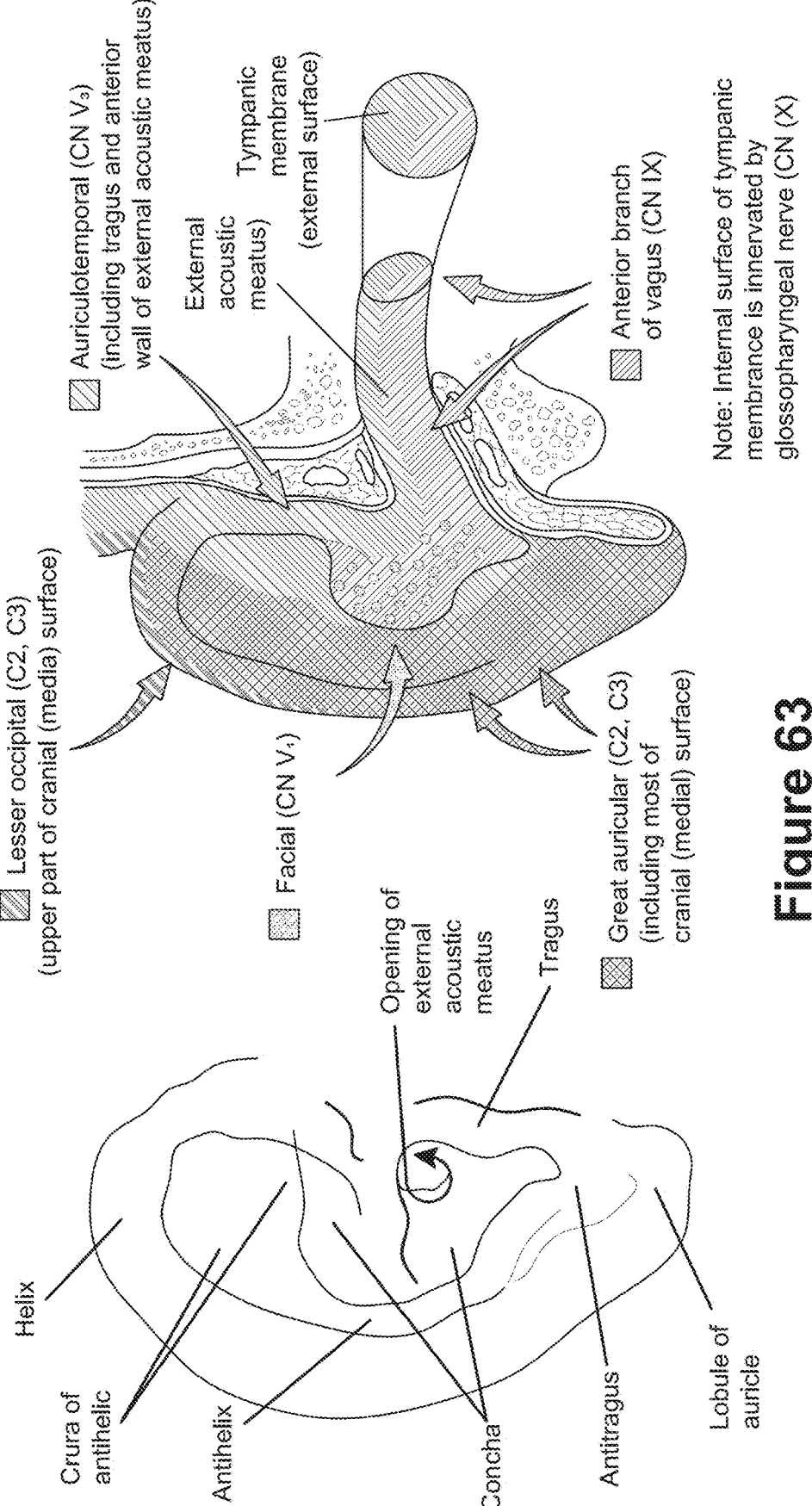
FIG. 63 illustrates various non-limiting potential locations for placement of galvanic stimulation electrodes on the ear.

In some embodiments, a stimulation modality can include galvanic stimulation. Galvanic vestibular stimulation (GVS) is a non-invasive technique that involves a weak direct current passing between surface electrodes placed on, for example, the mastoid behind the ear. GVS modulates the firing rate of vestibular afferents with perilymphatic cathodal currents causing an increase in firing rate and anodal currents causing a decrease. Bipolar binaural GVS can evoke a net pattern of firing across both vestibular organs that mimics a head motion in space. In some embodiments, the polarity of stimulation can be reversed, producing opposite effects on firing rate in the two vestibular organs, and thus reversing of direction of the apparent head motion. In some embodiments, placing the GVS electrodes away from the mastoids allows a sham stimulation, producing the same skin sensations under the electrodes as real GVS, but without stimulation of the vestibular organs. Galvanic stimulation can involve, for example, transcutaneous electrical stimulation on a desired anatomical target, including, for example, a surface of a portion of one or both ears, or proximate one or both ears. to effect galvanic vestibular stimulation. FIG. 63 illustrates various non-limiting potential locations for placement of galvanic stimulation electrodes on the ear, including the helix, the crura of the anthelix, the anthelix, the concha, the anthragus, the lobule of the auricle, the tragus, and the opening of the external acoustic meatus. In some embodiments, the desired anatomical target can be the mastoid process, just behind the ear canal and lateral to the styloid process, and/or one or both tragus. Galvanic stimulation in a location proximate the ear can advantageously stimulate the vestibular system as an alternative to caloric stimulation, bypassing the tympanic membrane to the semicircular canals.

Pain can drive sympathetic activity, and in some embodiments it can be beneficial to drive parasympathetic function (slow heart rate, stimulate gut motility, etc.) via vagal nerve stimulation. Trans-mastoid stimulation can target the vestibular system (via vestibular nerve to the pons). The ear canal sub-module stimulation can affect, for example, the anterior (trigeminal nerve) and posterior canal (vagus nerve) and/or tragus (vagal nerve).

Figure 64:
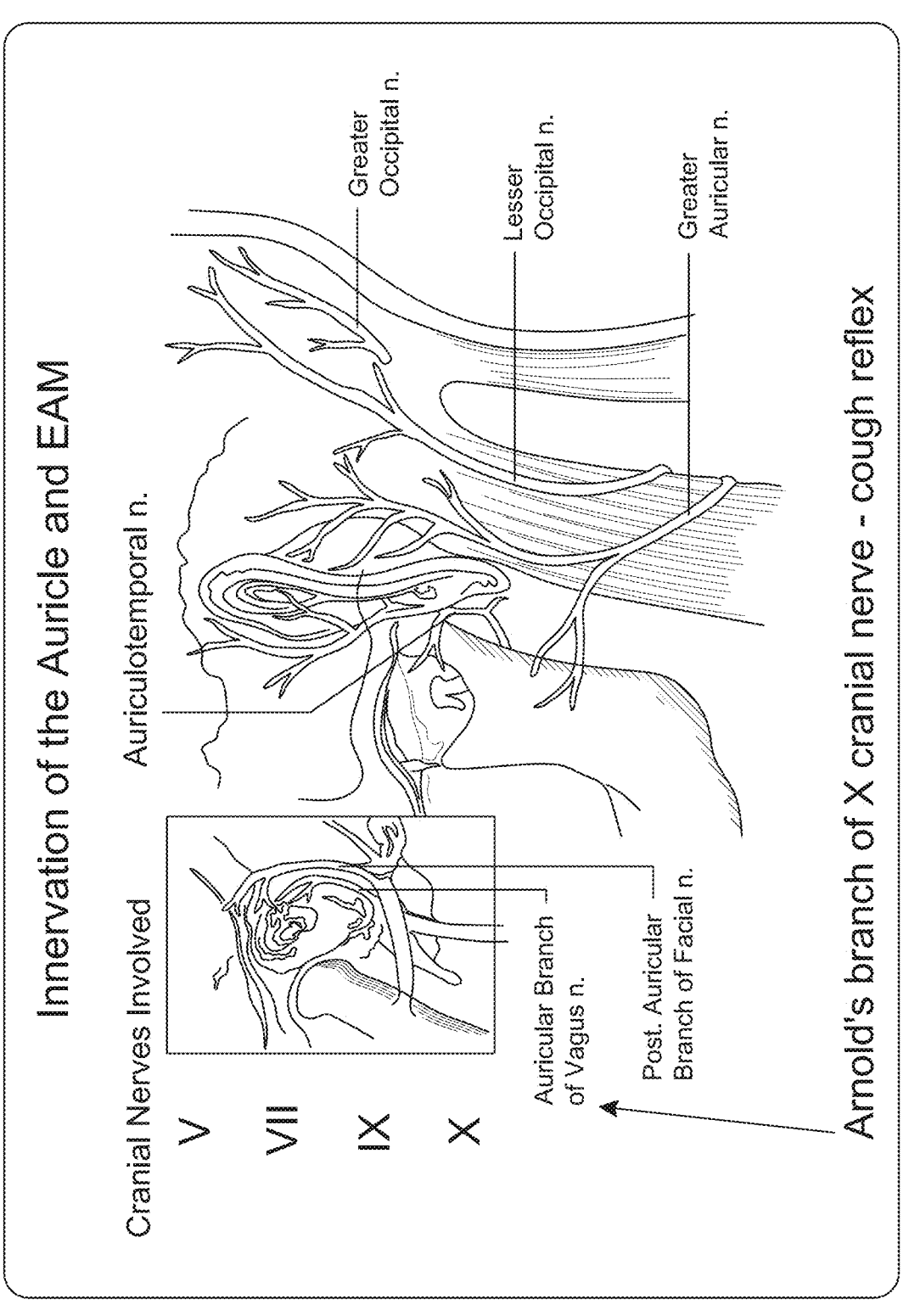
FIGS. 64 and 65 illustrate various nerves innervating the auricle and the external auditory meatus that can be stimulated using systems and methods disclosed herein.
Figure 65:
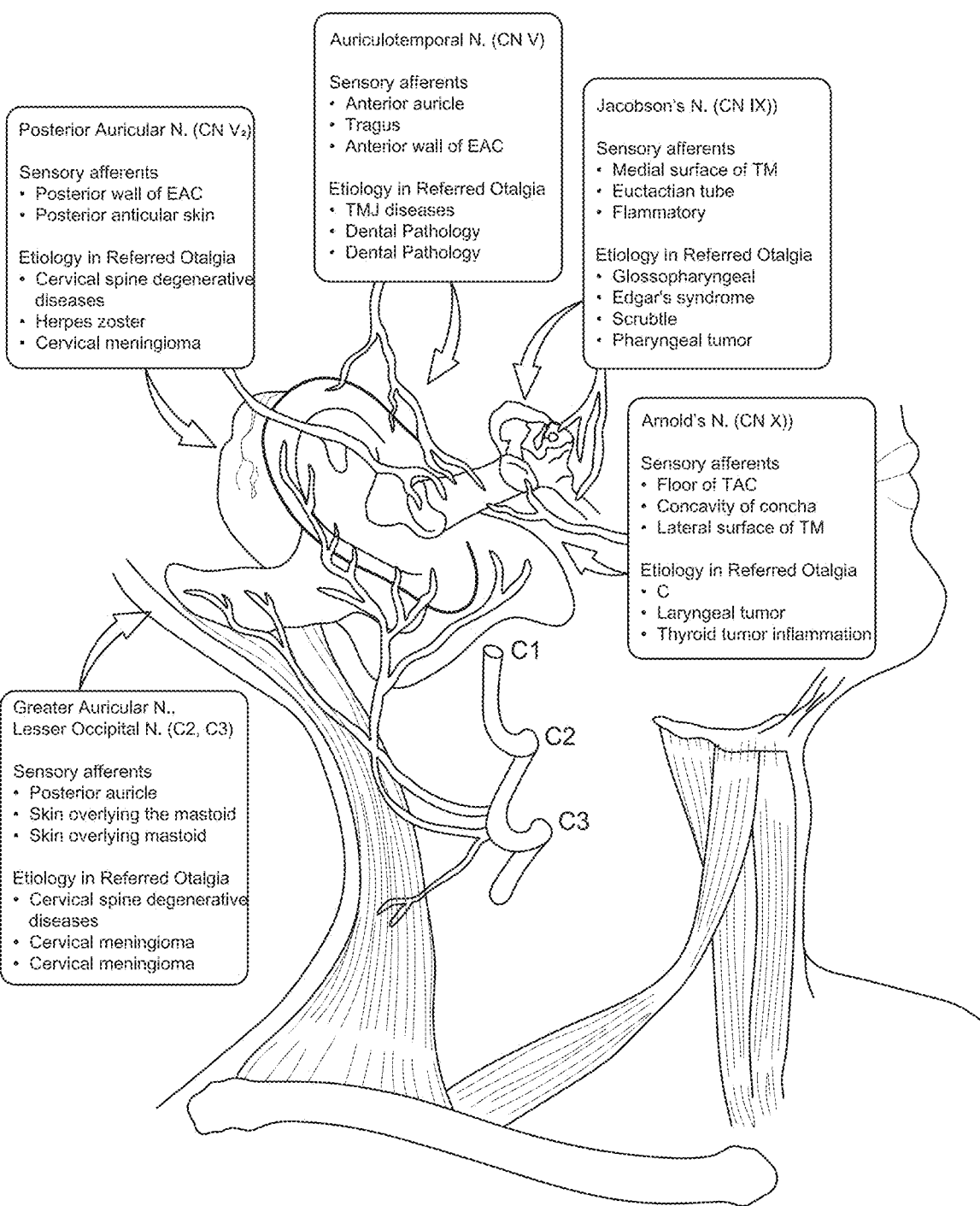

The ear canal itself is divided into 2 nerve distributions: Cranial Nerve V (trigeminal—anterior wall of canal) and Cranial Nerve X (vagus—posterior wall and tragus). By selectively electrically stimulating the posterior canal, the anterior canal, or the tragus or other locations for example, selective stimulation of specific nerves and CNS centers can occur. For example, the trigeminal nerve connects with the trigeminal nucleus, which is the pain processing Nucleus of the brainstem for the face and head. The auricular branch of the vagus Nerve (aka Arnold's nerve) connects with the brainstem vagal nuclei, including the nucleus tractus solitarius (an important processing center in brain associated with parasympathetic system). FIGS. 64 and 65 illustrate various nerves innervating the auricle and the external auditory meatus that can be stimulated using systems and methods disclosed herein, including any number of cranial nerves V, VII, IX, and X and branches thereof, including the auriculotemporal nerve, the greater occipital nerve, the lesser occipital nerve, the great auricular nerve, the auricular branch of the vagus nerve, the posterior auricular branch of the facial nerve, Arnold's branch of the vagus nerve, and others.

In some embodiments, GVS modalities can be utilized in combination with ear pressure regulation stimulation modalities to achieve a synergistic desired clinical result. In some embodiments, one, two, or more stimulation modalities can be combined with a visual illusion such as a display and/or 3D goggles to support the illusion of ascending to altitude or descending to depth. This can be achieved, in some embodiments, by increasing positive pressure as the galvanic stimulation and the visual stimulus create a sense of descending to depth (e.g., such as diving underwater) or by decreasing ear canal pressure when the illusion is targeting creating an illusion of ascending (e.g., taking off in a plane or flying above the clouds). In some embodiments, such effects can be useful for military or civilian flight training, or entertainment purposes such as enhanced movies, virtual reality games, and the like.

In some embodiments, GVS modalities can be utilized in combination with ear pressure regulation stimulation modalities to stimulate the vestibular system (including the. cerebellum and associated areas of the brain) in conjunction with the trigeminal system. In some cases, this leads to unexpectedly synergistic brainstem stimulation that may not be found in nature (e.g., unilateral negative canal pressure with simultaneous discharge of the ipsilateral vestibular system). By simultaneously stimulating the vestibular and trigeminal system, some embodiments can induce brain plasticity that can advantageously stimulate remapping of cortical maps and counteract the central changes associated with centrally-mediated chronic pain.

In some embodiments, GVS systems and methods described herein may use AC current or near DC current and use a maximum stimulation of, for example, about or less than about 5 mA, 4 mA, 3 mA, or 2.5 mA. In some cases, a stimulation dose can be from about 1 mA to about 2.5 mA. For example, a stimulation dose can be about 1, 1.5, 2.0, and 2.5 mA. In some cases, maximum stimulation can be applied without any time delay and with greater than 2.5 mA of current. In some cases, stimulation can be ramped up to the maximum stimulation current over a period of time. For example, stimulation can be ramped up from about 0 ms to about 600 msec. For example, stimulation can be ramped up in about 25, 75, 175, 300, or 600 msec. In some cases, stimulation can be terminated immediately after the response has been achieved. In some cases, stimulation can be ramped down. For example, stimulation can be ramped down from about 0 ms to about 600 ms. For example, stimulation can be ramped down over 25, 75, 175, 300, or 600 msec.

In some embodiments, devices and methods for transcutaneous vagus nerve stimulation can include a stimulation unit and a dedicated ear electrode, such as, for example, the NEMOS system from Cerbomed GmbH (Germany), and U.S. Pat. No. 7,797,042 to Dietrich et al., which is hereby incorporated by reference in its entirety. Impulses can be transferred via the ear electrode through the skin to a branch of the vagus nerve. Some embodiments can involve the combined application of a transcutaneous electrical stimulus to the surface of a portion of the human ear and emission of an acoustic signal into the auditory canal of the ear, such as those disclosed in U.S. Pat. No. 8,885,861 to Cerbomed GmbH, which is hereby incorporated by reference in its entirety. In some embodiments, devices and methods for the application of a transcutaneous electrical stimulus to the surface of a portion of the human ear can be as disclosed in U.S. Pat. App. Pub. No. 2014/0127666 to Cevette et al., which is hereby incorporated by reference in its entirety. The foregoing systems and methods that can involve GVS can be in some embodiments used in combination with ear pressure regulation stimulation therapies as disclosed herein, as well as other stimulation modalities to achieve synergistic results.

Coupling of Tactile Stimulus with Tone Sequence

In some embodiments, a tactile stimulus can be matched with an audible tone, with the tactile stimulus frequency potentially dropped by 1, 2, 3, or more octaves, to allow for an octave shift conversion of the tactile stimulus with a sequence of tones. In some embodiments, the octave shift conversion can be accomplished by a controller configured for pitch shifting. A sequence of tones could be any sequence, including a piece of music wherein each tone is matched with a corresponding tactile/haptic stimulus at the ear, on the body or both. The system could allow for entry of music or pre-determined tone sequence, which is converted into a corresponding sequence of haptic/tactile stimuli.

Test-Manipulate-Stimulate-Test

In some embodiments, disclosed herein is a stimulation system that includes a test, manipulate, and stimulate functionality. The system can be delivered, for example, by a mobile phone, tablet, or other device. The system might be presented as a therapy to enhance hearing wherein a short test (resembling the common audiogram test wherein a sequence of tones is delivered at certain intensities (levels of loudness)) to predetermine the status of hearing system is administered. The patient can then signal whether or not each tone(s) have been actually heard by the patient. This can be followed by application of a stimulus modality to the ear, followed by introduction of prescribed sequence of audible tones at or around the areas of "weakness" in the user's hearing system (as determined by the pre-screening).

In some embodiments, if a tone is not heard by the patient, a range of tones around that tone can be presented, to determine the actual target range of hearing loss. For example, if a patient has a 10 dB hearing loss at around 5 Khz, the system could be configured to present tones at 5.5 kHz and 4.5 kHz, followed by bringing these range ends closer to each other over consecutive sessions, thereby "zoning in" on the target range of loss. In some embodiments, the initial target range around the specific hearing loss data point is within about 20%, 15%, 10%, 5%, or less of the specific hearing loss data point, and subsequently narrowed to focus in on the target range of loss.

Tilt-Table Systems

In some embodiments, systems and methods as disclosed herein incorporating one, two or more stimulation modalities (including but not limited to pulses of pressure, warm/cold pulses of pressure or vibration) can incorporate a tilt table or similar device configured to orient a subject at one, two, or more target angles with respect to gravity (horizontal or vertical). The target angle to horizontal (or vertical) could be, for example, about 10°, 20°, 30°, 40°, 50°, 60°, 70°, 80°, 90°, 100°, 110°, 120°, 130°, 140°, 150°, 160°, or 170° degrees or ranges incorporating any of the two aforementioned angles. This can in some cases advantageously stimulate the vestibular system at target angles in space. The body and/or head of a subject can be moved to a desired position (e.g., back and to the right/left; forward and to the left/right; laterally flexed left/right; flexed forward/back). Such embodiments can be advantageous for users with different forms of dysautonomia (dysfunction of the autonomic nervous system), where commonly, regulation of blood pressure, for example is problematic. Dysautonomia can be primary, such as with, for example, postural orthostatic tachycardia syndrome (POTS), neurocardiogenic syncope (NCS), or multiple system atrophy (MSA); or secondary to other conditions such as adrenal insufficiency, diabetes, multiple sclerosis, rheumatoid arthritis, celiac disease, Sjogren's syndrome, lupus, or Parkinson's disease, for example. By stimulating the ear in this way, the vestibular and trigeminal pathways can be utilized to stimulate the brainstem, including the pons (which hosts parasympathetic nuclei).

Eye Movement Monitoring

In some embodiments, one, two, or more stimulation modalities can be incorporated as part of a system to monitor eye movements. U.S. Pat. No. 9,186,277 to George et al., incorporated by reference in its entirety, discloses in some embodiments a hybrid therapy, which combines pulses of air into the ear (insufflation) with caloric irrigation (warm/cold air used for the aforementioned purpose). Utilization of varied patterns of frequency and amplitude of pressure pulse waves at certain temperatures can advantageously stimulate the central nervous system (including but not limited to the brain and brainstem), via the vestibular system. The utricle and saccule (referred to as the otolithic organs) and the vestibular canals, as well as the cochlea, all share endolymph—a liquid/almost gel-like medium. By warming or cooling this medium and delivering vibratory, oscillatory or kinetic forces to the middle and inner ear (e.g., by way of the external ear through the device), receptors associated with balance (rotary and linear movement) and hearing (the cochlea and its receptors) can be advantageously stimulated. A non-limiting example of utilizing these systems and methods as a therapy is described above with tilt-table and similar systems that can advantageously stimulate the vestibular system at target angles in space, and where the body and/or head may be positioned into a certain position (e.g., back and to the right/left; forward and to the left/right; laterally flexed left/right; flexed forward/back) while patterns of energy are delivered into the ear canal. The stimulation can be unilateral or bilateral. Stimulation involving force and higher or lower temperatures for example may be matched or mismatched in each ear.

In some embodiments, including stimulation where the patient is positioned at a target angle in space to horizontal or vertical; and/or with stimulation for the treatment of canalithiasis and cupulolithiasis for example, treatment effects can be observed by monitoring eye movements, which can be achieved through systems such as VNG (video nystagmography). As such, systems and methods as disclosed herein can be advantageously combined with eye movement detection systems such as VNG, e.g., the VISUALEYES VNG system from Micromedical Technologies (Chatham, IL). For example, the caloric irrigation test involving warming or cooling of the ear can cause ocular nystagmus. This nystagmus can be accompanied by a sense of vertigo in the user. Combining stimulation with an eye monitoring device can be utilized to eliminate, mitigate, or prevent vertigo (and associated risk for fall or injury). For example, as the stimulation therapy is being applied, e.g., pulses of "warm/cold pressure" (flow of warm or cold air into air in specific patterns of frequency and amplitude) delivered into the ear canal (to, for example, stimulating the brainstem or liberating canaliths as described elsewhere herein, the eyes are monitored via the eye movement detection system to either modulate (increase or decrease) stimulation to increase efficacy and/or decrease adverse side effects. For example, detection of a pre-determined pattern of undesirable eye movement, e.g., significant nystagmus, can stop or reduce the warm pulses to avoid vertigo, or continue stimulation (e.g., for treatment of canalithiasis or cupulolithiasis where vertigo is a desired effect for confirmation that canaliths are in fact moving, and as such treatment is efficacious).

Randomization of Stimulation

In some embodiments, the stimuli from one, two, or more stimulation modalities as disclosed herein can be delivered through randomized or pseudorandomized stimulation signals. Any number of stimulation parameters can be randomized, including but not limited to stimulus waveforms (including but not limited to pressure waveforms), repetition rates, pulse width, pulse amplitude, burst frequency, stimulus frequency, amplitude, temperature, and/or others. In some embodiments, the randomized or pseudorandomized parameters can be preprogrammed into a control unit and selected randomly or pseudorandomly from a hardware or software controller, which can be configured to operably communicate with a stimulus generator of one, two, or more stimulation modalities. Not to be limited by theory, but randomization or pseudorandomization can prevent tolerance and decreased efficacy created by constant monotonous stimulation (also applicable to other modalities discussed herein). In some cases, therapeutic effects are subjected to significant neural plasticity in the brain. The brain can adapt to almost non-varying stimulation patterns, which disadvantageously diminishes therapeutic effects over extended periods of time. As such, it can be desirable to provide stimulation that reduce adaptation or desensitization effects.

Synchronizing Stimulation with the Cardiac Cycle

In some embodiments, any one, two, or more stimulation modalities as discussed herein can be synchronized with the cardiac cycle and/or electrical activity of the heart. For example, one or more stimulation modalities can be configured to fire in sync with a selected phase of the cardiac cycle, and/or adjust filing rate based on feedback information relating to the heart rate or other parameters. Systems and methods can synchronize with, for example, ECG (electrocardiography) sensors which measure the bio-potential generated by electrical signals that control the expansion and contraction of heart chambers; or PPG (photoplethysmography) sensors using a light-based technology to sense the rate of blood flow as controlled by the heart's pumping action.

Not to be limited by theory, this can be advantageous in some cases as the brain normally tunes out heart rate sensations. By synchronizing pulses of an insufflator and/or pulses of stimuli throughout other modalities, it can be possible in some embodiments to synergistically enhance the anti-nociceptive and nervous system stimulating effects of these modalities. Furthermore, by synchronizing output of all receptor-based stimuli (e.g., insufflation, galvanic, tones, tactile stimulation) to specific part of cardiac cycle, it can be possible to utilize innate habituating mechanisms of the brain (e.g., cancelling of irrelevant environmental stimuli) to couple painful areas (e.g., trigeminal system of the head in headache or painful area of limb in complex regional pain syndrome) to stimulus synchronized with the cardiac cycle to cause the brain to cancel out the pain.

In one embodiment, ear pressure regulation stimuli can be provided to the tympanic membrane in synchronization with systole or diastole, one can fire impulses into the trigeminal system of the brain and stimulate the brain to ignore pain signals from this area—thereby lowering head and facial pain (headache or facial pain syndromes). In some embodiments, stimulation can be synchronized with the P wave, QRS complex, T wave, or other electrical activity of a heart identified on EKG.

In some embodiments, one, two, or more stimulation modalities as described herein can be randomly synchronized with certain phases of the cardiac cycle, in order to counteract stimulation. For example, synchronizing stimulation with the diastole may function to enhance parasympathetic functions. In some cases, parasympathetic drive can be stimulated, in order to achieve any number of the following: slow heart rate (e.g., by forcing delay of the user's SA node activation) and lower blood pressure; drive gut motility (e.g., in constipation, irritable bowel syndrome, ileus, or other conditions); constrict pupils in light sensitivity; lubricate nasal and oral mucosa; and/or stimulate sexual function (e.g., erection in men and lubrication in females). In some embodiments, sympathetic drive can be stimulated. For example, synchronizing stimulation with the systole may function as an analgesic, as discussed herein.

Synchronization and Utilization of Heart Rate Variability as a Feedback Parameter In some embodiments, heart rate variability (HRV) can be utilized as a feedback parameter to assess treatment response to stimulation utilizing one, two, or more modalities as described herein. Heart rate variability is sometimes referred to as cycle length variability, RR variability (where R is a point corresponding to the peak of the QRS complex of the EKG wave; and RR is the interval between successive R waves), and heart period variability. It is the physiological phenomenon of variation in the time interval between heartbeats, and is measured by the variation in the beat-to-beat interval. HRV can be analyzed, for example, under time-domain, geometric, and frequency domain methods. HRV can assess autonomic adaptation to pain and other innervations, such as confirming an increase in vagal tone and confirm overall positive balance in sympathovagal balance.

In some embodiments, increased heart rate variability can signify increased parasympathetic response and/or decreased sympathetic response, which can be evidence in some cases of a positive therapeutic effect. Decreased heart rate variability can signify decreased parasympathetic response and/or increased sympathetic response, which can be evidence of stress, acute or chronic pain, myocardial infarction, diabetic neuropathy, or other conditions. In some embodiments, a system can sense an increase or decrease in HRV of about or more than about 5%, 10%, 15%, 20%, 25%, 30%, 35%, 40%, 45%, 50%, 75%, 100%, or more over a baseline value (or target desired HRV value) and institute a change in one, two, or more stimulation modality parameters accordingly. In some embodiments, the one, two, or more stimulation modalities can be configured to stimulate the parasympathetic nervous syndrome (e.g., via the vagus nerve), and a favorable response to therapy can be confirmed by sensing an increase in parasympathetic tone, such as an increase in HRV. In some embodiments, a vestibular stimulus (e.g., a galvanic stimulus to the mastoid) or receptor stimulus (e.g., insufflation to the ear and/or body stimulus via electrodes or tactile stimulus) can be synchronized to the heart rate and/or heart rate variability.

Synchronization and Utilization of Additional Feedback Parameters

In some embodiments, any one, two, or more stimulation modalities as discussed herein can be synchronized or otherwise adjusted with respect to one, two, or more inputs relating to a patient, including but not limited to physiologic reference points, e.g., the cardiac cycle and/or electrical activity of the heart as disclosed herein. In some embodiments, the input is a movement of the patient or lack thereof, such as kinetic or akinetic tremors (as associated with, for example, benign essential tremor, Parkinson's disease, Lewy body dementia, cerebellar disease, and/or other forms of dystonia or movement disorders including but not limited to chorea, tardive dyskinesia, seizures/epilepsy, spasticity, and Tourette's syndrome). As such, the system can detect a tremor by way of, for example, one, two, or more of the following: accelerometers (from a mobile device), gyroscopes, electromyography (needle or surface electrodes), any form of sensor on the body surface that can detect movement, direct reading from the cortex (e.g., somatosensory evoked potentials or EEG), and/or any transducer configured to convert kinetic oscillations or cyclical changes in muscle tone into sound, visual, or other feedback/forms of information. A sensor can measure, for example, tremor amplitude, latency, and/or frequency. In some embodiments, a subject can be placed into a low-sensory environment (e.g. a dark, quiet room; lying on their back in some cases), during which time the system can detect tremor and delivers one, two, or more stimuli such as pulses of energy (e.g., pulses of warm air into the canal to stimulate the ear) at a rate to match (synchronous pulses) or mismatch (asynchronous pulses) the tremor. This method can in some cases stimulate the brain's inhibitory network (primarily the basal ganglia) to inhibit activity at the rate of the external stimulus but due to the fact that the stimulus is relatively less intense than an actual muscle tremor, the brain is "exercised" with a stimulus that it can manage. Not to be limited by theory, systems and methods as disclosed herein can stimulate the basal ganglia in cases of dystonia where there is excess muscle tone and any stimulation of muscles might only exacerbate the subject's condition—e.g., drive more spasticity and muscle tone. As such, one, two, or more peripheral stimulation modalities (e.g., proximate the ear) can advantageously and in some cases non-invasively modulate the central nervous system and treat a movement disorder as noted above, without in some cases necessarily stimulating muscle counter-stimulation to the tremor.

Furthermore, in some embodiments, systems and methods as disclosed herein can treat acute or chronic pain, and be configured to stimulate the brain's default mode network. In some cases, one, two, or more stimulation modalities including but not limited to pulses at the ear and/or other parts of the body, including heart rate, bowels sounds, breathing rhythm and/or other physiologic rhythms can amplify enteroceptive awareness. This can be coupled in some embodiments with a meditative, hypnotic or directed instruction (either delivered by person or by automated system), which can in some cases further stimulate the brain's default mode network. The insula, a significant component of the brain's default mode network, is also associated with enteroceptive awareness. The ability to stimulate the brain's primitive vestibular system (e.g. with warming/cooling of air in the ear canal, coupled with tactile stimuli within the trigeminal system (e.g. by pulses of air pressure or vibration in the ear canal) while stimulating this part of the brain can be utilized to treat acute and chronic pain, and other psychopathology (e.g., anxiety, PTSD, depression, schizophrenia, etc.)

Closed Loop Feedback Systems

Figure 66:
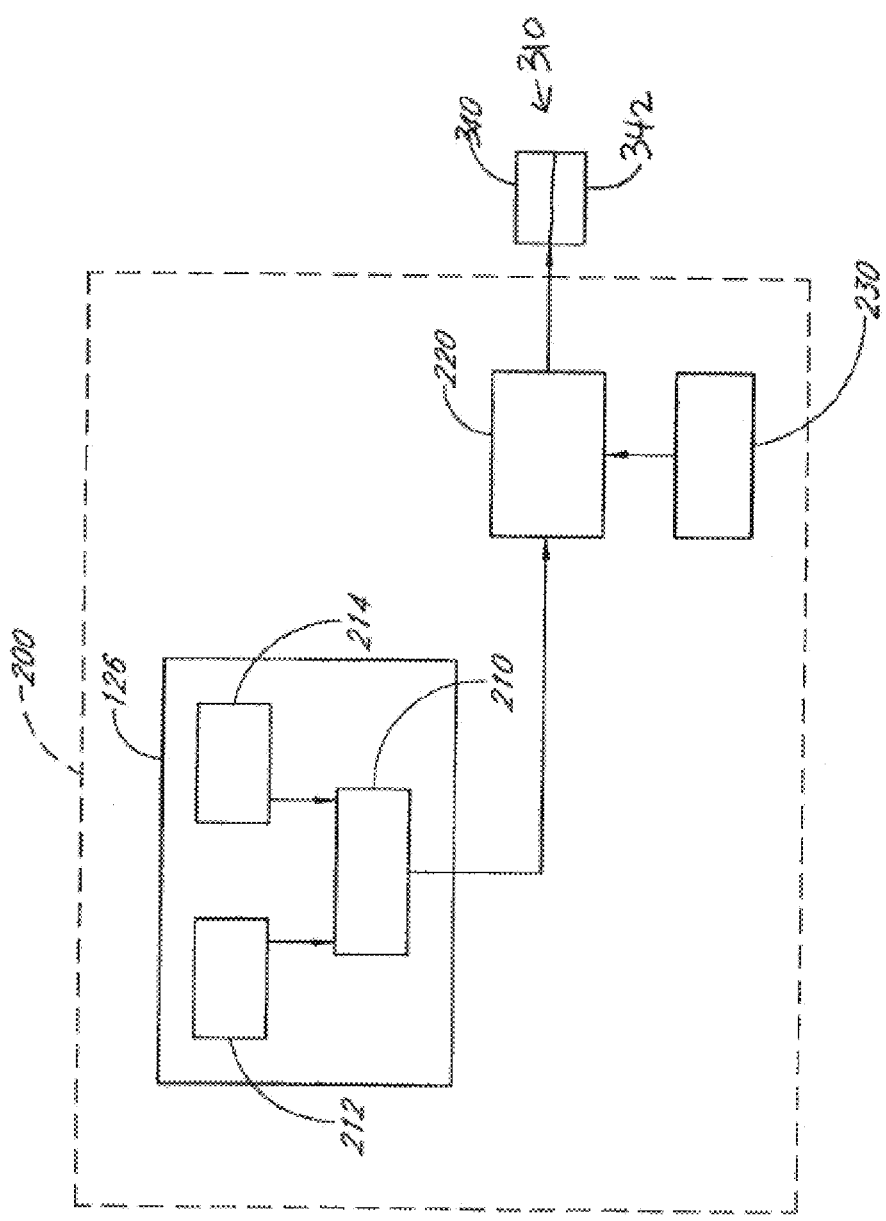
FIG. 66 is a schematic block diagram of a control circuit comprising a programmable controller for controlling a first stimulation modality and/or a second stimulation modality according to certain embodiments described herein.

FIG. 66 is a schematic block diagram of a control circuit 200 comprising a programmable controller 126 for controlling a first stimulation modality 340 and/or a second stimulation modality 342 according to certain embodiments described herein. The control circuit 200 can be configured to adjust parameters of the first stimulation modality 340 such that the stimulation corresponding to a predetermined stimulation profile to a target location, e.g., on or proximate the ear. In some embodiments, the stimulation profile could be an ear pressure differential. Similarly, the control circuit 200 can be configured to adjust the power or other parameters, as mentioned elsewhere in the application, of the second stimulation modality 342. If the second stimulation modality 342 is a galvanic stimulation modality, for example, the control circuit 200 could be configured to adjust the power, frequency, pulse rate, or other parameters. In some embodiments, the first stimulation modality 340 and second stimulation modality 342 could be controlled by a single controller, or a plurality of controllers, with each controller controlling a particular stimulation modality.

In certain embodiments, the programmable controller 126 can include one, two, or more logic circuits 210, a clock 212 coupled to the logic circuit 210, and an interface 214 coupled to the logic circuit 210. The clock 212 of certain embodiments provides a timing signal to the logic circuit 210 so that the logic circuit 210 can monitor and control timing intervals of the first stimulation modality and the second stimulation modality. Examples of timing intervals include, but are not limited to, total treatment times, and time intervals between pulses of the first and/or second stimulation modalities. In certain embodiments, the first stimulation modality 340 can be selectively turned on and off depending on HRV and other parameters. The second stimulation modality 342 can be similarly adjusted.

The interface 214 of certain embodiments provides signals to the logic circuit 210 which the logic circuit 210 uses to control the stimulation modalities. The interface 214 can comprise a user interface or an interface to a sensor monitoring at least one parameter of the treatment. In certain such embodiments, the programmable controller 126 is responsive to signals from the sensor to preferably adjust treatment parameters to optimize the measured response.

The programmable controller 126 can thus provide closed-loop monitoring and adjustment of various treatment parameters to optimize the stimulation. The signals provided by the interface 214 from a user are indicative of parameters that may include, but are not limited to, patient characteristics (e.g., skin type), response to HRV, synchronization to the cardiac cycle, target time intervals, or power or other measurements for the stimulation modalities.

In certain embodiments, the logic circuit 210 is coupled to a driver 220 for driving the first and/or second stimulation modalities. The energy source driver 220 is coupled to a power supply 230, which in certain embodiments comprises a battery or capacitive energy storage device and in other embodiments comprises an alternating current source. The energy source driver 220 is also coupled to the first stimulation modality 340 and/or second stimulation modality 342. The logic circuit 210 is responsive to the signal from the clock 212 and to user input from the user interface 214 to transmit a control signal to the driver 220. In response to the control signal from the logic circuit 210, the driver 220 adjusts and controls signals of the first stimulation modality 340 and the second stimulation modality 342. Other control circuits besides the control circuit 200 of FIG. 66 are compatible with embodiments described herein, and some embodiments involve three, four, or more stimulation modalities. In some embodiments, the control circuit 200 can be used to provide real-time positive and/or negative feedback.

In certain embodiments, the logic circuit 210 is responsive to signals from a sensor monitoring at least one parameter of the treatment to control the first and/or second stimulation modalities. For example, certain embodiments comprise EKG or PPG sensors in communication with a body structure to provide information regarding the cardiac cycle or HRV to the logic circuit 210. In such embodiments, the logic circuit 210 is responsive to the information from the sensor(s) to transmit a control signal to the driver 220 so as to adjust the parameters of the first and/or second stimulation modalities to keep, for example, HRV above a predetermined level. Other embodiments of sensors include other biomedical sensors including, but not limited to, thermocouples, a blood flow sensor, a blood gas (e.g., oxygenation) sensor, an ATP production sensor, or a cellular activity sensor. Such biomedical sensors can provide real-time feedback information to the logic circuit 210. In certain such embodiments, the logic circuit 210 is responsive to signals from the sensors to preferably adjust the parameters of the stimulation modalities to optimize the measured response. The logic circuit 210 can thus provide automatic real-time closed-loop monitoring and adjustment of various parameters of the stimulation modalities to optimize the combination therapy. In other embodiments, the control circuit 200 can be configured to provide manual closed-loop feedback. The sensors can also include biochemical sensors, EEG sensors, EMG sensors, NCT sensors, and/or other sensors.

Example Treatment Systems

Figure 67:
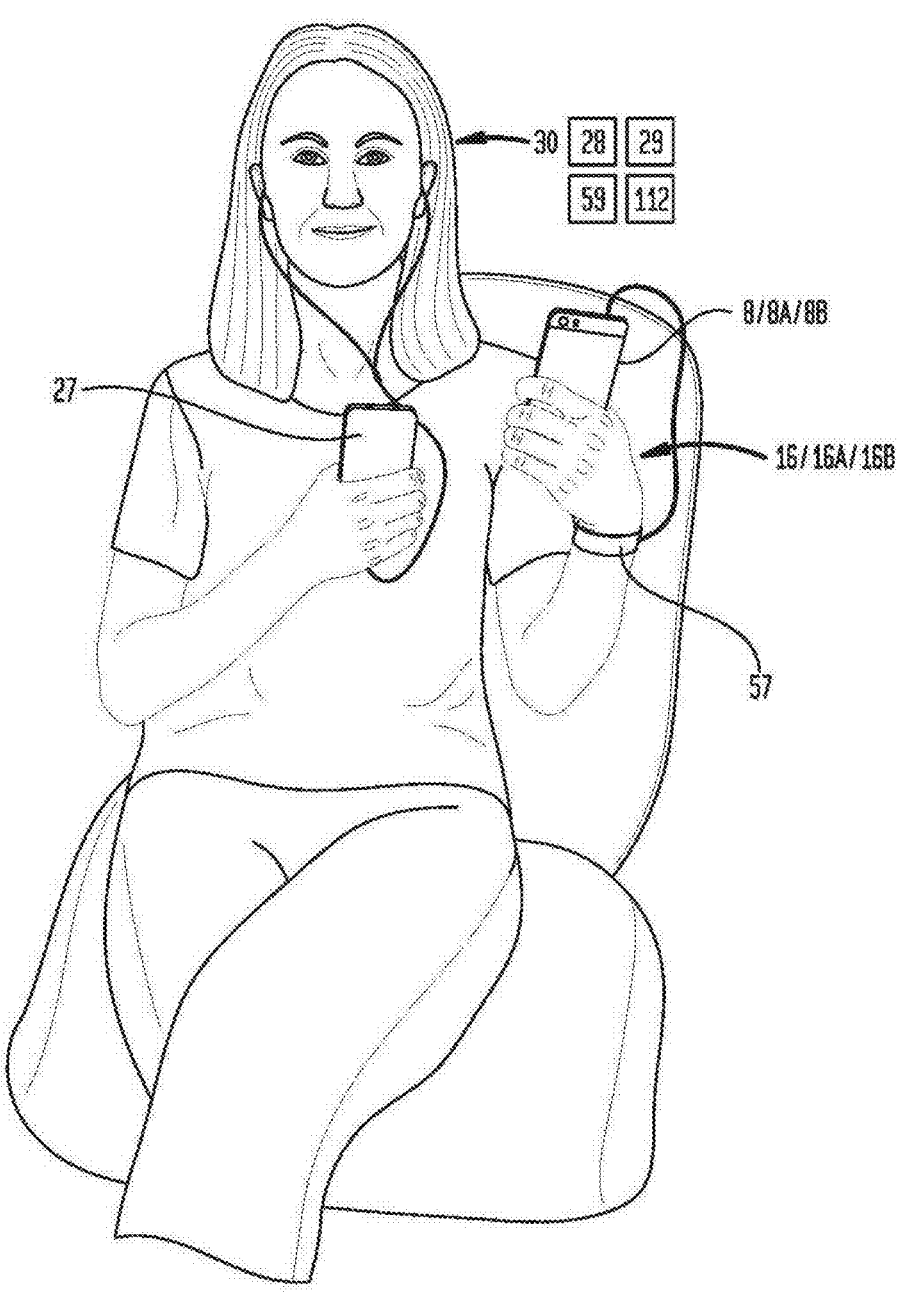
FIG. 67 illustrates a method of using a particular embodiment of a computer implemented treatment device control system.
Figure 68:
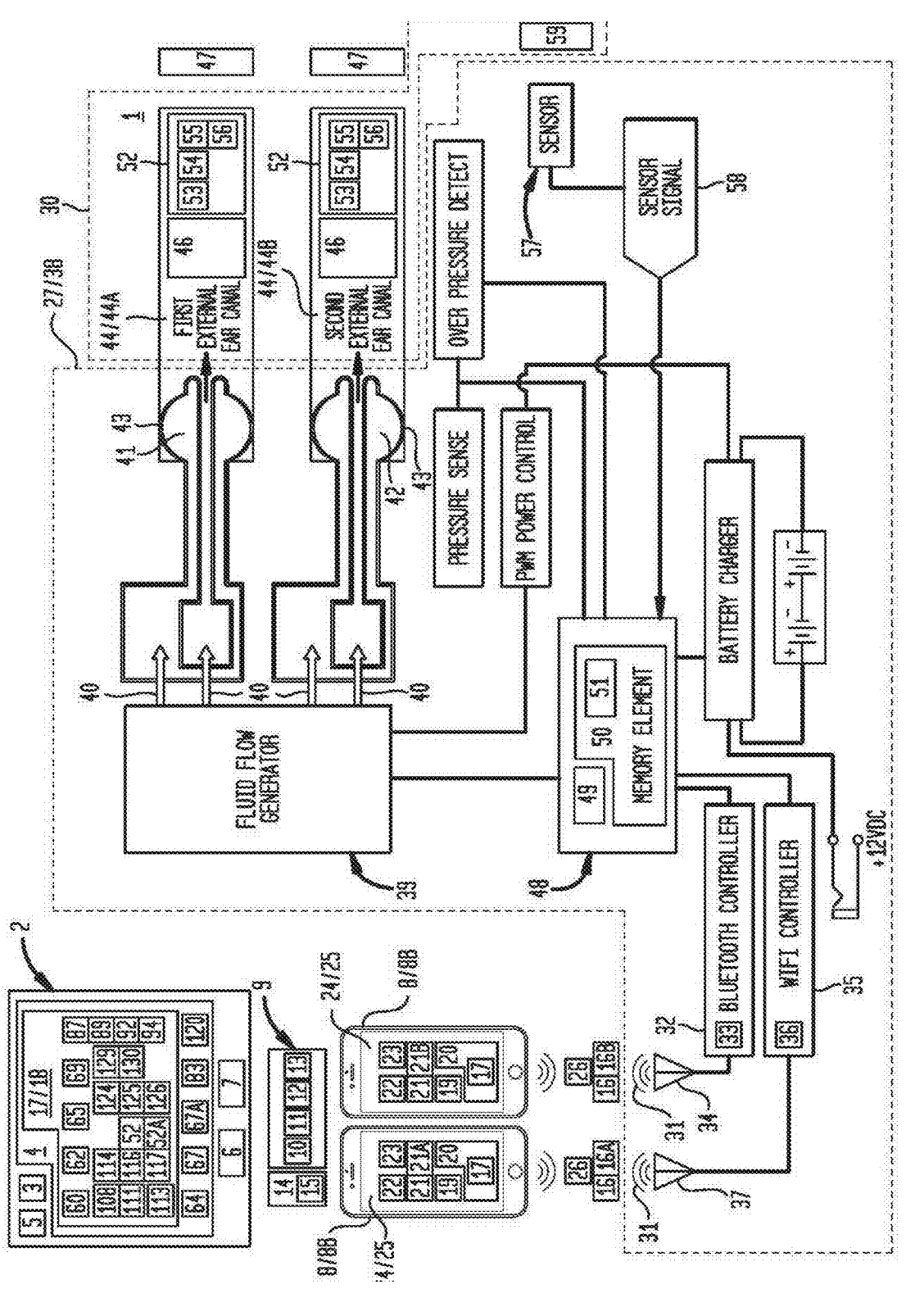
FIG. 68 is a block diagram of a particular embodiment of the computer implemented treatment device control system.
Figure 70:
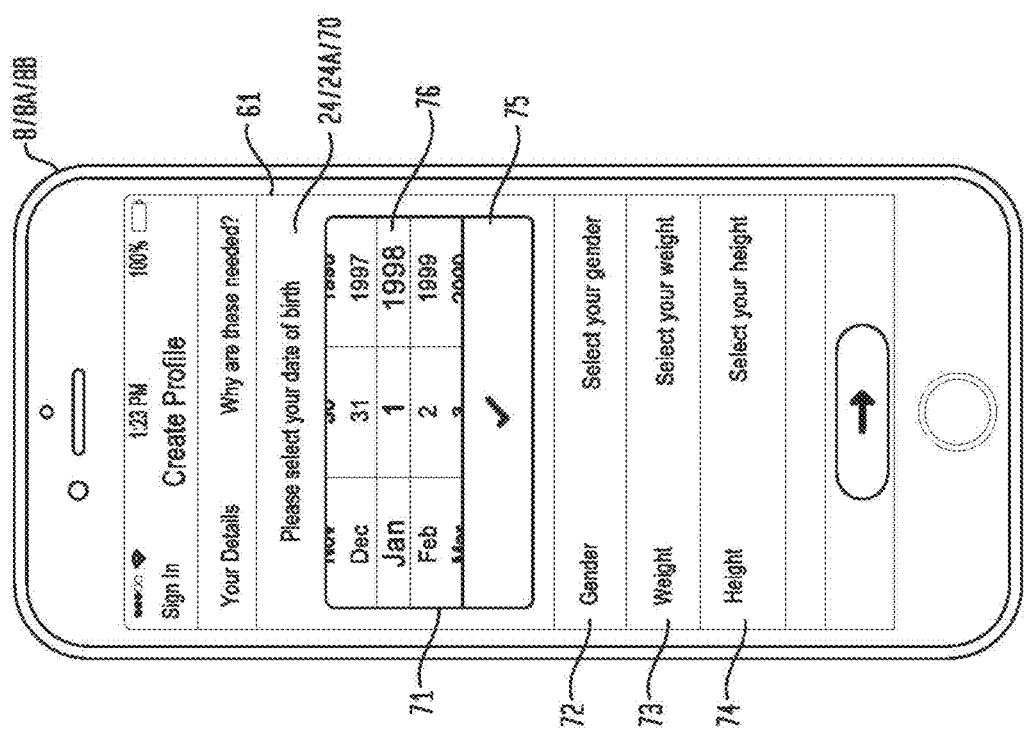
FIG. 70 illustrates a particular embodiment of a user interface including setup module in which user can enter a birthdate.

Now referring primarily to FIGS. 67 and 68, which illustrate a computer implemented treatment device control system (1) (also referred to as the "system") which may be distributed on one or more servers (2), each having a server processor (3), a server memory (4), a server operating system (5), a server input/output interface (6), and a server network interface (7) operatively communicating with one or more computing devices (8) via a network (9) including one or more of a public network (10), such as the Internet (11), a cellular-based wireless network (12), or a local network (13) (also individually and collectively referred to as a "network (9)"). Unless otherwise noted, reference numerals in FIGS. 67-98 refer to components that are the same as or generally similar to the components having the same reference numerals in the preceding figures. It will be understood that the systems and features shown in FIGS. 67-98 can be used with any of the embodiments described and/or contemplated herein. It will also be understood that any of the embodiments described and/or contemplated herein can be modified to be used with the systems and features disclosed in connection with FIGS. 67-98.

The network (9) supports a plurality of communication resources (14)(along with other communication resources made available in the future) to afford recording, transmission, or reproduction of images (whether still or moving images), sound relating to acoustical, mechanical or electrical frequencies, electronic mail, instant messaging, text messaging (such as short message service) multimedia messaging (such as multimedia message service) attributable to the execution of self-contained programs or pieces of software designed to fulfill particular purposes (also referred to as "applications" (15)), such as web applications, online applications, mobile applications, or the like, downloadable by a user (16) to one or more computing devices (8).
The Treatment Device Control Program Again referring primarily to FIGS. 67 and 68, the server (2) can include a server processor (3) communicatively coupled to the server memory (4) containing a treatment device control program (17) (also referred to as the "program (17)") which is described below in the general context of computer-executable instructions such as program modules (18) which utilize routines, programs, objects, components, data structures, or the like, to perform particular functions or tasks or implement particular abstract data types, however, it is not intended that any embodiment be limited to a particular set of computer-executable instructions or protocols.

As to particular embodiments, the program (17) can be downloaded in whole from the server (2) to a first computing device (8A) having a computing device processor (19) communicatively coupled to a computing device memory element (20) to discretely confer all of the program functions (21) of the program (17) to the first computing device (8A) for use only by a first user (16A), or as to other embodiments, the program (17) can be downloaded in part to a first computing device (8A) for use by a first user (16A) and in part to a second computing device (8B) for use by a second user (16B) to discretely confer a first portion of the program functions (21A) of the program (17) to the first computing device (8A) and discretely confer a second portion of the functions (21B) of the program (17) to the second computing device (8B) for integrated or coordinated use of the first computing device (8A) by the first user (16A) and the second computing device (8B) by the second user (16B). The program (17) can operatively communicate with the server (2) over the network (9) to communicatively couple the first computing device (8A) with the server (2) to coordinate or pair operation of the first computing device (8A) with operation of a second computing device (8B).

As to particular embodiments, the program (17) can also be loaded to and contained in whole or in part in the local memory element (20) of the first or second computing devices (8A)(8B) (or a plurality of computing devices (8)) from one or more of: a computer disk, universal serial bus flash drive, or other computer readable medium, without communication with a server (2) or use of any network (9).

In some embodiments, the computing device (8) may comprise a desktop or mobile computer devices. The computing device, in some instances, can include a computing device processor (19) communicatively coupled to a computing device memory element (20). The computing device memory element (20) may contain in whole or in part the program (17) or can perform browser based processing in downloaded computing device content (22) and without sacrificing the breadth of the foregoing includes personal computers, slate, tablet or pad computers, and cellular telephones or camera/cell phones, and programmable consumer electronics.

Again referring primarily to FIG. 67, each of the one or more computing devices (8) can, but need not necessarily, include an Internet browser (23) (also referred to as a "browser") such as Microsoft's INTERNET EXPLORER®, GOOGLE CHROME®, MOZILLA®, FIREFOX®, or the like, which functions to download and render computing device content (22) formatted in "hypertext markup language" (HTML). In this environment, the one or more servers (2) can contain the program (17) which implements the most significant portions of one or more graphical user interface(s)(24) including one or more menus (25) including a combination of text and symbols to represent options selectable by user command (26) to execute one or more program functions (21) of the program (17). As to these embodiments, the one or more computing devices (8) can use the Internet browser (23) to display downloaded computing device content (22) and to relay selected user commands (26) back to the one or more servers (2). The one or more servers (2) can respond by formatting new menus (25) for the respective graphical user interfaces (24) (as shown in the illustrative examples of FIGS. 69 through 98 further described below).

Again referring primarily to FIGS. 67 and 68, in some embodiments, the one or more servers (2) can be used as sources of computing device content (22). The one or more servers (2) may be configured to implement the graphical user interface (24) placed upon each of the one or more computing devices (8). In some embodiments, each of the one or more computing devices (8) can run the appropriate portions of the program (17) implementing the corresponding program functions (21) including but not limited to the depiction of the graphical user interfaces (24).

In some embodiments, the machine readable medium may comprise any medium capable of non-volatile storage of machine readable code in a format readable by a mechanical device and without sacrificing the breadth of the forgoing a magnetic media, an optical media, a non-volatile memory, or the like, or combinations thereof.
The Treatment Device Now referring primarily to FIGS. 67 and 68, embodiments of the computer implemented treatment device control system (1) can further include a treatment device (27). In some embodiments, the treatment device (27) may comprise any device which can pair operation with a computing device (8) (or a first and second computing devices (8A) (8B)) containing the program (17). The program (17) may (in whole or in part) control the device to treat a condition (28) or alleviate symptoms (29) of a condition (28).

In some embodiments, a condition (28) may comprise any physical or mental feature or function of a user (16).

In some embodiments, a symptoms (29) may comprise subjective evidence of a condition (27) of a user (16).

In some embodiments, the subject (30) may comprise an animal (whether human or non-human) subjected to the operation of a treatment device. A subject (30) may be the user (16) of the computing device (8) or the subject (30) can be discrete from the user (16) of computing device (8).

In some embodiments, the term wireless may comprise using electromagnetic waves (31) rather than some form of wire to carry a signal over all or a part of a communication path and without sacrificing the breadth of the foregoing can include BLUETOOTH® enabled in the ISM band from 2400-2480 MHz or Wi-Fi® enabled in one or more channels in the 2.4 GHz band, or the like, or combinations thereof, for the exchange of data over the communication path.

As to particular embodiments, the treatment device (27) can, but need not necessarily, include a BLUETOOTH® controller (32) (as shown in the illustrative example of FIG. 68 a Texas Instruments CC2540 BLUETOOTH® System-on-Chip) including the associated BLUETOOTH® transceiver (33) and BLUETOOTH® antenna (34). As to particular embodiments, the treatment device (27) can, but need not necessarily, include a Wi-Fi® controller (35) and the associated Wi-Fi® receiver (36) and Wi-Fi® antenna (37). As to some embodiments, the treatment device (27) can provide both a BLUETOOTH® controller (32) and a Wi-Fi® controller (35) including the associated transceivers (33)(36) and antennas (34)(37).

The treatment device (27) can be placed in the active condition by a user (16) such that the treatment device (27) seeks a connection with a computing device (8) containing or having access to the program (17) within the range of the transceiver (33)(36)(or vice versa). The program (17) can cause pairing of the computing device (8) with the treatment device (27).

In some instances, a treatment device (27) can be an external ear canal pressure regulation device (38) including a fluid flow generator (39) capable of generating a fluid flow (40) and one or more of a first earpiece (41) and a second earpiece (42) each fluidicly coupled or discretely fluidicly coupled to the fluid flow generator (39), each earpiece (41)(42) can have an earpiece external surface (43) configured to sealably engage an external ear canal (44) of an ear (45) as a barrier between an external ear canal pressure (46) and an ambient pressure (47). The external ear canal pressure regulation device (38) can further include a treatment device controller (48) including a treatment device processor (49) communicatively coupled with a treatment device memory element (50) containing a treatment device computer code (51) executable to control the fluid flow generator (39) to generate a pre-selected pressure differential (52) (whether positive or negative) between the external ear canal pressure (46) and the ambient pressure (47) which can be generated as a pre-selected static pressure differential (53), as pre-selected pressure waves (54) having pre-selected amplitude (55) or pre-selected frequency (56), or combination thereof in which a pre-selected static pressure differential (52) can be generated and superimposed by a pressure wave (54) having a pre-selected frequency (56) and pre-selected amplitude (55). The external ear canal pressure regulation device (38) can, but need not necessarily, further include a physiological parameter sensor (57) which generates a sensor signal (58) which varies based on change in a sensed physiological parameter (59) receivable by the treatment device controller (48) which further functions to synchronize operation of the fluid flow generator (39)(in regard to amplitude (55) and frequency (56) of the pressure differential (52) generated in the external ear canal (44) with the sensed physiological parameter (59). U.S. Pat. No. 9,039,639 is hereby incorporated by reference herein as an illustrative example of the structure and function of an external ear canal pressure regulation device (38).

The Graphical User Interface

Now referring primarily to FIGS. 68 through 98, the program (17) in part includes a user interface module (60) executable to generate a user interface (24) which can, but need not necessarily, be a graphical user interface (24A) displayed on the display surface (61) of a computing device (8) which allows a user (16) to execute by user command (26) one or more program functions (21) of the program (17). The user command (26) can, as illustrative examples, be: selection of one or more control icon(s), entry of text into one or more fillable fields, voice command, keyboard stroke, mouse button point and click, touch on a touch screen, or otherwise, or combinations thereof (individually and collectively referred to as a "user command").

The Signup Module

Figure 69:
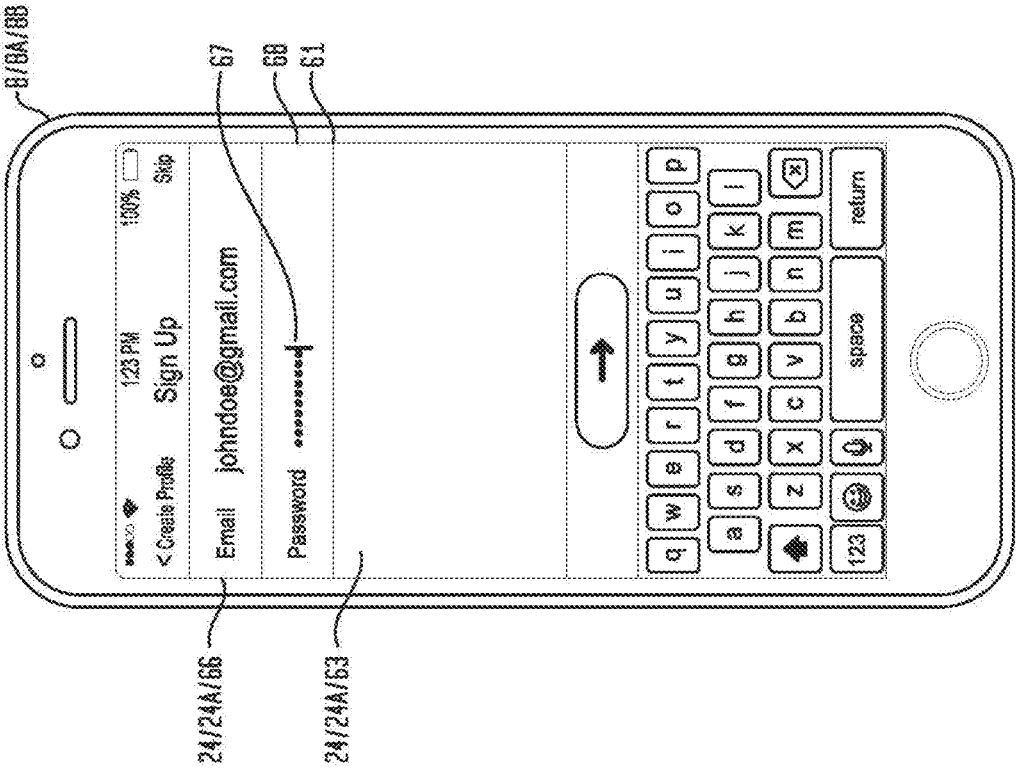
FIG. 69 illustrates a particular embodiment of a user interface including a signup and login menu.
Figure 72:
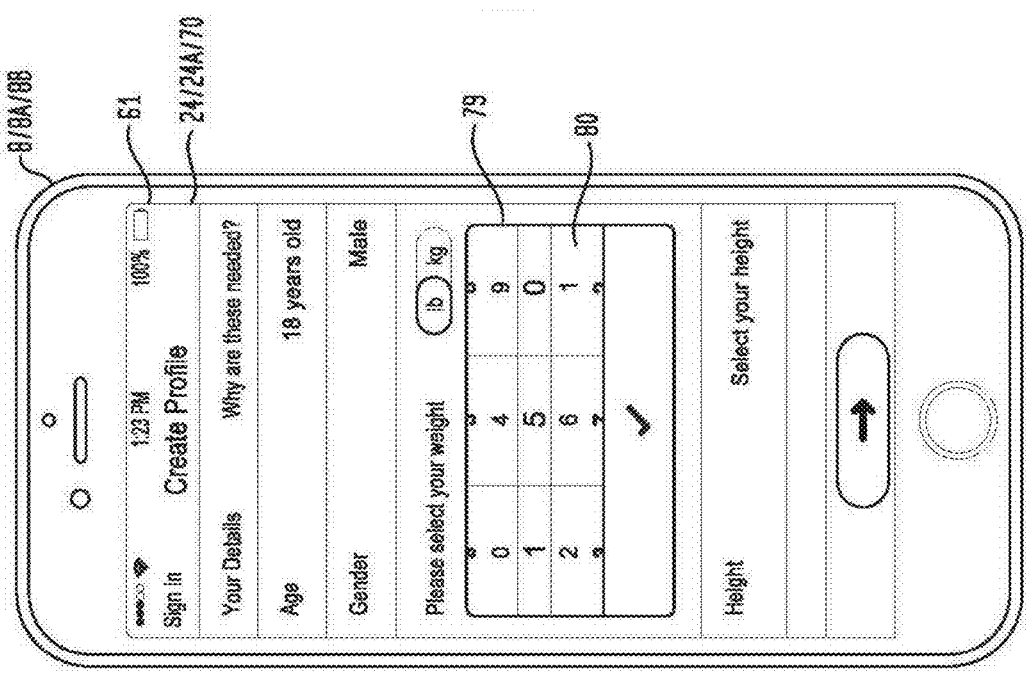
FIG. 72 illustrates a particular embodiment of a user interface including a setup menu in which the user can enter weight.
Figure 71:
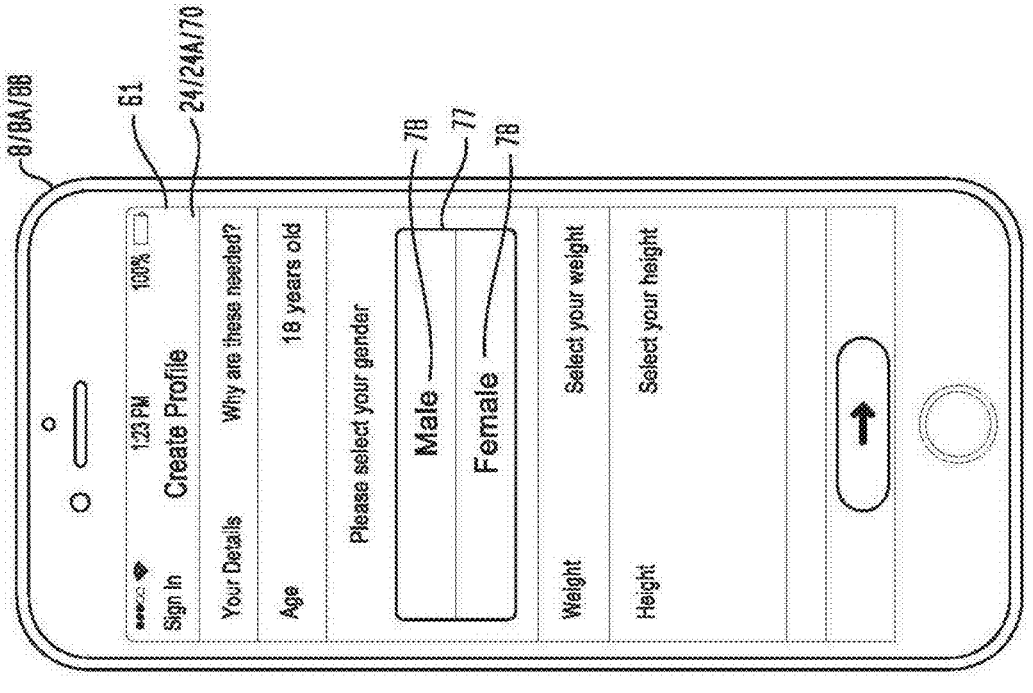
FIG. 71 illustrates a particular embodiment of a user interface including a setup menu in which the user can enter a gender.

Now referring primarily to FIGS. 68 and 69, embodiments of the program (17) can, but need not necessarily, include a sign up module (62) which upon execution depicts a sign up menu (63) on the display surface (61) of a computing device (8) which by user command (26) allows the user (16) to create an account (64) which allows a user (16) to authenticate to the system (1) and potentially receive authorization to access resources (14) provided by or connected to the system (1) and to load the program (17) in whole or in part to the computing device (8).

The Login Module.

Now referring primarily to FIGS. 68 and 69, embodiments of the program (17) can, but need not necessarily, include a login module (65) which upon execution depicts a login menu (66) which by user command (26) allows the user (16) to log in to an account (64). To log in to an account (64), a user (16) is typically required to authenticate oneself with a user identifier (67) or other credentials for the purposes of accounting, security, logging, and resource management. Once the user has logged on, the system (1) will often use a user identifier (67) such as an integer to refer to them, rather than their user name, through a process known as identity correlation. As one illustrative example, in Unix® systems, the user name is correlated with the user identifier (67).

In some embodiments, the user identifier (67) may comprise integers or characters or combination thereof unique to a user (16) which by operation of the login module (65) can be matched by the server (2) or computing device (8) to the stored data structures (67A) of that user (16). In the illustrative example of FIG. 69, the log in module (65) depicts a user identifier (67) entered into a user identifier field (68).

The Setup Module

Now referring primarily to FIGS. 68 through 74, embodiments of the program (17) can, but need not necessarily, include a setup module (69) which by user command (26) allows settings or values to be assigned to the program (17) or the computing device (8). Certain embodiments can, but need not necessarily, be provided with presets which provide settings or values automatically assigned by or to the program (17) outside of user intervention. For the sake of brevity, the particular illustrative example depicted in FIGS. 69 through 74 and further described below, include only a first computing device (8A); this not intended to preclude embodiments in which the operation of a first computing device (8A) coordinates the operation of a plurality of second computing devices (8B) in a computer administrator-computer user relationship within the system (1), or embodiments in which a first computing device (8A) and a second computing device (8B) have respective operation coordinated by the system (1) in which the first user (16A) and the second user (16B) have respectively parent-child, educatorstudent, physician-patient or other relationships in which the program functions (21) are discretely allocated between the first computing device (8A) used by the first user (16A) and a second computing device (8B) used by a second user (16B).

Now referring primarily to FIGS. 68 through 74, the setup module (69) can function to display a setup menu (70) on the display surface (61) of a computing device (8) of a user (16) by which the user (16) by user command (26) inputs one or more of: age status (71), gender status (72), weight status (73), and height status (74) of the subject (30) that will interact with the treatment device (27). While the embodiment illustrated in FIGS. 69 through 74 respectively depict an age status field (75) in which age status values (76) (month, day, year) can be selected by user command (26), a gender status field (77) in which gender status values (78)(male, female) can be selected by user command (26), a weight status field (79) in which weight status values (80)(pounds or kilograms) can be select by user command (26), a height status field (81) in which height status values (82) can be selected by user command (26); this illustrative example is not intended to preclude depiction of additional or alternate status fields or status values relating to anatomical or physiological attributes of a user or medicaments taken by a user which may be relevant to controlled operation of a treatment device.

Figure 74:
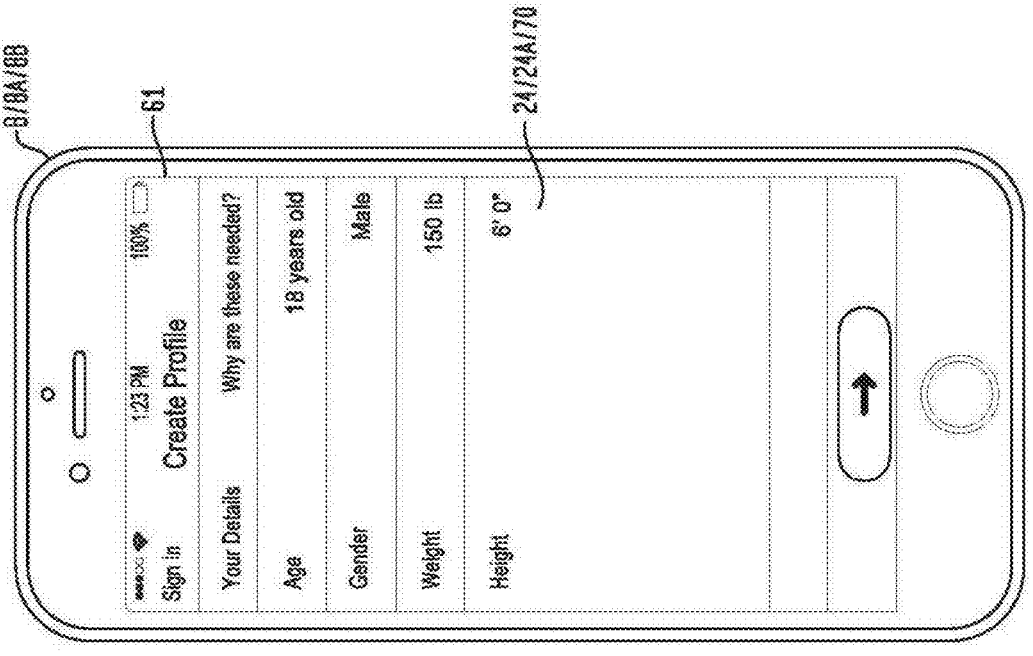
FIG. 74 illustrates a particular embodiment of a user interface including a setup menu which allows user input to be confirmed and matched to a user identifier to create a user profile.
Figure 73:
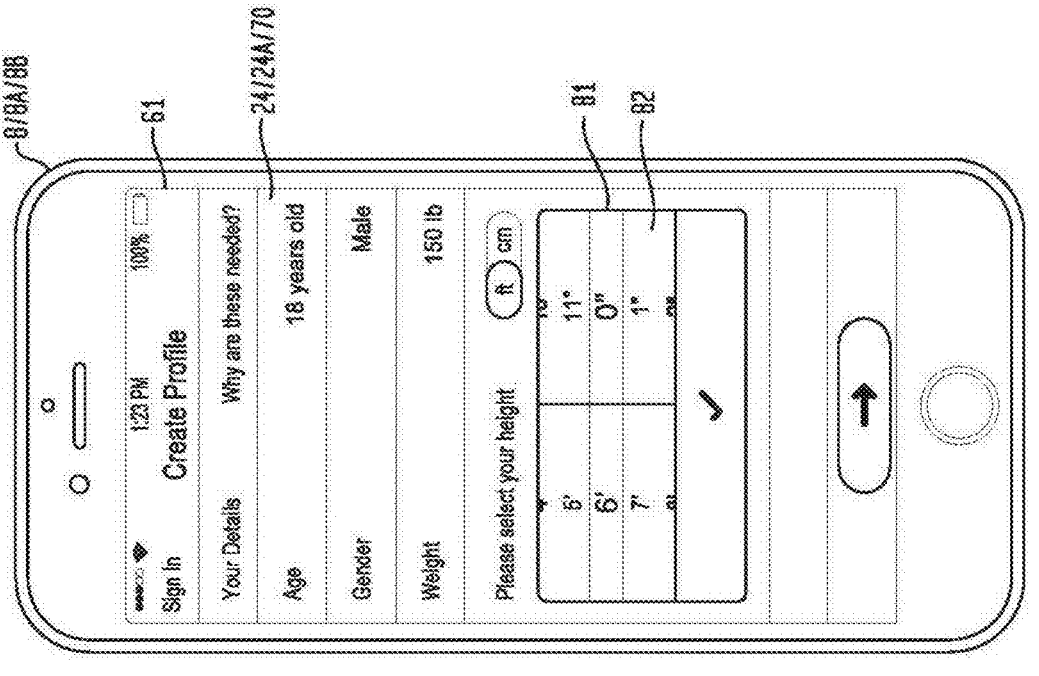
FIG. 73 illustrates a particular embodiment of a user interface including a setup menu in which the user can enter height.

Now referring primarily to FIGS. 68 and 74, as to particular embodiments, the set up module (69) can further function to match the status values (76)(78)(80)(82) input by user command (26) into the set up menu (70) with the user identifier (67) to create a user profile (83) which can be stored remotely in the server memory (2) or locally in the computing device memory element (20).

Figure 75:
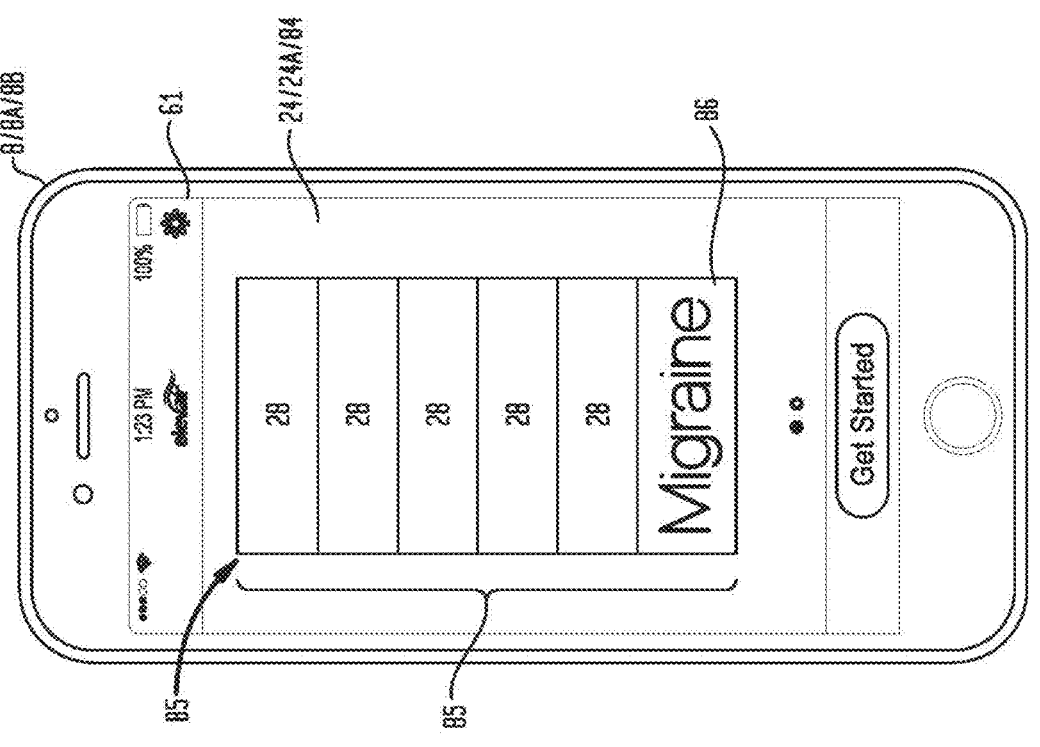
FIG. 75 illustrates a particular embodiment of a user interface including a setup menu which allows the user to select a condition to associate with operation of a treatment device.

Now referring primarily to FIGS. 68 and 75, as to particular embodiments, the set up module (69) can further function to depict on the display surface (61) of the computing device (8) a condition selection menu (84) which allows by user command (26) selection of a condition (28) to be associated with the operation of a treatment device (27). As shown in the illustrative example of FIG. 75, the condition selection menu (84) depicts a conditions list (85) including a plurality of conditions (28) selectable by the user (16). As one illustrative example, the conditions list (85) includes the condition (28) identified as "Migraine (86)."

Now referring primarily to FIGS. 68 and 76 through 81, the program (17), can but need not necessarily, include a condition symptoms assessment module (87) executable upon selection of a condition (28) in the condition selection menu (84) to download and depict in the display surface (61) of the computing device (8) one of a plurality of condition symptom menus (88) matched to the selected condition (28). The condition symptom menu (88) allows the user (16) to enter indications of condition symptoms (89) and for the condition symptoms assessment module (87) to receive indications of condition symptoms (89).

Now referring primarily to FIGS. 76 through 80, as to particular embodiments, the condition symptom menu (88) can, but need not necessarily, depict in whole or in part an anatomical representation (90) corresponding in whole or in part the subject (30). As shown in the illustrative example of FIG. 76, the anatomical representation (90) can by user command (26) be rotated to depict in whole or in part the anatomical surface (91) corresponding to the subject (30).

Now referring primarily to FIGS. 76 through 81 which illustrates operation of the condition symptoms assessment module (87) executed based upon selection of the condition (28) identified as Migraine (86) in the condition selection menu (84). However, this illustrative example is not intended to preclude embodiments of the condition symptom menu (88) based upon selection of any one of a numerous and varied conditions (28) such as: asthma, hypertension, hyperglycemia, or the like.

Figure 76:
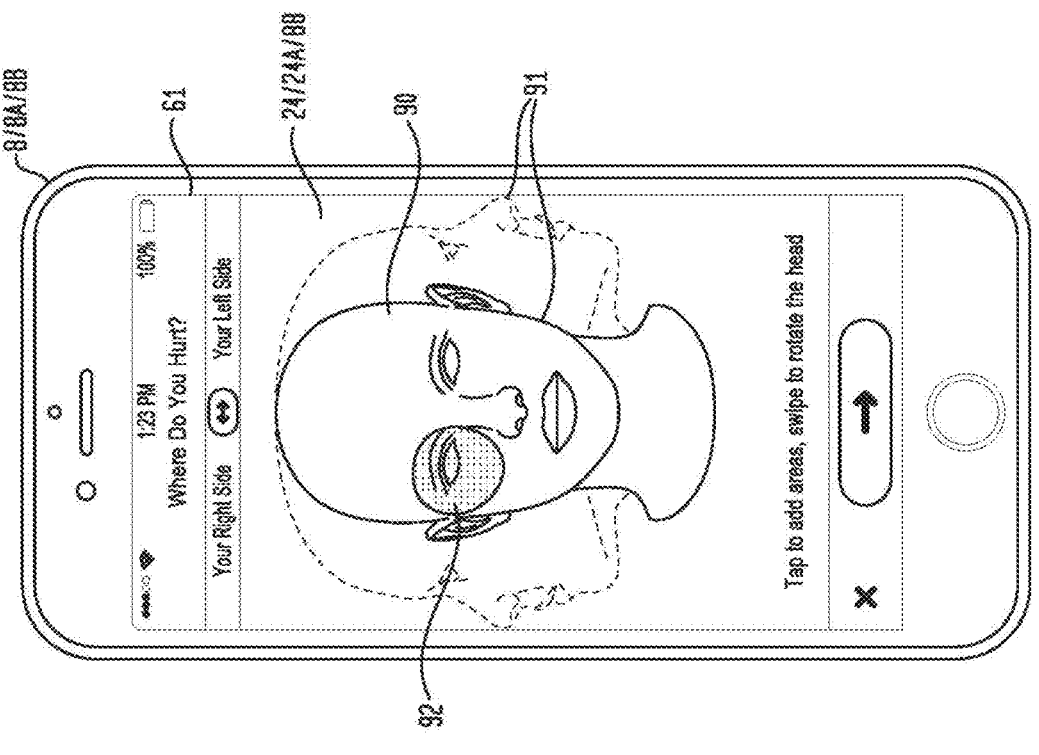
FIG. 76 illustrates a particular embodiment of a user interface including condition symptom menu which allows the user to enter indications of condition symptoms at a location in an anatomical representation.
Figure 77:
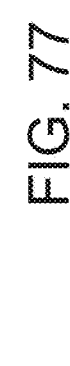
FIG. 77 illustrates a particular embodiment of a user interface including a condition symptom intensity scale which allows a user to indicate condition symptom intensity.

Now referring primarily to FIGS. 76 and 77, as an illustrative example relating to the condition (28) of Migraine (86), the condition symptoms assessment module (87) can function to download and depict in the display surface (61) of the computing device (8) an anatomical representation (90) of the head and neck. The user (16) can by user command (26) indicates a condition symptom location (92)(which in the example of FIG. 76 can be by touch on the display surface (61) of the computing device (8) over the portion of the anatomical representation (90) or can be by circumscribing the area in which the condition symptom (28) occurs).

Now referring to primarily to FIG. 77, the condition symptoms assessment module (87) can further function to depict a condition symptom intensity scale (93) which by user command (26) allows an indication of symptom intensity (94). In the illustrative example, the user (16) by user command (26) has indicated a condition symptom location (92) in the anatomical representation (90) over the eye (95) causing the condition symptoms assessment module (87) to depict a condition symptom intensity scale (93) in the form of a numerical scale (96) having a numerical values (97) of between zero indicating absence of condition symptoms (28) and indicating severe condition symptoms (28). In the example, the user (16) has provided an indication of condition symptom intensity (94) corresponding to the numerical value (97) seven.

Figure 78:
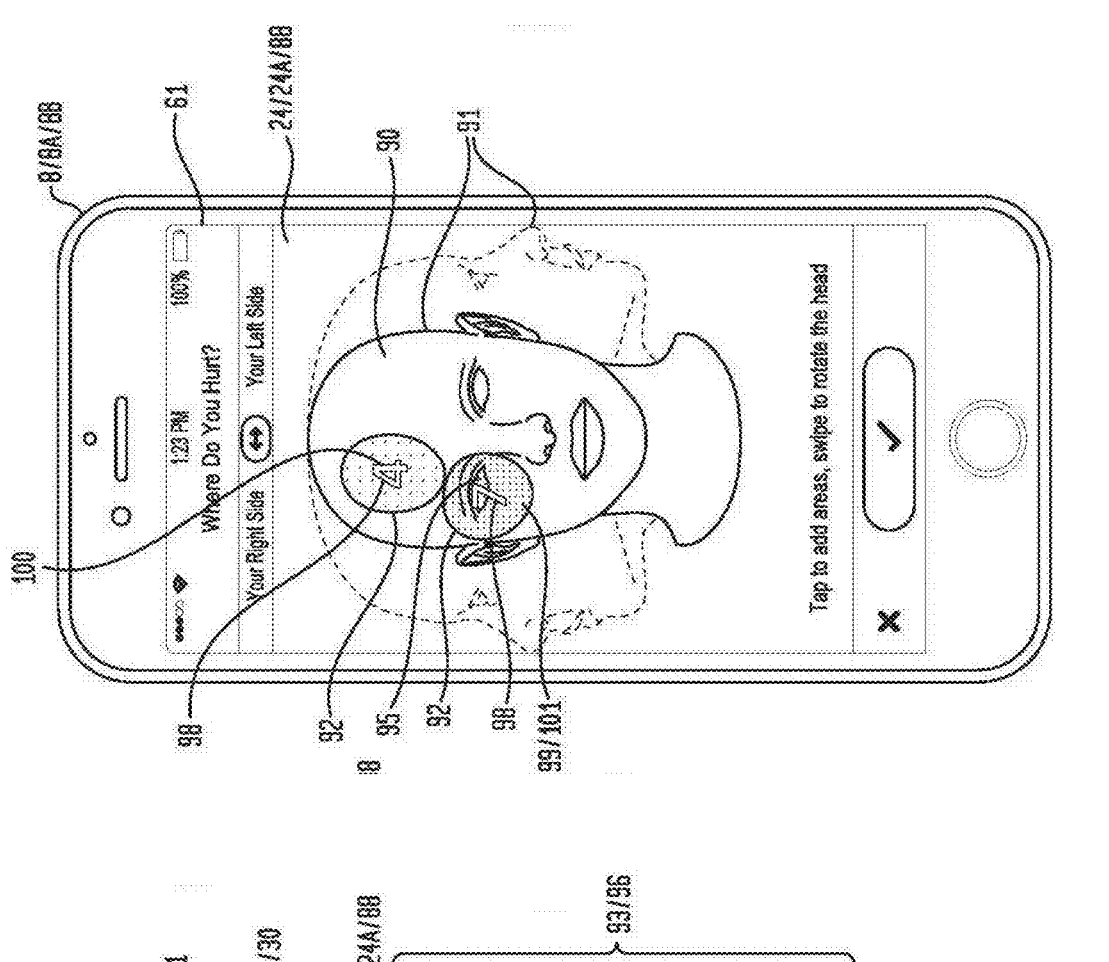
FIG. 78 illustrates a particular embodiment of a user interface including a condition symptom menu which allows the user to enter indications of condition symptoms at a plurality of locations in an anatomical representation.

Now referring primarily to FIGS. 68 and 78, the condition symptoms assessment module (87) can further function to allow the user (16) to select a plurality of condition symptom locations (92) in the anatomical representation (90) by user command (26) and by further depictions of the condition symptom intensity scale (93)(as shown in the example of FIG. 77) provide indications of condition symptom intensity (94) associated with each condition symptom location (92). As to particular embodiments, the numerical value (97) associated with the indication of condition symptom intensity (94) can be depicted as numeral (98) within the bounded area of the condition symptom location (92). As to particular embodiments, the numerical value (97) associated with the indication of condition symptom intensity (94) can be further associated with other sensorial perceivable indicia (99) in graded relation to indication of condition symptom intensity (94). In the illustrative example of FIG. 78, the user (16) indication of condition symptoms (89) in the areas of the eye (95) and the forehead (100) and the condition symptoms assessment module (87) has further functioned to depict the condition symptom locations (92) along with a numeral (98) corresponding to the selected numerical value (97) and further differentiates indications of condition symptom intensity (94) by graded shading (101) based on numerical value (97) (with increasingly darker shading correlated with increased indication of condition symptom intensity (94)). This illustrative example of depicting numerals (98) or graded shading (101) is not intended to preclude other sensorial perceivable indicia (99) in graded relation to indications of condition symptom intensity (94) such as graded illumination or a graded range of color.

Figure 80:
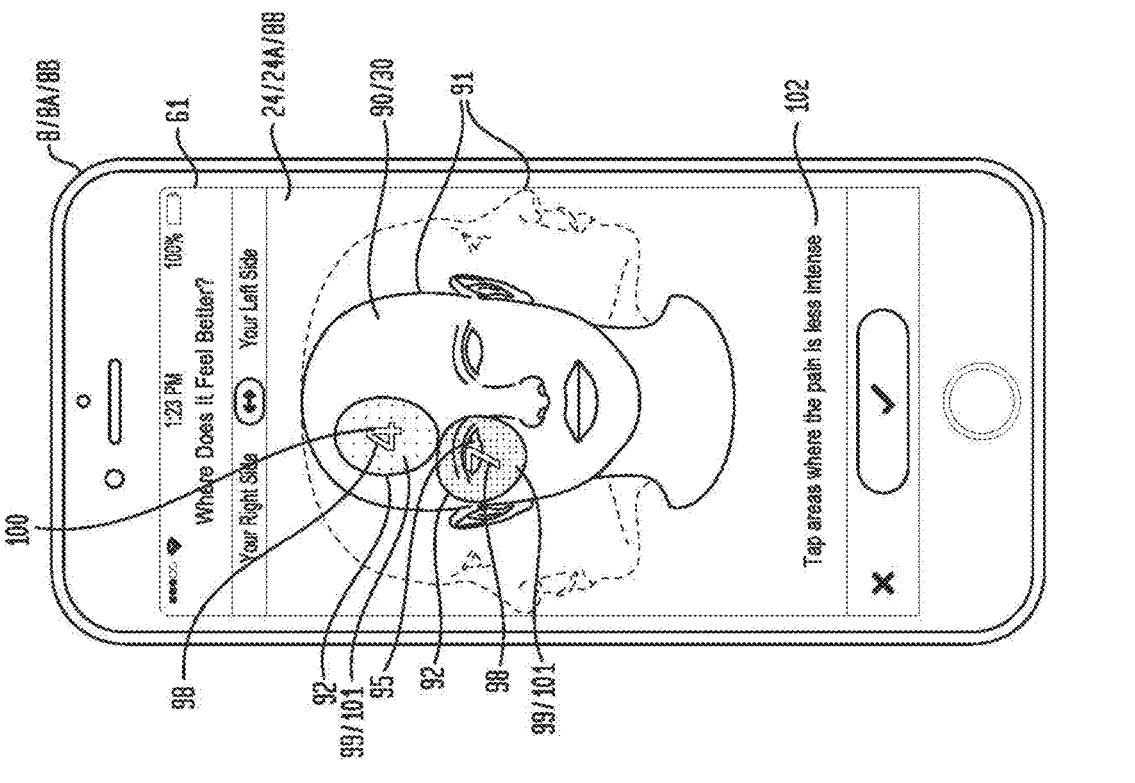
FIG. 80 illustrates a particular embodiment of a user interface including a condition symptom menu which allows a user to indicate condition symptom intensity by comparison between two or more locations in the anatomical representation as to which of the two or more locations has lesser condition symptom intensity.
Figure 80:
Figure 79:
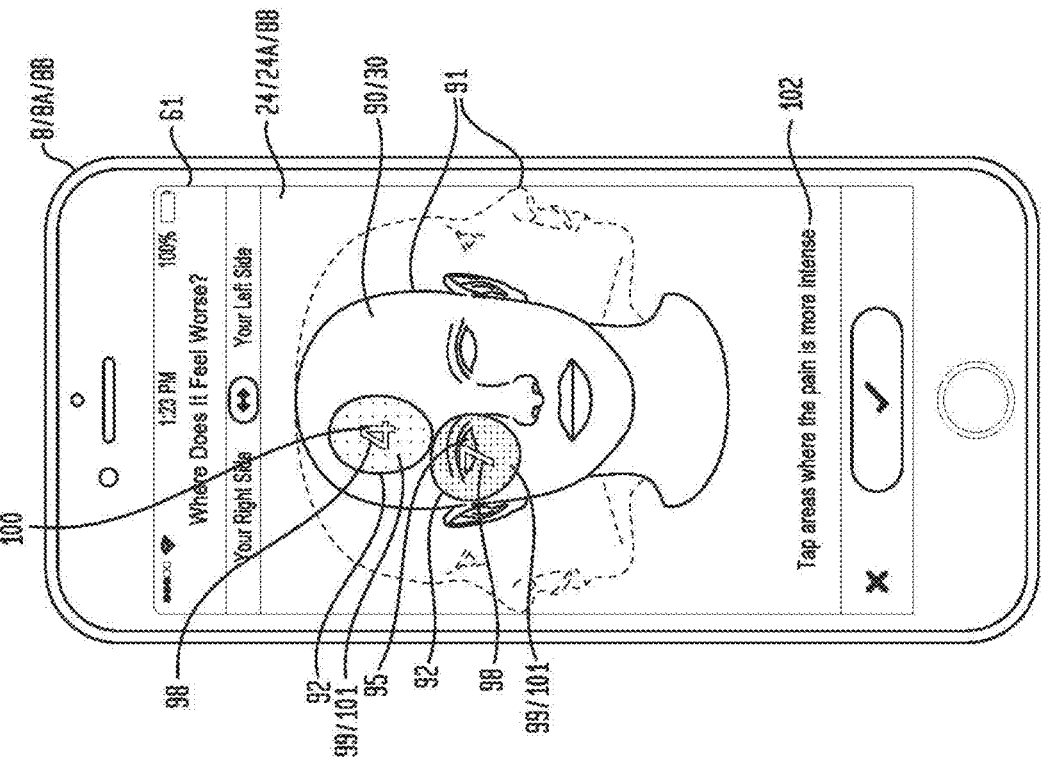
FIG. 79 illustrates a particular embodiment of a user interface including a condition symptom menu which allows a user to indicate condition symptom intensity by comparison between two or more locations in the anatomical representation as to which of the two or more locations has greater condition symptom intensity.

Now referring primarily to FIGS. 68 and 79 through 80, which provides an illustrative example in which the user (16) has indicated more than one condition symptom location (92) (the eye (95) and the forehead (100)). As to particular embodiments, the condition symptoms assessment module (87) can function to obtain indications of condition symptom intensity (94) by comparison between a pair of symptom condition locations (92). As an example, the condition symptoms assessment module (87) can depict one or more symptom condition inquiries (102) to obtain relative indications of condition symptom intensity (94) between the pair of condition symptom locations (92). As shown in the illustrative example of FIG. 83 the symptom condition inquiry (102) tasks the user to "tap where the condition symptom is more intense" or "tap where the condition symptom is less intense".

Figure 81:
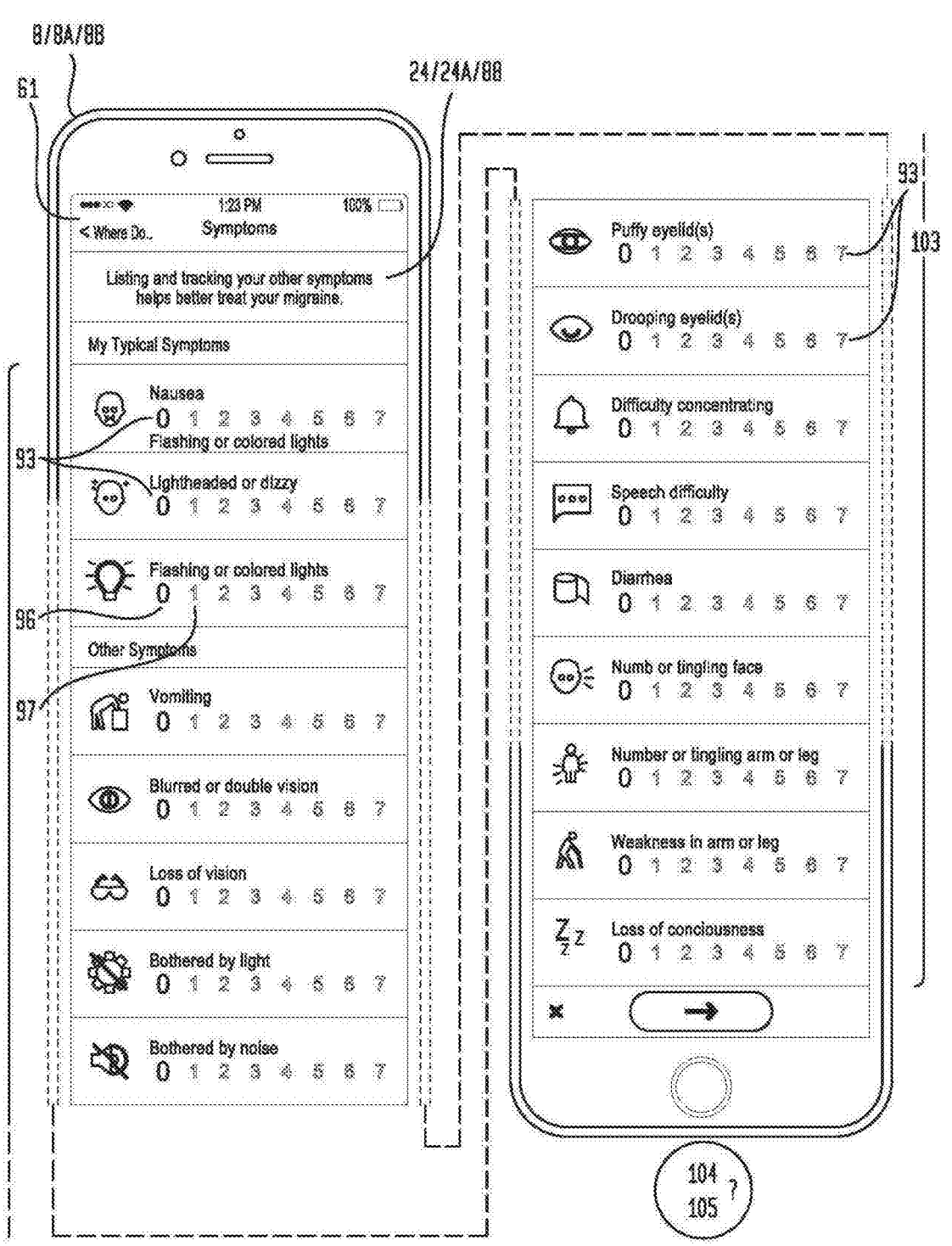
FIG. 81 illustrates a particular embodiment of a user interface including a condition symptom menu which allows a user to select condition symptom intensity in each of a plurality of listed condition symptoms.

Now referring primarily to FIGS. 68 and 81, the condition symptoms assessment module (87) can further function to depict a list of condition symptoms (103) with or without an associated condition symptom intensity scale (93). In the illustrative example, the user (16) has prior selected the condition (28) Migraine (86) and the condition symptoms assessment module (87) functions to depict a list of condition symptoms (103) associated with the condition (28) Migraine (86) along with a condition intensity scale (93) in the form of a numerical scale (96) having a numerical values (97) of between zero indicating absence of condition symptoms (29) and ten indicating severe condition symptoms (29).

Depending on the condition (28) selected by the user (16) additional condition symptom menus (88) relating to condition symptom frequency (104) or condition symptom duration (105) can be depicted by the condition symptoms assessment module (87) which by user command (26) can provide indications of conditions symptom frequency (106) or indications of condition symptom duration (107) which can be processed to subsequently effect operation of the treatment device (27).

Figure 82:
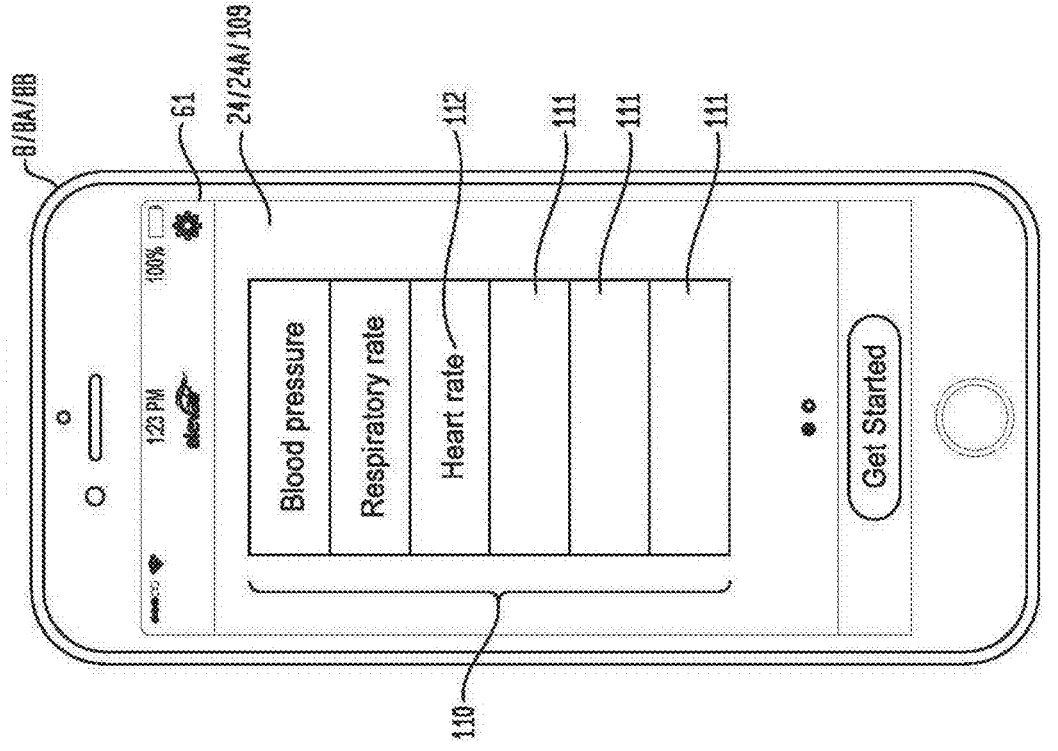
FIG. 82 illustrates a particular embodiment of a user interface including a physiological parameter synchronization menu in which the user can select a physiological parameter to coordinate operation of a treatment device with a sensed physiological parameter.

Now referring primarily to FIGS. 68 and 82, as to particular embodiments, the program (17) can further include a physiological parameter synchronization module (108) which can function to depict a physiological parameter synchronization menu (109) on the display surface (61) of the computing device (8). In some embodiments, the physiological parameter can comprise a measurable variable of the subject (30), such as the following illustrative examples: pulse rate, respiratory rate, body temperature, blood pressure, or the like. The physiological parameter synchronization menu (109) can depict a list of physiological parameters (110) selectable by user command (26) to provide indications of a sensed physiological parameter (111) to be synchronized with operation of the treatment device (26). In the example of FIG. 82, the user (16) has selected the physiological parameter (59) "heart rate" (112) which provides indications of a sensed physiological parameter (111) of "heart rate" (112) to the physiological parameter synchronization module (108) which can be processed to coordinate operation of the treatment device (26) with the sensed physiological parameter (111) of "heart rate" (112). In the example of the external ear canal pressure regulation device (38), pressure wave frequency (56) within the external ear canal (44) can be correlated or matched to the sensed heart rate (112). As to this embodiment or similar embodiments, the system (1) can further include physiological parameter sensors (57) which can be applied to the subject's (30) finger, wrist, neck or ear lobe. The physiological parameter sensor (57) can generate a sensor signal (58) as above described which can be processed by the physiological parameter synchronization module (108) to measure the sensed physiological parameter (59). However, this illustrative example, is not intended to preclude operation of a treatment device (26) synchronized with other sensed physiological parameters (59). In some instances, the synchronization can include an interdependence of the variable quantities of a sensed physiological parameter (59) and treatment parameter (113) administered by a treatment device (26).

Now referring primarily to FIGS. 68 and 83 through 95, the program (17) can further include a treatment device control module (114) executable to control a treatment device (27) based on indications of condition symptoms (89) of a condition (28) received by the condition symptoms assessment module (87). As to particular embodiments, the treatment device (27) can be placed in the active condition by a user (16) such that the treatment device (27) seeks a connection with a computing device (8) containing or having access to the program (17). The treatment device control module (114) can further function to cause wireless pairing of the computing device (8) with the treatment device (27) using electromagnetic waves (31) rather than some form of wire to carry a signal over all or a part of the communication path between the computing device (8) and the treatment device (27). However, the example of wireless communication does not preclude embodiments in which the computing device (8) and the treatment device (27) are conventionally wired to carry the signals. As to other embodiments, the treatment device control module (114) can operatively communicate with the server (2) over the network (9) to communicatively couple the computing device (8) with the treatment device (27) and coordinate or pair operation of the computing device (8) with operation of treatment device (27) as part of an internet of things.

Figure 83:
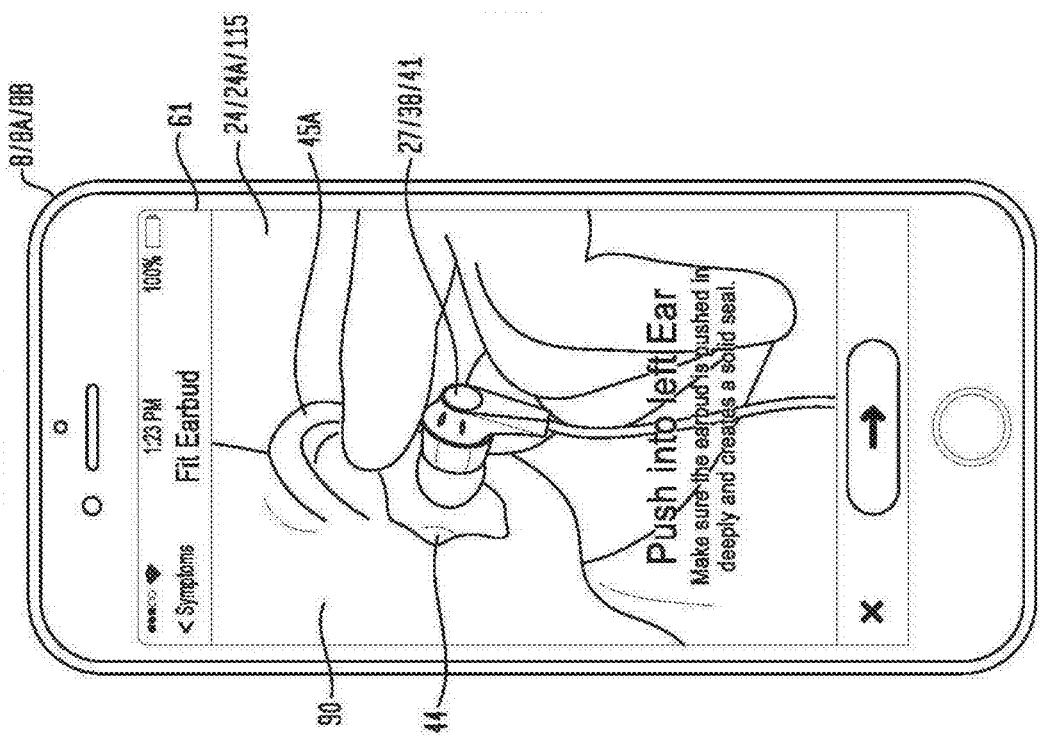
FIG. 83 illustrates a particular embodiment of a user interface including a treatment device operating menu serially depicting stepwise use of the treatment device including a first earpiece engaged with the external ear canal of a first ear.
Figure 84:
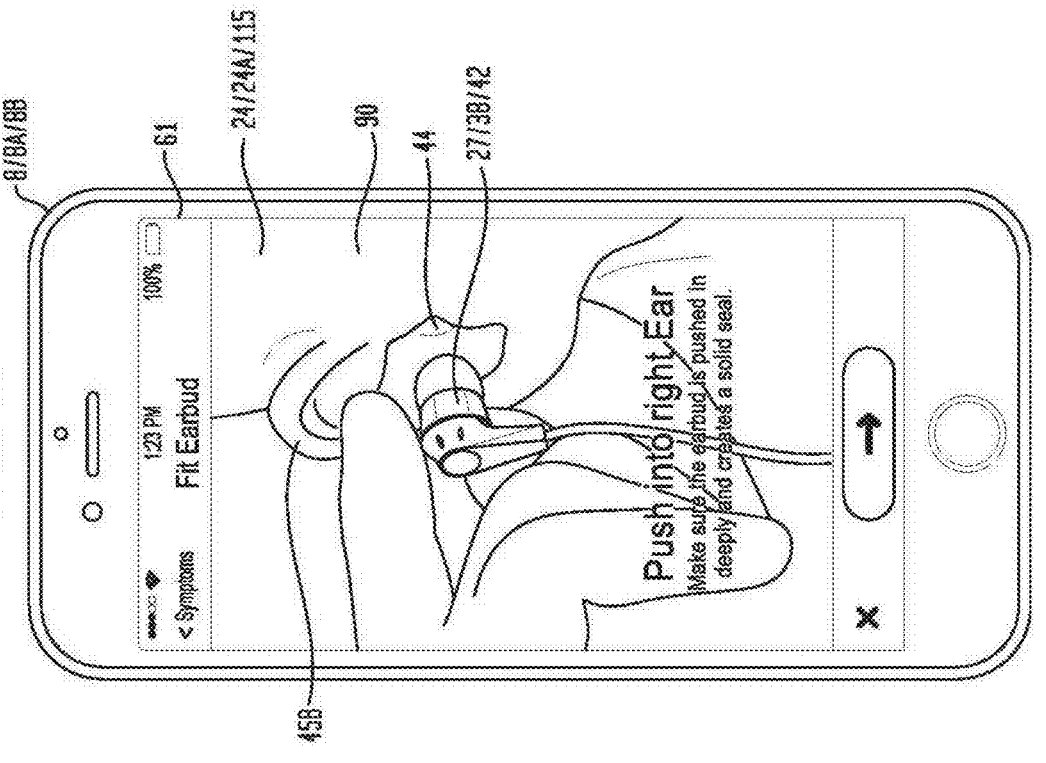
FIG. 84 illustrates a particular embodiment of a user interface including a treatment device operating menu serially depicting stepwise use of the treatment device including a second earpiece engaged with the external ear canal of a second ear.
Figure 87:
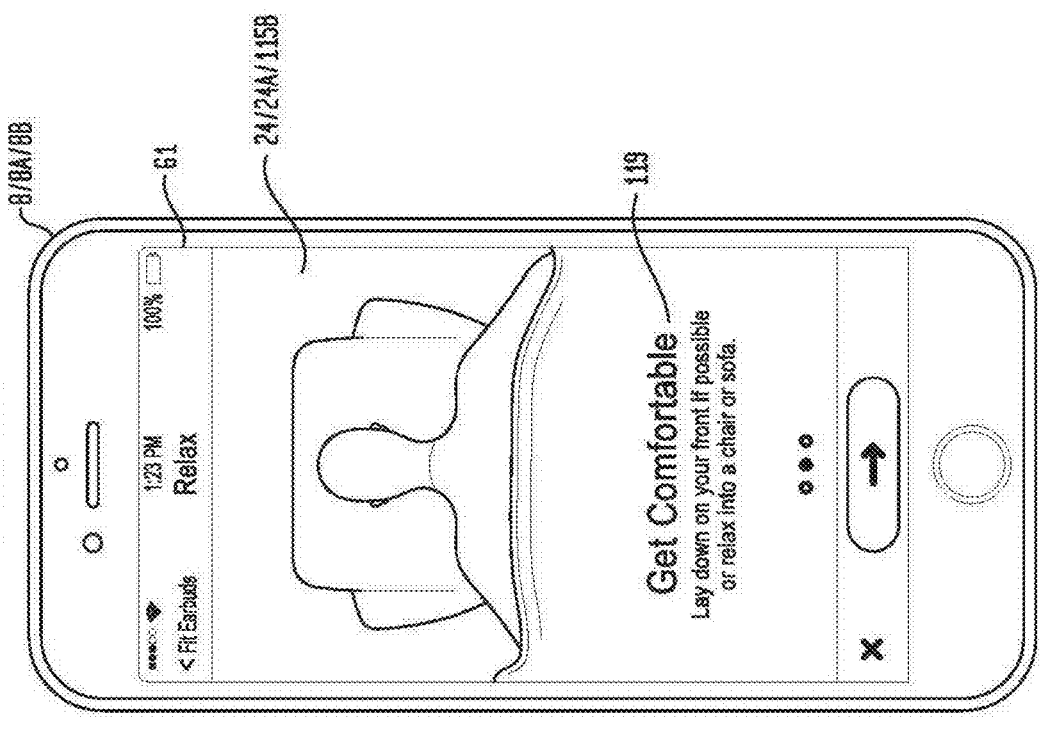
FIG. 87 illustrates a particular embodiment of a user interface including a treatment device operating menu which serially depicts adjusting environmental conditions in which the treatment device operates illustrating the position of the user in relation to the environment.
Figure 86:
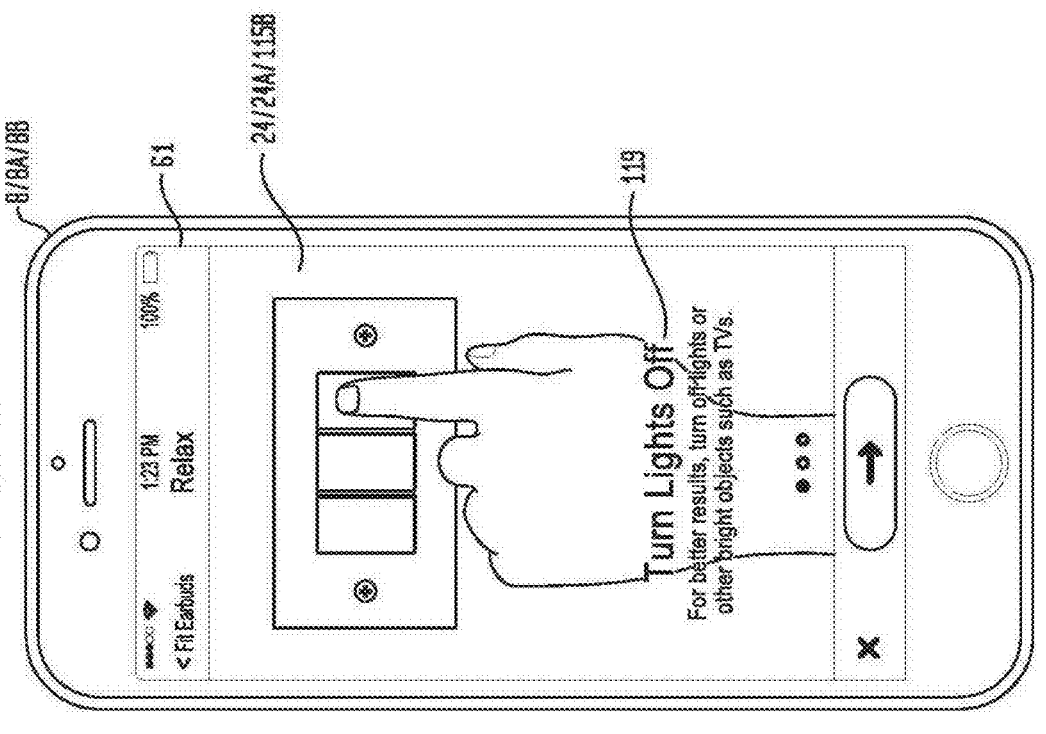
FIG. 86 illustrates a particular embodiment of a user interface including a treatment device operating menu which serially depicts adjusting environmental conditions in which the treatment device operates illustrating adjustment of ambient lighting conditions.

Now referring primarily to FIGS. 68 and 83 and 84, the treatment device control module (114) can further function to depict a treatment device operating menu (115) on the display surface (61) of the computing device (8). The treatment device operating menu (115) can provide a serial depiction of instructions on how to use the treatment device (27) in relation to the subject (30). In the illustrative example shown by the Figures the treatment device (27) encompasses the above described external ear canal pressure regulation device (38) having a first earpiece (41) and a second earpiece (42) and the treatment device operating menu (115) serially depicts engaging the first earpiece (41) with the external ear canal (44) of the first ear (45A) of the subject (30)(as shown in the illustrative example of FIG. 83) and further depicts engaging the second earpiece (42) with the external ear canal (44) of the second ear (45B) of the subject (as shown in the illustrative example of FIG. 84).

Figure 85:
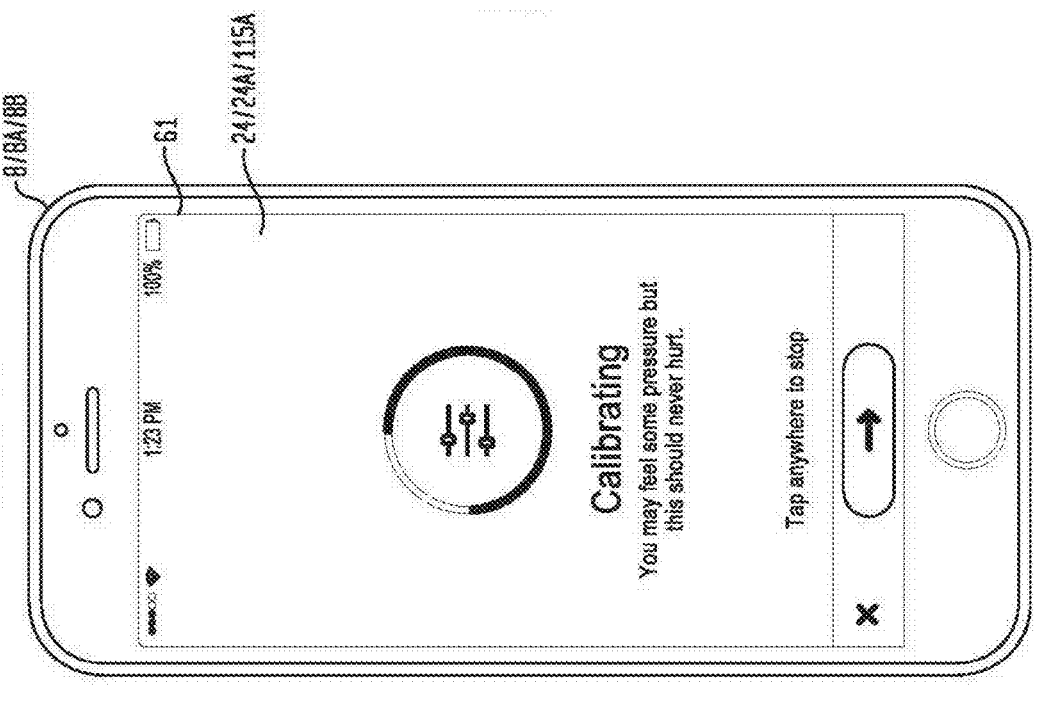
FIG. 85 illustrates a particular embodiment of a user interface including a treatment device operating menu which depicts example steps in calibrating the treatment device.

Now referring primarily to FIGS. 68 and 85, the treatment device control module (114) can further function to depict the operating menu (115) in a calibration mode (115A) which by user command (26) causes the treatment control module (114) to quantitatively measure an operating parameter (116) of the treatment device (27) and compare the measured operating parameter (116) to an operating parameter standard (117) for the treatment device (27) to assure that the treatment device (27) will operate within the operating parameters (116) selected by the treatment device control module (114). As one illustrative example in the context of the external ear canal pressure regulation device (38), the treatment device control module (114) can operate the fluid flow generator (39) of the external ear canal pressure regulation device (38) to generate and measure the pressure differential (52) generated in the first external ear canal (44A) over a period of time (118) and compare the measured pressure differential (52) to a standard pressure differential (52A). If the measured pressure differential (52) matches or deviates from the standard pressure differential (52A) within accepted limits, then the treatment device (27) repeats the process for the second external ear canal (44B) and if the measured pressure differential (52) matches or deviates from the standard pressure differential (52A) within accepted limits for the second external ear canal (44B), the external ear canal pressure regulation device (38) can be by function of the treatment device control module (114) determined to be calibrated.

Now referring primarily to FIGS. 68 and 86 through 88, the treatment device control module (114) can further function to provide serially depiction in the treatment device operating menu (115) of an environmental condition mode (115B) which provides instruction of how to adjust the environmental conditions (119) prior to operation of the treatment device (27) to treat a condition (28) or alleviate condition symptoms (29) of the condition (28). In the illustrative example in which the user (16) has selected the condition (28) Migraine (86), the treatment device operating menu (115) can depict instructions to adjust the environmental conditions (119) by "turn off lights" and "lay down on your front" and "close or cover your eyes."

Figure 89:
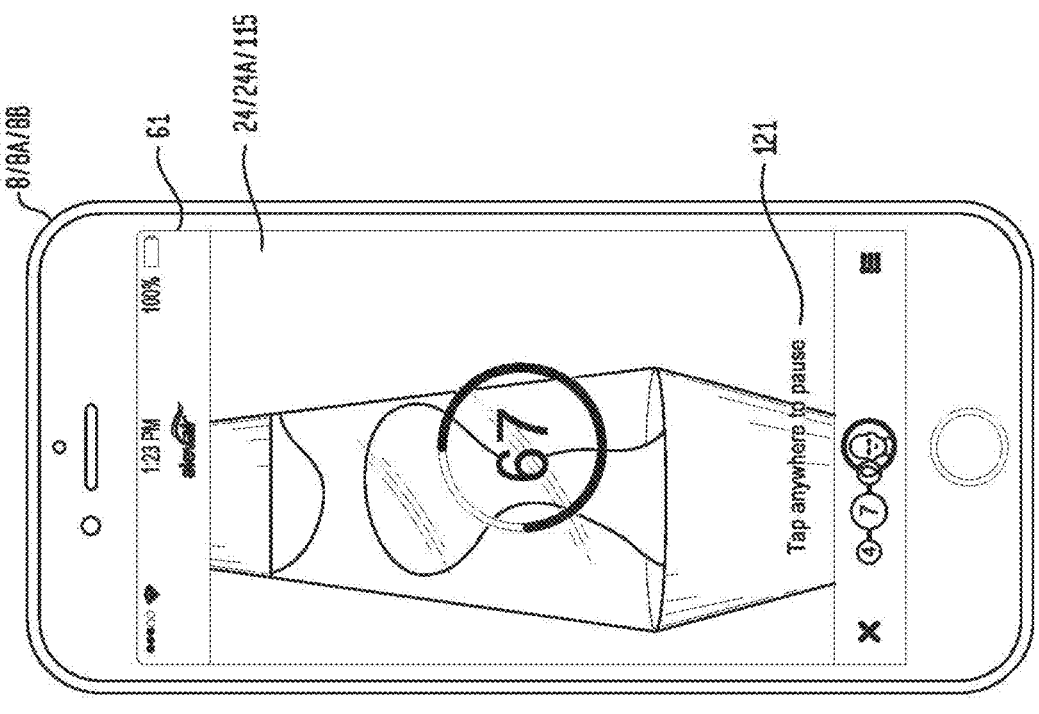
FIG. 89 illustrates a particular embodiment of a user interface including a treatment device operating menu which depicts a pause treatment icon.
Figure 89:
Figure 88:
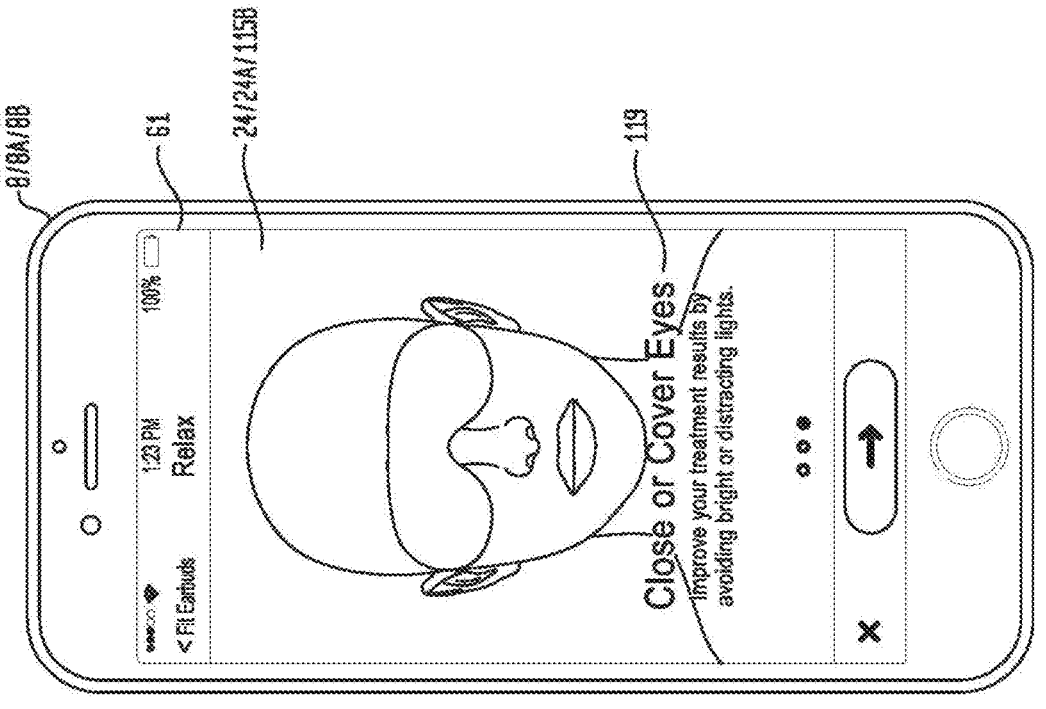
FIG. 88 illustrates a particular embodiment of a user interface including a treatment device operating menu which serially depicts adjusting environmental conditions in which the treatment device operates.

Now referring primary to FIGS. 68 and 89, the treatment device control module (114) can further function to operate the treatment device (27) to treat the condition (28) or alleviate condition symptoms (29) based on received indications of condition symptoms (89). The treatment device control module (114) can further function to cross reference indications of condition symptoms (89) of a condition (28) against a plurality of treatment device operating profiles (120) associated with the condition (28) and the treatment device (27) stored in the computing device memory (20) or the server memory (4). The treatment device control module (114) can further function to load the selected treatment device operating profile (120) for the treatment device (27). The treatment device control module (114) can further function to operate the treatment device (27) in accordance with the loaded treatment device operating profile (120).

Figure 90:
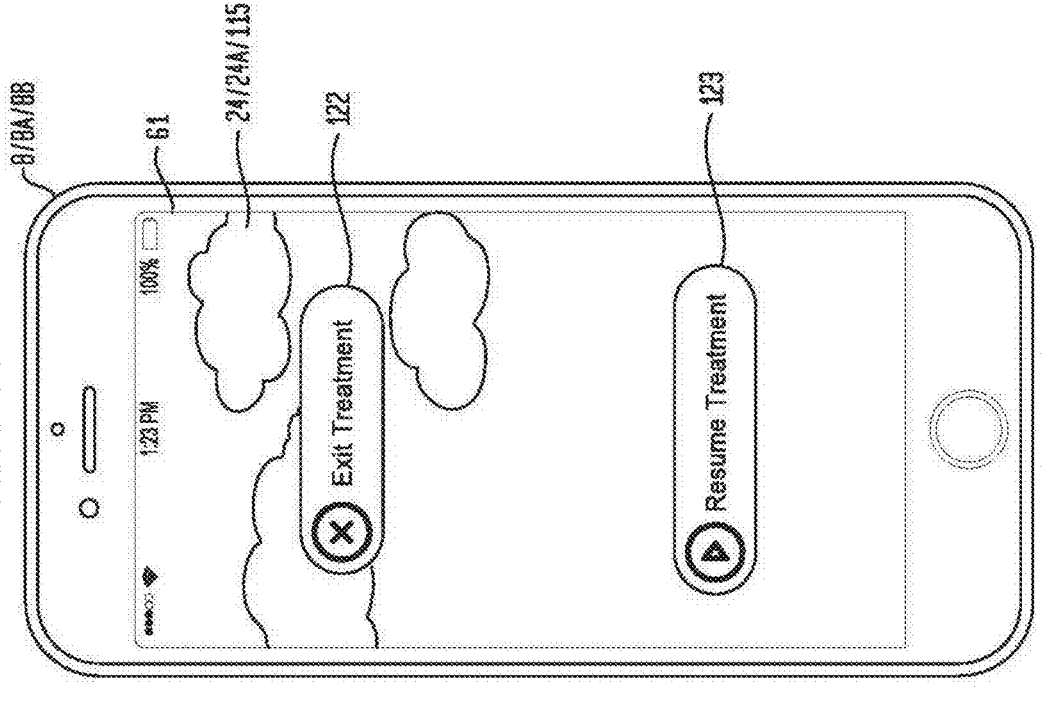
FIG. 90 illustrates a particular embodiment of a user interface including a treatment device operating menu which depicts a resume treatment icon and an exit treatment icon.

Now referring primarily to FIGS. 68 and 89 and 90, the treatment device control module (114) can further depict in treatment device operating menu (115) a treatment pause icon (121)(as shown in the illustrative example of FIG. 89) which by user command (26) causes the treatment control module (114) to pause operation of the treatment device (27) during application of the treatment device operating profile (120). Upon a user command (26) to pause operation of the treatment device (27) the treatment device control module (114) can further function to depict in the treatment device operating menu (115) a treatment exit icon (122) and a treatment resume icon (123) (as shown in the illustrative example of FIG. 90) which by user command (26) respectively causes the treatment device control module (114) to terminate administration of the treatment device operating profile (120) or resume administration of the treatment device operating profile (120).

Figure 91:
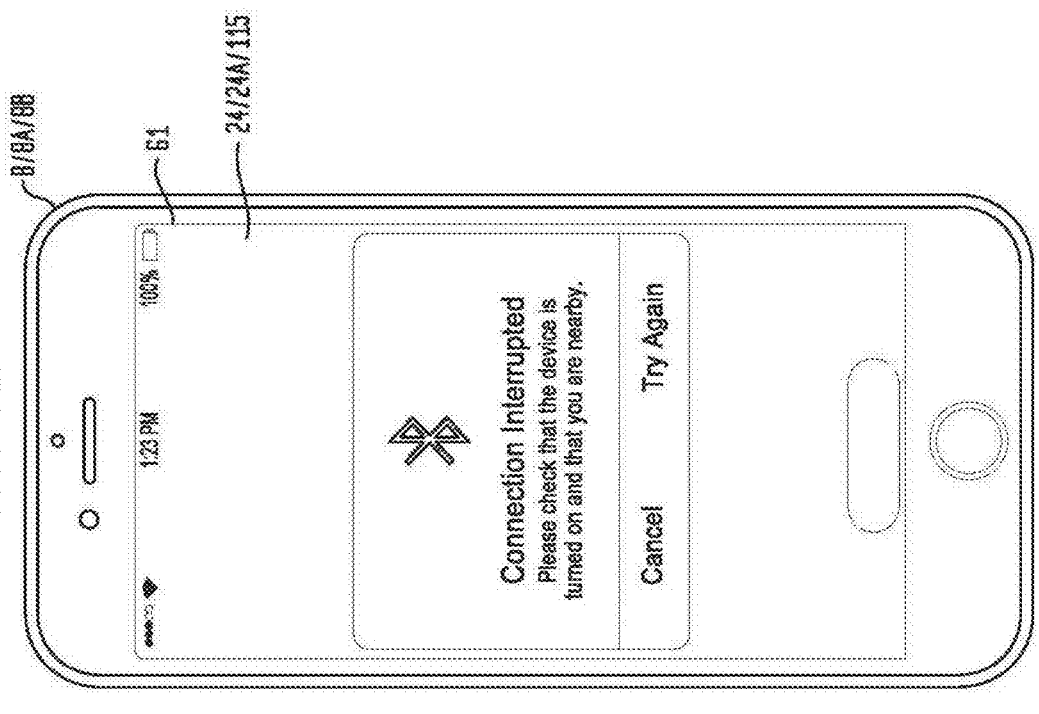
FIG. 91 illustrates a particular embodiment of a user interface including a treatment device operating menu which depicts a connection interrupt.
Figure 93:
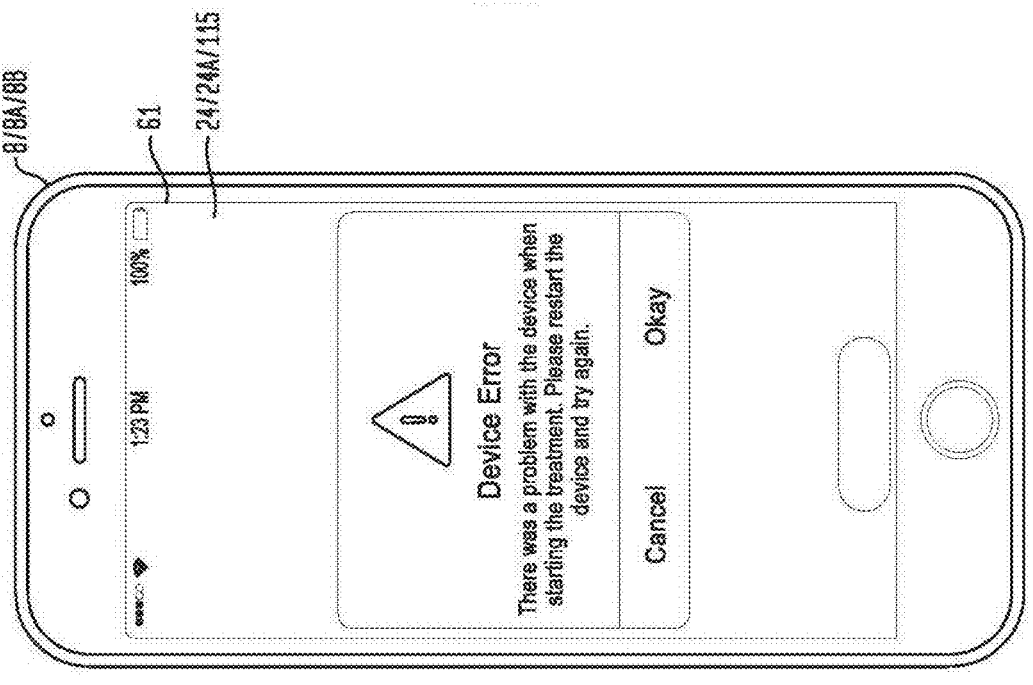
FIG. 93 illustrates a particular embodiment of a user interface including a treatment device operating menu which depicts a treatment device error.
Figure 92:
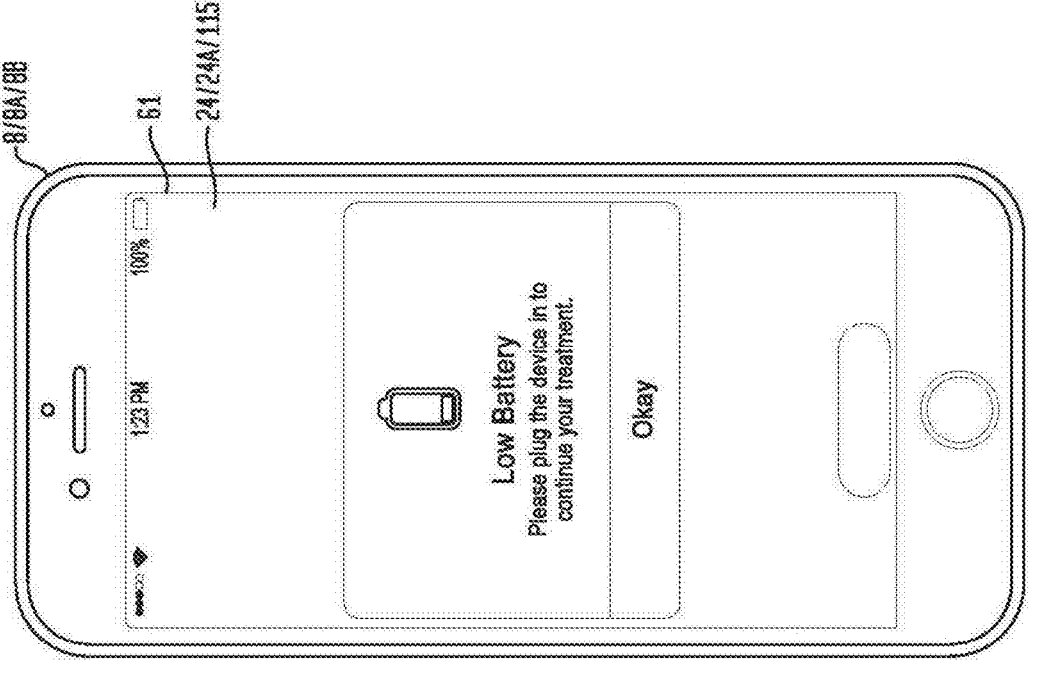
FIG. 92 illustrates a particular embodiment of a user interface including a treatment device operating menu which depicts a low battery.
Figures 94, 95:
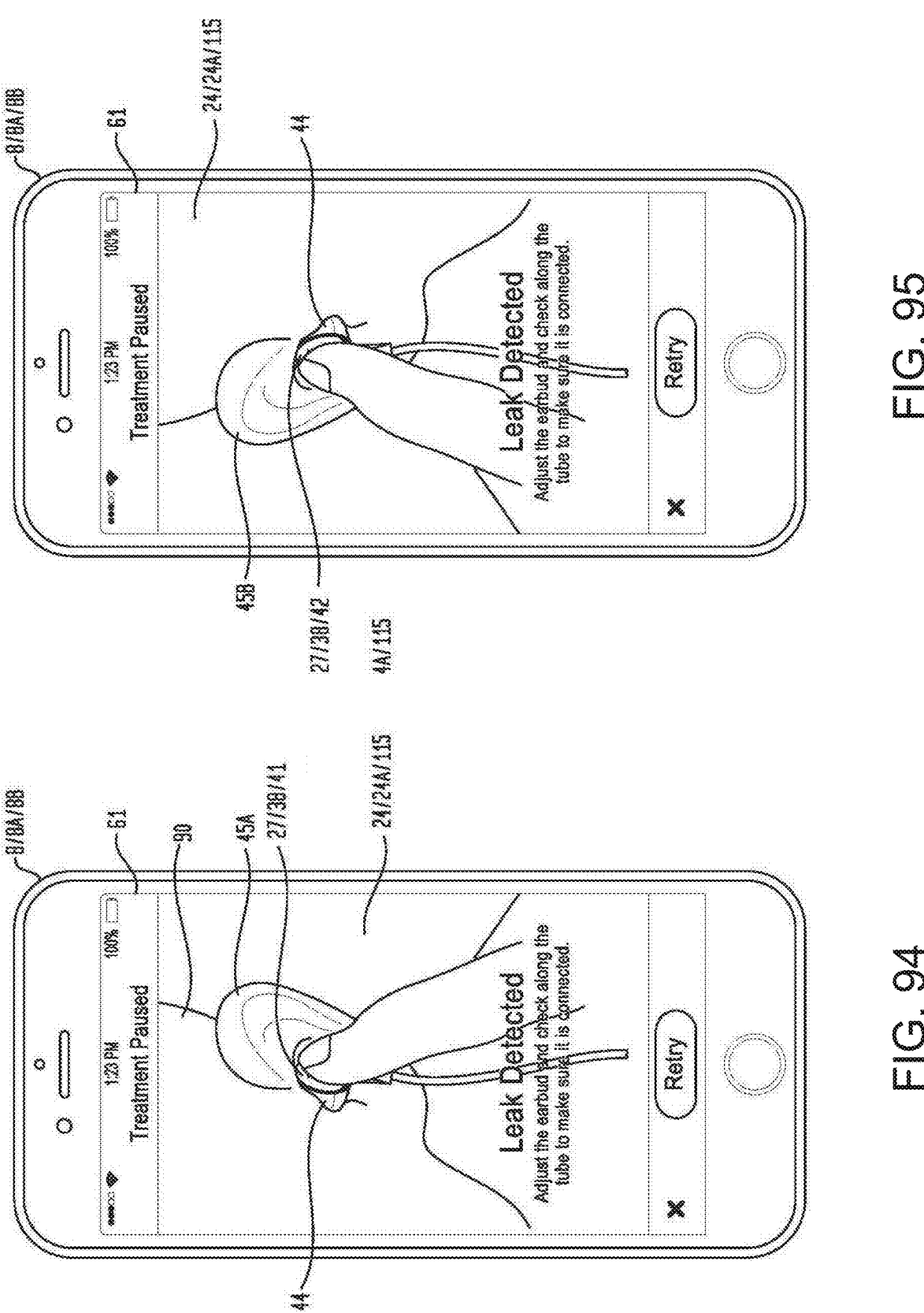
FIG. 94 illustrates a particular embodiment of a user interface including a treatment device operating menu which depicts a leak detected in a first earpiece.
FIG. 95 illustrates a particular embodiment of a user interface including a treatment device operating menu which depicts a leak detected a second earpiece.

Now referring primarily to FIGS. 68 and 91 through 95, as to particular embodiments, the treatment device control module (114) whether during calibration of the treatment device (27) or during administration of a treatment device operating profile (120), can continue to quantitatively measure one or more operating parameters (116) of the treatment device (27) and compare the measured operation parameter (116) against an operating parameter standard (117) or against the treatment device operation profile (120) to assure that the treatment device (27) administers treatment or operates consistent with the selected treatment device operating profile (120). In the illustrative example in which the subject (30) has selected the condition (28) Migraine (86), the treatment device operating menu (115) can depict instructions to manipulate or alter the computing device (8) or the treatment device (27) such that the treatment device operation profile (120) can be successfully administered. In the illustrative example of FIGS. 94 and 95, the pre-selected pressure differential (52) generated by the treatment device (27) and measured by the treatment device control module (114) is not consistent with the treatment device operation profile (120) and the treatment device control module (114) function to depict in the treatment device operating menu (115) and instruction to inspect for leaks or adjust the first earpiece (41) in relation to the first external ear canal (44A)(as shown in the example of FIG. 94). If the pressure differential (52) generated by the external ear canal pressure regulation device (38) and measured by the treatment device control module (114) remains inconsistent with the treatment device operation profile (120), the treatment device control module (114) can further depict in the treatment device operating menu (115) an instruction to inspect for leaks or adjust the second earpiece (42) in relation to the second external ear canal (44B)(as shown in the illustrative example of FIG. 95). As to particular embodiments, the treatment device control module (114) can further depict in the treatment device operating menu (115) instructions or warnings that the communication between the computing device (8) and the treatment device (27) has been interrupted (as shown in the example of FIG. 91) or that the battery of the computing device or the treatment device (27) may be low (as shown in the example of FIG. 92) or that there is a computing device (8) error or a treatment device (27) error (as shown in the example of FIG. 93).

Figure 96:
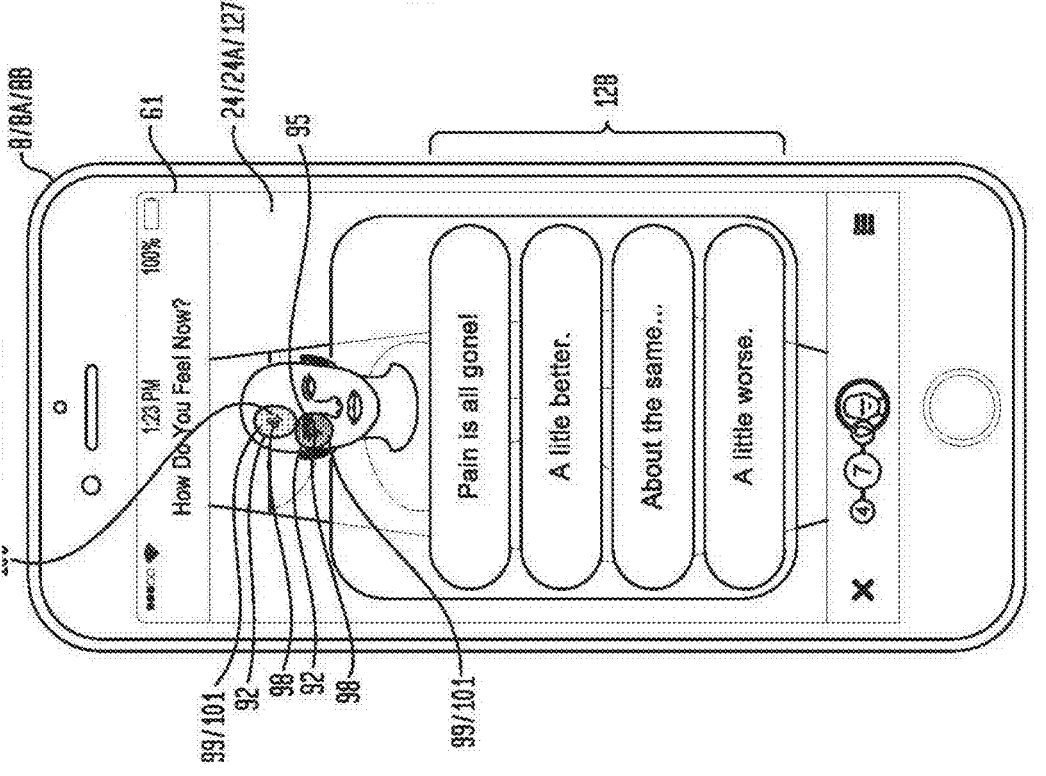
FIG. 96 illustrates a particular embodiment of a user interface including a condition symptom tracking menu which allows user to enter indications of condition symptom severity after operating the treatment device compared to condition symptom severity prior to operating the treatment device.

Now referring primarily to FIGS. 68 and 96, embodiments of the program (17) can, but need not necessarily, include a condition symptom tracking module (124) which receives indications of condition symptom relief (125) or non-relief (126) based on prior control of the treatment device (27) to administer the treatment device operating profile(s)(120) to the subject (31). The condition symptom tracking module (124) can function to depict a condition symptom tracking menu (127) on the display surface (61) of the computing device (8). As shown in the illustrative example of FIG. 96, the condition symptom tracking menu (127) can depict indications of condition symptoms (89) entered into the condition symptom menu (88) including depiction of the anatomical representation (90) with condition symptom locations (92) and indications of condition symptom intensity (94), frequency (104) or duration (105) prior entered into the condition symptom menu (88) associated with the condition (28) Migraine (86). The user (16) can by user command (26) select one of the condition symptom locations (92) to cause the condition symptom tracking module (124) to further depict a condition symptom relief scale (128) having a range from complete relief of a condition symptom (29) (shown in the example of FIG. 96 as "pain all gone") at the condition symptom location (92) to complete non-relief of a condition symptom (29) (shown in the example of FIG. 96 as "a little worse") at the condition symptom location (92). The subject (31) can repeat the process for each of the condition symptom locations (92).

Figure 97:
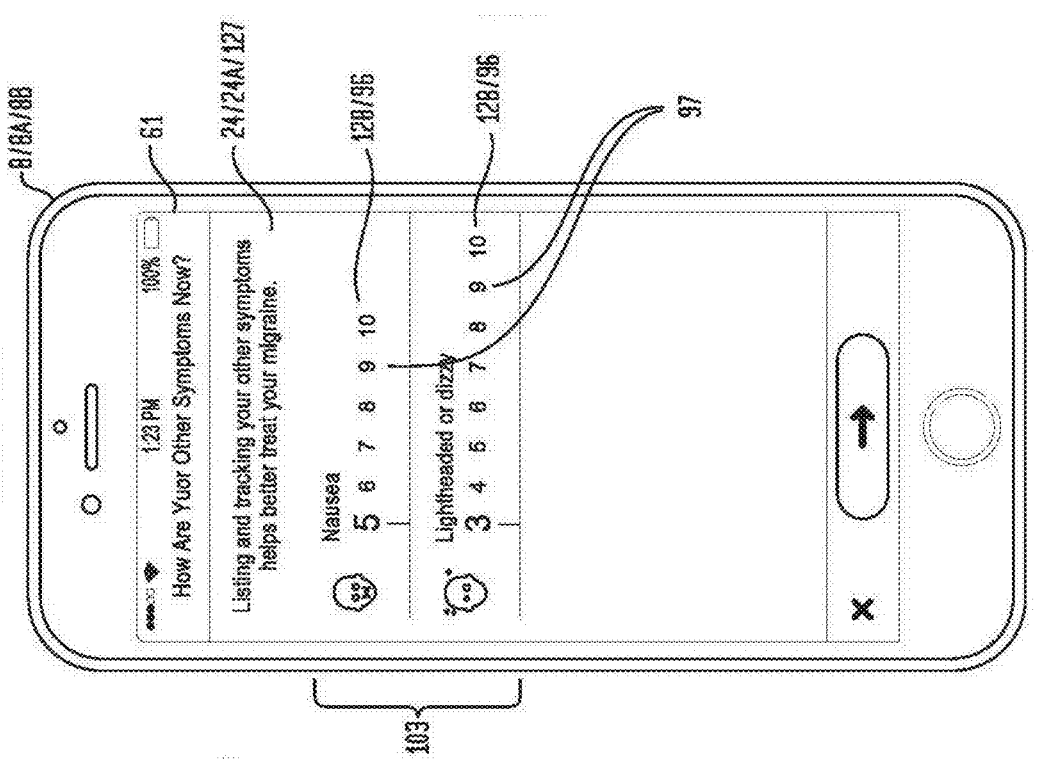
FIG. 97 illustrates a particular embodiment of a user interface including a condition symptom tracking menu which allows user to enter indications of condition symptom severity after operating the treatment device compared to condition symptom severity prior to operating the treatment device.
Figure 97:

Now referring primarily to FIGS. 68 and 97, the condition symptom tracking module (124) can, but need not necessarily, function to depict the list of condition symptoms (103) associated with the condition (28) Migraine (81) along with a condition intensity relief scale (128) in the form of a numerical scale (96) having the numerical values (97) prior entered into the condition symptom menu (88). The subject (31) can adjust the numerical value (97) associated with each condition symptom (29) to provide current and indications of condition symptom intensity (94), frequency (104) or duration (105) after the treatment device control module (114) has administered one or more of the treatment device operating profiles (120) to the subject (31).

Again referring to FIGS. 68 and 96 and 97, the treatment control module (114) can analyze indications of condition symptom relief (125) or non-relief (126) entered into the condition symptom tracking menu (127) by cross referencing condition symptom relief or non-relief (125)(126) against a plurality of treatment device operating profiles (120) associated with the condition (28) and the treatment device (27) stored in the computing device memory (20) or the server memory (4). Based on indications of condition symptom relief (125) or non-relief (126), the treatment control module (114) can subsequently alter control of the treatment device (27) toward increasing indications of condition symptom relief (125) or away from indications of condition symptom non-relief (126).

Figure 98:
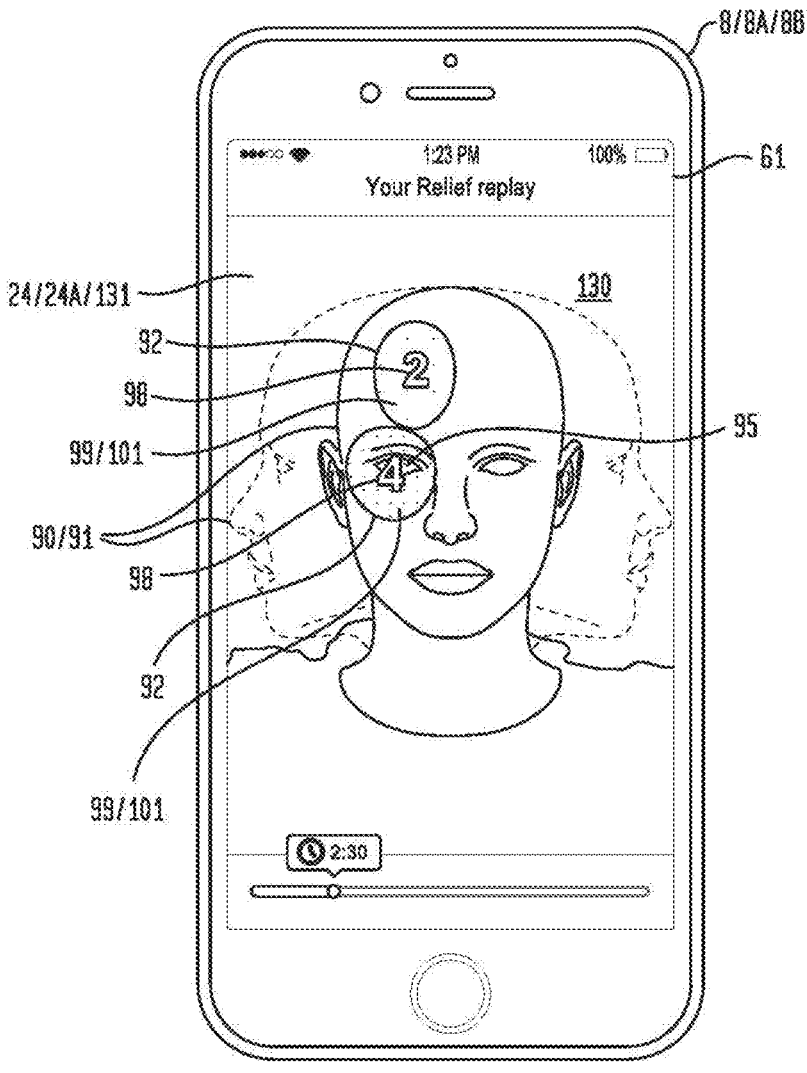
FIG. 98 illustrates a particular embodiment of a user interface including a condition symptom replay menu which allows a user to create a condition symptom relief video based on the indications of condition symptoms entered into the condition symptom menu and depicted in the anatomical representation replayable on the display surface of the computing device.

Now referring primarily to FIGS. 68 and 98, embodiments of the program (17) can, but need not necessarily, include a condition symptom relief replay module (129) executable to create a condition symptom relief video (130) replayable in a condition symptom replay menu (131) on the display surface (61) of the computing device (8) based on the indications of condition symptoms (89) entered into the condition symptom menu (88) and depicted in the anatomical representation (90) with condition symptom locations (92) and indications of condition symptom intensity (94), frequency (104) or duration (105) and the indications of condition symptom relief or non-relief (125)(126) entered into the condition symptom tracking module (124). The condition symptom relief video (130) illustrates change in condition symptoms (29) achieved by administration of the of treatment device operating profiles (120) by the treatment control module (114).

As can be easily understood from the foregoing, the basic concepts of the present disclosure may be embodied in a variety of ways. The disclosure involves numerous and varied embodiments of a treatment device control system (1) and methods for making and using such treatment device control system.

Example Treatment System

Figure 99:
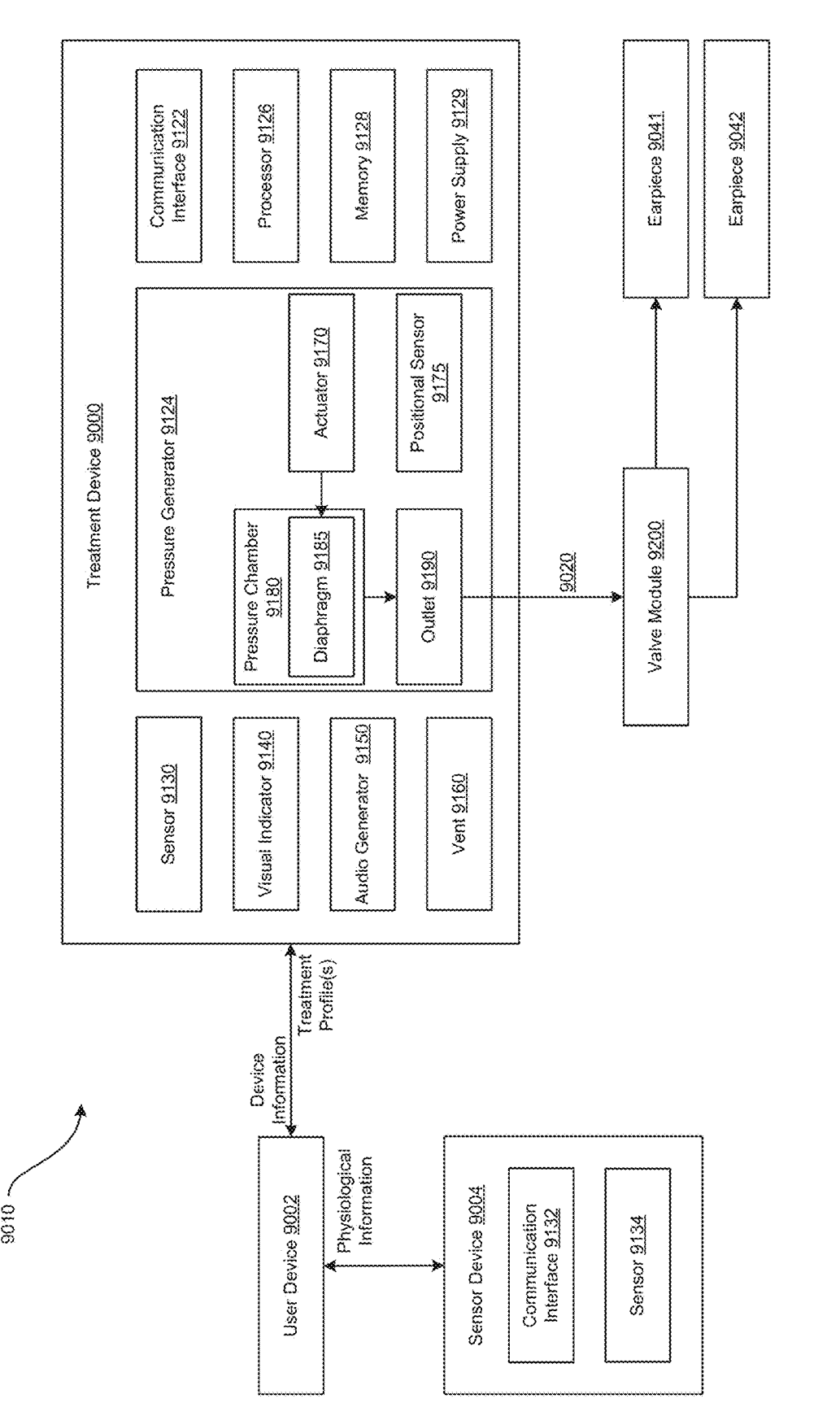
FIG. 99 illustrates a block diagram of an example treatment system having a treatment device in communication with other systems and devices.
Figure 100:
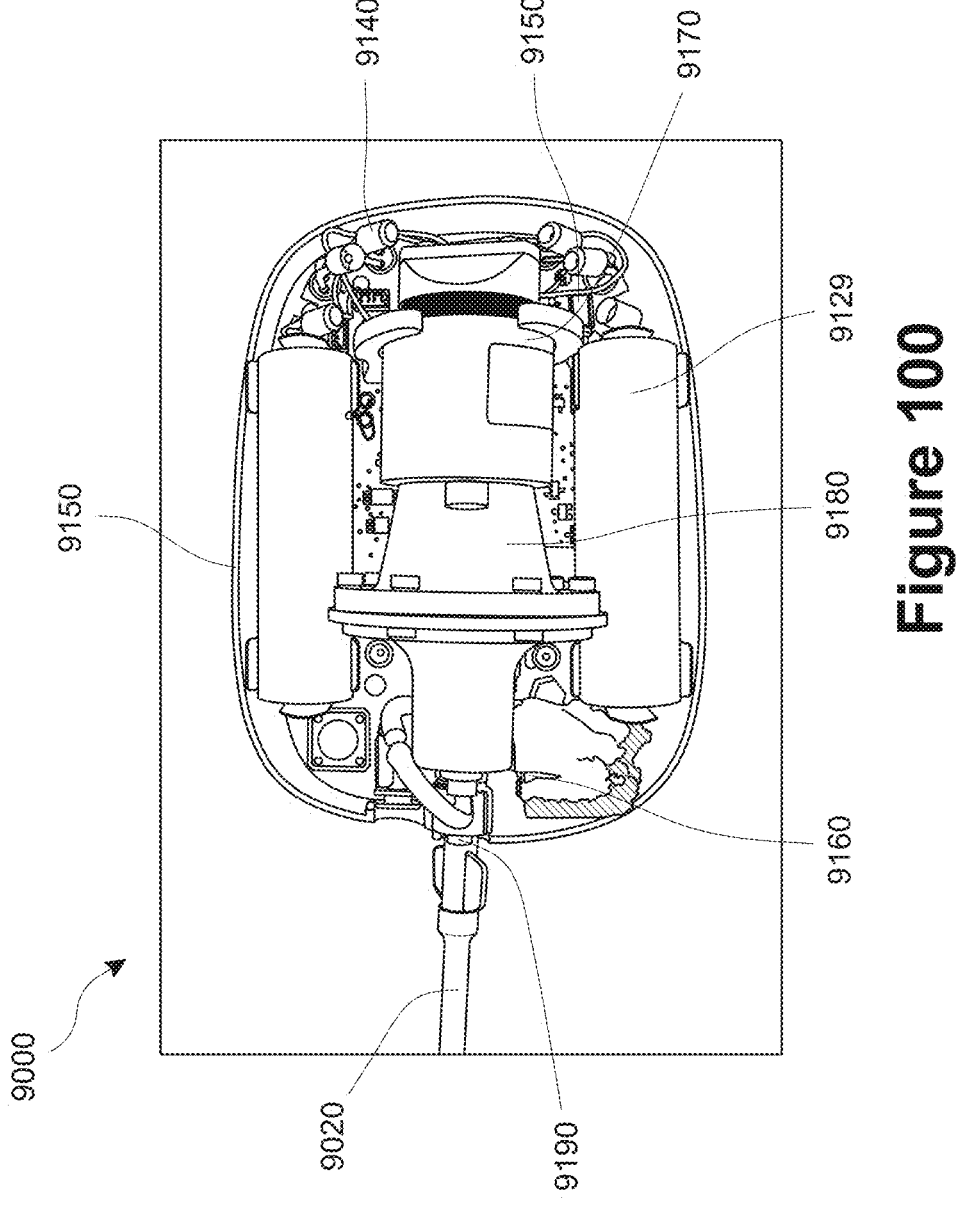
FIG. 100 illustrates an example treatment device.

FIGS. 99 and 100 illustrate a treatment device 9000, according to some embodiments. In particular, FIG. 99 is a block diagram of an example treatment system 9010 including a treatment device 9000. The treatment device 9000 may be in communication with at least one of a user device 9002, valve module 9200, and earpieces 9041, 9042. The treatment device 900 can include a wireless communication interface 9122 for communicating with the user device 9002, for example. In some cases a wired communication link can be used. In some embodiments, the user device and treatment device can be merged into a single device (e.g., sharing the same housing). Thus, the wireless communication interface 9122 can be omitted in some embodiments. In some embodiments, the one or more earpieces 9041, 9042 and/or the valve module 9200 can be part of the treatment device 9000. FIG. 100 is a top view of an example treatment device 9000 of FIG. 99, shown in an open configuration. Unless otherwise noted, reference numerals in FIGS. 99 and 100 refer to components that are the same as or generally similar to the components having the same reference numerals in the remaining figures discussed herein. While treatment system 9010 shown in FIG. 99 incorporates features not shown in other treatment systems discussed herein, it will be understood that the features described with reference to treatment system 9010 (e.g., shown in FIGS. 99 and 100) can be used with any of the embodiments described and/or contemplated herein. Any one of the treatment systems disclosed herein can be modified to include any one of the features of treatment device 9000. For example, any treatment device disclosed herein can include a pressure generator 9124, a valve module 9200, and/or any additional features, as shown and described with reference to FIGS. 99 and 100. It will also be understood that any feature, structure, material, step, or component of any embodiment described and/or illustrated herein can be used with or instead of any other feature, structure, material, step, or component of any embodiment of the treatment system 9010 and/or the treatment device 9000 of FIGS. 99 and 100.

General Overview

Shown in FIG. 99, and described herein, is an example embodiment of a treatment system 9010 comprising a treatment device 9000 and one or more earpieces 9041, 9042 configured to be inserted into a user's ear canal. The treatment device 9000 can include a housing 9005 (as shown in FIG. 100) that encloses or supports at least some components of the treatment system 9010.

The treatment device 9000 can include an outlet 9190 configured to connect the treatment device 9000 to the one or more earpieces 9041, 9042. For example, the outlet 9190 can be connected to a tubing 9020 that is in fluid communication with the one or more earpieces 9041, 9042 via a fluid flow path. The treatment device 9000 may apply pressure through one or more of the tubing 9020 and earpiece(s) 9041, 9042 to affect the user's ear canal.

In some embodiments, the tubing 9020 can be removably coupled to at least a portion of the treatment device 9000 (e.g., the outlet 9190) and/or to one or more earpieces 9041, 9042. For example, the tubing 9020 may utilize a lure lock configuration to removably attach the tubing 9020 to a corresponding locking structure on the treatment device 9000. The treatment system 9010, in some implementations, may comprise two or more sets of tubing 9020 having various configurations, such as different lengths, different diameters, different cross-sectional areas, etc. A user may select a particular tubing 9020 based on the user's needs and attach the selected tubing 9020 to the treatment device 9000. The sets of tubing 9020 can be interchangeable.

As illustrated and described herein, the treatment device 9000 can include at least one processor 9126 and computer-readable memory 9128, which can have executable instructions that are executable by the at least one processor 9126 to perform the functions of the treatment device 9000 described herein. The treatment device 9000 can receive one or more of the pressure treatment parameter profiles or parameters for treatment based on a pressure treatment parameter profile, as described herein. In some implementations, the pressure treatment parameter profiles can be stored in the memory 9128 on the treatment device. The treatment device 9000 can receive an instruction from the user device as a selection of one of the treatment profiles stored in memory. The at least one processor 9126 can operate the pressure generator 9124 to produce the pressure according to the selected pressure treatment parameter profile. In some instances, the pressure treatment parameter profiles can be stored on the user device 9002. When a treatment profile is selected (e.g., based on symptom information), the user device 9002 can send information based on the selected treatment profile (e.g., pressure set points, timing information for periods of stable or variable or oscillating pressure) to the treatment device 9000, which can implement the treatment according to the treatment profile based on the received information. In some instances, the user device 9002 can select a treatment profile, and the treatment profile can be sent to the treatment device 9000. The memory 9128 can store an active treatment profile, which can be implemented by the treatment device 9000.

The treatment device 9000 can be powered by a power source 9129 such as a battery power cell or any other suitable power source. The treatment device 9000 can include a charging port. A connector can be inserted into the charging port to charge the battery power cell of the treatment device 9000. The connector can be electrically coupled to a power source (e.g., wall outlet) by a wired connection. In some instances, the power supply 9129 can be charged using wireless charging (e.g., inductive charging).

In some embodiments, the treatment device 9000 can include one or more sensors 9130 configured to detect one or more operating conditions of the treatment device 9000. The sensor 9130 may be configured to detect any condition described herein. For example, the sensor 9130 may comprise a pressure sensor that is configured to measure the pressure within at least a portion of the treatment device 9000 and/or the user's ear (e.g., in the external ear canal). The pressure sensor can measure the pressure in the tubing 9020, the valve module 9200, the pressure chamber 9180, earpiece 9041 and/or 9042, or any other suitable pressurized location, which can provide information regarding corresponding pressure in the ear. The at least one processor 9126 may monitor the pressure measured by the sensor 9130 and can control a pressure generator 9124 (e.g., pump) to achieve the pressures set by a pressure treatment parameter profile.

The treatment device 9000 can use the pressure sensor 9130 to detect a leak, such as when the earpiece is not sealed properly in the user's ear. The treatment device 9000 may utilize any feature, structure, material, step, or component of any embodiment described and/or illustrated herein to detect and/or correct a leak condition. In some embodiments, if the pressure measured by the sensor 9130 does not increase or decrease as expected (e.g., within an acceptable threshold) when the pressure generator 9124 attempts to change the pressure, or if the measured pressure is changing (e.g., outside of an acceptable threshold) when the pressure generator 9124 is trying to hold the pressure steady, the treatment device 9000 can determine that a leak is likely present. In some embodiments, when a leak is detected, the at least one processor 9126 may perform any procedure described herein to correct the leak condition and/or indicate to the user the presence of the leak condition.

The treatment device 9000, in some implementations, can include one or more visual indicators 9140 and/or one or more audio generators 9150, as described in further detail herein. The one or more visual indicators 9140 and/or audio generators 9150 can be in electrical communication with the at least one processor 9126.

In some embodiments, the treatment device 9000 may be configured to determine internal temperature information of one or more components of the treatment device 9000. For example, the treatment device 9000 may include one or more temperature sensors. The temperature sensor may be configured to determine a temperature of one or more components of the pressure generator 9124 (e.g., the actuator 9170 or the diaphragm 9185). The temperature sensor may determine the temperature information by any suitable approaches to measure and determine temperature of an object.

The temperature sensor can transmit the sensed temperature information to the at least one processor 9126. The at least one processor 9126 may be configured to receive the information and to utilize the temperature information to determine whether the temperature system 9010 should proceed with treatment. The temperature value can be communication to the at least one processor 9126 such that the temperature value may be compared to a threshold value. In some embodiments, the treatment system 9010 may compare the temperature value with the threshold value to determine an operating condition of the treatment system and whether the treatment system 9010 should proceed with treatment. In some embodiments, if the temperature value exceeds the threshold value (e.g., if the voice coil motor or other actuator becomes too hot), the treatment system 9010 may alert a user, reduce treatment performance to decrease the internal temperature, and/or turn off treatment.

Pressure Generator

As shown in FIGS. 99 and 100, and described herein, in some embodiments, the treatment device 9000 can also include a pressure generator 9124. The pressure generator 9124 may include a pump powered by an actuator 9170. For example, the actuator 9170 may comprise an electric motor, a voice coil motor, a piezoelectric actuator, a linear actuator, a motor with a worm screw, or the like. An H-bridge can be used to control the direction of current flow to control the direction of actuation of the actuator. For example, the H-bridge can include four switches, where a first pair of switches can be closed to apply current in a first direction to drive the actuator in a first direction (e.g., to produce an increase in pressure). A second pair of switches can be closed to apply current in a second direction to drive the actuator in a second direction (e.g., to reduce pressure (or increase an amount of negative pressure)).

The pressure generator 9124 can include a pressure chamber 9180 that encloses or supports at least some components of the pressure generator 9124. For example, at least a portion of the pump may be enclosed within the pressure chamber 9180. In some embodiments, the actuator 9170 is integrated into the pressure chamber 9180. The pump can be a rotary diaphragm pump or other diaphragm pump, a piezoelectric pump, a peristaltic pump, a piston pump, a syringe pump, a rotary vane pump, a liquid ring pump, a scroll pump, a diaphragm pump operated by a piezoelectric transducer, a pump operated by a voice coil actuator, or any other suitable pump or micropump or any combinations of the foregoing. As illustrated in FIGS. 99 and 100, the pump may comprise a diaphragm 9185 housed within the pressure chamber 9180. In some embodiments, the actuator 9170 may be configured to move the diaphragm 9185 within the pressure chamber 9180. As the diaphragm 9185 is moved within the pressure chamber 9180, an internal volume of the pressure chamber 9180 can change. The change in the internal volume may cause a resultant pressure change within the tubing 9020, the earpiece(s) 9041, 9042, and/or one or both of the user's ear canal(s). For example, an increase in pressure within at least one of the tubing 9020, the earpiece 9041, 9042, and one or more ear canals of the user may occur as the actuator 9170 moves the diaphragm 9185 in a first direction. By way of another example, a decrease in pressure may result when the actuator 9170 moves the diaphragm 9185 in a second direction. As discussed herein, the tubing 9020 and/or earpieces 9041, 9042 may be connected in fluid communication to the treatment device 9000 through the outlet 9190. The pressure generator 9124 can produce a positive pressure that is higher than ambient pressure and a negative pressure that is lower than ambient pressure. In some instances negative pressure therapy can be highly effective, such as by pulling on the tympanic membrane.

As described herein, the treatment device 9000 is configured to operate in one or more operating modes. The pressure generator 9124 may be configured to generate treatment parameter profiles that oscillate between various pressure values (e.g., between positive and negative pressure values). The treatment system 9010 can activate the pressure generator 9124 to provide or achieve a particular set point or target level of pressure within one or both of the ear canals of a user. The treatment system 9010 may perform any treatment method or treatment pressure profile disclosed herein. The processor 9126 may operate the treatment device 9000 differently depending on a selected mode of operation. For example, the pressure generator 9124 can be operated continuously based on feedback from the sensor 9130 that measures pressure in the fluid flow path. In some embodiments, the processor 9126 may alter the pressure generator 9124 in response to a sensed condition. By way of example, a pressure treatment parameter profile can supply a pressure set point (e.g., negative 0.75 PSI). The processor 9126 can operate the actuator to increase the negative pressure, and the processor 9126 can monitor the pressure measured by the sensor 9130. When the measured pressure reaches negative 0.75 PSI, the processor 9126 can stop the actuator 9170. The processor 9126 can monitor the measured pressure and operate the actuator 9170 in response to maintain the negative 0.75 PSI. Movement of the user, movement of the treatment device 9000, etc. can cause pressure variations, and the actuator can control the pressure to compensate for those variations.

If the system is not able to produce a threshold pressure, the system can determine that a leak (e.g., a gross leak) is present. The threshold pressure can be 0.25 PSI, 0.5 PSI, 0.75 PSI, 1.0 PSI, 1.5 PSI, 2.0 PSI, or any values therebetween, or any ranges bounded by any combination of these values. The threshold pressure can be 30%, 40%, 50%, 60%, 70%, 80%, 90%, 95% of the set point pressure, or any values therebetween, or any range of percentages bounded by any combination of these values. In some embodiments, if operating the actuator 9170 results in a measured pressure change that is less than the expected pressure change by a threshold amount, the system can determine that a leak (e.g., a gross leak) is present. The threshold amount can be 30%, 40%, 50%, 60%, 70%, 80%, 90%, 95% of the expected pressure change, or any values therebetween, or any ranges bounded by any combination of these values.

In some instances, the pressure generator 9124 may include an oscillation generator (e.g., an electromagnetic restrictive transducer). The electromagnetic restrictive transducer may be configured to facilitate the generation of rapid oscillations during the application of one or more treatment parameter profiles, as described herein. The electromagnetic restrictive transducer, in some embodiments, can be engaged with at least one of the pressure chamber 9180, the diaphragm 9185, and the actuator 9170 to generate a rapid oscillation (e.g., 50 Hz, 100 Hz, 150 Hz, 200 Hz, 250 Hz, 300 Hz, or any values therebetween or any ranges bounded by these values). In some implementations, the actuator (e.g., a voice coil motor) can induce a baseline pressure that is not at ambient pressure, and the electromagnetic restrictive transducer can superimpose the oscillation over the baseline pressure.

Positional Sensor

The treatment device 9000, in some instances, may be configured to determine at least one of a position, orientation, and motion information of one or more components of the treatment device 9000. In some embodiments, as shown in FIG. 99, the treatment device 9000 may include one or more positional sensors 9175. The positional sensor 9175 may be configured to determine a position of one or more components of the pressure generator 9124 (e.g., the actuator 9170 or the diaphragm 9185).

The positional sensor 9175 can transmit the sensed information to the at least one processor 9126. The at least one processor 9126 may be configured to receive the information and to utilize the position and/or orientation information to determine an expected pressure value during a treatment procedure. The expected pressure value can be communication to the at least one processor 9126 such that the expected pressure value may be compared to an actual pressure value determined by a pressure sensor (e.g., sensor 9130). In some embodiments, the treatment system 9010 may compare an expected pressure value with an actual pressure value to determine an operating condition of the treatment system (such as a slow leak or gross leak), as described herein.

The positional sensor 9175 may determine the position, orientation, and/or motion information by any suitable approaches to measure and determine the position and orientation of an object in three-dimensional space. In some embodiments, the positional sensor 9175 may capture position and/or orientation information of one or more components of the pressure generator 9124 by an external tracking system, such as, by way of non-limiting example, an optical tracking system. For example, an optical tracking system and/or inertial sensors (for example, gyroscope sensors and/or accelerometers) can be configured to obtain one or more of position, orientation, and motion information of the actuator 9170 and/or diaphragm 9185. In some instances, the actuator 9170 and/or diaphragm 9185 may include visual markers that provide placement and/or location indications to a positional sensor 9175. For example, the actuator 9170 and/or diaphragm 9185 may be annotated with positional indicators (e.g., depth indications) along at least a portion of the actuator 9170 and/or diaphragm 9185 to orient a positional sensor 9175 interacting with the actuator 9170 and/or diaphragm 9185. The positional sensor 9175, in some implementations, can determine when the actuator 9170 and/or the diaphragm 9185 is at a zero pressure position (e.g., a center position). In some embodiments, the actuator 9170 and/or the diaphragm may comprise two or more visual indicators to indicate to the positional sensor 9175 when the actuator 9170 and/or the diaphragm 9185 is at a position close to the zero pressure position. So the system can act in anticipation of reaching the zero pressure position (e.g., to vent the pressure chamber to ambient pressure, or to slow down the actuator to more smoothly approach or cross the zero-pressure position). Indicator(s) can be used to identify other positions, such as when the actuator is pegged at the limit of its motion, or when it is close to being pegged. Indicator(s) may be active (e.g., light-emitting diodes, infrared red sources, etc.) and/or passive (e.g., optically recognizable colors patterns). In some cases, the indicator(s) can be the natural structure of the moving component (e.g., wrapped wire, end cap, etc.). By way of example, a voice coil motor can include a moving shaft that has conductive wire coiled around the shaft, and an end cap positioned at the end of the shaft. The conductive wire can be a different color than the end cap (e.g., copper vs. black), and the transition between the conductive wire and end cap can be the visual indicator used to determine the position of the actuator.

The positional sensor 9175 can include a photo detector (e.g., optical sensor) that is sensitive to light. When light from an indicator on a movable portion of the pressure generator 9124 (e.g., the diaphragm or actuator component) is detected by the photo detector, the signal from the photo detector can be used to determine the position of the movable portion. A light source can be used to illuminate the area that is visible to the photo detector. By way of example, a light source (e.g., visible light or IR light) can illuminate the shaft of a voice coil motor, and light can reflect from the voice coil motor to a photo detector. The photo detector can be positioned at a location so that when the color of the reflected light received by the photo detector changes (e.g., from copper to black or vice versa) that can indicate that the actuator shaft is at a position that corresponds to zero pressure (e.g., a center position for the actuator).

Venting Structure

The treatment device 9000, in some instances, can include a vent 9160. The vent 9160 can provide an opening to permit gas to flow between the atmosphere and at least a portion of the treatment device 9000. The vent 9160 may open a fluid pathway between the atmosphere and at least a portion of the treatment device 9000 by any suitable approaches. For example, the processor 9126 can selectively open and close a fluid pathway, such as, by way of non-limiting example, a solenoid valve. In some embodiments, the information from the positional sensor 9175 may be used to open the vent when the pressure generator is at a zero-pressure state (e.g., when the actuator 9170 and/or the diaphragm 9185 is at a center or zero-pressure position). This can be done to reset the pressure generator. During some pressure treatment profiles, the target pressure can cross the zero-pressure (e.g., ambient pressure) state. For example, as the target pressure transitions from a positive pressure to a negative pressure, the actuator can cross the zero-pressure position. The positional sensor 9175 can be used to determine when the actuator is at the zero-pressure position, and the vent can be opened (e.g., by actuating the solenoid valve) to vent the pressure chamber to ambient pressure to reset the pressure generator. When the pressure set point (e.g., from a treatment profile) is zero differential pressure (e.g., ambient pressure), the vent 9160 can be opened and the actuator 9170 can be driven to the zero pressure position (e.g., as determined by the positional sensor 9175).

The vent 9160 may selectively open a fluid pathway between the external atmosphere and the pressure chamber 9180 and/or outlet 9190. When the vent 9160 opens, the vent 9160 can be configured to equalize the pressure within the pressure chamber 9180 and/or outlet 9190 with atmospheric pressure. For example, in some instances when the pressure within the pressure chamber 9180 is greater than atmospheric pressure, the vent 9160 may open and gas may be expelled to the atmosphere to decrease the pressure within the pressure chamber 9180. By way of another example, in some embodiments, when the pressure within the pressure chamber 9180 is less than atmospheric pressure, the vent 9160 may open and gas may flow into the pressure chamber 9180 from the atmosphere to increase the pressure within the pressure chamber 9180. The treatment system 9010, in some instances, may utilize the vent 9160 to correct a leak condition, as discussed herein.

In some instances, the actuator can become pegged at the end of its range of motion. For example, during a negative pressure sustained dwell, the system can try to maintain a negative pressure (e.g., negative 0.5 PSI) in the ear for sustained amount of time. If a slow leak is present, the actuator 9170 may need to continue moving the diaphragm 9185 to maintain the negative 0.5 PSI of pressure. At some point, and actuator 9170 can reach the end of its range of motion so that it can no longer maintain the negative pressure at 0.5 PSI. The positional sensor 9175 can be used to determine when the actuator 9170 is pegged, or close to being pegged. In some cases, the actuator can have an electrical operational range (e.g., driving voltage range) can the actuator can be determined to pegged when the limit of the electrical operational range is reached. When the actuator 9170 becomes pegged, the system can reset the pressure generator 9124 and then return to applying the specified pressure differential. For example, the vent 9160 can be opened, and the actuator 9170 can be moved to the zero-pressure differential position (e.g., as determined using the positional sensor 9175). Then the vent 9160 can be closed, and the actuator 9170 can be moved to again apply the negative 0.5 PSI of pressure, but without being pegged. The treatment can be interrupted for only a short time to reset the pressure generator, such as for a time of 0.1, 0.2, 0.5, 0.8, 1.0, 2.0, or 3.0 seconds, or any values therebetween, or any ranges bounded by those values.

In some embodiments, a dampening component (not shown), such as a noise dampening component, can be interposed between the vent 9160 and the atmosphere. The dampening component can reduce the noise generated by the treatment device 9000 during operation. In some implementations, the treatment device 9000 can communicate information, such as information related to provision of pressure therapy, to one or more remote devices.

Valve Module

The treatment device 9000, in some instances as described herein, may be configured to selectively apply treatment to one or both ears at the same or different times during a treatment session, without the user needing to reposition the ear plug. The device can have a right earpiece (e.g., 9041) and a left earpiece (e.g., 9042). In some embodiments, as shown in FIG. 99, the treatment device 9000 may include one or more valve modules 9200. The valve module 9200 may be configured to selectively establish fluid communication between the treatment device 9000 and one or more earpieces 9041, 9042.

The valve module 9200 can open a fluid flow pathway to at least one earpiece 9041, 9042. The at least one earpiece 9041, 9042 may then be configured to apply selective pressure treatment to the respective ear canal. Pressure generated by the pressure generator 9124 may be transferred along the tubing 9020 and towards the earpiece(s) having an opened fluid pathway. The valve module 920 can have a right configuration that is configured to provide an open fluid pathway to a right earpiece (e.g., 9041) only. In the right configuration the fluid pathway to the left earpiece (e.g., 9042) can be closed. The valve module 920 can have a left configuration that is configured to provide an open fluid pathway to a left earpiece (e.g., 9042) only. In the left configuration the fluid pathway to the right earpiece (e.g., 9041) can be closed. In some embodiments, the valve module 920 can have a both configuration, where fluid pathways are open to both the right earpiece (e.g., 9041) and the left earpiece (e.g., 9042). In some instances, a closed configuration can close the fluid pathways to the right and left earpieces.

The valve module 9200 may selectively establish fluid communication with one or more earpieces 9041, 9042 by any suitable approaches to selectively open and close a fluid pathway. For example, the valve module 9200 may comprise a first position that is configured to open a fluid pathway to the earpiece located in the user's right ear canal and to close a fluid pathway to the earpiece located in the user's left ear canal. The valve module 9200 may comprise a second position that is configured to open a fluid pathway to the earpiece located in the user's left ear canal and to close a fluid pathway to the earpiece located in the user's right ear canal. The valve module 9200 may comprise a third position that is configured to open the fluid pathways to both earpieces located in the user's left ear canal and the user's right ear canal. The valve module 9200 may comprise a fourth position that is configured to close the fluid pathways to both the earpieces located in the user's left ear canal and the user's right ear canal.

In some embodiments, the valve module may be manually actuated by a user to selectively establish a fluid communication between one or more earpieces 9041, 9042. The valve module 9200, in some instances, may comprise a switch that may comprise multiple positions to selectively close one or more fluid pathways. A manual actuator can be manipulated by the user to transition the valve module between the right configuration and the left configuration, and in some cases to the both configuration and/or to the closed configuration. A rotatable stopcock valve with a manual actuator can be used.

In some embodiments, the valve module 9200 may be automated and configured to be controlled by the treatment system 9010. For example, the treatment system 9010 may be configured control the selective opening and closing of the valve module 9200 based on the treatment profile without requiring user interaction. The valve module 9200 can be electronically actuated between the right configuration and the left configuration, and in some cases to the both configuration and/or the closed configuration as well. The treatment device 9000, in some implementations, may comprise a wired connection to valve module 9200. The wired connection may be configured to send signal to an actuator configured to toggle the valve module 9200 between various valve module 9200 positions, as described herein. The wired connection can supply power to one or more electronic actuators to selectively set the configuration of the valve module 9200. For example, two solenoid valves can be used: one for opening and closing the pathway to the right earpiece, and another for opening and closing the pathway to the left earpiece. In some implementations, a rotating stopcock valve can be driven by an electronic actuator. The wire(s) can run inside the tube, outside the tube, or can be embedded inside the wall of the tubing.

In some embodiments, the valve module 9200 may comprise a wireless receiver (e.g., Bluetooth) configured to receive position information and automatically selectively open and/or close one or more fluid pathways in response to the received position information. The valve module 9200 can have a power supply (e.g., a battery) for powering the electronic actuator.

In various embodiments discussed herein, treatment can be transitioned from one ear to the other. If the system has a single earpiece, the user can be provided an instruction to move the earpiece from one ear to the other side. If the system has two earpieces and a manual valve module 9200, the user can be provided with an instruction to toggle the valve module 9200 manually to change the treatment from one ear to the other side. If the system has two earpieces and an automated valve module 9200, the system can toggle the valve module 9200 without any involvement from the user. Similarly, in various embodiments discussed herein, the system can select whether to provide treatment to the right ear or left ear. If the system has a single earpiece, the user can be provided an instruction to insert the earpiece into the selected ear. If the system has two earpieces and a manual valve module 9200, the user can be instructed to use both earpieces and to put the manual valve module 9200 in the selected configuration. If the system has two earpieces and an automated valve module 9200, the user can be instructed to use both earpieces, and the system can select which earpiece to use for treatment without any involvement from the user.

As illustrated in FIG. 99, the valve module 9200 may reside along the tubing 9200, external to the treatment device 9000. For example, the tubing 9020 may comprise a single fluid pathway connected to the treatment device 9000 and then split into two or more fluid pathways at the connection with the valve module 9200. Each of the two or more fluid pathways may be connected to a particular earpiece and may be selectively opened and closed by the valve module 9200. However, while the valve module 9200 is illustrated in FIG. 99 as residing outside of the housing 9005 of the treatment device 9000, it will be understood by one of ordinary skill in the art that the valve module 9200 may be located within the housing 9005. For example, the valve module 9200 may be connected to the outlet 9190 with two or more tubings 9020 extending therefrom.

In some embodiments, the system can include two pressure generators 9124, one for applying pressure through the right earpiece (e.g., 9041) and the other for applying pressure through the left ear (e.g., 9041). This configuration can enable different pressures to be applied simultaneously to the different ears. Also, with this configuration, the system could select whether to apply treatment to the right ear or left ear by controlling which pressure generator is driven.

Visual Indicator

With continued reference to FIGS. 99 and 100, in various embodiments, the treatment device 9000 may include an information output element, which can communicate information to the user. The information output element can be one or more visual indicators 9140. The one or more visual indicators 9140 may be configured to signal one or more operating or failure conditions of treatment system 9010, according to some embodiments. The one or more visual indicators 9140 may provide an indication regarding a different operating or failure condition. In some implementations, one or more active (for example, lit) visual indicators 9140 can represent a certain operation condition for the treatment system 9010. For example, a visual indicator 9140 can provide an indication as to presence of leaks in the treatment system 9010. As another example, one or more visual indicators 9140 can provide an indication as to the remaining capacity or life of a power source, such as batteries, and an active battery visual indicator 9140 can represent a low capacity. In some embodiments, the one or more visual indicators 9140 can represent a combination of one or more of the above operating or failure conditions of the treatment system 9140 or other operating or failure conditions for the treatment system 9140. The visual indicator(s) can provide different colors, different patterns, different flashing or pulsing rates, or other visual differences between output information that the treatment device 9000 is not yet paired (e.g., with the user device), that the treatment device 9000 is attempting to pair (e.g., with the user device), that the treatment device 9000 has successfully paired (e.g., with the user device), that the power supply 9129 (e.g., battery) is being charged, that the power supply 9128 (e.g., battery) is running low, that a gross leak was detected, that a slow leak was detected, input requested from the user (e.g., to input updated pain symptom information) and/or normal treatment operation.

In some instances, when the treatment device 9000 is performing treatment, the visual indicator 9140 can illuminate at least a portion of the treatment device 9000 with green light, such as light of 500 nm to 570 nm, or light of 520 nm to 550 nm, or of light of about 535 nm. The green light can have a therapeutic effect, such as for relief of migraine headache pain, other pain syndromes, and/or other neurological disorders. During treatment, the treatment device 9000 can be lit up to provide a relatively dim light source to the user. Often, during a migraine episode, the subject can be sensitive to light. So lights in the room can be turned off, while the visual indicator 9140 on the treatment device 9000 can provide a dim light source. Also, as the light transitions in color, or intensity, or pattern, etc. the light transitions can be gradual, because the migraine patient is often sensitive to light. Light pulses or transitions can occur over the course of 0.5 seconds, 1.0 second, 1.5 seconds, 2 seconds, 3 seconds, 5 seconds, 7 seconds, 10 seconds, 15 seconds or more, or any values therebetween, or any ranges bounded by these values. The housing can be translucent, so that the light source(s) inside the housing can illuminate the housing, for example, so that the whole treatment device housing emits light. The application running on the user device (e.g., smartphone) can cause the display of the user device to turn on and off gradually, similar to the discussion above with regards to the gradual light pulses.

With reference to FIG. 100, the one or more visual indicators 9140 may comprise one or more light sources, such as LEDs, configured to illuminate at least a portion of the housing 9005. The one or more visual indicators 9140 can, for instance, be of a different color, two different colors (for example, two indicators can share the same color), or same color. The visual indicators 9140 may be located within the housing 9005. The visual indicators 9140 may be configured to selectively activate.

In some embodiments, the one or more information output elements (e.g., the visual indicators 9140) may include visual, audible, tactile, and other types of indicators or alarms configured to signal to the user various operating conditions. Such conditions include system on/off, standby, pause, normal operation, earpiece problem, leak, error, and the like. The treatment system 9010 may include speakers, displays, light sources, etc., or combinations thereof.

Audio Generator

The treatment device 9000, in some embodiments, may include one or more audio generators 9150. The one or more audio generators 9150 may be configured to signal one or more audio commands or information to a user. The one or more audio generators 9150 may provide an indication to the user when the treatment system 9010 requests information from the user. The one or more audio generators 9150 can provide therapeutic audio signals (e.g., tones) to the user.

The one or more audio generators 9150 may be located within the housing 9005, as illustrated in FIG. 100. The audio generator 9150 may generate a sound that is configured to be propagated through the tubing 9020 to an earpiece 9041, 9042 located within the user's ear. The propagation of the audio along the fluid (e.g., air) in the tubing 9020 and through the earpiece 9041, 9042 advantageously allows the user to hear an audio cue even during a treatment procedure. For example, a user wearing the earpieces may be unable to hear an audio cue generated by an external device not connected to the earpieces(s), such as audio from the user device (e.g., smartphone). The use of the tubing 9020 to propagate the sound (e.g., audio cue) generated by the audio generator 9150 permits the sound to travel directed towards the user's ear canal to be heard by the user. However, while the audio generator 9150 is illustrated in FIGS. 99 and 100 as residing within of the housing 9005 of the treatment device 9000, it will be understood by one of ordinary skill in the art that the audio generator 9150 may be located outside the housing 9005. For example, the audio generator 9150 may be connected to the outlet 9190, tubing 9020, and/or other structure located outside the housing 9005. In some embodiments, the audio generator 9150 can be positioned on or near the pressure chamber 9180, on or near the outlet 9190, etc. The audio generator 9150 can be a speaker, a vibrator, or other suitable element that can produce sounds.

As discussed herein, the treatment system 9010 may utilize the one or more audio generators 9150 for an audio treatment that uses sounds (e.g., to stimulate therapeutic neurological responses). The treatment system 9010 may use an audio treatment parameter profiles that include information indicative of parameters for the audio treatment (e.g., different tones, volumes, and durations, for sounds at different times). The one or more audio generators 9150 may be configured to introduce various tone frequencies, such as tones known to have therapeutic effects. The tones may be within audible or inaudible ranges. For example, an audio treatment parameter profile may incorporate a 500 Hz tone for the treatment of acoustic myogenic disorder. In some instances, the audio generator 9150 may provide music known to have therapeutic effects.

The treatment system 9010 can provide an audio treatment parameter profile in isolation or in combination with any other treatment profile discussed herein. For example, in some embodiments, the treatment system 9010 may superimpose a generator audio cue with the pressure therapy. The supplemental therapies can improve or harmonize with the foundation therapy. For example, a negative pressure therapy configured stretch a muscle may be followed by an audio cue that causes the stretched muscle to reflex. The reflex may trigger and stimulate receptors on the muscle to provide a therapeutic effect. A synergy can be produced in many instances where the combination of therapies can have therapeutic results that are superior to the sum of results of the individual therapies.

Examples of Specific Therapeutic Indications

Treatment of Tonic Tensor Tympani Syndrome/Hyperacusis

The tensor tympani arises from the cartilaginous portion of the auditory tube, and the adjoining part of the great wing of the sphenoid, as well as from the osseous canal in which it is contained. Passing backward through the canal, it ends in a slender tendon which enters the tympanic cavity, makes a sharp bend around the extremity of the septum, known as the processus cochleariformis, and is inserted into the neck of the malleus, near its root. The tensor tympani is the larger of the two muscles of the tympanic cavity, the other being the stapedius. Innervation of the tensor tympani is from the tensor tympani nerve, a branch of the mandibular division of the trigeminal nerve.

The tympanic reflex helps prevent damage to the inner ear by muffling the transmission of vibrations from the tympanic membrane to the oval window. The tympanic reflex manifests, for example, when a loud sound causes reflexive contraction of the tensor tympani muscle to dampen sound by arresting the tympanic membrane and ossicular chain. When this muscle is stretched it fires muscle spindle stretch receptor-generated impulses into the trigeminal nerve system, which can have an antinociceptive effect.

In some embodiments, external ear pressure regulation can treat or prevent tonic tensor tympani syndrome. Tonic tensor tympani syndrome (TTTS) is an involuntary, anxiety-based condition where the reflex threshold for tensor tympani muscle activity is reduced, causing a frequent spasm. This can trigger aural symptoms from tympanic membrane tension, middle ear ventilation alterations and trigeminal nerve irritability. TTTS can potentially cause the distinctive symptoms of acoustic shock, which can develop after exposure to an unexpected loud sound perceived as highly threatening. Hyperacusis is a dominant AS symptom.

Not to be limited by theory, external ear pressure regulation, such as via negative pressure, induces stretch of the tonic tensor tympani muscle. Furthermore, by combining stretch with another therapeutic modality such as auditory stimulation (e.g., introduction of a loud sound), certain embodiments can cause the muscle to reflexively fire while it is loaded in an eccentric position (e.g., the muscle is stretched, then caused to contract in that position). The audio tone can be applied through the ear (e.g., through an earpiece of a treatment system), or through bone conduction (e.g., though the mastoid bone). In some cases, the subject can be instructed to chew, talk, yell, or otherwise create a noise or tone to trigger the muscle reflex.

In some embodiments, the stretch can occur at pre-set intervals. In some embodiments, by randomly stretching and releasing the muscle (via unique and randomized pressure patterns), the muscle spindles can discharge, sending unique signals to the brain and trigeminal system and creating an enhanced therapeutic effect.

Treatment of Hearing Loss

In some embodiments, systems and methods as disclosed herein can treat or prevent hearing loss, including, for example, conductive hearing loss; sensorineural hearing loss; and/or mixed hearing loss. Conductive hearing loss can be due to pathology associated with the ear canal, ear drum, or middle ear and its bony structures, such as the malleus, incus, and stapes. Sensorineural hearing loss is typically due to problems of the inner ear, also known as nerve-related hearing loss. Mixed hearing loss refers to a combination of conductive and sensorineural hearing loss, and typically indicates there may be damage in the outer or middle ear and in the inner ear (cochlea) or auditory nerve.

Types of conductive hearing loss include congenital absence of ear canal or failure of the ear canal to be open at birth, congenital absence, malformation, or dysfunction of the middle ear structures. Conventional therapies include surgical correction, amplification with a bone conduction hearing aid, or a surgically implanted, osseointegrated device (for example, the Baha or Ponto System), or a hearing aid, depending on the status of the hearing nerve.

Other causes of conductive hearing loss include infection; tumors; middle ear fluid from infection or Eustachian tube dysfunction; foreign body; and trauma (as in a skull fracture). Acute infections can be treated with antibiotic or antifungal medications. Chronic ear infections, chronic middle fluid, and tumors can require surgery. If there is no response to initial medical therapy, infectious middle ear fluid is usually treated with antibiotics—while chronic non-infectious middle ear fluid is treated with surgery (or pressure equalizing tubes).

A genetic form of conductive hearing loss is otosclerosis, in which there is bony fixation of the stapes (the third little bone of hearing in the middle ear), where sound can't get to the middle ear. Otosclerosis usually presents with hearing loss in early adulthood. Otosclerosis can in some cases be successfully managed with surgery to replace the immobile stapes with a mobile stapes prosthesis or with a hearing aid. The measles virus may contribute to stapes fixation in those with a genetic predisposition to otosclerosis. The incidence of otosclerosis may be decreasing in some communities due to measles vaccination. Otosclerosis (a hereditary disorder in which a bony growth forms around a small bone in the middle ear, preventing it from vibrating when stimulated by sound) usually causes a conductive hearing loss, a hearing loss caused by a problem in the outer or middle ear. Less frequently, otosclerosis may cause a sensorineural hearing loss (damaged sensory cells and/or nerve fibers of the inner ear), as well as a conductive hearing loss.

Sensorineural hearing loss can result from, for example, acoustic trauma (or exposure to excessively loud noise), which may respond to medical therapy with corticosteroids to reduce cochlea hair cell swelling and inflammation to improve healing of these injured inner ear structures. Sensorineural hearing loss can occur from head trauma or abrupt changes in air pressure such as in airplane descent, which can cause inner ear fluid compartment rupture or leakage, which can be toxic to the inner ear. There has been variable success with emergency surgery when this happens.

Sudden sensorineural hearing loss, presumed to be of viral origin, is an otologic emergency that is medically treated with corticosteroids. Bilateral progressive hearing loss over several months, also diagnosed as autoimmune inner ear disease, is managed medically with long-term corticosteroids and sometimes with drug therapy. Autoimmune inner ear disease is when the body's immune system misdirects its defenses against the inner ear structures to cause damage in this part of the body.

Fluctuating sensorineural hearing loss may be from unknown cause or associated with Meniere's Disease. Symptoms of Meniere's disease are hearing loss, tinnitus (or ringing in the ears), and vertigo. Meniere's disease may be treated medically with a low-sodium diet, diuretics, and corticosteroids. If the vertigo is not medically controlled, then various surgical procedures are used to eliminate the vertigo.

A treatment device can apply pressure to stretch the tympanic membrane to improve mobility thereof. The treatment device can be applied as a continuous passive mobility device for improving mobility of the tympanic membrane, such as after a surgery (e.g., middle ear surgery). The treatment device can apply various combinations of pressure profiles, such as similar to the relaxation session or supplemental session discussed herein, such as without requesting feedback from the user regarding symptom information.

The treatment device can also apply targeted tones to "exercise" the nerve pathways for those tones. The tones can be applied through the ear (e.g., through an earpiece of the treatment device) or by bone conduction (e.g., through the mastoid bone). Applying the tones through bone conduction can be beneficial because the tones can bypass the tympanic membrane which can have limited mobility, which would dampen the tones. In some cases the tones can be applied through the ear after the pressure treatment has stretched the tympanic membrane to improve mobility thereof during the tone portion of the treatment. In some cases an audio gram can be performed to identify which tones the patent has hearing loss for, and those tones can then be applied during treatment to build up the neurological pathways associated with those tones.

Treatment of Trigeminal Neuralgia

In some embodiments, systems and methods as disclosed herein can involve one, two, or more stimulation modalities to treat or prevent trigeminal neuralgia. Trigeminal neuralgia (TN), also called tic douloureux, is a chronic pain condition that affects the trigeminal or 5th cranial nerve, one of the most widely distributed nerves in the head. TN is a form of neuropathic pain (pain associated with nerve injury or nerve lesion.) The typical or "classic" form of the disorder (called "Type 1" or TN1) causes extreme, sporadic, sudden burning or shock-like facial pain that lasts anywhere from a few seconds to as long as two minutes per episode. These attacks can occur in quick succession, in volleys lasting as long as two hours. The "atypical" form of the disorder (called "Type 2" or TN2), is characterized by constant aching, burning, stabbing pain of somewhat lower intensity than Type 1. Both forms of pain may occur in the same person, sometimes at the same time. The intensity of pain can be physically and mentally incapacitating. In some embodiments, acoustic stimulation, and/or other stimulation modalities as disclosed herein can stimulate the trigeminal nerve to reduce or eliminate pain and other symptoms associated with trigeminal neuralgia. In some embodiments, the stimulation modality can be combined with pharmacologic therapy for an unexpected synergistic effect. The pharmacologic therapy could include, for example, carbamazepine, oxcarbazepine, valproic acid, phenytoin, gabapentin, baclofen, pregabalin, or other therapeutic agents.

Treatment of Serous Otitis Media

Acute otitis media is a potentially painful infection of the middle ear, especially common in children. Otitis media can include the buildup of serous fluid on or proximate the tympanic membrane. In some embodiments, one or more stimulation modalities as disclosed herein can be utilized to treat otitis media. In some embodiments, caloric stimulation modalities can be utilized, e.g., cooling or heating for soothing, cooling to counteract inflammation and provide analgesia akin to ice to the tympanic membrane can provide analgesia. In some embodiments, caloric (cooling or heating) stimulation can be applied proximate a bone such as the temporal bone. In some embodiments, insufflation stimulation modalities can gently mechanically stimulate the tympanic membrane to counteract the outward bulging caused by the infectious process. A pumping action of insufflation may in some cases also advantageously promote clearing of effusion in the middle ear. In some embodiments, the stimulation modalities can be synergistic with, and co-administered with antibiotic therapy regiments. One, two, or more stimulation modalities as disclosed herein can also be utilized for therapy.

Treatment of Canalithiasis, Cupulothiasis, and Vertigo

Epley has previously described a method for liberating otoconia from the canals, a common cause of benign paroxysmal positional vertigo (BPPV). Epley's maneuver includes a series of maneuvers including head-turning that position the head (and vestibular canals) in a position so as to allow the canaliths to leave the canals and enter the utricle and saccule. In some cases, the canaliths can become stuck/adhered to the sidewalls (endolymphatic sac) of the canals, which prevents them from being liberated from the canal—in this manner, vertigo can persist when the otoconia fall back into the canals. In some embodiments, one, two, or more stimulation modalities can be utilized to apply, for example, pulses of pressure, oscillations, and/or vibration into the endolymph of the semicircular canal advantageously utilizing the continuity of the connection between the tympanic membrane-ossicular chain-oval window. Energy can be delivered, for example, via this chain (e.g., originating from the device through the aforementioned series of structures) to the endolymph and perilymph which the cochlea and vestibular canals share. In some embodiments, systems and methods can unexpectedly and synergistically enhance this process by, in some cases, warming the endolymph by heating the ear canal and consequently the endolymph of the vestibular canals.

Treatment of Chronic Pain Syndromes

In some embodiments, one, two, or more stimulation modalities associated with the ear as disclosed herein can be combined with a stimulation modality at the ear, or another non-ear anatomical location to effect somatotopic neural remapping.

In some embodiments, an auditory stimulus can be presented concurrent with, before, and/or after a stimulus to the ear, or a non-ear anatomical location of which acute or chronic pain, inflammation, and/or other symptoms are experienced by a patient. Not to be limited by theory, but association and neural priming can allow for the stimulation of the CNS associated with a first sensory modality to be synergistically amplified by stimulation of a second sensory modality. The tactile stimulus can be delivered to any part of the ear or other anatomical location on the human body. For example, the first sensory modality could be vibration of the ear, while the second sensory modality could be tones delivered by bone conduction.

In some embodiments, because there is a large gap between auditory (20 Hz-20 kHz) and tactile ranges (0 Hz-1,000 Hz), for the "gap range", the tactile stimulus (in embodiments where synchrony is desired) can be dropped by a selected number of octaves to allow for tone matching. In some embodiments, at least two, three, or more matched stimuli are delivered, such as an audible tone, a tactile stimulus dropped by one octave, and a tactile stimulus dropped by two octaves. In some embodiments, a tone and/or pressure pattern might be delivered to the ear while a tactile stimulus is delivered over a first symptomatic region as well as an second asymptomatic region of the body. This can advantageously create a change (e.g., an improvement) in the perceived symptoms from the symptomatic body region.

In some embodiments, a first stimulus presented at the ear (including but not limited to oscillation, vibration, pulsing, and the like) can be matched with a second stimulus at an anatomical location elsewhere on the body other than the ear (e.g., neck, upper or lower extremities, face, chest, torso, back, abdomen, pelvis, genitals, visceral organs, or the like). Not to be limited by theory, areas that have undergone cortical remapping (such as in chronic pain), can be remapped by coupling one, two, or more stimulus modalities at the receptor-rich ear canal to a tactile stimulus modality at the other anatomical location on the body. Tactile stimuli on the body can be generated in various ways. For example, tactile stimuli can produce a matching or asynchronous stimulus including a haptic device (e.g., a vibratory motor), transcutaneous or percutaneous electrical stimulus (e.g., surface electrode, needle-electrode), evoked potential generating device, or pulsed sound or shockwave device for example. In some embodiments, the stimuli at the other anatomical location on or in the body could be caloric (warm or cold stimulation). The stimulus to the other anatomical location can be delivered, for example, between about 0 Hz and about 1,000 Hz. In some embodiments, the stimulus presented at the ear can be delivered at the same or substantially the same frequency at that of the tactile stimulus at the different anatomical location on the body. In some embodiments, the pain is associated with reflex sympathetic dystrophy, complex regional pain syndrome, fibromyalgia, diabetic neuropathy, sciatica, trauma, or other pain syndromes. In some embodiments, the other anatomical location is adjacent a joint, nerve, or muscle (e.g., a shoulder, knee, cervical spine, thoracic spine, lumbosacral spine, elbow, hip, foot, ankle, or other site), and can be synchronized with a stimulation modality associated with the ear to advantageously allow for less painful and potentially longer and more efficacious stimulation therapy sessions. In some embodiments, the non-ear stimulation modality can be configured to cause limb muscle contraction.

Neural Maintenance and Rehabilitation

In some embodiments, one, two, or more stimulation modalities associated with the ear as disclosed herein can be utilized to treat or prevent degeneration from low-stimulus environments. For example, "exercise" galvanic stimulation via bone conduction, among others, may be beneficial for comatose patients, patients in a vegetative state, patients in intensive care units, postoperative patients recovering from anesthesia, patients suffering a concussion, stroke, TIA, or other neurologic injury.

In some embodiments, one, two, or more stimulation modalities associated with the ear as disclosed herein can be incorporated with oculomotor training as a form of brain rehabilitation and/or eye-motor training. While a stimulus, e.g., when warm or cool media is delivered to the ear, the eyes can develop nystagmus (a classic "wobbling" of the eyes). This nystagmus can be overcome (sometimes with much difficulty) if the subject is presented with a visual target to focus on. In this way, the "higher brain centers" (including, for example, the frontal eye field center of the frontal cortex) can be recruited to "override" the lower vestibulo-ocular pathways. Precise stimulation, including but not limited to intentional pulses of warm air, may cause nystagmus. A short burst (e.g., about or less than about 10, 9, 8, 7, 6, 5, 4, 3, 2, or 1 second) of warm air may be sufficient to only produce a short volley of nystagmus. More persistent (e.g., about or at least about 15, 20, 25, 30, 45, 60, or more seconds) warming or cooling may produce more robust and persistent nystagmus. As such, duration of nystagmus desired can be advantageously produced.

In some embodiments, systems can include a screen, projected image, or image inside some form of goggles (including any visual target presented in the visual field that a subject can stare at). As nystagmus is brought on via stimulation, an image can be presented at a certain time, which can require that the subject overrides the nystagmus to acquire the focal point. This can in some cases take an effort that is proportionate to the extent, duration and amplitude of the nystagmus. While the subject's eyes are oscillating from side-to-side (the classic nystagmus pattern), the user's vision can be blurry because the eyes may not settle on a focal point. If the subject's eyes continue to oscillate, they can experience blurry vision. Forcing the subject to utilize the brain to focus on a point while their eyes are oscillating can advantageously train the brain (including but not limited to the frontal lobe) and oculomotor system. This can have advantages as a therapy for, e.g., brain injury, stroke, concussion, sporting performance and other conditions of the brain, such as depression and other numerous conditions described elsewhere herein.

Nystagmus typically has slow and fast phases. In some embodiments, warming the right ear will allow the fast phase of the nystagmus as the eyes move toward the right (and slow phase toward the left); and vice versa. In some embodiments, with the use of one, two, or more stimulation modalities, a fixed target can be presented so that the user is forced to stare at a fixed point to override their nystagmus. However, in some embodiments the visual target can be moving and need not be fixed. The visual target can also move "against the current" of the eyes. For example, if the eyes are being driven slowly toward the left, a target might appear in the left visual field causing the user's brain to saccade (fast eye movement) toward the left. The visual target can then slowly move toward the opposite direction, causing the user to have to concentrate to slowly move the eyes toward the right (where the brain is trying to quickly move them). In other words, in some embodiments, an oculomotor training tool can be configured to couple fixed or moving visual targets with a stimulation system, e.g., a stimulation modality that cools/warms the ear canal and/or other forms of stimulation as described herein. In some embodiments, the system can optionally include elements configured to record and track eye movements, including functionality that can compare how the user's eyes behave in relation to the visual target (e.g., whether they are successful in overriding the nystagmus or not, and if not, how are their eyes failing.)

Postoperative Recovery

In some embodiments, one, two, or more stimulation modalities (e.g., including ear pressure regulation stimulation modalities) can be applied before, during, or after an ENT procedure to reduce post-surgical scarring of the tympanic membrane.

Treatment Effects

Beneficial physiological effects may include, without limitation, reduction of pain, improved rate of healing, reduction of inflammation, improved neurologic function, including strength, sensation, vision, hearing, olfactory, taste, cranial nerve function, cognition, gait, and balance, and the like. Other non-limiting possible treatment effects can include enhancement of a number of cell-related activities: cell replication, cell metabolism, protein synthesis, ATP production, mitochondria replication, phagocytosis, and photodissociation of oxygenated hemoglobin. Effects may include, for example: capillary formation, parasympathetic nervous system stimulation, increased endorphin release, increased production and release of adrenal steroids, reduction in pain and in inflammation, reduction of tissue edema, and immune system stimulation. In some embodiments, a beneficial effect could include slowing or preventing the otherwise irreversible loss of neurons due to neurodegeneration after a primary destructive event, whether the neurodegeneration is due to disease mechanisms associated with the primary destructive event or secondary destructive event. In some embodiments, systems and methods as disclosed herein could treat a wide variety of psychiatric conditions or other disorders, including dysthymia, depression, anxiety, bipolar disorder, mania, schizophrenia, schizoaffective disorder, obsessive-compulsive disorder, panic disorder, post-traumatic stress disorder, phobias, anorexia, bulimia, Tourette's syndrome, insomnia, hypersomnia, and others. In some embodiments, systems and methods as disclosed herein can treat or prevent neuropathic craniofacial pain syndromes such as neuralgias, for example trigeminal neuralgia; temporomandibular joint syndrome; headache syndromes such as migraine headaches, chronic daily headaches, cluster headaches, muscle tension headaches, post-traumatic headaches, or chronic paroxysmal hemicranias; endolymphatic hydrops; vertigo, labyrinthitis, and Meniere's disease; tinnitus; syndromes resulting from brain injury; syndromes resulting from impaired neurologic function, including cognitive disorders such as attention deficit disorder, emotional disorders such as anxiety disorders, or seizure disorders; phantom limb; middle ear disorders; inner ear disorders; or the like, or combinations thereof.

In some embodiments, stimuli from the first stimulation modality and the second stimulation modality are administered concurrently. In other embodiments, at least a portion of the first stimulation modality is administered prior to, or following the administration of the second stimulation modality, or in alternating pulses in some embodiments.

In certain embodiments, the treatment may be terminated after one treatment period (also referred to herein as a treatment session), while in other embodiments, the treatment may be repeated for at least two, three, four, five, ten, or even more treatment periods. The time between subsequent treatment periods can be at least about five minutes, at least two in a 24-hour period, at least about 1 to 2 days, or at least about one week. The length of treatment time and frequency of treatment periods can depend on several factors, including the functional recovery of the patient. In certain embodiments, one or more treatment parameters can be adjusted in response to a feedback signal from a device monitoring the patient.

Clinical Example

An insufflator device was used in a clinical setting with 30 subjects, all of whom were reporting for treatment while suffering from acute migraine. The treatment device brought about a 67% complete pain resolution rate at the 2-hour, post treatment end-point. Users reported a consistently favorable and very comfortable experience with the device and treatment method. Overall, results appeared to demonstrate a, treatment option for acute migraine with appealing safety profile as an alternative or adjunct to drug treatment.

Table 1 (shown below) contains the descriptive statistics (mean, standard deviation, median, maximum and minimum) for the pain severity ratings at the different time points, the descriptive statistics of the changes between pre-treatment and the post-treatment time points, and the number of patients pain free at the different post-treatment time points.

TABLE 1

| Pain severity ratings at the different time points, changes between pre-treatment and all post-treatment time points, and number of patients pain free | | | |
|---|---|---|---|
| Time point | Descriptive statistics mean ± standard deviation median (range) | Changes from pre-treatment mean ± standard deviation median (range) | Number of patients pain free and their percentage |
| Pre-treatment | 7.2 ± 1.3 7 (5-10) | — | — |
| Immediately Post-Treatment | 1.4 ± 2.2 0 (0-8) | 5.8 ± 2.4 6 (1.10) | 18 (60%) |
| 2 Hrs Post-Treatment | 1 ± 1.7 0 (0-7) | 6.2 ± 1.7 6 (2-10) | 20 (66.7%) |
| 24 Hrs Post-Treatment | 0.8 ± 1.6 0 (0-7) | 6.5 ± 1.7 7 (3-9) | 15 (50%) |

The therapeutic mechanism of action may result from stimulation of sensory receptors. For example, the stimulation may occur at the tympanic membrane, the ear canal, the middle ear, and/or the inner ear. The tympanic membrane and external ear canal have overlapping sensory innervation by cranial nerves V, VII, IX and X, whereas the middle ear is supplied by cranial nerves V and IX, and the vestibulocochlear nerve (cranial nerve VIII) contains afferent fibers from the sensory organs of inner ear. With respect to vestibulocochlear contributions, it is noted that since both vestibular (saccule) and auditory (cochlea) transducers are situated in the close proximity of stapes, the movement of stapes has been shown to stimulate the cochlea as well as the vestibule (saccule). The therapeutic, antinociceptive effects may be mediated via one or more of the following potential pathways: auriculotemporal nerve afferent modulation of sensory traffic within the trigeminal nucleus caudalis (TNC) and other sites including the sensory thalamus and cortex; vestibulocochlear nerve to vestibular nucleus to thalamus to parieto-insular vestibular cortex; vagus nerve afferent modulation of sensory traffic within the TNC, rostral sensory modulatory centers, and autonomic centers including the nucleus tractus solitarius.

The treatment device may include one or more features directed towards usability and risk mitigation. For example the treatment device may: 1) be safe for unsupervised personal use; 2) deliver well-controlled, consistent, treatment patterns, 3) deliver a comfortable experience in a population characteristically sensitive to most sensory stimuli (especially touch/pressure, sound and light); and 4) deliver the most efficacious treatment possible.

With respect to safety, a risk may include the potential tympanic membrane rupture caused by overpressure. Studies have demonstrated that the minimum overpressure value required to produce minor or moderate tympanic membrane rupture is around 2.9-5.1 psi (20-35 kPa). Furthermore, devices used in the field of otology and audiometry employ pressure ranges of +0.9 psi to −1.2 psi. As outlined by the American Speech-Language-Hearing Association Working Group on Aural Acoustic-Immittance Measurements, with regard to pneumatic systems, Type 1 and 2 instruments must be able to make pressure changes between +200 and −600 daPa, and that the instruments should not produce more than 600 daPa or less than 800 daPa (e.g., +9 psi and −1.2 psi) as they might cause damage to otherwise weakened tympanic membranes. The device, in some embodiments, may be equipped with an active safety mechanism. For example, the active safety mechanism may comprise an electronic circuit configured to compare a pressure sensor signal (reflecting current pressure within the system) to a maximum positive pressure threshold (e.g., +0.8 psi) and a maximum negative pressure threshold (e.g., −0.8 psi). These pressure limits may include a functional range below those known to pose threat to tympanic membrane integrity. In the event the pressure signal exceeds either threshold, in some embodiments, power to the device pressure modulator is disabled. During treatment the current measured pressure is compared to the desired target pressure. If the resulting error signal exceeds +/−0.1 psi, or if at any time the measured pressure exceeds +/−0.8 psi, the pressure modulator is stopped.

In some instances, the device can produce a negligible noise profile. 85 dB of noise is widely accepted as the level at which damage to the hearing system may occur. Normal conversation typically occurs around 60 dB, while rustling of leaves or whispering occurs around 20 dB. The device may be devoid of any primary sources of noise (e.g. motor noise and vibration). The user can be exposed to secondary noise limited to that generated by the movement of air within the sealed ear canal, which is much less than 20 dB (below the level of whispering).

In some embodiments, the potential for user pain or discomfort by excessive pressure may be mitigated by using a simple, pretreatment calibration test. The pretreatment calibration test can include exposing the patient to the maximal ranges of function in both the positive and negative pressure ranges and asking the patients for any sign of pain or discomfort through the range of pressures.

With respect to efficacy, the results of this study evidence efficacy rates potentially superior to widely used oral medications for migraine treatment. Notwithstanding widespread regard for triptans as treatment for acute migraine, for a large proportion of patients, they are ineffective (they provide 2 hour headache freedom in only around 30% of patients and a sustained pain response up to 24 hours in only 20%). By comparison, this study reports impressive rates around 67% and 50%, respectively.

These results appeared to demonstrate a promising, novel, treatment option for acute migraine with appealing safety profile as an alternative or adjunct to drug treatment. Furthermore, they strongly suggest that the treatment device is a well-tolerated, non-invasive therapeutic device, sufficiently designed to provide a comfortable treatment for acute migraine with an appealing safety profile. In some embodiments, the treatment device may include a user interface design based on smart phone technology.

ADDITIONAL EXAMPLES

The following numbered examples are not an exhaustive list, and additional example embodiments are disclosed and covered by this disclosure.

1. A system for treating a medical condition associated with pain, the system comprising:
a treatment device configured to apply pressure to an ear of a patient, the treatment device comprising:
an earpiece;
a pressure generator configured to apply pressure through the earpiece to an external ear canal of the ear to move the tympanic membrane of the ear; and
a wireless communication interface configured to receive instructions, wherein the pressure generator is responsive to the instructions received by the communication interface to change the applied pressure in the ear;
a user device that is separate from the treatment device, the user device comprising:
a user interface configured to output information to a user and to receive input information from the user; and
a wireless communication interface configured to communicate wirelessly with the communication interface of the treatment device;
at least one computer hardware processor; and
computer-readable memory storing instructions that are executable by the at least one computer hardware processor to cause the system to:
receive first pain information via the user interface;
provide instructions to operate the treatment device to administer pressure treatment to the ear according to a pressure treatment parameter profile for a first treatment phase;
receive second pain information via the user interface after the first treatment phase;
select a pressure treatment parameter profile for a second treatment phase based at least in part on the second pain information; and
provide instructions to operate the treatment device to administer pressure treatment to the ear according to the selected pressure treatment parameter profile for the second treatment phase.

2. The system of Example 1, wherein the treatment device is configured to administer varying frequencies of oscillation of pressure and/or vibrations to the ear.

3. The system of Example 1, wherein the first pain information comprises one or more pain intensity values for one or more corresponding pain locations on a head, wherein the second pain information comprises one or more pain intensity values for one or more corresponding pain locations on the head, and wherein the instructions are executable by the at least one computer hardware processor to cause the system to:
compare the second pain information to the first pain information; and
select the pressure treatment parameter profile for the second treatment phase based at least in part on the comparison of the second pain information to the first pain information.

4. The system of Example 1, wherein the second pain information comprises an indication of pain reduction or non-reduction, and wherein the instructions are executable by the at least one computer hardware processor to cause the system to select the pressure treatment parameter profile for the second treatment phase based at least in part on the indication of pain reduction or non-reduction.

5. The system of Example 4, wherein the instructions are executable by the at least one computer hardware processor to cause the system to select the pressure treatment parameter profile for the second treatment phase to be the same as the pressure treatment parameter profile for the first treatment phase in response to the second pain information comprising an indication of pain reduction.

6. The system of Example 4, wherein the instructions are executable by the at least one computer hardware processor to cause the system to select the pressure treatment parameter profile for the second treatment phase to be different than the pressure treatment parameter profile for the first treatment phase in response to the second pain information comprising an indication of pain non-reduction.

7. The system of any one of Examples 1 to 6, wherein the instructions are executable by the at least one computer hardware processor to cause the system to select the pressure treatment parameter profile for the second treatment phase based at least in part on effectiveness data stored in the memory for at least one available pressure treatment parameter profile that is stored in the memory.

8. The system of Example 7, wherein the effectiveness data is based at least in part on a determined effectiveness of the at least one available pressure treatment parameter profile during a prior treatment for the patient.

9. The system of any one of Examples 1 to 8, wherein the instructions are executable by the at least one computer hardware processor to cause the system to update effectiveness data that is stored in the memory and associated with the pressure treatment parameter profile for the first treatment phase based at least in part on the second pain information.

10. The system of any one of Examples 1 to 9, wherein the instructions are executable by the at least one computer hardware processor to cause the system to provide instructions from the communication interface of the user device to the communication interface of the treatment device to operate the treatment device to administer pressure treatment to the ear according to one or more pressure treatment parameter profiles for one or more treatment phases prior to the first treatment phase.

11. The system of any one of Examples 1 to 10, wherein the user device comprises a smart phone.

12. A system for controlling a treatment device that is configured to apply pressure to an ear of a patient, the system comprising:
a user interface configured to output information to a user and to receive input information from the user;
at least one computer hardware processor;

computer-readable memory storing instructions that are executable by the at least one computer hardware processor to cause the system to:

receive pain information via the user interface;

select a pressure treatment parameter profile based at least in part on the pain information; and provide instructions to operate the treatment device to administer pressure treatment to the ear according to the selected pressure treatment parameter profile.

13. The system of Example 12, wherein the pain information comprises one or more pain intensity values for one or more corresponding pain locations on a head.

14. The system of any one of Examples 12 to 13, wherein the instructions are executable by the at least one computer hardware processor to cause the system to:

analyze the pain information and determine a pain category for the pain; and select the pressure treatment parameter profile based at least in part on the determined pain category.

15. The system of Example 14, wherein the memory stores a plurality of available pressure treatment parameter profiles and effectiveness data for one or more of the available pressure treatment parameter profiles, wherein the effectiveness data is indicative of a determined effectiveness of the one or more of the available pressure treatment parameter profiles for one or more pain categories.

16. The system of any one of Examples 12 to 15, wherein the received pain information is the initial pain information for a treatment session, and the selected pressure treatment parameter profile is the initial pressure treatment parameter profile for the treatment session.

17. The system of any one of Examples 12 to 15, wherein the instructions are executable by the at least one computer hardware processor to cause the system to provide instructions to operate the treatment device to administer pressure treatment to the ear according to a pressure treatment parameter profile for a prior treatment phase before receiving the pain information.

18. The system of Example 17, wherein the pain information comprises an indication of pain reduction or non-reduction after the prior treatment phase, and wherein the instructions are executable by the at least one computer hardware processor to cause the system to select the pressure treatment parameter profile based at least in part on the indication of pain reduction or non-reduction.

19. The system of Example 18, wherein the instructions are executable by the at least one computer hardware processor to cause the system to select the pressure treatment parameter profile to be the same as the pressure treatment parameter profile for the prior treatment phase in response to the pain information comprising an indication of pain reduction.

20. The system of Example 18, wherein the instructions are executable by the at least one computer hardware processor to cause the system to select the pressure treatment parameter profile to be different than the pressure treatment parameter profile for the prior treatment phase in response to the pain information comprising an indication of pain non-reduction.

21. The system of any one of Examples 17 to 20, wherein the instructions are executable by the at least one computer hardware processor to cause the system to:

receive prior pain information before the prior treatment phase;

compare the pain information to the prior pain information; and select the pressure treatment parameter profile based at least in part on the comparison of the pain information to the prior pain information.

22. The system of Example 21, wherein the prior pain information comprises one or more pain intensity values for one or more corresponding pain locations on a head, and wherein the second pain information comprises one or more pain intensity values for one or more corresponding pain locations on the head.

23. The system of any one of Examples 17 to 22, wherein the instructions are executable by the at least one computer hardware processor to cause the system to update effectiveness data that is stored in the memory for the pressure treatment parameter profile for the prior treatment phase based at least in part on the pain information.

24. The system of Example 23, wherein the instructions are executable by the at least one computer hardware processor to cause the system to:

update the effectiveness data to indicate that the pressure treatment parameter profile for the prior treatment phase was not effective; and at a later time provide instructions to operate the treatment device to administer pressure treatment to the ear according to the same pressure treatment parameter profile from the prior treatment phase to reevaluate that pressure treatment parameter profile.

25. The system of any one of Examples 17 to 24, wherein the memory stores a plurality of available pressure treatment parameter profiles, and wherein the instructions are executable by the at least one computer hardware processor to cause the system to:

determine that the pressure treatment parameter profile for the prior treatment phase was ineffective based at least in part on the pain information; and replace the pressure treatment parameter profile for the prior treatment phase with a new pressure treatment parameter profile.

26. The system of any one of Examples 17 to 25, wherein the instructions are executable by the at least one computer hardware processor to cause the system to determine that the pressure treatment parameter profile for the prior treatment phase was ineffective based at least in part on the pain information, wherein the pressure treatment parameter profile for the prior treatment phase is one of a kinetic profile type or an akinetic profile type, and wherein the selected pressure treatment parameter profile is the other of the akinetic profile type or the kinetic profile type.

27. The system of any one of Examples 17 to 26, wherein the instructions are executable by the at least one computer hardware processor to cause the system to:

determine that the pressure treatment parameter profile for the prior treatment phase was ineffective based at least in part on the pain information;

select the pressure treatment parameter profile to be different than the pressure treatment parameter profile for the prior treatment phase;

receive subsequent pain information after administration of the pressure treatment to the ear according to the selected pressure treatment parameter profile;

determine that the selected pressure treatment parameter profile was ineffective based at least in part on the subsequent pain information;

output an instruction via the user interface for the patient to change the treatment from one ear to the other ear.

28. The system of Example 27, wherein the instructions are executable by the at least one computer hardware processor to cause the system to provide instructions to operate the treatment device to administer pressure treatment to the other ear according to a pressure treatment parameter profile that is known to be effective for the patient.

29. The system of any one of Examples 12 to 28, wherein the instructions are executable by the at least one computer hardware processor to cause the system to select the pressure treatment parameter profile based at least in part on effectiveness data that is stored in the memory for at least one available pressure treatment parameter profile that is stored in the memory.

30. The system of Example 29, wherein the effectiveness data is based at least in part on a determined effectiveness of the at least one available pressure treatment parameter profile during a prior treatment for the patient.

31. The system of any one of Examples 29 to 30, wherein the effectiveness data is based at least in part on a determined effectiveness of the at least one available pressure treatment parameter profile for a general population.

32. The system of any one of Examples 12 to 31, wherein the selected pressure treatment parameter profile comprises applying negative pressure to the ear.

33. The system of any one of Examples 12 to 32, wherein the selected pressure treatment parameter profile comprises oscillating the applied pressure to the ear about a negative pressure baseline.

34. The system of any one of Examples 12 to 33, wherein the instructions are executable by the at least one computer hardware processor to cause the system to:

receive a command via the user interface to modify the pressure intensity for the pressure treatment parameter profile; and provide instructions to operate the treatment device to administer the pressure treatment to the ear according to the pressure treatment parameter profile with the modified pressure intensity.

35. The system of Example 34, wherein the instructions are executable by the at least one computer hardware processor to cause the system to provide instructions to operate the treatment device to administer pressure treatment to the ear according to a subsequent pressure treatment parameter profile with an unmodified pressure intensity.

36. The system of Example 34, wherein the instructions are executable by the at least one computer hardware processor to cause the system to provide instructions to operate the treatment device to administer pressure treatment to the ear according to a subsequent pressure treatment parameter profile with the modified pressure intensity.

37. The system of any one of Examples 12 to 36, wherein the instructions are executable by the at least one computer hardware processor to cause the system to display a visual indicator associated with the selected pressure treatment parameter profile during administration of the pressure treatment to the ear according to the selected pressure treatment parameter profile.

38. The system of any one of Examples 12 to 37, wherein the user interface comprises a display, and wherein the instructions are executable by the at least one computer hardware processor to cause the system to:

display a head on the display;

receive one or more selections via the user interface of one or more pain locations on the head; and receive input via the user interface of one or more pain intensity values that correspond to the one or more pain locations.

39. The system of Example 38, wherein the instructions are executable by the at least one computer hardware processor to cause the system to:

receive a selection of a mirrored configuration or a flipped configuration;

in the mirrored configuration, display a right side of the head on a right side of the display, and display a left side of the head on a left side of the display;

in the flipped configuration, display the right side of the head on the left side of the display, and display the left side of the head on the right side of the display.

40. The system of any one of Examples 38 to 39, wherein the one or more pain locations are selected from between 10 and 30 available pain zones on the head.

41. The system of any one of Examples 38 to 40, wherein the instructions are executable by the at least one computer hardware processor to cause the system to display a visual representation of the one or more selected pain locations and the one or more corresponding pain intensity values on the head.

42. The system of any one of Examples 12 to 41, wherein the user interface comprises a display, and wherein the instructions are executable by the at least one computer hardware processor to cause the system to display a face on the head, wherein an expression of the face is based at least in part on the pain information.

43. The system of Example 42, wherein the instructions are executable by the at least one computer hardware processor to cause the system to change the expression of the face as additional pain information is received during a treatment session.

44. The system of Example 43, wherein the instructions are executable by the at least one computer hardware processor to cause the system to display an accelerated visual summary of the treatment session after the treatment session is completed.

45. The system of Example 44, wherein the instructions are executable by the at least one computer hardware processor to cause the system to receive a command via the user interface to share the accelerated visual summary of the treatment session on social media.

46. The system of Example 45, wherein the memory stores a connectedness score for the patient, and wherein the instructions are executable by the at least one computer hardware processor to cause the system to increase the connectedness score in response to the command to share the accelerated visual summary of the treatment session on social media.

47. The system of any one of Examples 12 to 46, wherein the memory stores a proactivity score for the patient, and wherein the instructions are executable by the at least one computer hardware processor to cause the system to increase the proactivity score for the patient in response to a treatment session using the treatment device.

48. The system of any one of Examples 12 to 47, wherein the memory stores an understanding score for the patient, and wherein the instructions are executable by the at least one computer hardware processor to cause the system to:

receive input via the user interface;

provide information regarding headache pain via the user interface in response to the input; and increase the understanding score for the patient.

49. The system of any one of Examples 12 to 48, wherein the instructions are executable by the at least one computer hardware processor to cause the system to:

receiving associated symptom information via the user interface, wherein the associated symptom information relates to one or more additional symptoms that are associated with headache pain; and select the pressure treatment parameter profile based at least in part on the associated symptom information.

50. The system of any one of Examples 12 to 49, wherein the user interface comprises a display, and wherein the instructions are executable by the at least one computer hardware processor to cause the system to:

display a listing of available associated symptoms that are associated with headache pain, wherein the listing has a first order;

receive one or more selections via the user interface of one or more of the available associated symptoms;

at a later time, display the listing of available associated symptoms having a second order that is different than the first order, wherein the second order is based at least in part on the one or more selections of one or more of the available associated symptoms.

51. The system of any one of Examples 12 to 50, wherein the instructions are executable by the at least one computer hardware processor to cause the system to upload information regarding the treatment to a server that is configured to aggregate treatment info from multiple users.

52. The system of any one of Examples 12 to 51, comprising a treatment device that comprises:

an earpiece configured to seal against the ear; and a pressure generator configured to apply pressure through the earpiece to an external ear canal of the ear to move the tympanic membrane of the ear.

53. The system of Example 52, comprising a single housing that includes the pressure generator, the user interface, the at least one computer hardware processor, and the computer-readable memory.

54. The system of Example 52, comprising a user device having a first housing, the user device comprises the user interface, the at least one computer hardware processor, and the computer-readable memory, wherein the treatment device comprises a second housing that is separate from the first housing.

55. The system of Example 54, wherein treatment device comprises a communication interface configured to receive instructions, wherein the pressure generator is responsive to the instructions received by the communication interface to change the applied pressure in the ear, and wherein the at least one computer hardware processor is communicatively coupled to a controller communication interface that is configured to communicate with the communication interface of the treatment device.

56. The system of Example 55, wherein the controller communication interface and the communication interface of the treatment device are configured to communicate wirelessly.

57. The system of any one of Examples 54 to 56, wherein the user device comprises a smart phone.

58. A system for treating a medical condition associated with pain, the system comprising:

a treatment device configured to apply pressure to an ear of a patient, the treatment device comprising:

an earpiece;

a pressure generator configured to apply pressure through the earpiece to an external ear canal of the ear to move the tympanic membrane of the ear; and a wireless communication interface configured to receive instructions, wherein the pressure generator is responsive to the instructions received by the communication interface to change the applied pressure in the ear;

a user device that is separate from the treatment device, the user device comprising:

a user interface configured to output information to a user and to receive input information from the user;

a wireless communication interface configured to communicate wirelessly with the communication interface of the treatment device;

at least one computer hardware processor; and computer-readable memory storing instructions that are executable by the at least one computer hardware processor to cause the system to:

receive pain information via the user interface, the pain information comprising one or more pain intensity values for one or more corresponding pain locations on a head;

determine whether to apply pressure treatment to a right ear or a left ear of the patient based at least in part on the pain information;

provide an instruction via the user interface to position the earpiece of the treatment device in the determined ear for treatment; and provide instructions to operate the treatment device to apply pressure treatment to the determined ear.

59. The system of Example 58, wherein the instructions are executable by the at least one computer hardware processor to cause the system to:

analyze the pain information to determine that all the one or more pain locations are on either a right side of the head or a left side of the head;

determine to apply the pressure treatment to the right ear in response to a determination that all the one or more pain locations are on the right side of the head; and determine to apply the pressure treatment to the left ear in response to a determination that all the one or more pain locations are on the left side of the head.

60. The system of Example 58, wherein the instructions are executable by the at least one computer hardware processor to cause the system to:

analyze the pain information to determine that the one or more pain locations are on both a right side of the head and a left side of the head;

determine to apply the pressure treatment to the right ear in response to a determination that a highest pain intensity value is on the right side of the head; and determine to apply the pressure treatment to the left ear in response to a determination that the highest pain intensity value is on the left side of the head.

61. The system of Example 58, wherein the instructions are executable by the at least one computer hardware processor to cause the system to:

analyze the pain information to determine that the one or more pain locations are on both a right side of the head and a left side of the head;

determine aggregate pain intensity values for the right side and the left side;

determine to apply the pressure treatment to the right ear in response to a determination that the right side aggregate pain intensity value is higher than the left side aggregate pain intensity value; and determine to apply the pressure treatment to the left ear in response to a determination that the left side aggregate pain intensity value is higher than the right side aggregate pain intensity value.

62. The system of Example 58, wherein the instructions are executable by the at least one computer hardware processor to cause the system to:

analyze the pain information to determine that the one or more pain locations are on both a right side of the head and a left side of the head;

determine whether the right side or left side has a higher number of pain locations;

determine to apply the pressure treatment to the right ear in response to a determination that the right side has the higher number of pain locations; and determine to apply the pressure treatment to the left ear in response to a determination that the left side has the higher number of pain locations.

63. The system of Example 58, wherein the instructions are executable by the at least one computer hardware processor to cause the system to:

analyze the pain information to determine that the pain is symmetrical on the right side of the head and the left side of the head; and determine to apply the pressure treatment to the left ear.

64. The system of Example 58, wherein the instructions are executable by the at least one computer hardware processor to cause the system to:

analyze the pain information to determine that the one or more pain locations are on both a right side of the head and a left side of the head; and determine to apply the pressure treatment to the left ear.

65. The system of Example 58, wherein the instructions are executable by the at least one computer hardware processor to cause the system to:

receive updated pain information after administration of pressure treatment; and determine whether to switch the pressure treatment from the one ear to the other ear based at least in part on the updated pain information;

66. The system of Example 65, wherein the instructions are executable by the at least one computer hardware processor to cause the system to provide an instruction via the user interface to change the earpiece of the treatment device from one ear to the other in response to a change of the one or more pain intensity values and/or the one or more pain locations.

67. The system of any one of Examples 58 to 66, wherein the instructions are executable by the at least one computer hardware processor to cause the system to:

receive information regarding associated symptoms via the user interface; and determine the ear for treatment based at least in part on the information regarding the associated symptoms.

68. The system of any one of Examples 58 to 67, wherein the user device comprises a smart phone.

69. A system for treating a medical condition associated with pain, the system comprising:

a treatment device configured to apply pressure to an ear of a patient, the treatment device comprising:

an earpiece;

a pressure generator configured to apply pressure through the earpiece to an external ear canal of the ear to move the tympanic membrane of the ear;

a pressure sensor configured to measure pressure in the external ear canal of the ear; and a wireless communication interface configured to receive instructions, wherein the pressure generator is responsive to the instructions received by the communication interface to change the applied pressure in the ear;

a user device that is separate from the treatment device, the user device comprising:

a user interface configured to output information to a user and to receive input information from the user;

a wireless communication interface configured to communicate wirelessly with the communication interface of the treatment device;

at least one computer hardware processor; and computer-readable memory storing instructions that are executable by the at least one computer hardware processor to cause the system to:

provide instructions to operate the treatment device to increase pressure in the ear towards a maximum target pressure;

receive an input from the user via the user interface before the pressure reaches the maximum target pressure; and set a maximum treatment pressure that is lower than the maximum target pressure.

70. The system of Example 69, wherein the maximum target pressure can be a maximum positive pressure or a maximum negative pressure.

71. The system of any one of Examples 69 to 70, wherein the instructions are executable by the at least one computer hardware processor to cause the system to provide instructions to the treatment device to reduce the pressure in the ear in response to the user input.

72. The system of any one of Examples 69 to 71, wherein the instructions are executable by the at least one computer hardware processor to cause the system to:

provide instructions from the communication interface of the user device to the communication interface of the treatment device to operate the treatment device to increase pressure in the ear towards a reduced maximum target pressure;

receive an indication from the treatment device that the reduced maximum target pressure was measured by the pressure sensor; and set the maximum treatment pressure to the reduced maximum target pressure.

73. The system of Example 72, wherein the instructions are executable by the at least one computer hardware processor to cause the system to:

receive a pressure value from the treatment device, wherein the pressure value was taken at the time of the input received by the user interface; and determine the reduced maximum target pressure based at least in part on the pressure value that was taken at the time of the input.

74. The system of any one of Examples 69 to 73, wherein the instructions are executable by the at least one computer hardware processor to cause the system to:

receive demographic information from the patient;

determine the maximum target pressure based at least in part on the demographic information.

75. The system of Example 74, wherein the demographic information comprises at least one of gender, age, weight, and height.

76. The system of any one of Examples 69 to 75, wherein the instructions are executable by the at least one computer hardware processor to cause the system to:

receive pressure values from the treatment device as the pressure increases toward the maximum target pressure;

analyze the received pressure values to determine whether there is a leak; and provide an instruction via the user interface to reapply the earpiece in response to a determination that there was a leak.

77. The system of any one of Examples 69 to 76, wherein the user device comprises a smart phone.

78. A system for treating a medical condition associated with pain, the system comprising:

a treatment device configured to apply pressure to an ear of a patient, the treatment device comprising:

an earpiece;

a pressure generator configured to apply pressure through the earpiece to an external ear canal of the ear to move the tympanic membrane of the ear; and a wireless communication interface configured to receive instructions, wherein the pressure generator is responsive to the instructions received by the communication interface to change the applied pressure in the ear;

a user device that is separate from the treatment device, the user device comprising:

a user interface configured to output information to a user and to receive input information from the user, wherein the user interface comprises a display;

a wireless communication interface configured to communicate wirelessly with the communication interface of the treatment device;

at least one computer hardware processor; and computer-readable memory storing instructions that are executable by the at least one computer hardware processor to cause the system to:

receive pain information via the user interface;

display a head having a face with an expression, wherein an expression of the face is based at least in part on the pain information.

79. The system Example 78, wherein the instructions are executable by the at least one computer hardware processor to cause the system to:

receive additional pain information after at least a portion of a treatment session; and change the displayed expression of the face based at least in part on the additional pain information.

80. The system of any one of Examples 78 to 79, wherein the instructions are executable by the at least one computer hardware processor to cause the system to:

receive the pain information by:

receiving one or more selections via the user interface of one or more pain locations on the head; and receiving input via the user interface of one or more pain intensity values that correspond to the one or more pain locations.

81. The system of Example 80, wherein the one or more pain locations are selected from between 10 and 30 available pain zones on the head.

82. The system of any one of Examples 80 to 81, wherein the instructions are executable by the at least one computer hardware processor to cause the system to:

receive a selection of a mirrored configuration or a flipped configuration;

in the mirrored configuration, display a right side of the head on a right side of the display, and display a left side of the head on a left side of the display;

in the flipped configuration, display the right side of the head on the left side of the display, and display the left side of the head on the right side of the display.

83. The system of any one of Examples 80 to 82, wherein the instructions are executable by the at least one computer hardware processor to cause the system to display a visual representation of the one or more selected pain locations and the one or more corresponding pain intensity values on the head.

84. The system of any one of Examples 78 to 83, wherein the user device comprises a smart phone.

85. A system for treating a medical condition associated with pain, the system comprising:

a treatment device configured to apply pressure to an ear of a patient, the treatment device comprising:

an earpiece;

a pressure generator configured to apply pressure through the earpiece to an external ear canal of the ear to move the tympanic membrane of the ear; and a wireless communication interface configured to receive instructions, wherein the pressure generator is responsive to the instructions received by the communication interface to change the applied pressure in the ear;

a user device that is separate from the treatment device, the user device comprising:

a user interface configured to output information to a user and to receive input information from the user, wherein the user interface comprises a display;

a wireless communication interface configured to communicate wirelessly with the communication interface of the treatment device;

at least one computer hardware processor; and computer-readable memory storing instructions that are executable by the at least one computer hardware processor to cause the system to:

provide instructions to operate the treatment device to administer pressure treatment to the ear for a treatment session;

receive pain information via the user interface at multiple times during the treatment session; and after the treatment session is completed, display an accelerated visual summary of the treatment session on the display of the user interface.

86. The system of Example 85, wherein the pain information comprises one or more pain intensity values for one or more corresponding pain locations on a head.

87. The system of Example 86, wherein the one or more pain intensity values and/or the one or more pain locations change during the treatment session, and wherein the accelerated visual summary of the treatment session includes a visual indication of the changing one or more pain intensity values and/or the one or more pain locations.

88. The system of any one of Examples 85 to 86, wherein the accelerated visual summary of the treatment session includes a displayed visual indication associated with one or more pressure treatment parameter profiles applied during one or more treatment phases of the treatment session.

89. The system of any one of Examples 85 to 88, wherein the accelerated visual summary of the treatment session includes a displayed head having a face, wherein an expression of the face is based at least in part on the pain information, and wherein the expression of the face changes during the accelerated visual summary of the treatment session to represent reduction of pain resulting from the treatment.

90. The system of any one of Example 85 to 89, wherein the accelerated visual summary of the treatment session is provided as a video played on the display.

91. The system of any one of Example 85 to 90, wherein the instructions are executable by the at least one computer hardware processor to cause the system to receive a command via the user interface to share the accelerated visual summary of the treatment session on social media.

92. The system of Example 91, wherein the memory stores a connectedness score for the patient, and wherein the instructions are executable by the at least one computer hardware processor to cause the system to increase the connectedness score in response to the command to share the accelerated visual summary of the treatment session on social media.

93. A system for treating a medical condition associated with pain, the system comprising:

a treatment device configured to apply pressure to an ear of a patient, the treatment device comprising:

an earpiece;

a pressure generator configured to apply pressure through the earpiece to an external ear canal of the ear to move the tympanic membrane of the ear; and a wireless communication interface configured to receive instructions, wherein the pressure generator is responsive to the instructions received by the communication interface to change the applied pressure in the ear;

a user device that is separate from the treatment device, the user device comprising:

a user interface configured to output information to a user and to receive input information from the user;

a wireless communication interface configured to communicate wirelessly with the communication interface of the treatment device;

at least one computer hardware processor; and computer-readable memory storing instructions that are executable by the at least one computer hardware processor to cause the system to:

store at least one of a proactivity score, a connectedness score, and an understanding score for the patient in the computer-readable memory; and at least one of:

increase the proactivity score for the patient in response to a treatment session using the treatment device;

increase the connectedness score in response to a command received by the user interface to share condition information with others; and increase the understanding score in response to a command received by the user interface to access information regarding headache pain.

94. The system of Example 93, wherein the instructions are executable by the at least one computer hardware processor to cause the system to increase the connectedness score in response to a command received by the user interface to share an accelerated visual summary of a treatment session.

95. The system of any one of Example 93 to 94, wherein the instructions are executable by the at least one computer hardware processor to cause the system to increase the connectedness score in response to a command received by the user interface to chare the condition information on social media.

96. A system for treating a medical condition associated with pain, the system comprising:

a treatment device configured to apply pressure to an ear of a patient, the treatment device comprising:

an earpiece;

a pressure generator configured to apply pressure through the earpiece to an external ear canal of the ear to move the tympanic membrane of the ear; and a wireless communication interface configured to receive instructions, wherein the pressure generator is responsive to the instructions received by the communication interface to change the applied pressure in the ear;

a user device that is separate from the treatment device, the user device comprising:

a user interface configured to output information to a user and to receive input information from the user;

a wireless communication interface configured to communicate wirelessly with the communication interface of the treatment device;

at least one computer hardware processor; and computer-readable memory storing instructions that are executable by the at least one computer hardware processor to cause the system to:

store prescription information in the memory, wherein the prescription is indicative of a prescription for a medication;

receive medication consumption information via the user interface, wherein the medication consumption information is indicative of consumption of the medication by the patient; and compare the medication consumption information to the prescription information to determine whether the medication consumption was proper or improper under the prescription.

97. The system of Example 96, wherein the instructions are executable by the at least one computer hardware processor to cause the system to:

store a proactivity score in the memory; and increase the proactivity score in response to a determination that the medication consumption was proper under the prescription.

98. The system of Example 96, wherein the instructions are executable by the at least one computer hardware processor to cause the system to output an alert via the user interface in response to a determination that the medication consumption was improper.

99. The system of any one of Examples 1 to 98, wherein the treatment device is configured to apply pressure to the ear to treat migraine headache pain.

100. The system of any one of Examples 1 to 99, wherein the treatment device includes an earpiece that is configured to insert into the external ear canal of the ear.

101. The system of any one of Examples 1 to 99, wherein the treatment device includes an earpiece that fits over the ear.

102. A computer-implemented method comprising:

receiving condition symptom information via a user interface;

selecting a treatment parameter profile based at least in part on the condition symptom information; and providing instructions to operate a treatment device to administer treatment to a patient according to the selected treatment parameter profile.

103. A computer-implemented method comprising:

receiving condition symptom information relating to one or more symptoms of a condition of a patient; and determine whether to apply treatment to a right ear or a left ear of the patient based at least in part on the condition symptom information.

104. A computer-implemented method comprising:

providing instructions to a pressure treatment device to increase pressure in the ear towards a maximum target pressure;

receiving an input via the user interface before the pressure reaches the maximum target pressure; and setting a maximum treatment pressure value that is lower than the maximum target pressure.

105. A computer-implemented method comprising:

receiving condition symptom information for a condition affecting a body portion of a patient, wherein the condition symptom information is received through a user interface that has a display; and displaying an anatomical representation of the body portion on the display, wherein an appearance of the anatomical representation of the body portion is based at least in part on the condition symptom information.

106. A computer-implemented method comprising:

provide instructions to operate a treatment device to administer treatment to a patient for a treatment session;

receive condition symptom information for a condition affecting a body portion of a patient at multiple times during the treatment session, wherein the condition symptom information is received through a user interface that has a display; and after the treatment session is completed, display an accelerated visual summary of the treatment session on the display of the user interface.

107. A computer-implemented method comprising:

storing at least one of a proactivity score, a connectedness score, and an understanding score for a patient in a computer-readable memory; and at least one of:

increase the proactivity score for the patient in response to a treatment session using a treatment device for treating a medical condition;

increase the connectedness score in response to a command received by a user interface to share information with others relating to the medical condition; and increase the understanding score in response to a command received by the user interface to access information regarding the medical condition.

108. A computer-implemented method comprising:

storing a proactivity score for a patient in a computer-readable memory;

storing prescription information in the memory, wherein the prescription is indicative of a prescription for a medication;

receiving medication consumption information via the user interface, wherein the medication consumption information is indicative of consumption of the medication by the patient;

comparing the medication consumption information to the prescription information to determine whether the medication consumption was proper or improper under the prescription; and increasing the proactivity score in response to a determination that the medication consumption was proper under the prescription.

109. A computer-readable memory storing instructions that are executable by at least one computer hardware processor to perform the computer-implemented method of any one of the preceding method Examples.

110. A system for controlling a treatment device, the system comprising:

a user interface configured to output information to a user and to receive input information from the user;

at least one computer hardware processor;

the computer-readable memory of Example 109, wherein the memory stores instructions that are executable by the at least one computer hardware processor to provide instructions to operate the treatment device.

111. The system of Example 110, further comprising a treatment device.

112. The system of Example 110, further comprising a treatment device that is configured to administer treatment to an ear of the patient.

113. The system of Example 112, wherein the treatment device is configured to administer at least one of a pressure treatment, a vibration treatment, and a temperature treatment to the ear.

114. The system of any one of Examples 111 to 113, wherein the treatment device comprises:

an earpiece; and a pressure generator configured to apply pressure through the earpiece to an external ear canal of the ear to move the tympanic membrane of the ear.

115. The system of Example 114, comprising a single housing that includes the pressure generator, the user interface, the at least one computer hardware processor, and the computer-readable memory.

116. The system of Example 114, comprising a user device having a first housing, the user device comprises the user interface, the at least one computer hardware processor, and the computer-readable memory, wherein the treatment device comprises a second housing that is separate from the first housing.

117. The system of Example 116, wherein treatment device comprises a communication interface configured to receive instructions, wherein the pressure generator is responsive to the instructions received by the communication interface to change the applied pressure in the ear, and wherein the at least one computer hardware processor is communicatively coupled to a controller communication interface that is configured to communicate with the communication interface of the treatment device.

118. The system of Example 117, wherein the controller communication interface and the communication interface of the treatment device are configured to communicate wirelessly.

119. The system of any one of Examples 116 to 118, wherein the user device comprises a smart phone.

120. A system for controlling a treatment device, the system comprising:

a user interface configured to output information to a user and to receive input information from the user;

a controller configured to cause the system to:

receive symptom information via the user interface;

select a treatment parameter profile based at least in part on the symptom information; and provide instructions to operate the treatment device to administer treatment according to the selected treatment parameter profile.

121. The system of Example 120, wherein the controller includes at least one computer hardware processor, and computer-readable memory storing instructions that are executable by the at least one computer hardware processor to operate the system.

122. The system of Example 120, wherein the controller includes special purpose circuitry that is configured to operate the system.

123. The system of any one of Examples 120 to 122, wherein the system comprises a treatment device.

124. The system of Example 123, wherein the treatment device is configured to apply pressure to an ear of a user.

125. The system of any one of Examples 123 to 124, wherein the treatment device is configured to treat a neurological disorder.

126. The system of any one of Examples 123 to 125, wherein the treatment device is configured to treat migraine headache pain.

127. The system of any one of Examples 120 to 126, wherein the symptom information comprises one or more pain intensity values for one or more corresponding pain locations.

128. The system of any one of Examples 120 to 127, wherein the system stores, in computer-readable memory, a plurality of available treatment parameter profiles and effectiveness data for one or more of the available treatment parameter profiles.

129. The system of Example 128, wherein the effectiveness data is indicative of a determined effectiveness of the one or more of the available treatment parameter profiles for one or more pain categories.

130. The system of any one of Examples 120 to 129, wherein the symptom information includes an indication of symptom relief or non-relief after a prior treatment phase, and wherein the controller causes the system to select the treatment parameter profile based at least in part on the indication of symptom relief or non-relief.

131. The system of Example 130, wherein the controller selects the same treatment parameter profile as the prior treatment phase in response to an indication of symptom relief.

132. The system of Example 130, wherein the controller selects a different treatment parameter profile than the treatment parameter profile from the prior treatment phase in response to an indication of symptom non-relief.

133. The system of any one of Examples 130 to 132, wherein the controller causes the system to:
  receive prior symptom information before the prior treatment phase;
  compare the symptom information to the prior symptom information; and
  select the treatment parameter profile based at least in part on the comparison of the symptom information to the prior symptom information.

134. The system of any one of Examples 130 to 133, wherein the controller causes the system to update effectiveness data that is stored in memory for the treatment parameter profile of the prior treatment phase, wherein the effectiveness data is based at least in part on the symptom information received after use of the treatment parameter profile.

135. The system of Example 134, wherein the controller causes the system to:
  update the effectiveness data to indicate that the treatment parameter profile for the prior treatment phase was effective; and
  during a later treatment session, receive later symptom information that is similar to the symptom information; and
  provide instructions to operate the treatment device to administer treatment according to the same pressure treatment parameter profile from the prior treatment phase during the later treatment session.

136. The system of any one of Examples 130 to 135, wherein the controller is configured to cause the system to:
  determine that the treatment parameter profile for the prior treatment phase was ineffective based at least in part on the symptom information; and
  replace the treatment parameter profile from the prior treatment phase with a new treatment parameter profile.

137. The system of any one of Examples 120 to 136, wherein the controller is configured to cause the system to select the pressure treatment parameter profile based at least in part on effectiveness data that is stored in computer-readable memory for at least one available treatment parameter profile that is stored in the memory.

138. The system of Example 137, wherein the effectiveness data is based at least in part on a determined effectiveness of the at least one available treatment parameter profile during a prior treatment for the patient.

139. The system of any one of Examples 137 to 138, wherein the effectiveness data is based at least in part on a determined effectiveness of the at least one available treatment parameter profile for a general population.

140. The system of any one of Examples 120 to 139, wherein the user interface comprises a display, and wherein the controller is configured to cause the system to:
  display an indicia of a body portion on the display;
  receive one or more selections via the user interface of one or more symptom locations on the indicia of the body portion;
  receive input via the user interface of one or more symptom intensity values that correspond to the one or more symptom locations.

141. The system of Example 140, wherein the controller is configured to cause the system to display a visual representation of the one or more selected symptom locations and/or the one or more symptom intensity values on the indicia of the body portion.

142. The system of any one of Examples 140 to 141, wherein controller is configured to cause the condition of the displayed indicia of the body portion to change based at least in part on the symptom information.

143. The system of any one of Examples 120 to 142, wherein the controller is configured to cause the system to determine a location for treatment based at least in part on symptom information received from the user via the user interface.

144. The system of Example 143, wherein the controller is configured to cause the system to provide an instruction via the user interface to position the treatment device at the determined location for treatment.

145. The system of any one of Examples 143 to 144, wherein the controller is configured to cause the system to provide instructions to operate the treatment device to apply treatment to the determined location on the user's body.

146. The system of any one of Examples 120 to 145, wherein the controller is configured to cause the system to:
  operate the treatment device to apply increasing treatment towards a maximum target treatment level;
  receive an input from the user via the user interface before the treatment reaches the maximum target treatment level; and
  set a maximum treatment level that is lower than the maximum target pressure.

147. The system of Example 146, wherein the controller is configured to cause the system to operate the treatment device to apply increasing treatment towards a reduced maximum target treatment level.

148. The system of any one of Examples 120 to 147, wherein the controller is configured to cause the system to:
  operate the treatment device to perform a treatment session;
  receive symptom information at multiple times during the treatment session; and
  after the treatment session, display an accelerated visual summary of the treatment session on a display of the user interface.

149. The system of Example 148, wherein the accelerated visual summary of the treatment session comprises a relief replay video.

150. The system of any one of Examples 120 to 149, wherein the system includes a user device and a treatment device that in communication with the user device.

151. The system of Example 150, wherein the treatment device is in wireless communication with the user device.

152. The system of any one of Examples 150 to 151, wherein the controller includes at least one processor on the user device.

153. The system of any one of Examples 150 to 151, wherein the controller includes at least one processor on the treatment device.

154. The system of any one of Examples 150 to 151, wherein the controller includes processors on both the user device and the treatment device.

155. A computer-implemented system, comprising
a memory element containing a program;
a processor communicatively coupled to said memory element, said program executable by said processor to:
receive indications of condition symptoms of a condition;
compare said indications of condition symptoms to a plurality of treatment device operating profiles of a treatment device contained in said memory element;
select one of said plurality of treatment device operating profiles based on comparison of said indications of condition symptoms to said plurality of treatment device operating profiles; and
operate said treatment device to administer said one of said plurality of treatment operating profiles.

156. The system of Example 155, wherein said program is further executable to:
receive indications of condition symptom relief or non-relief of said condition subsequent to administration of said one of said plurality of treatment operating profiles by said treatment device;
compare said indications of condition symptom relief or non-relief of said condition symptoms of said condition to said plurality of treatment device operating profiles of said treatment device contained in said memory element;
select one of said plurality of treatment device operating profiles based on comparison of said indications relief or non-relief to said plurality of treatment device operating profiles; and
operate said treatment device to administer said one of said plurality of treatment operating profiles to a subject.

157. The system of Example 156, wherein said program is further executable to:
depict a graphical user interface on the display surface of a computing device; and
receive said indications of condition symptoms and said indications of condition symptom relief or non-relief of said condition generated by user command in said graphical user interface.

158. The system of Example 157, wherein said program is further executable to:
depict an anatomical representation of a subject in said graphical user interface; and
receive indications of condition symptom location generated by user command in said graphical user interface identifying condition symptom locations on said anatomical representation of said subject.

159. The system of Example 158, wherein said program is further executable to:
depict condition symptom locations on said anatomical representation of said subject;
depict a condition symptom intensity scale corresponding to one of said condition symptom locations in said graphical user interface; and
receive indications of symptom intensity corresponding to one of said condition symptom locations generated by user command selecting a symptom intensity in said condition symptom intensity scale.

160. The system of Example 159, wherein said program is further executable to:
serially combine a plurality of said anatomical representations including said indications of condition symptoms and said indications of condition symptom relief or non-relief into a condition symptom replay video; and
playing said condition symptom replay video in said graphical user interface depicted on said display surface of said computing device.

161. The system of Example 155, wherein said program is further executable to:
measure a sensed physiological parameter of said subject;
synchronize administration of one of said plurality of treatment operating profiles to a sensed physiological parameter of said subject.

162. A method of treating a patient, comprising:
sealably engaging a first external ear canal of a first ear with a first earpiece external surface of the first earpiece, generating a first fluid flow between the first fluid flow generator and the first axial earpiece conduit, and one or more of: regulating a first pressure differential between a first external ear canal pressure of a first ear and an ambient pressure; delivering oscillations to the first ear; and delivering vibrations to the first ear; and
stimulating one or more nerves associated with the ear via a stimuli other than an external ear canal pressure differential.

163. The method of Example 162, wherein the stimuli comprises galvanic stimuli.

164. The method of Example 162, wherein the stimuli comprises acoustic stimuli.

165. The method of Example 164, wherein the acoustic stimuli comprises bone conduction proximate the mastoid bone.

166. The method of Example 164, wherein the acoustic stimuli comprises air conduction.

167. The method of Example 162, wherein the stimuli comprises caloric stimuli.

168. The method of Example 162, further comprising randomizing at least one of the pressure differential and the stimuli.

169. The method of Example 162, further comprising pseudo-randomizing at least one of the pressure differential and the stimuli.

170. The method of Example 162, further comprising synchronizing at least one of the pressure differential and the stimuli with electrical activity of the heart.

171. The method of Example 170, wherein synchronizing at least one of the pressure differential and the stimuli with electrical activity of the heart comprises synchronizing the stimuli with systole of the cardiac cycle.

172. The method of Example 170, wherein synchronizing at least one of the pressure differential and the stimuli with electrical activity of the heart comprises synchronizing the stimuli with systole of the cardiac cycle.

173. The method of Example 162, further comprising sensing heart rate variability of the patient, and adjusting at least one of the pressure differential and the stimuli based off the heart rate variability.

174. The method of Example 162, for treating or preventing tonic tensor tympani syndrome.

175. The method of Example 162, for treating or preventing hearing loss.

176. The method of Example 162, for treating or preventing trigeminal neuralgia.

177. The method of Example 162, for treating or preventing acute pain.

178. The method of Example 162, for treating or preventing chronic pain.

179. A method of treating a patient, comprising:

stimulating one or more nerves associated with an ear via a first stimuli modality; and stimulating one or more nerves associated with the ear via a second stimuli modality different from the first stimuli modality, wherein the first stimuli modality and the second stimuli modality is selected from the group consisting of: ear canal pressure regulation; galvanic vestibular stimulation; acoustic stimulation; bone conduction stimulation; and caloric stimulation.

180. The method of Example 179, further comprising randomizing at least one of the first stimuli and the second stimuli.

181. The method of Example 179, further comprising pseudo-randomizing at least one of the first stimuli and the second stimuli.

182. The method of Example 179, further comprising synchronizing at least one of the first stimuli and the second stimuli with electrical activity of the heart.

183. The method of Example 179, wherein synchronizing the first stimuli and the second stimuli with electrical activity of the heart comprises synchronizing the stimuli with systole of the cardiac cycle.

184. The method of Example 179, wherein synchronizing the first stimuli and the second stimuli with electrical activity of the heart comprises synchronizing the stimuli with diastole of the cardiac cycle.

185. The method of Example 179, further comprising sensing heart rate variability of the patient, and adjusting at least one of the pressure differential and the stimuli based off the heart rate variability.

186. The method of Example 179, wherein the first stimuli modality comprises acoustic stimulation, and wherein the method further comprises shifting the frequency of the second stimuli modality by one or more octaves relative to the first stimuli modality.

187. A method of treating pain, comprising:

stimulating one or more nerves associated with an ear via a first stimuli modality at a first location on or proximate an ear; and concurrently stimulating one or more nerves at a second location where pain is present, wherein combined stimulation is sufficient to effect somatotopic remapping and reduce pain at the second location.

188. A multi-modality medical stimulation system, comprising:

a first stimulus generator configured to stimulate one or more nerves associated with an ear via a first stimuli modality; and a second stimulus generator configured to stimulate one or more nerves associated with an ear via a second stimuli modality;

wherein the first stimuli modality and the second stimuli modality is selected from the group consisting of: ear canal pressure regulation; galvanic vestibular stimulation; acoustic stimulation; bone conduction stimulation; and caloric stimulation.

189. The stimulation system of Example 188, further comprising a controller configured to operably communicate with the first stimulus generator and the second stimulus generator and synchronize pulses of fluid flow with a part of a patient's cardiac cycle.

190. The stimulation system of Example 188, further comprising a controller configured to operably communicate with the first stimulus generator and the second stimulus generator and adjust outputs of the first stimulus generator and the second stimulus generator upon receiving heart rate variability information of a patient from one or more sensors.

191. The stimulation system of Example 188, further comprising a randomization controller configured to operably communicate with the first stimulus generator and the second stimulus generator and randomize pulses of fluid flow.

192. The stimulation system of Example 188, configured to pitch shift a frequency of a first stimuli modality relative to the second stimuli modality.

193. An external ear canal pressure regulation system, comprising:

a first fluid flow generator capable of generating a first fluid flow;

a first earpiece having a first axial earpiece conduit which communicates between a first earpiece first and second ends earpiece second ends, said first axial earpiece conduit fluidicly coupled to said first fluid flow generator, said first earpiece having a first compliant earpiece external surface configured to sealably engage a first external ear canal of a first ear as a first barrier between a first external ear canal pressure and an ambient pressure;

said first fluid flow generator capable of generating a first pressure differential between said first external ear canal pressure and said ambient pressure, said first pressure differential having a first pressure differential amplitude and a first pressure differential amplitude oscillation frequency;

a first pressure sensor which generates a first pressure sensor signal which varies based upon change in said first pressure differential; and a controller configured to operably communicate with the first fluid flow generator and synchronize pulses of fluid flow with a part of a patient's cardiac cycle.

194. An external ear canal pressure regulation system, comprising:

a first fluid flow generator capable of generating a first fluid flow;

a first earpiece having a first axial earpiece conduit which communicates between a first earpiece first and second ends earpiece second ends, said first axial earpiece conduit fluidicly coupled to said first fluid flow generator, said first earpiece having a first compliant earpiece external surface configured to sealably engage a first external ear canal of a first ear as a first barrier between a first external ear canal pressure and an ambient pressure;

said first fluid flow generator capable of generating a first pressure differential between said first external ear canal pressure and said ambient pressure, said first pressure differential having a first pressure differential amplitude and a first pressure differential amplitude oscillation frequency;

a first pressure sensor which generates a first pressure sensor signal which varies based upon change in said first pressure differential; and

a controller configured to operably communicate with the first fluid flow generator and adjust the fluid flow upon receiving heart rate variability information of a patient from one or more sensors.

195. An external ear canal pressure regulation system, comprising:

a first fluid flow generator capable of generating a first fluid flow;

a first earpiece having a first axial earpiece conduit which communicates between a first earpiece first and second ends earpiece second ends, said first axial earpiece conduit fluidicly coupled to said first fluid flow generator, said first earpiece having a first compliant earpiece external surface configured to sealably engage a first external ear canal of a first ear as a first barrier between a first external ear canal pressure and an ambient pressure;

said first fluid flow generator capable of generating a first pressure differential between said first external ear canal pressure and said ambient pressure, said first pressure differential having a first pressure differential amplitude and a first pressure differential amplitude oscillation frequency;

a first pressure sensor which generates a first pressure sensor signal which varies based upon change in said first pressure differential; and a randomization controller configured to operably communicate with the first fluid flow generator and randomize pulses of fluid flow.

196. A method of treating hearing loss, comprising:

delivering a sequence of audible tones to a patient, the tones comprising variable frequencies and intensities;

assessing which of the tones were actually heard by the patient;

stimulating one or more nerves associated with an ear via a first stimuli modality at a first location on or proximate an ear at or around frequencies that were not actually heard by the patient.

204. A computer implemented system, comprising:

a processor communicatively coupled to a memory element containing a program including one or more of:

a setup module executable to allow selection of a condition associated with the operation of a treatment device;

condition symptoms assessment module executable upon selection of said condition to receive indications of condition symptoms of said condition; and a treatment device control module executable to control a treatment device based on indications of condition symptoms received by said condition symptoms assessment module.

205. The system of Example 204, further comprising a condition symptom tracking module executable to receive indications of condition symptom relief or non-relief based on prior control of the treatment device by the treatment device control module.

206. The system of Example 205, further comprising a condition symptom relief replay module executable to create a condition symptom relief video based on received said indications of condition symptoms and subsequently received indications of condition symptom relief or non-relief.

207. The system of Example 204, wherein said program further comprises a physiological parameter synchronization module executable to coordinate operation of said treatment device with a sensed physiological parameter of a subject.

208. The system of Example 206, wherein said program further comprises a user interface module executable to depict a graphical user interface on the display surface of a computing device which by user command generates indications of condition symptoms of said condition and indications of condition symptom relief or non-relief based on prior control of the treatment device by the treatment device control module.

OTHER VARIATIONS

Various other modifications, adaptations, and alternative designs are of course possible in light of the above teachings. Therefore, it should be understood at this time that within the scope of the appended claims the embodiments may be practiced otherwise than as specifically described herein. It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "regulating external ear pressure" includes "instructing the regulation of external ear pressure." The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

Each of the processes, methods, instructions, applications and algorithms described in the preceding sections may be embodied in, and fully or partially automated by, code modules executed by one or more computer systems or computer processors comprising computer hardware. The code modules (or "engines") may be stored on any type of non-transitory computer-readable medium or computer storage device, such as hard drives, solid state memory, optical disc, and/or the like. The systems and modules may also be transmitted as generated data signals (for example, as part of a carrier wave or other analog or digital propagated signal)

on a variety of computer-readable transmission mediums, including wireless-based and wired/cable-based mediums, and may take a variety of forms (for example, as part of a single or multiplexed analog signal, or as multiple discrete digital packets or frames). The processes and algorithms may be implemented partially or wholly in application-specific circuitry. The results of the disclosed processes and process steps may be stored, persistently or otherwise, in any type of non-transitory computer storage such as, for example, volatile or non-volatile storage.

User interfaces described herein are optionally presented (and user instructions may be received) via a user computing device using a browser, other network resource viewer, a dedicated application, or otherwise. Various features described or illustrated as being present in different embodiments or user interfaces may be combined into the same embodiment or user interface. Commands and information received from the user may be stored and acted on by the various systems disclosed herein using the processes disclosed herein. While the disclosure may reference to a user hovering over, pointing at, or clicking on a particular item, other techniques may be used to detect an item of user interest. For example, the user may touch the item via a touch screen, or otherwise indicate an interest. The user interfaces described herein may be presented on a user terminal, such as a laptop computer, desktop computer, tablet computer, smart phone, virtual reality headset, augmented reality headset, or other terminal type. The user terminals may be associated with user input devices, such as touch screens, microphones, touch pads, keyboards, mice, styluses, cameras, etc. While the foregoing discussion and figures may illustrate various types of menus, other types of menus may be used. For example, menus may be provided via a drop down menu, a tool bar, a pop up menu, interactive voice response system, or otherwise.

In general, the terms "engine" and "module", as used herein, refer to logic embodied in hardware or firmware, or to a collection of software instructions, possibly having entry and exit points, written in a programming language, such as, for example, Java, Lua, C or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software modules configured for execution on computing devices may be provided on a computer readable medium, such as a compact disc, digital video disc, flash drive, or any other tangible medium. Such software code may be stored, partially or fully, on a memory device of the executing computing device. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware. Generally, the modules described herein refer to logical modules that may be combined with other modules or divided into sub-modules despite their physical organization or storage. Electronic data sources can include databases, volatile/non-volatile memory, and any memory system or subsystem that maintains information.

The various features and processes described above may be used independently of one another, or may be combined in various ways. All possible combinations and subcombinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments.

Conditional language used herein, such as, among others, "can," "could," "might," "may," "for example," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is otherwise understood with the context as used in general to convey that an item, term, etc. may be either X, Y or Z. Thus, such conjunctive language is not generally intended to imply that certain embodiments require at least one of X, at least one of Y and at least one of Z to each be present.

The term "a" as used herein should be given an inclusive rather than exclusive interpretation. For example, unless specifically noted, the term "a" should not be understood to mean "exactly one" or "one and only one"; instead, the term "a" means "one or more" or "at least one," whether used in the claims or elsewhere in the specification and regardless of uses of quantifiers such as "at least one," "one or more," or "a plurality" elsewhere in the claims or specification.

The term "comprising" as used herein should be given an inclusive rather than exclusive interpretation. For example, a general purpose computer comprising one or more processors should not be interpreted as excluding other computer components, and may possibly include such components as memory, input/output devices, and/or network interfaces, among others.

While certain example embodiments have been described, these embodiments have been presented by way of example only, and are not intended to limit the scope of the disclosure. Nothing in the description is intended to imply that any particular element, feature, characteristic, step, module, or block is necessary or indispensable. The novel methods and systems described herein may be embodied in a variety of other forms; furthermore, various omissions, substitutions, and changes in the form of the methods and systems described herein may be made without departing from the spirit of the inventions disclosed herein. The accompanying claims and their equivalents are intended to cover such forms or modifications as would fall within the scope and spirit of certain of the inventions disclosed herein.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

It should be emphasized that many variations and modifications may be made to the above-described embodiments, the elements of which are to be understood as being among other acceptable examples. All such modifications and variations are intended to be included herein within the scope of the disclosure. The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated.

What is claimed is:

1. A system for treating a medical condition associated with pain, the system comprising:
   at least one earpiece;
   a pressure generator coupled to the earpiece and configured to apply pressure through the at least one earpiece to move a tympanic membrane of either a right or left ear of a user;
   computer-readable memory storing a plurality of pressure treatment parameter profiles and effectiveness data associated with each of the plurality of pressure treatment profiles;
   a user interface configured to output information to the user and to receive input information from the user; and
   at least one computer hardware processor;
   wherein the computer-readable memory stores instructions that are executable by the at least one computer hardware processor to cause the system to:
      receive first pain information via the user interface, the first pain information comprising a first pain location on a head of the user;
      operate the pressure generator to administer pressure treatment to either the right or left ear according to a first pressure treatment parameter profile for a first treatment phase, the first pressure treatment parameter profile selected from the plurality of pressure treatment parameter profiles based on each of the effectiveness data of the plurality of pressure treatment parameter profiles and the first pain information;

receive second pain information via the user interface after the first treatment phase, the second pain information comprising a second pain location on the head of the user;
      update the effectiveness data associated with the first pressure treatment profile based at least in part on the second pain information;
      select a second pressure treatment parameter profile from the plurality of pressure treatment parameter profiles for a second treatment phase based at least in part on a comparison of the second pain information to the first pain information and based on each of the effectiveness data of the plurality of pressure treatment parameter profiles;
      determine whether to apply the second treatment phase to the right ear or the left ear based at least in part on the comparison of the second pain information to the first pain information; and
      operate the pressure generator to administer pressure treatment to at least one of the right ear or the left ear according to the second pressure treatment parameter profile for the second treatment phase, wherein the second pressure treatment parameter profile comprises at least one of a second time duration, a second pressure pulse frequency, or a second pressure amplitude being different than at least one of a first time duration, a first pressure pulse frequency, or a first pressure amplitude of the first pressure treatment parameter profile.

2. The system of claim 1, wherein the effectiveness data is based at least in part on a determined effectiveness of at least one available pressure treatment parameter profile during a prior treatment for the user.

3. The system of claim 1, wherein the instructions are executable by the at least one computer hardware processor to cause the system to:
   send the effectiveness data for the first pressure treatment parameter profile to a remote optimization system that is configured to receive effectiveness information from a plurality of users; and
   receive at least one additional pressure treatment parameter profile that is optimized to be generally effective for pain relief based on the effectiveness information from the plurality of users.

4. The system of claim 1, wherein the instructions are executable by the at least one computer hardware processor to cause the system to:
   determine that the first pressure treatment parameter profile for the first treatment phase was ineffective based at least in part on the second pain information; and
   replace the first pressure treatment parameter profile used for the first treatment phase with a new pressure treatment parameter profile in the computer-readable memory.

5. The system of claim 1, wherein the instructions are executable by the at least one computer hardware processor to cause the system to administer pressure treatment to the ear according to one or more pressure treatment parameter profiles for one or more treatment phases prior to the first treatment phase.

6. The system of claim 1, wherein the user interface comprises a display, and wherein the instructions are executable by the at least one computer hardware processor to cause the system to:
   display a head image on the display;
   receive one or more selections via the user interface of one or more pain locations on the head image;

receive input via the user interface of one or more pain intensity values that correspond to the one or more pain locations;

wherein the one or more pain locations comprise the first and second pain locations; and wherein the one or more pain intensity values comprise a first pain intensity value corresponding with the first pain location and a second pain intensity value corresponding with the second pain location;

wherein the first pain information comprises the first pain intensity value at the first pain location; and wherein the second pain information comprises the second pain intensity value at the second pain location.

7. The system of claim 6, wherein the instructions are executable by the at least one computer hardware processor to cause the system to:

receive a selection of a mirrored configuration or a flipped configuration;

in the mirrored configuration, display a right side of the head image on a right side of the display, and display a left side of the head image on a left side of the display; and in the flipped configuration, display the right side of the head image on the left side of the display, and display the left side of the head image on the right side of the display.

8. The system of claim 6, wherein the instructions are executable by the at least one computer hardware processor to cause the system to display a visual representation of the one or more selected pain locations and the one or more corresponding pain intensity values on the head image on the display.

9. The system of claim 6, wherein the instructions are executable by the at least one computer hardware processor to cause the system to:

display a first expression on a face of the head image on the display, wherein the first expression is based at least in part on the first pain information; and change to a second expression on the face of the head image on the display, wherein the second expression is based at least in part on the second pain information.

10. The system of claim 6, wherein the instructions are executable by the at least one computer hardware processor to cause the system to:

store a pain information for multiple treatment phases of a treatment session; and display an accelerated visual summary of the pain information of the treatment session after the treatment session is completed.

11. The system of claim 1, wherein the instructions are executable by the at least one computer hardware processor to cause the system to:

operate the pressure generator to increase pressure in the ear towards a maximum target pressure;

receive an input from the user via the user interface before the pressure reaches the maximum target pressure; and set a maximum treatment pressure that is lower than the maximum target pressure.

12. The system of claim 11, wherein the instructions are executable by the at least one computer hardware processor to cause the system to:

operate the pressure generator to increase the pressure in the ear towards a reduced maximum target pressure, wherein the reduced maximum target pressure is based at least in part on a pressure value that was taken at a time of the input from the user;

receive an indication that the reduced maximum target pressure was reached without intervention from the user; and set the maximum treatment pressure to the reduced maximum target pressure that was reached.

13. The system of claim 1, further comprising a pressure sensor, wherein the instructions are executable by the at least one computer hardware processor to cause the system to:

provide a prompt to the user via the user interface to attach the earpiece to the ear;

operate the pressure generator to perform a plurality of negative pressure pulses;

measure a resulting pressure using the pressure sensor; and determine whether the earpiece has sealed on the ear based at least in part on the measured resulting pressure.

14. The system of claim 1, further comprising a pressure sensor, wherein the instructions are executable by the at least one computer hardware processor to cause the system to:

operate the pressure generator to administer pressure treatment to the ear according to a pressure treatment parameter profile;

measure a resulting pressure using the pressure sensor;

determine that a leak is present based at least in part on the measured resulting pressure; and operate the pressure generator in response to the leak determination to perform a reseating pressure profile that includes a plurality of negative pressure pulses.

15. The system of claim 14, wherein the instructions are executable by the at least one computer hardware processor to cause the system to:

measure the resulting pressure during the reseating pressure profile;

determine that the earpiece has reseated to resolve the leak based on the measured resulting pressure; and return to operating the pressure generator to administer pressure treatment to the ear according to the pressure treatment parameter profile.

16. The system of claim 14, wherein the instructions are executable by the at least one computer hardware processor to cause the system to:

measure the resulting pressure during the reseating pressure profile;

determine that the reseating pressure profile did not resolve the leak based on the measured resulting pressure; and provide a prompt to the user via the user interface to manually reseat the earpiece.

17. The system of claim 1, further comprising a pressure sensor, wherein the instructions are executable by the at least one computer hardware processor to cause the system to:

operate the pressure generator to administer pressure treatment to the ear according to a pressure treatment parameter profile;

measure a resulting pressure using the pressure sensor;

compare the measured resulting pressure to an expected pressure; and determine that a leak is present when the measured resulting pressure is different from the expected pressure by more than a threshold amount.

18. The system of claim 17, wherein the instructions are executable by the at least one computer hardware processor to cause the system to:

determine that a minor leak is present when the measured resulting pressure is different from the expected pressure by more than the threshold amount and by less than a gross threshold amount; and continue operating the pressure generator to administer pressure treatment to the ear according to the pressure treatment profile to complete the treatment phase.

19. The system of claim 17, wherein the instructions are executable by the at least one computer hardware processor to cause the system to:

determine that a gross leak is present when the measured resulting pressure is different from the expected pressure by more than the threshold amount and also by more than a gross threshold amount; and discontinue the treatment phase and prompt the user to manually reseat the earpiece.

20. The system of claim 1, further comprising a pressure sensor, wherein the instructions are executable by the at least one computer hardware processor to cause the system to:

operate the pressure generator to increase pressure towards a target pressure;

measure a resulting pressure using the pressure sensor;

determine that the measured resulting pressure did not rise above a threshold pressure value; and prompt the user via the user interface to reseat the earpiece.

21. The system of claim 1, wherein the first pain information comprises one or more pain intensity values, and wherein the second pain information comprises one or more pain intensity values.

22. The system of claim 1, wherein the second pressure treatment parameter profile is different than the first pressure treatment parameter profile.

23. The system of claim 1, wherein the instructions are executable by the at least one computer hardware processor to cause the system to determine whether to apply pressure treatment to a right ear or a left ear of the user based at least in part on the first pain information.

24. The system of claim 23, wherein the instructions are executable by the at least one computer hardware processor to cause the system to provide an instruction via the user interface to position the earpiece in the right ear or the left ear for treatment.

25. The system of claim 1, wherein the instructions are executable by the at least one computer hardware processor to cause the system to:

determine that the first pressure treatment parameter profile was ineffective based at least in part on the second pain information; and output an instruction via the user interface for the user to change the treatment from one ear to another ear.

26. The system of claim 1, wherein the instructions are executable by the at least one computer hardware processor to cause the system to determine to apply the second treatment phase to a different ear than the first treatment phase based at least in part on the second pain location being on an opposite side of the head of the user than the first pain location.

27. The system of claim 26, wherein the instructions are executable by the at least one computer hardware processor to cause the system to operate the pressure generator to administer pressure treatment to the different ear according to the second treatment phase.

28. The system of claim 2, wherein:

the second pressure treatment parameter profile is selected based at least in part on at least one factor outputted by at least one machine learning algorithm that is trained with effectiveness information from a plurality of users; and the at least one factor being based at least in part on the effectiveness data inputted into the at least one machine learning algorithm.

29. The system of claim 3, wherein:

the at least one additional pressure treatment parameter profile is based at least in part on at least one factor outputted by at least one machine learning algorithm that is trained with the effectiveness information from the plurality of users;

the at least one factor being based at least in part on the effectiveness data inputted into the at least one machine learning algorithm; and the second pressure treatment parameter profile comprising one of the at least one additional pressure treatment parameter profile.

30. The system of claim 3, wherein:

the determination for whether to apply the second treatment phase to the right ear or the left ear is based at least in part on at least one factor outputted by at least one machine learning algorithm that is trained with the effectiveness information from the plurality of users; and the at least one factor being based at least in part on the effectiveness data inputted into the at least one machine learning algorithm.

31. The system of claim 1, wherein the instructions are executable by the at least one computer hardware processor to cause the system to:

receive third pain information via the user interface after the second treatment phase, the third pain information comprising a third pain location on the head of the user; and update the effectiveness data associated with the second pressure treatment profile based at least in part on the third pain information.

\* \* \* \* \*